US011633459B2

(12) United States Patent
Hogendorf et al.

(10) Patent No.: US 11,633,459 B2
(45) Date of Patent: *Apr. 25, 2023

(54) GIP DERIVATIVES AND USES THEREOF

(71) Applicant: Novo Nordisk A/S, Bagsvaerd (DK)

(72) Inventors: Wouter Frederik Johan Hogendorf, Valby (DK); Henning Thoegersen, Farum (DK); Nicholas Raymond Cox, Seattle, WA (US); Patrick J. Knerr, Plainfield, IN (US); Richard Dimarchi, Carmel, IN (US); Brian Finan, Indianapolis, IN (US); Jesper F. Lau, Farum (DK); Steffen Reedtz-Runge, Bikeroed (DK); Fa Liu, Sammamish, WA (US)

(73) Assignee: Novo Nordisk A/S, Bagsvaerd (DK)

( * ) Notice: Subject to any disclaimer, the term of this patent is extended or adjusted under 35 U.S.C. 154(b) by 48 days.

This patent is subject to a terminal disclaimer.

(21) Appl. No.: 17/052,702

(22) PCT Filed: May 3, 2019

(86) PCT No.: PCT/EP2019/061413
§ 371 (c)(1),
(2) Date: Nov. 3, 2020

(87) PCT Pub. No.: WO2019/211451
PCT Pub. Date: Nov. 7, 2019

(65) Prior Publication Data
US 2022/0000982 A1 Jan. 6, 2022

Related U.S. Application Data

(60) Provisional application No. 62/666,916, filed on May 4, 2018.

(30) Foreign Application Priority Data

May 17, 2018 (EP) .................................... 18172827

(51) Int. Cl.
*A61K 38/00* (2006.01)
*A61K 38/22* (2006.01)
*A61P 3/10* (2006.01)
*A61K 38/26* (2006.01)
*C07K 14/645* (2006.01)

(52) U.S. Cl.
CPC .......... *A61K 38/2235* (2013.01); *A61K 38/26* (2013.01); *A61P 3/10* (2018.01); *C07K 14/645* (2013.01)

(58) Field of Classification Search
CPC ............ A61K 2300/00; A61K 38/2235; A61K 38/26; A61P 3/10; C07K 14/575; C07K 14/645
See application file for complete search history.

(56) References Cited

U.S. PATENT DOCUMENTS

| 9,453,062 B2 * | 9/2016 | Ma ............................ A61P 3/10 |
| 9,556,250 B2 | 1/2017 | Garibay et al. |
| 9,868,772 B2 | 1/2018 | Dimarchi et al. |
| 10,087,229 B2 | 10/2018 | Asami et al. |
| 10,253,078 B2 | 4/2019 | Shelton et al. |
| 10,604,555 B2 * | 3/2020 | Hogendorf ........... C07K 14/605 |
| 2017/0320927 A1 * | 11/2017 | Sauerberg ............... A61P 27/02 |

FOREIGN PATENT DOCUMENTS

| JP | 2013514323 A | 4/2013 |
| JP | 2015528795 A | 10/2015 |
| JP | 2016520511 A | 7/2016 |
| JP | 2018500282 A | 1/2018 |
| WO | 0058360 A2 | 10/2000 |
| WO | 2005082928 A2 | 9/2005 |
| WO | 10011439 A2 | 1/2010 |
| WO | 10016935 A2 | 2/2010 |
| WO | 10016938 A2 | 2/2010 |
| WO | 10016940 A2 | 2/2010 |
| WO | 10016944 A2 | 2/2010 |
| WO | 2011094337 A1 | 8/2011 |
| WO | 2011143208 A1 | 11/2011 |
| WO | 2011143209 A1 | 11/2011 |
| WO | 2012036962 A2 | 3/2012 |
| WO | 2012055770 A1 | 5/2012 |
| WO | 2012088379 A2 | 6/2012 |

(Continued)

OTHER PUBLICATIONS

Irwin et al. GIP(Lys16PAL) and GIP(Lys37PAL): Novel Long-Acting Acylated Analogues of Glucose-Dependent Insulinotropic Polypeptide with Improved Antidiabetic Potential. J. Med. Chem. 2006, 49, 3, 1047-1054 (Year: 2006).*
Baggio et al.,"Biology of Incretins: GLP-1 and GIP," Gastroenterology, 2007, vol. 132, pp. 2131-2157.
Finan et al.,"Reappraisal of GIP Pharmacology for Metabolic Diseases," Feature Review. Trends in Molecular Medicine, 2016, vol. 22, No. 5, pp. 359-376.
Irwin et al., "GIP(Lys16PAL) and GIP(Lys37PAL): Novel Long-Acting Acylated Analogues of Glucose-Dependent Insulinotropic Polypeptide with Improved Antidiabetic Potential 11" Journal of Medicinal Chemistry, 2006, vol. 49, No. 3, pp. 1047-1054.
Dirks, "Brain tumor stem cells: bringing order to the chaos of brain cancer", Journal Clinical Oncology, Jun. 2008, vol. 26, No. 17, pp. 2916-2924.

(Continued)

*Primary Examiner* — Aradhana Sasan
*Assistant Examiner* — Mercy H Sabila
(74) *Attorney, Agent, or Firm* — Leon Y. Lum

(57) ABSTRACT

The present invention relates to novel peptides that are derivatives of glucose-dependent insulinotropic polypeptide (GIP) analogues having improved physical stability in solution and a protracted profile of action. More particular the invention relates to such peptides that are agonists at the GIP receptor and to their use in weight management or for treatment of diseases such as obesity, diabetes or non-alcoholic steatohepatitis (NASH).

19 Claims, No Drawings
Specification includes a Sequence Listing.

(56) References Cited

FOREIGN PATENT DOCUMENTS

| WO | 2012167744 A1 | 12/2012 | | |
|---|---|---|---|---|
| WO | 2013003449 A2 | 1/2013 | | |
| WO | 2013164483 A1 | 11/2013 | | |
| WO | WO-2013164483 A1 * | 11/2013 | ............... | A61P 1/04 |
| WO | 2014158900 A1 | 10/2014 | | |
| WO | 14192284 A1 | 12/2014 | | |
| WO | 15022420 A1 | 2/2015 | | |
| WO | 2015022400 A1 | 2/2015 | | |
| WO | 2015067715 A2 | 5/2015 | | |
| WO | 2015067716 A1 | 5/2015 | | |
| WO | 2016034186 A1 | 3/2016 | | |
| WO | 16066744 A2 | 5/2016 | | |
| WO | 2016138335 A1 | 9/2016 | | |
| WO | 2016205488 A1 | 12/2016 | | |
| WO | 2017160669 A1 | 9/2017 | | |
| WO | 17210168 A1 | 12/2017 | | |
| WO | 2018220123 A1 | 12/2018 | | |

OTHER PUBLICATIONS

Lopez-Lazaro, "The migration ability of stem cells can explain the existence of cancer of unknown primary site. Rethinking metastasis", Oncoscience, May 2015, vol. 2, No. 5, pp. 467-475.

Tran et al., "Survival comparison between glioblastoma multiforme and other incurable cancers", Journal of Clinical Neuroscience, Apr. 2010, vol. 17, No. 4, pp. 417-421.

* cited by examiner

GIP DERIVATIVES AND USES THEREOF

CROSS-REFERENCE TO RELATED APPLICATIONS

This application is a 35 U.S.C. § 371 National Stage application of International Application PCT/EP2019/061413 (WO2019/211451), filed May 3, 2019, which claims priority to European Patent Application 18172827.0, filed May 17, 2018, this application further claims priority under 35 U.S.C. § 119 of U.S. Provisional Application 62/666,916, filed May 4, 2018, the contents of all above-named applications are incorporated herein by reference.

TECHNICAL FIELD

The present application relates to novel peptides that are derivatives of glucose-dependent insulinotropic polypeptide (GIP) analogues with improved physical stability in solution and a protracted profile of action, and to the pharmaceutical use of the GIP derivatives.

INCORPORATION-BY-REFERENCE OF THE SEQUENCE LISTING

The Sequence Listing, entitled "180016 sequence listing_ST25", is 58.669 bytes, was created on 9 Apr. 2019 and is incorporated herein by reference.

BACKGROUND

Glucose-dependent insulinotropic polypeptide (GIP, also known as gastric inhibitory peptide) is one of two endogenous incretins and is a 42 amino acid peptide hormone released from intestinal K-cells following food intake. GIP and the other incretin, glucagon-like Peptide-1 (GLP-1), are gut enteroendocrine cell-derived hormones accounting for the incretin effect, which estimated to account for over 70% of the total insulin response to an oral glucose challenge.

Due to the incretin effect, the GIP receptor has become an attractive drug target in the treatment of metabolic diseases such as obesity and diabetes, with GIP receptor agonists either as a standalone, in combination with GLP-1 receptor agonists, or in combination with GLP-1/glucagon receptor co-agonists. GIP itself has a short plasma half-life due to dipeptidyl peptidase-4 (DPP-IV) mediated inactivation, and poor physical stability due to high tendency to form fibrils in solution.

Patent applications disclosing different GIP receptor agonists or and their potential medical uses are described, such as e.g. disclosed in WO 2016/066744, WO 2016/034186, WO 2012/055770, and WO 2012/167744. Also GIP/GLP-1 receptor co-agonists and their medical use have been studied in e.g. WO 2013/164483, and WO 2014/192284.

The derivatives of the present invention provide novel modified GIP analogues with a protracted profile of action in addition to providing improved stability.

SUMMARY

The invention relates to derivatives of GIP analogues that have a lysine at a position corresponding to position 24 of hGIP(1-31) (SEQ ID NO: 3).

In some embodiments, the derivatives comprise a GIP analogue having a lysine at a position corresponding to position 24 of hGIP(1-31) (SEQ ID NO: 3) and a negatively charged modifying group attached to the epsilon amino group of said lysine.

In some embodiments, the derivatives comprise a GIP analogue having a lysine at a position corresponding to position 24 of hGIP(1-31) (SEQ ID NO: 3), a negatively charged modifying group attached to the epsilon amino group of said lysine, and may comprise up to 7 further amino acid substitutions, i.e. also to be described as a maximum of 8 substitutions as compared to hGIP(1-31).

In some embodiments, the derivatives comprise a GIP analogue having a lysine at a position corresponding to position 24 of hGIP(1-31) (SEQ ID NO: 3), a negatively charged modifying group attached to the epsilon amino group of said lysine, and may comprise up to 7 further amino acid substitutions, wherein the substitutions are at one or more of the positions corresponding to positions 1, 2, 14, 16, 18, 20 and/or 31 of Formula I.

The invention furthermore relates to pharmaceutical compositions comprising such derivatives of GIP analogues and pharmaceutically acceptable excipients, as well as the medical use of said derivatives.

In a first aspect, the invention relates to derivatives of GIP analogues that are capable of activating the GIP receptor. In a further aspect, the derivatives of GIP analogues are selective at activating the human GIP receptor over the human GLP-1 receptor and the human glucagon receptor.

Also or alternatively, in a second aspect, the invention relates to derivatives of GIP analogues that are active in vivo alone or in combination with a GLP-1 receptor agonist.

Also or alternatively, in a third aspect, the invention relates to derivatives of GIP analogues with improved pharmacokinetic properties.

Also or alternatively, in a fourth aspect, the invention relates to derivatives of GIP analogues with improved physical stability.

Also or alternatively, in a fifth aspect, the invention relates to derivatives of GIP analogues with improved chemical stability.

DESCRIPTION

The invention relates to derivatives of GIP analogues that have a lysine at a position corresponding to position 24 of hGIP(1-31) (SEQ ID NO: 3). In one aspect, the derivatives of the present invention comprise a lysine at a position corresponding to position 24 of hGIP(1-31) (Formula I; SEQ ID NO: 3) and a negatively charged modifying group attached to the epsilon amino group of said lysine.

In another aspect, the derivatives of the invention comprise a lysine at a position corresponding to position 24 of hGIP(1-31) (Formula I; SEQ ID NO: 3), a negatively charged modifying group attached to the epsilon amino group of said lysine, and wherein Formula I may comprise up to 7 further amino acid substitutions also described as a maximum of 8 substitutions as compared to hGIP(1-31).

In another aspect, the derivatives of the invention comprise a lysine at a position corresponding to position 24 of hGIP(1-31) (Formula I; SEQ ID NO: 3), a negatively charged modifying group attached to the epsilon amino group of said lysine, and wherein Formula I may comprise up to 7 further amino acid substitutions, wherein the substitutions are at one or more of the positions corresponding to positions 1, 2, 14, 16, 18, 20 and/or 31 of Formula I.

In addition, the invention relates to pharmaceutical compositions comprising such derivatives of GIP analogues and pharmaceutically acceptable excipients, as well as the medical use of said derivatives.

In one aspect, the invention relates to derivatives of GIP analogues that are capable of activating the GIP receptor. In a further aspect, the derivatives of GIP analogues are selective at activating the human GIP receptor over the human GLP-1 receptor and the human glucagon receptor. The term "selective" for the GIP receptor over the GLP-1 receptor and glucagon receptor refer to derivatives that display at least 10 fold, such as at least 50 fold, at least 500 fold, or at least 1000 fold higher potency for the GIP receptor over the GLP-1 receptor and glucagon receptor as measured in vitro in a potency assay for receptor function, such as a CRE luciferase functional potency assay, and compared by $EC_{50}$ values.

Also or alternatively, the invention relates to derivatives of GIP analogues that are active in vivo alone or in combination with a GLP-1 receptor agonist.

Also or alternatively, in one aspect, the invention relates to derivatives of GIP analogues with improved pharmacokinetic properties.

Also or alternatively, in one aspect, the invention relates to derivatives of GIP analogues with improved physical stability.

Also or alternatively, in one aspect, the invention relates to derivatives of GIP analogues with improved chemical stability.

In what follows, Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

Unless otherwise indicated in the specification, terms presented in singular form generally also include the plural situation.

Also described herein are derivatives, derivatives of GIP analogues, pharmaceutical compositions and uses thereof in which open ended terms like "comprises" and "comprising" are replaced with closed terms such as "consists of", "consisting of", and the like.

Compound/Product
GIP Receptor Agonist

A receptor agonist may be defined as a compound that binds to a receptor and elicits a response typical of the natural ligand (see e.g. "Principles of Biochemistry", A L Lehninger, D L Nelson, M M Cox, Second Edition, Worth Publishers, 1993, page 763).

As described herein, a "GIP receptor agonist" may be defined as a compound which is capable of activating the GIP receptor.

GIP Analogues

The term "hGIP(1-42)" as used herein refers to the human glucose-dependent insulinotropic polypeptide, the sequence of which is included in the sequence listing as SEQ ID NO: 1. The peptide having the sequence of SEQ ID NO: 1 may also be designated native hGIP or hGIP.

The term "hGIP(1-31)" as used herein refers to a truncated version of hGIP(1-42), comprising amino acids 1-31 of hGIP(1-42), the sequence of hGIP(1-31) is included in the sequence listings as SEQ ID NO: 2.

The term "GIP analogue" as used herein refers to a peptide, or a compound, which is a variant of hGIP(1-31). The term "variant" is used for peptides comprising at least one amino acid substitution as compared to hGIP(1-31) and is capable of activating the GIP receptor.

The term "substitution" as used herein refers to one amino acid being replaced by another in the backbone of the peptide. In one aspect, amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids. In one aspect, the GIP analogues of the derivatives of the invention may comprise substitutions of one or more unnatural and/or non-amino acids, e.g., amino acid mimetics, into the sequence of the GIP analogue.

GIP analogues of the derivatives of the invention may be described by reference to i) the number of the amino acid residue in hGIP(1-31) or hGIP(1-42) which corresponds to the amino acid residue which is changed (i.e., the corresponding position in hGIP(1-31) or hGIP(1-42)), and to ii) the actual change. For example, [Lys24]-hGIP(1-31) refers to a GIP analogue in which position 24 of hGIP(1-31) has been replaced by a lysine.

In one aspect, the GIP analogues of the derivatives of the invention comprise a lysine residue at the position corresponding to position 24 of hGIP(1-31) as described by formula I: Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-Lys-Trp-Leu-Leu-Ala-Gln-Lys-Gly. Formula I is included in the sequence listings as SEQ ID NO: 3 and may also be designated [Lys24]-hGIP(1-31).

Also or alternatively, in one aspect, the GIP analogues of the derivatives of the invention comprise a maximum of eight amino acid substitutions as compared to hGIP(1-31), wherein position 24 is always a lysine accounting for one substitution and up to seven further substitutions at positions other than at position 24. In a further aspect, the GIP analogues of the derivatives of the present invention comprise up to seven, six, five, four, three, two, or one amino acid substitution(s) as compared to hGIP(1-31). In one aspect, said substitutions are present at one or more of positions corresponding to position 1, 2, 14, 16, 18, 20, and 31 of Formula I as described herein by Formula II: $X_1$-$X_2$-Glu-Gly-Thr-Phe-Ile-Ser-Asp-Tyr-Ser-Ile-Ala-$X_{14}$-Asp-$X_{16}$-Ile-$X_{18}$-Gln-$X_{20}$-Asp-Phe-Val-Lys-Trp-Leu-Leu-Ala-Gln-Lys-$X_{31}$. Formula II is included in the sequence listings as SEQ ID NO: 48. In one aspect, the GIP analogues of the derivatives of the invention may be in the form of C-terminal carboxylic acids or amides.

Also or alternatively, in one aspect, the GIP analogues of the derivatives of the present invention comprise a C-terminal extension to Formula I or Formula II. In a further aspect, the GIP analogues of the derivatives of the invention comprise a C-terminal extension described by Formula III: Lys-$X_{33}$-$X_{34}$-Asp-Trp-Lys-His-Asn-Ile-Thr-Gln, wherein $X_{33}$ is Lys or Glu; $X_{34}$ is Asn, Glu, or Asp. The C-terminal extension is attached to Formula I or Formula II via an amide bond from the C-terminal carboxylic acid of Formula I or Formula II to the N-terminal amino group of Formula III. Formula III is included in the sequence listings as SEQ ID NO: 51.

The following are non-limiting examples of suitable analogue nomenclature.

As an example, [Aib2,Nle14,Arg18,Lys24]-hGIP(1-31) comprises 4 substitutions as compared to hGIP(1-31). As a further example, [D-Tyr1,Aib2,Nle14,Arg18,Lys24,Pro31]-hGIP(1-31) comprises 6 substitutions as compared to hGIP(1-31). Similarly, [D-Tyr1,Aib2,Nle14,Arg18,Lys24, Pro31]-hGIP(1-31) amide comprises 6 substitutions as compared to hGIP(1-31) as the number of substitutions refer to the backbone.

Analogues "comprising" certain specified changes may comprise further changes, when compared to the respective formula. In a particular embodiment, the analogue "has" the specified changes.

As is apparent from the above examples, amino acid residues may be identified by their full name, their one-letter code, and/or their three-letter code. These three ways are fully equivalent.

The expressions "a position equivalent to" or "a position corresponding to" may be used to characterise the site of change in a variant GIP sequence by reference to a given sequence, e.g. hGIP(1-31), or hGIP(1-42).

The term "peptide", as e.g. used in the context of the GIP analogues of the derivatives of the invention, refers to a compound which comprises a series of amino acids interconnected by amide (or peptide) bonds.

Amino acids are molecules containing an amino group and a carboxylic acid group, and, optionally, one or more additional groups, often referred to as a side chain.

The term "amino acid" includes proteinogenic (or coded or natural) amino acids (amongst those the 20 standard amino acids), as well as non-proteinogenic (or non-coded or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (alpha-aminoisobutyric acid), Nle (norleucine), as well as the D-isomers of the proteinogenic amino acids. Non-limiting examples of D-isomers of a proteinogenic amino acid is the D-isomers of tyrosine or alanine, which can be written as D-Tyr or D-Ala, respectively.

In what follows, all amino acids of the GIP analogues of derivatives of the invention for which the optical isomer is not stated is to be understood to mean the L-isomer (unless otherwise specified).

GIP Derivatives

The term "derivative" as used herein in the context of a GIP analogue means a chemically modified GIP analogue, in which one or more substituents have been covalently attached to the peptide backbone.

In one aspect of the invention, the substituent may be an N-terminal substituent.

Also or alternatively, in one aspect, the substituent may be a modifying group or, alternatively, referred to as a protracting moiety or albumin binding moiety.

The term "N-terminal substituent" or "modifying group" as used herein, means a chemical moiety or group replacing a hydrogen atom.

In one aspect, the derivative of a GIP analogue comprises a substituent covalently attached to the alpha-amino group of the amino acid residue in the N-terminus of the analogue. In one aspect, the N-terminal substituent is an alkanoyl or acyl group. In a particular aspect, the N-terminal substituent is an acetyl group. As an example of an N-terminal substituted amino acid is Ac-Tyr at position 1. Such acetylation would not count as a substitution in the peptide backbone compared with hGIP(1-31), because the amino acid in the GIP analogue is the native Tyr, e.g. N{1}-acetyl-[Aib2, Nle14,Arg18,Lys24]-hGIP(1-31) comprises 4 substitutions as compared to hGIP(1-31).

Also or alternatively, in one aspect, the GIP analogue comprises a modifying group covalently attached to the amino acid residue corresponding to position 24 of hGIP(1-31) or hGIP(1-42). In a further aspect, the modifying group is capable of forming non-covalent conjugates with proteins, e.g. albumin, thereby promoting the circulation of the derivative with the blood stream, and also having the effect of protracting the time of action of the derivative, due to the fact that the conjugate of the GIP derivative and albumin is only slowly disintegrated to release the active pharmaceutical ingredient.

The modifying group may be covalently attached to a lysine residue of the GIP analogue by acylation, i.e. via an amide bond formed between a carboxylic acid group of the modifying group and the epsilon amino group of said lysine group. The amino group of lysine could also be coupled to an aldehyde of the modifying group by reductive amination.

In one aspect, the modifying group is covalently attached to a lysine residue at a position corresponding to position 24 of hGIP(1-31) or hGIP(1-42) by acylation, i.e. via an amide bond formed between a carboxylic acid group of the modifying group and the epsilon amino group of the lysine residue.

In one embodiment, the modifying group is defined by A-B-C- wherein A- is a lipophilic moiety with a negatively charged moiety at the distal end and B-C- is a linker. In one embodiment, the modifying group is defined by A-B-C- wherein A- is a lipophilic moiety with a negatively charged moiety at the distal end and B-C- is a linker comprising at least one negatively charged moiety.

The term "lipophilic moiety" as used herein, means an aliphatic hydrocarbon chain of 8 to 30 carbon atoms, preferably 10 to 28 carbon atoms, more preferably 12-24 carbon atoms, even more preferably 14 to 20 carbon atoms, most preferably 16 or 18 carbon atoms, wherein said hydrocarbon may contain additional substituents.

The term "negatively charged moiety" as used herein, means a negatively chargeable chemical moiety being negatively charged at physiological pH (7.4). Examples of negatively charged moieties are carboxylic acids or isosteres thereof, such as sulfonic acids or tetrazoles. In a preferred embodiment, the negatively charged moiety is a carboxylic acid moiety.

The term "distal" as used herein, means most remote (terminal) from the point of attachment of A- to B-.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The derivatives of the invention have GIP activity. This term refers to the ability to bind to the GIP receptor and initiate a signal transduction pathway resulting in insulinotropic action or other physiological effects as is known in the art. For example, the derivatives of the invention can be tested for GIP activity or stability using the assay described in Examples 1-6 herein.

Pharmaceutically Acceptable Salt, Amide, or Ester

The derivatives of the invention may be in the form of a pharmaceutically acceptable salt, or amide.

Salts are e.g. formed by a chemical reaction between a base and an acid, e.g.: $2NH_3+H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the modifying group of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In one aspect, the derivative of the invention is in the form of a pharmaceutically acceptable salt, preferably in the form of a sodium salt. Also or alternatively, in one aspect, the derivative of the invention is in the form of a pharmaceutically acceptable amide, preferably with an amide group at the C-terminus of the peptide.

Functional Properties

In a first functional aspect, the derivatives of the invention have a good potency at the GIP receptor. Preferably they are potent GIP receptor agonists as is reflected by their ability to activate the GIP receptor. Also, or alternatively, in a second functional aspect, they have an in vivo effect on body weight, food intake and glucose tolerance both alone and in combination with a GLP-1 receptor agonist. Also, or alternatively, in a third functional aspect, they have improved pharmacokinetic properties. Also, or alternatively, in a fourth functional aspect, the derivatives of the invention are physically stable. Also, or alternatively, in a fifth functional aspect, the derivatives of the invention are chemically stable.

Biological Activity—In Vitro Potency

According to the first functional aspect, the derivatives of the invention, as well as the constituent GIP analogues such as [Lys24]-hGIP(1-31) or analogues thereof, are biologically active, or potent at the human GIP receptor.

In one embodiment, potency and/or activity refers to in vitro potency, i.e. performance in a functional GIP receptor assay, more in particular to the capability of activating the human GIP receptor.

The in vitro potency may, e.g., be determined in a medium containing membranes expressing the human GIP receptor, and/or in an assay with whole cells expressing the human GIP receptor.

For example, the response of the human GIP receptor may be measured in a reporter gene assay, e.g. in a stably transfected BHK cell line that expresses the human GIP receptor and contains the DNA for the cAMP response element (CRE) coupled to a promoter and the gene for firefly luciferase (CRE luciferase). When cAMP is produced as a result of activation of the GIP receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 2 as described herein.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a further particular embodiment, the derivative of the invention has an in vitro potency determined using the method of Example 2 corresponding to an $EC_{50}$ at or below 5000 pM, more preferably below 900 pM, even more preferably below 500 pM, or most preferably below 200 pM.

In a further particular embodiment, the derivatives of the invention are capable of activating the GIP receptor selectively over the human GLP-1 receptor and the human glucagon receptor. The term "selectively" when used in relation to activation of the GIP receptor over the GLP-1 receptor and glucagon receptor refer to derivatives that display at least 10 fold, such as at least 50 fold, at least 500 fold, or at least 1000 fold better potency for the GIP receptor over the GLP-1 receptor and glucagon receptor as measured in vitro in a potency assay for receptor function, such as an CRE luciferase functional potency assay, and compared by $EC_{50}$ values. The term "better potency" of the derivatives of the invention at the GIP receptor over the GLP-1 receptor and the glucagon receptor is determined by the ratio of the $EC_{50}$ values at the GLP-1 receptor versus GIP receptor or glucagon receptor versus GIP receptor, respectively.

Biological Activity—In Vivo Pharmacology

According to a second functional aspect, the GIP derivatives of the invention, as well as the constituent GIP analogues such as [Lys24]-hGIP(1-31) or analogues thereof, are potent in vivo, which may be determined as is known in the art in any suitable animal model, as well as in clinical trials.

The diet-induced obese (DIO) mouse is one example of a suitable animal model, and the effect on body weight, food intake and glucose tolerance can be assessed during sub-chronic dosing in this model. The effect of the GIP derivatives of the invention on body weight, food intake and glucose tolerance may be determined in such mice in vivo, e.g. as described in Example 6 herein. Food intake can be assessed by single housing animals and weighing food consumed per day. This model can also be used to evaluate effects on glucose tolerance by performing an oral or i.p. glucose tolerance test (OGTT or IPGTT). These tests are performed by administration of a glucose load orally or i.p. to semi-fasted animals and subsequent blood glucose measured for up to three hours.

Pharmacokinetics Profile

According to the third functional aspect, the derivatives of the invention have improved pharmacokinetic properties such as increased terminal half-life.

Increasing terminal half-life means that the compound in question is eliminated slower from the body. For the derivatives of the invention this entails an extended duration of pharmacological effect.

The pharmacokinetic properties of the derivatives of the invention may suitably be determined in vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half-Life In Vivo in Minipigs

According to the third functional aspect, the derivatives of the invention have improved pharmacokinetic properties.

In a particular embodiment, the pharmacokinetic properties may be determined as terminal half-life ($t_{1/2}$) in vivo in minipigs after i.v. administration, e.g. as described in Example 3 herein.

In particular embodiments, the terminal half-life in minipigs is at least 24 hours, preferably at least 40 hours, even more preferably at least 60 hours.

Physical Properties

According to the fourth functional aspect, the derivative of the invention has improved physical stability in solution. The term "physical stability" refers to the tendency of the polypeptide to form biologically inactive and/or insoluble aggregates, e.g. amyloid fibrils or gels.

In a particular embodiment, the improved physical stability may be determined by measuring lag-time and/or recovery in a Thioflavin T (ThT) fibrillation assay, e.g. as described in Example 4 herein.

In a further particular embodiment, the derivative of the invention has more than 70 percent recovery in a ThT fibrillation assay, preferably more than 90 percent recovery, even more preferably more than 95 percent recovery, or most preferably more than 98 percent recovery, such as shown in Example 4 described herein.

In a further particular embodiment, the derivative of the invention has a lag-time in the ThT fibrillation assay of more than 10 hours, preferably more than 20 hours, even more preferably more than 45 hours, such as shown in Example 4 described herein.

In a particular embodiment, the improved physical stability may be determined by Dynamic Light Scattering stability index (DLS-SI) assay, e.g. as described in Example 4 herein.

In a further particular embodiment, the derivative of the invention has a low DLS-SI value in a DLS-SI assay, preferably less than 7, more preferably less than 2, such as shown in Example 4 herein.

In a further particular embodiment, the derivative of the invention shows no or little precipitation in a DLS-SI assay, preferably no precipitation, such as shown in Example 4 herein.

Chemical Properties

According to the fifth functional aspect, the derivatives of the invention have improved chemical stability. The term "chemical stability" refers to chemical (in particular covalent) changes in the polypeptide structure leading to formation of chemical degradation products, such as high molecular weight proteins (HMWPs), deamidation, isomerization and hydrolysis products potentially having a reduced biological potency, and/or increased immunogenic effect as compared to the intact polypeptide.

In a particular embodiment, the improved chemical stability may be determined by measuring the content of HMWP and/or purity loss, by measuring the amount of chemical degradation products at various time-points after exposure to different environmental conditions, e.g. by SEC-HPLC, and/or LCMS, e.g. as described in Example 5 herein.

In a further particular embodiment, the derivative of the invention has a purity loss per month of less than 35 percent, preferably less than 15 percent, more preferably less than 7 percent, such as shown in Example 5 described herein.

In a further particular embodiment, the derivative of the invention has a formation of HMWP's per month of less than 4 percent, preferably less than 2 percent, more preferably less than 1 percent, such as shown in Example 5 described herein.

Additional particular embodiments of the derivatives of the invention are described in the section headed "particular embodiments".

Production Processes

The production of peptides like hGIP(1-31) and hGIP analogues is well known in the art.

The GIP analogues of the derivatives of the invention (or fragments thereof), such as [Lys24]-hGIP(1-31) or an analogue or fragment thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430.

Specific examples of methods of preparing a number of the derivatives of the invention are included in the experimental part.

Pharmaceutical Compositions

Injectable compositions comprising derivatives of the present invention can be prepared using the conventional techniques of the pharmaceutical industry which involve dissolving and mixing the ingredients as appropriate to give the desired end product. Thus, according to one procedure, a derivative of this invention is dissolved in a suitable buffer at a suitable pH so precipitation is minimised or avoided. The injectable composition is made sterile, for example, by sterile filtration.

Pharmaceutical compositions comprising a derivative of the invention or a pharmaceutically acceptable salt, or amide thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The formulation of pharmaceutically active ingredients with various excipients is known in the art, see e.g. Remington: The Science and Practice of Pharmacy (e.g. $19^{th}$ edition (1995), and any later editions).

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The treatment with a derivative according to the present invention may also be combined with one or more additional pharmacologically active substances, e.g. selected from GLP-1 receptor agonists, or GLP-1/glucagon receptor co-agonists.

In one aspect of the invention, the derivative of the invention is combined with a GLP-1 receptor agonist. The compounds may be supplied in a single-dosage form wherein the single-dosage form contains both compounds, or in the form of a kit-of-parts comprising a preparation of the derivative of the invention as a first unit dosage form and a preparation of the GLP-1 receptor agonist as a second unit dosage form.

Non-limiting examples of GLP-1 receptor agonists to be combined with the derivative of the present invention are liraglutide, semaglutide, exenatide, dulaglutide, lixisenatide, taspoglutide, and albiglutide. Semaglutide is a GLP-1 receptor agonist that may be prepared as described in WO2006/097537, Example 4 and is also known as $N^{6,26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid), 34-L-arginine]human glucagon-like peptide 1(7-37), see WHO Drug Information Vol. 24, No. 1, 2010 (SEQ ID NO: 57).

Non-limiting examples of GLP-1/glucagon receptor co-agonists are described in WO 2014/170496 e.g. see present SEQ ID NO: 52, 53, 54, 55, or 56.

Pharmaceutical Indications

The present invention also relates to a derivative of a GIP analogue, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(iv) weight maintenance after successful weight loss (either drug induced or by diet and exercise)—i.e. prevention of weight gain after successful weight loss.

(v) prevention and/or treatment of liver disorders, such as hepatic steatosis, non-alcoholic fatty liver disease (NAFLD), non-alcoholic steatohepatitis (NASH), liver inflammation or fatty liver.

In a particular embodiment, the indication is Type 2 diabetes, and/or obesity.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the derivative of the present invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the derivative of a GIP analogue for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the derivative of a GIP analogue for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

PARTICULAR EMBODIMENTS

The invention may be further described by the following non-limiting embodiments:

1. A derivative of a GIP analogue comprising Formula I (SEQ ID NO: 3):

(I)
Tyr-Ala-Glu-Gly-Thr-Phe-Ile-Ser-Asp-Tyr-Ser-Ile-

Ala-Met-Asp-Lys-Ile-His-Gln-Gln-Asp-Phe-Val-Lys-

Trp-Leu-Leu-Ala-Gln-Lys-Gly, wherein a modifying group is covalently attached to the side chain of the epsilon amino group of the lysine at position 24, the modifying group being defined by A-B-C-, wherein A- is a lipophilic moiety with a negatively charged moiety at the distal end and B-C- is a linker; and wherein the GIP analogue has a maximum of 8 amino acid substitutions as compared to hGIP(1-31) (SEQ ID NO: 2), or a pharmaceutically acceptable salt, or amide thereof.

2. The derivative according to embodiment 1 comprising Formula II (SEQ ID NO: 48):

(II)
$X_1$-$X_2$-Glu-Gly-Thr-Phe-Ile-Ser-Asp-Tyr-Ser-Ile-Ala- $X_{14}$-Asp-$X_{16}$-Ile-$X_{18}$-Gln-$X_{20}$-Asp-Phe-Val-Lys-Trp-Leu-

Leu-Ala-Gln-Lys-$X_{31}$, wherein Formula II comprises any amino acid at positions $X_1$, $X_2$, $X_{14}$, $X_{16}$, $X_{18}$, $X_{20}$, and/or $X_{31}$; and wherein the GIP analogue has a maximum of 8 amino acid substitutions as compared to hGIP(1-31) (SEQ ID NO: 2).

3. The derivative according to any one of embodiments 1-2 comprising Formula II, wherein the amino acids at positions $X_1$, $X_2$, $X_{14}$, $X_{16}$, $X_{18}$, $X_{20}$, and/or $X_{31}$ are selected from (SEQ ID NO: 49):

$X_1$ is Tyr or D-Tyr;
$X_2$ is Aib, Ala, or D-Ala;
$X_{14}$ is Leu, Nle, Asp or Met;
$X_{16}$ is Lys or Ala;
$X_{18}$ is Arg or His;
$X_{20}$ is Gln, Glu or Aib;
$X_{31}$ is Gly or Pro.

4. The derivative according to any one of the preceding embodiments comprising Formula II, wherein the amino acids at positions $X_1$, $X_2$, $X_{14}$, $X_{16}$, $X_{18}$, $X_{20}$, and/or $X_{31}$ are selected from (SEQ ID NO: 64):

$X_1$ is Tyr or D-Tyr;
$X_2$ is Aib, Ala, or D-Ala;
$X_{14}$ is Leu, Nle, or Met;
$X_{16}$ is Lys or Ala;
$X_{18}$ is Arg or His;
$X_{20}$ is Gln, Glu or Aib;
$X_{31}$ is Gly or Pro.

5. The derivative according to any one of the preceding embodiments comprising formula II, wherein the amino acids at positions $X_1$, $X_2$, $X_{14}$, $X_{16}$, $X_{18}$, $X_{20}$, and/or $X_{31}$ are selected from (SEQ ID NO: 63):

$X_1$ is Tyr or D-Tyr;
$X_2$ is Aib or Ala;
$X_{14}$ is Nle, Asp or Leu;
$X_{16}$ is Lys or Ala;
$X_{18}$ is Arg or His;
$X_{20}$ is Gln, Glu or Aib;
$X_{31}$ is Gly or Pro.

6. The derivative according to any one of the preceding embodiments comprising formula II, wherein the amino acids at positions $X_1$, $X_2$, $X_{14}$, $X_{16}$, $X_{18}$, $X_{20}$, and/or $X_{31}$ are selected from (SEQ ID NO: 50):

$X_1$ is Tyr or D-Tyr;
$X_2$ is Aib or Ala;
$X_{14}$ is Nle;
$X_{16}$ is Lys or Ala;
$X_{18}$ is Arg or His;
$X_{20}$ is Gln, Glu or Aib;
$X_{31}$ is Gly or Pro.

7. The derivative according to any one of the preceding embodiments wherein the derivative is represented by Formula II, wherein the amino acids at positions $X_1$, $X_2$, $X_{14}$, $X_{16}$, $X_{18}$, $X_{20}$, and/or $X_{31}$ are selected from (SEQ ID NO: 65):

$X_1$ is Tyr, Ac-Tyr, D-Tyr or Ac-D-Tyr;
$X_2$ is Aib, Ala, or D-Ala;
$X_{14}$ is Leu, Nle, Asp or Met;
$X_{16}$ is Lys or Ala;
$X_{18}$ is Arg or His;
$X_{20}$ is Gln, Glu or Aib;
$X_{31}$ is Gly or Pro or a pharmaceutically acceptable salt, or amide thereof.

8. The derivative according to any one of the preceding embodiments, wherein the GIP analogue has a maximum of 7 amino acid substitutions as compared to hGIP(1-31) (SEQ ID NO: 2).

9. The derivative according to any one of preceding embodiments wherein the GIP analogue has a maximum of 6 amino acid substitutions as compared to hGIP(1-31) (SEQ ID NO: 2).

10. The derivative according to any one of the preceding embodiments, wherein the GIP analogue has a maximum of 5 amino acid substitutions as compared to hGIP(1-31) (SEQ ID NO: 2).

11. The derivative according to any one of the preceding embodiments, wherein the GIP analogue has a maximum of 4 amino acid substitutions as compared to hGIP(1-31) (SEQ ID NO: 2).

12. The derivative according to any one of the preceding embodiments, wherein the GIP analogue has a maximum of 3 amino acid substitutions as compared to hGIP(1-31) (SEQ ID NO: 2).

13. The derivative according to any one of the preceding embodiments, wherein the GIP analogue has a maximum of 2 amino acid substitutions as compared to hGIP(1-31) (SEQ ID NO: 2).

14. The derivative according to any one of the preceding embodiments, wherein the GIP analogue has a maximum of 1 amino acid substitutions as compared to hGIP(1-31) (SEQ ID NO: 2).

15. The derivative according to embodiments 1-12, wherein the GIP analogue has 3 to 6 amino acid substitutions as compared to hGIP(1-31) (SEQ ID NO: 2).

16. The derivative according to any one of the preceding embodiments, wherein the modifying group is A-B-C-, wherein A- is a lipophilic moiety with a negatively charged moiety at the distal end and B-C- is a linker comprising at least one negatively charged moiety.

17. The derivative according to any one of the preceding embodiments, wherein the linker B-C- comprises 1 to 6 negatively charged moieties.

18. The derivatives according to any one of the preceding embodiments, wherein the linker B-C- comprises 1 to 4 negatively charged moieties.

19. The derivatives according to any one of the preceding embodiments, wherein the at least one negatively charged moiety in the linker B-C- is selected from gamma-Glu, Glu and/or Asp.

20. The derivatives according to any one of the preceding embodiments, wherein the at least one negatively charged moiety in the linker B-C- is gamma-Glu.

21. The derivative according to any one of the preceding embodiments, wherein
A- is Chem.1

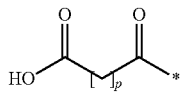

Chem. 1 p is an integer in the range of 14-20;
wherein * denotes the position of an amide bond connecting A- and B-.

22. The derivative according to any one of the preceding embodiments, wherein
B- is Chem. 2

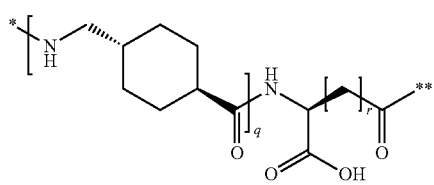

Chem. 2 q is an integer in the range of 0-1;
r is an integer in the range of 1-3;
wherein * denotes the position of the amide bond connecting A- and B-, and ** denotes the position of an amide bond connecting B- and C-.

23. The derivative according to any one of the preceding embodiments, wherein
C- is selected from Chem. 3 and Chem. 4

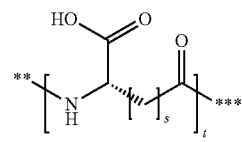

Chem. 3

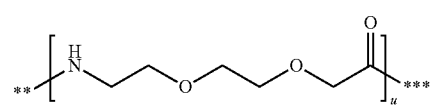

Chem. 4 s is an integer in the range of 1-3;
t is an integer in the range of 1-4;
u is an integer in the range of 1-3;
wherein  denotes the position of the amide bond connecting B- and C-, and * denotes the position of an amide bond connecting C- and the epsilon amino group of the lysine at position 24.

24. The derivative according to any one of the preceding embodiments, wherein the modifying group is defined by A-B-C-, wherein
A- is Chem.1

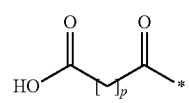

Chem. 1 p is an integer in the range of 14-20;
wherein * denotes the position of an amide bond connecting A- and B-;
B- is Chem. 2

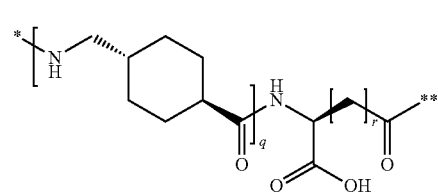

Chem. 2 q is an integer in the range of 0-1;
r is an integer in the range of 1-3;
wherein * denotes the position of the amide bond connecting A- and B-, and ** denotes the position of an amide bond connecting B- and C-;
C- is selected from Chem. 3 and Chem. 4

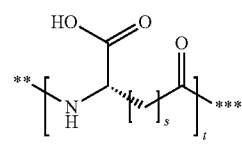

Chem. 3

-continued

Chem. 4

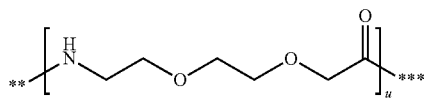

s is an integer in the range of 1-3;
t is an integer in the range of 1-4;
u is an integer in the range of 1-3;
wherein  denotes the position of the amide bond connecting B- and C-, and * denotes the position of an amide bond connecting C- and the epsilon amino group of the lysine at position 24.

25. The derivative according to any one of embodiments 21 or 24, wherein A- is Chem. 1 and p is 16-18.

26. The derivative according to any one of embodiments 22 or 24, wherein B- is Chem. 2, q is 0-1, and r is 2.

27. The derivative according to any one of embodiments 23-24, wherein C- is Chem. 3.

28. The derivative according to embodiment 27, wherein C- is Chem. 3. and s is 2.

29. The derivative according to any one of embodiments 27-28, wherein C- is Chem. 3. and t is 2-3.

30. The derivative according to any one of embodiments 23-24, wherein C- is Chem. 4.

31. The derivative according to embodiment 30, wherein C- is Chem. 4. and u is 2.

32. The derivative according to any one of embodiments 1-24, wherein the modifying group A-B-C- is selected from:

Chem. 5

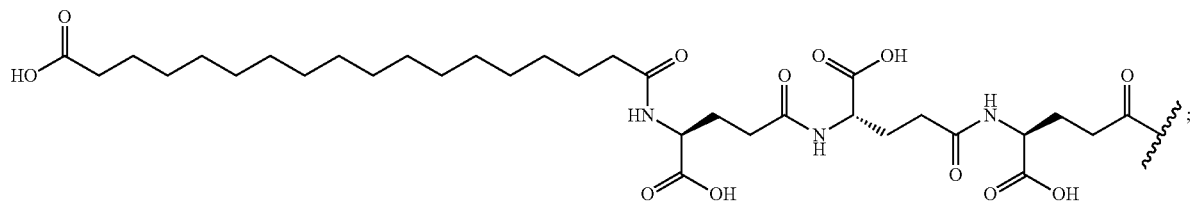

Chem. 6

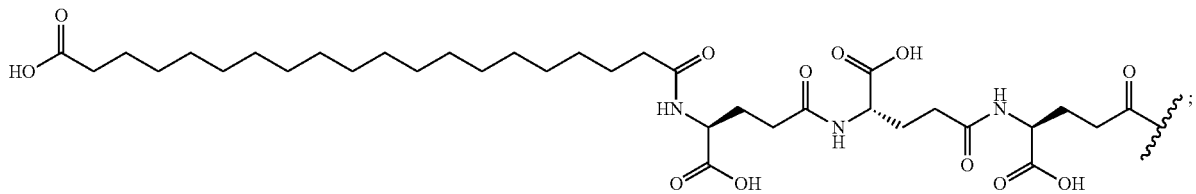

Chem. 7

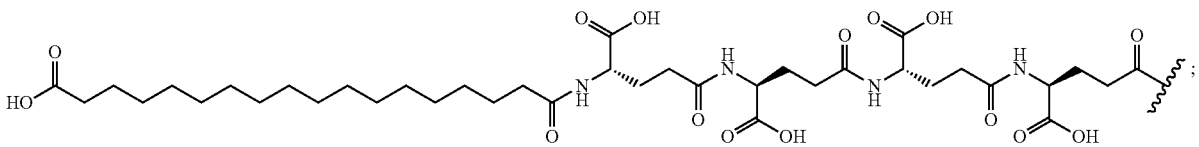

Chem. 8

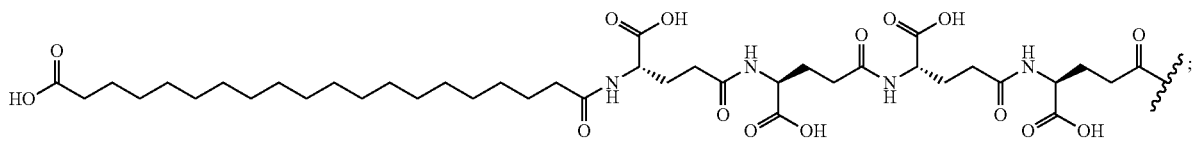

Chem. 9

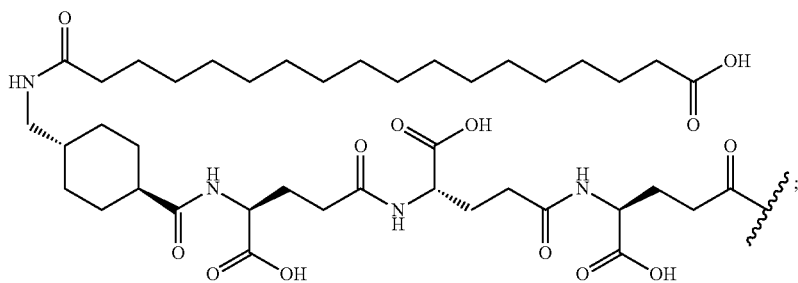

-continued
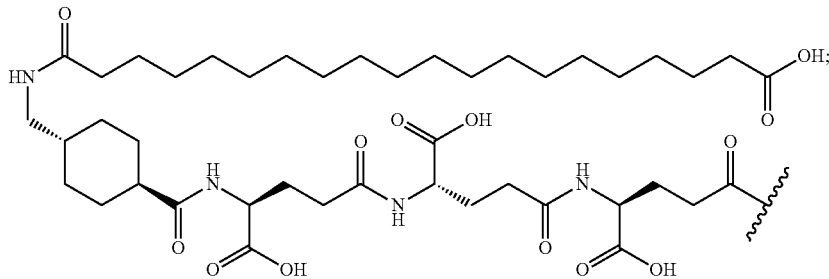
Chem. 10
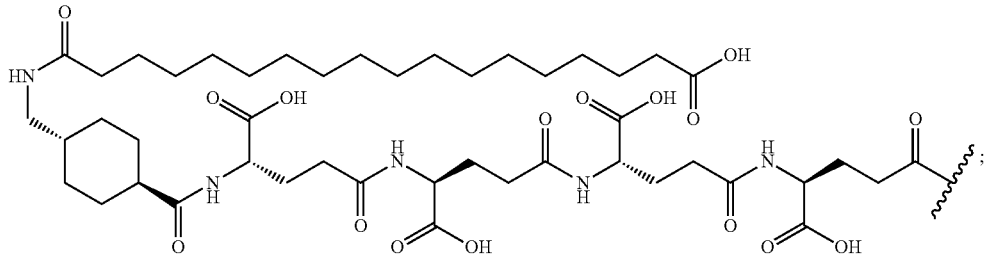
Chem. 11
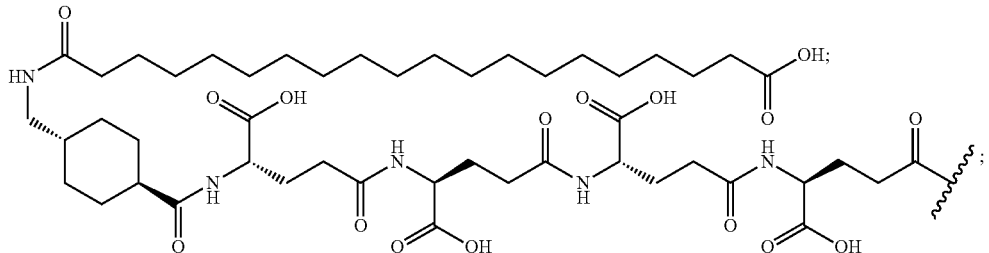
Chem. 12
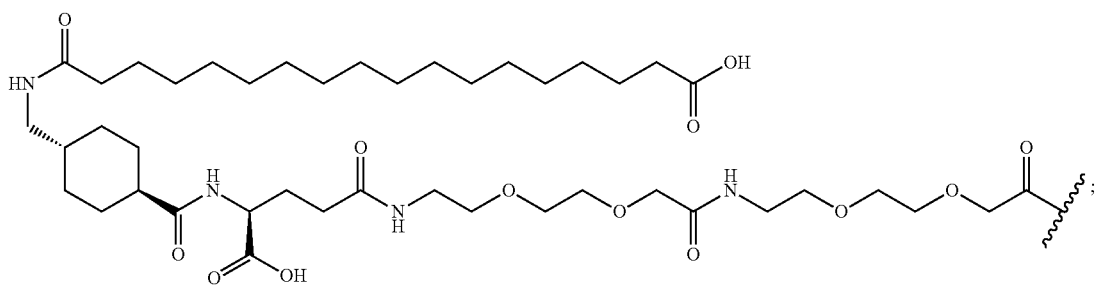
Chem. 13
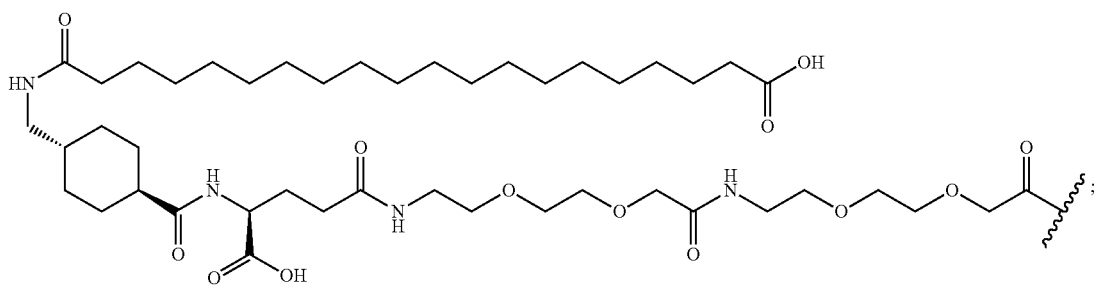
Chem. 14

-continued

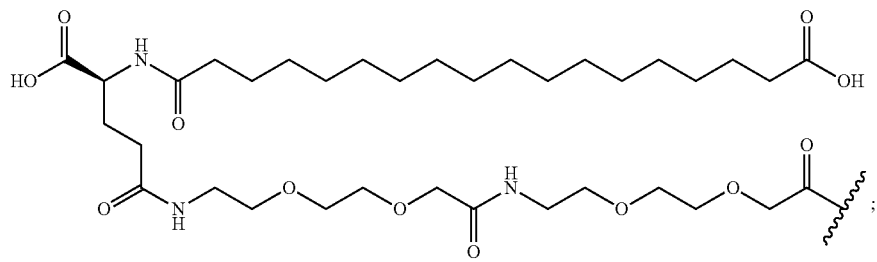

Chem. 15

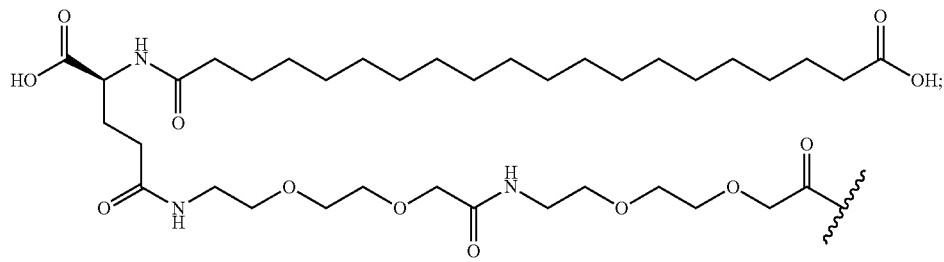

Chem. 16

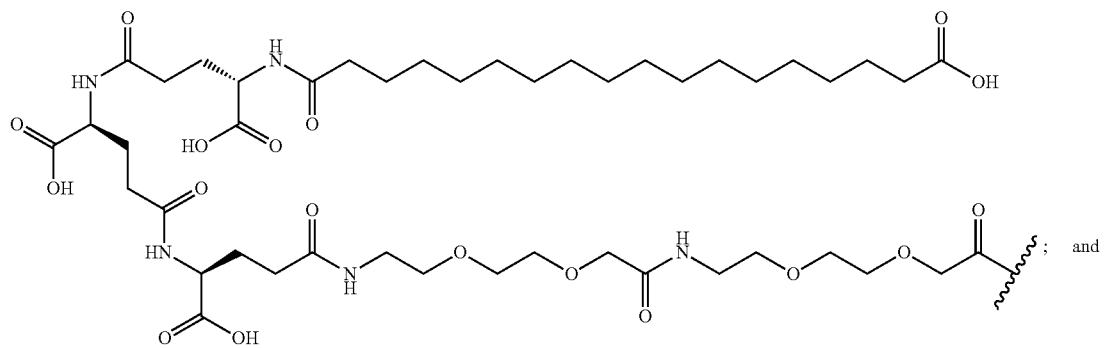

Chem. 17

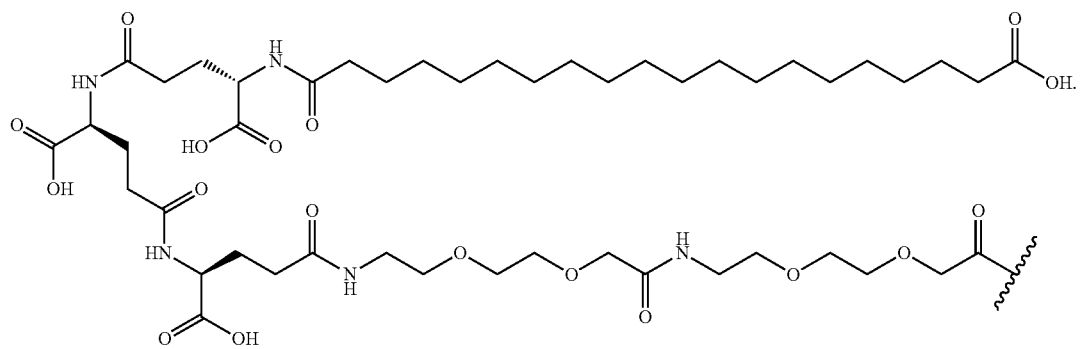

Chem. 18

33. The derivative according to any one of embodiments 2-32, wherein $X_1$ is Tyr.
34. The derivative according to any one of embodiments 2-32, wherein $X_1$ is D-Tyr.
35. The derivative according to any one of embodiments 2-34, wherein $X_2$ is Aib.
36. The derivative according to any one of embodiments 2-34, wherein $X_2$ is Ala.
37. The derivative according to any one of embodiments 2-34, wherein $X_2$ is D-Ala.
38. The derivative according to any one of embodiments 2-37, wherein $X_{14}$ is Leu.
39. The derivative according to any one of embodiments 2-37, wherein $X_{14}$ is Nle.
40. The derivative according to any one of embodiments 2-37, wherein $X_{14}$ is Asp.
41. The derivative according to any one of embodiments 2-37, wherein $X_{14}$ is Met.
42. The derivative according to any one of embodiments 2-41, wherein $X_{16}$ is Lys.
43. The derivative according to any one of embodiments 2-41, wherein $X_{16}$ is Ala.
44. The derivative according to any one of embodiments 2-43, wherein $X_{18}$ is Arg.
45. The derivative according to any one of embodiments 2-43, wherein $X_{18}$ is His.
46. The derivative according to any one of embodiments 2-45, wherein $X_{20}$ is Gln.
47. The derivative according to any one of embodiments 2-45, wherein $X_{20}$ is Glu.
48. The derivative according to any one of embodiments 2-45, wherein $X_{20}$ is Aib.

49. The derivative according to any one of embodiments 2-48, wherein $X_{31}$ is Gly.
50. The derivative according to any one of embodiments 2-48, wherein $X_{31}$ is Pro.
51. The derivative according to any one of the preceding embodiments, wherein a peptide defined by Formula III (SEQ ID NO: 51) is attached to the C-terminal of Formula I or Formula II via an amide bond from the C-terminal carboxylic acid group of Formula I or Formula II to the N-terminal amino group of Formula III:

Lys-$X_{33}$-$X_{34}$-Asp-Trp-Lys-His-Asn-Ile-Thr-Gln     (III), wherein
$X_{33}$ is Lys, Glu;
$X_{34}$ is Asn, Glu, or Asp.
52. The derivative according to embodiment 51, wherein $X_{33}$ is Lys.
53. The derivative according to embodiment 51, wherein $X_{33}$ is Glu.
54. The derivative according to any one of embodiments 51-53, wherein $X_{34}$ is Asn.
55. The derivative according to any one of embodiments 51-53, wherein $X_{34}$ is Glu.
56. The derivative according to any one of embodiments 51-53, wherein $X_{34}$ is Asp.
57. The derivative according to any one of the preceding embodiments, wherein the N-terminal amino acid is acylated.
58. The derivative according to any one of the preceding embodiments, wherein the N-terminal amino acid is acetylated.
59. The derivative according to any one of embodiments 2-33, 35-58, wherein $X_1$ is Ac-Tyr.
60. The derivative according to any one of embodiments 2-32, 34-58, wherein $X_1$ is Ac-D-Tyr.
61. The derivative according to any one of the preceding embodiments, wherein the GIP analogue is a C-terminal carboxylic acid or C-terminal amide.
62. The derivative according to any one of the preceding embodiments, wherein the GIP analogue is a C-terminal carboxylic acid.
63. The derivative according to any one of embodiments 2-49, 57-62, wherein $X_{31}$ is Gly-OH.
64. The derivative according to any one of embodiments 2-48, 50, 57-62, wherein $X_{31}$ is Pro-OH.
65. The derivative according to any one of embodiments 1-61, wherein the GIP analogue is a C-terminal amide.
66. The derivative according to any one of embodiments 2-49, 57-61, 65, wherein $X_{31}$ is Gly-$NH_2$.
67. The derivative according to any one of embodiments 2-48, 50, 57-61, 65, wherein $X_{31}$ is Pro-$NH_2$.
68. The derivative according to any one of the preceding embodiments selected from:
N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Lys24]-hGIP(1-31) (Compound 1, SEQ ID NO: 6)

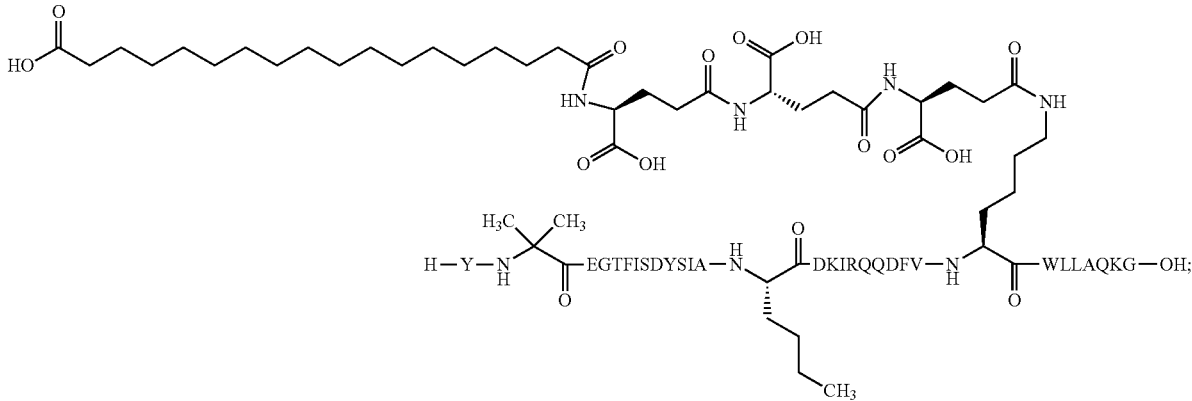

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24]-hGIP(1-31) (Compound 2; SEQ ID NO: 7)

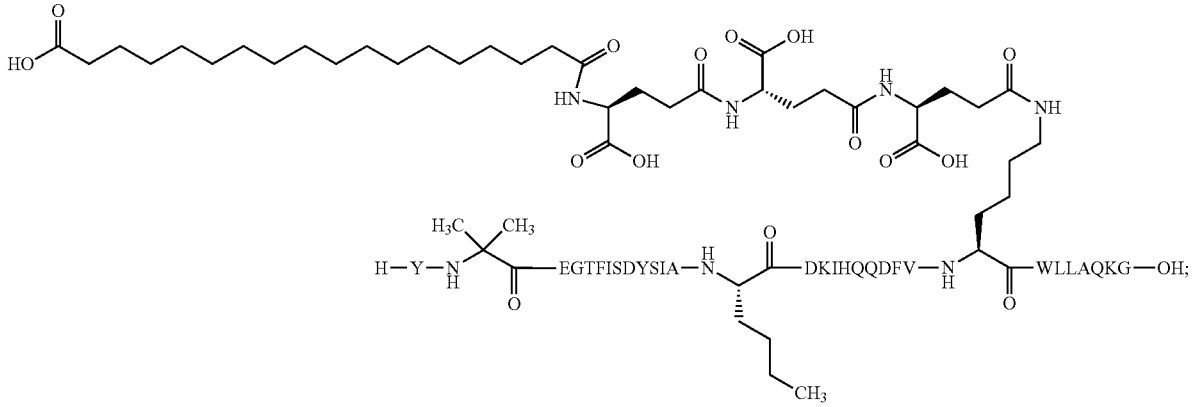

N{Epsilon-24}-[2-[2-[2-[[2-[2-[2-[[(4S)-4-carboxy-4-[[4-[(19-carboxynonadecanoylamino) methyl]cyclohexanecarbonyl]amino]butanoyl]amino]ethoxy]ethoxy]acetyl]amino]ethoxy]ethoxy]acetyl]-[Aib2,Nle14,Arg18,Lys24]-hGIP(1-31) (Compound 3; SEQ ID NO: 8)

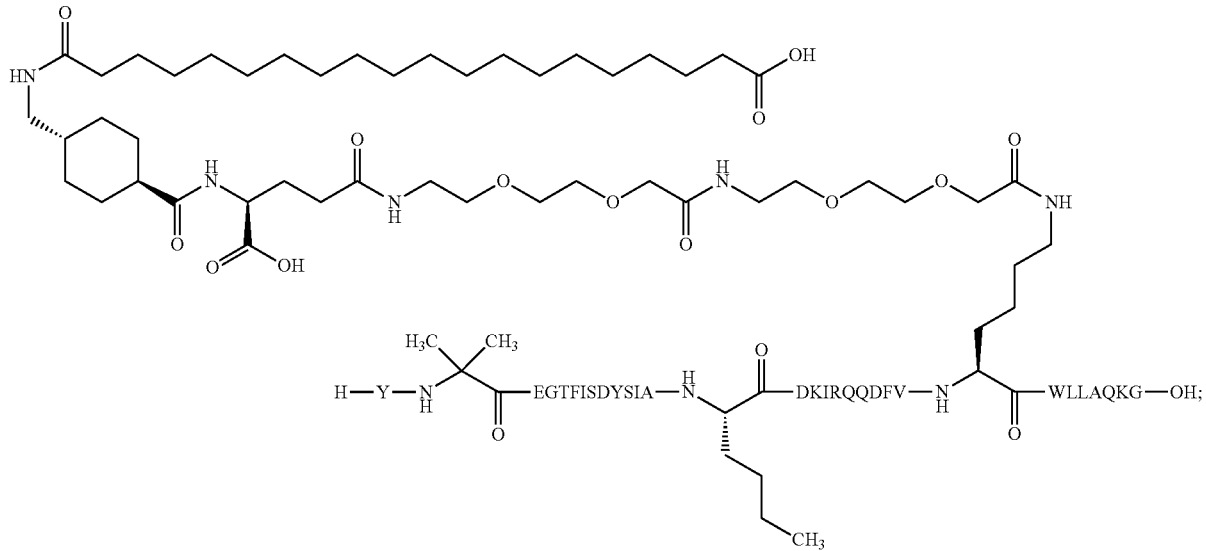

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[Aib2,Nle14,Arg18,Lys24]-hGIP(1-31) (Compound 4; SEQ ID NO: 9)

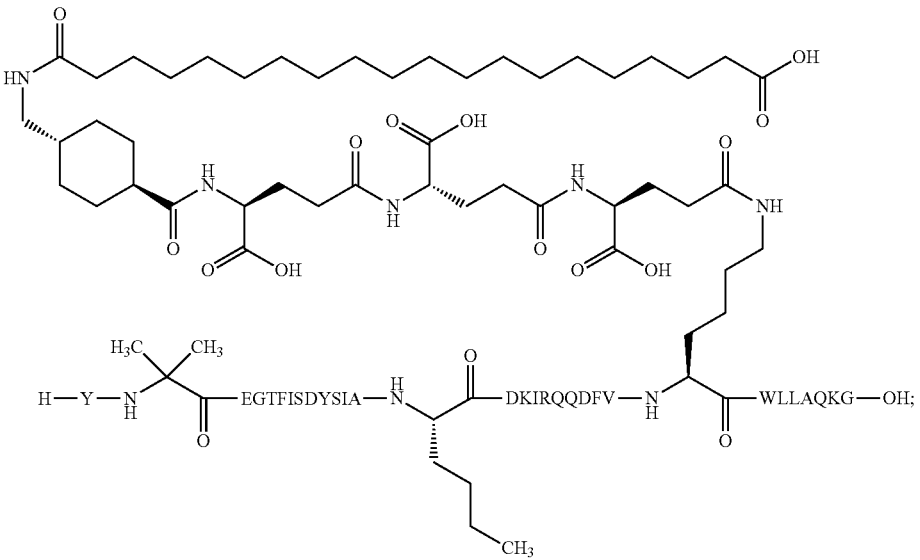

N{1}-acetyl, N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[D-Tyr1,Aib2,Nle14,Arg18,Lys24]-hGIP(1-31) (Compound 5; SEQ ID NO: 10)

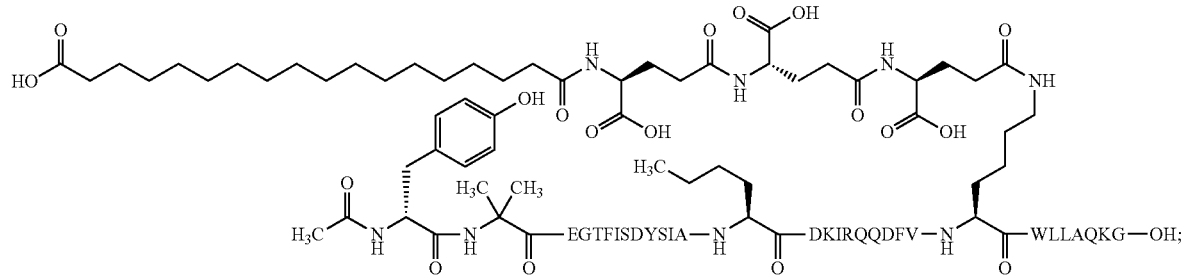

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[D-Tyr1,Aib2,Nle14,Arg18,Lys24]-hGIP(1-31) (Compound 6; SEQ ID NO: 11)

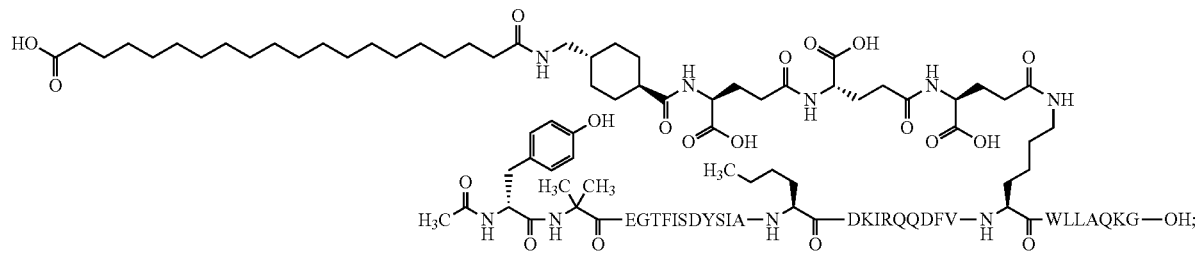

N{1}-acetyl,N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[D-Tyr1,Nle14,Arg18,Lys24]-hGIP(1-31) (Compound 7; SEQ ID NO: 12)

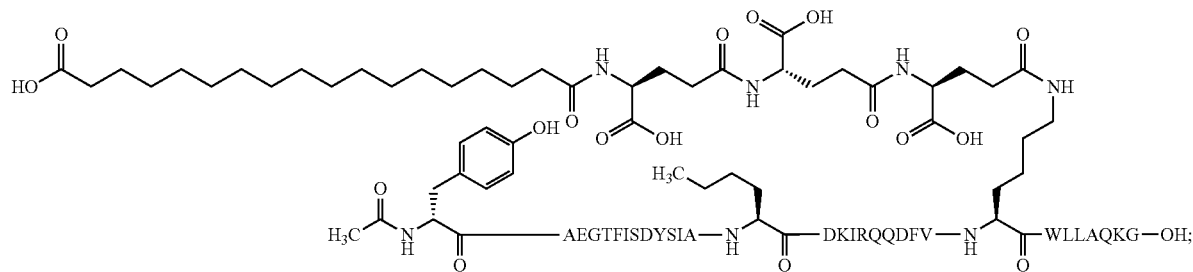

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]-butanoyl]amino]butanoyl]amino]butanoyl]-[D-Tyr1,Nle14,Arg18,Lys24]-hGIP(1-31) (Compound 8; SEQ ID NO: 13)

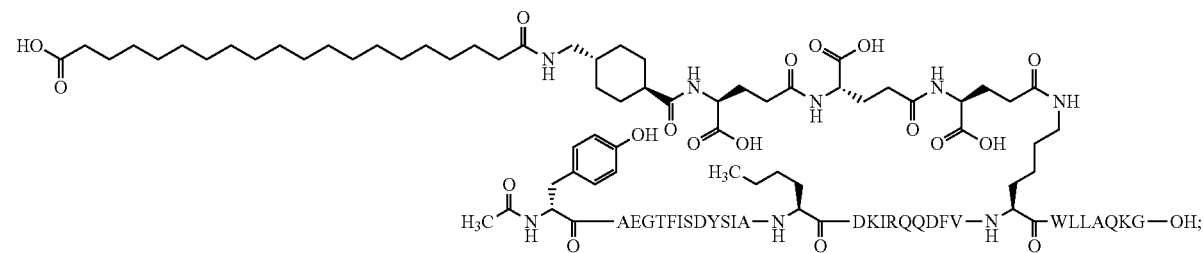

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Glu20,Lys24]-hGIP(1-31) (Compound 9; SEQ ID NO: 14)

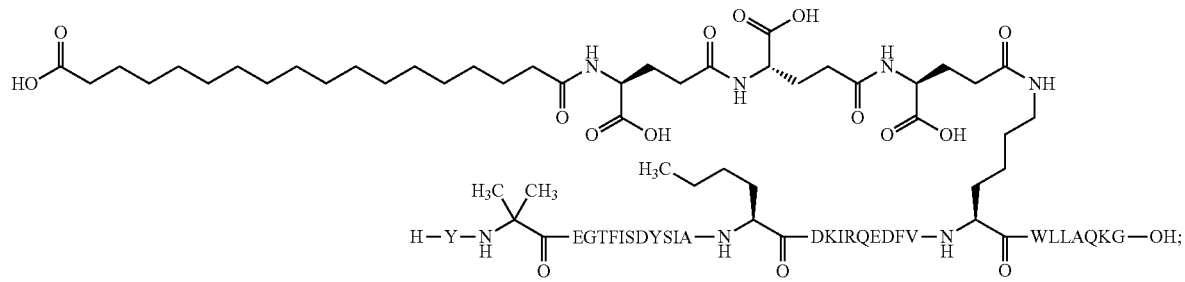

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Arg18,Glu20,Lys24]-hGIP(1-31) (Compound 10; SEQ ID NO: 15)

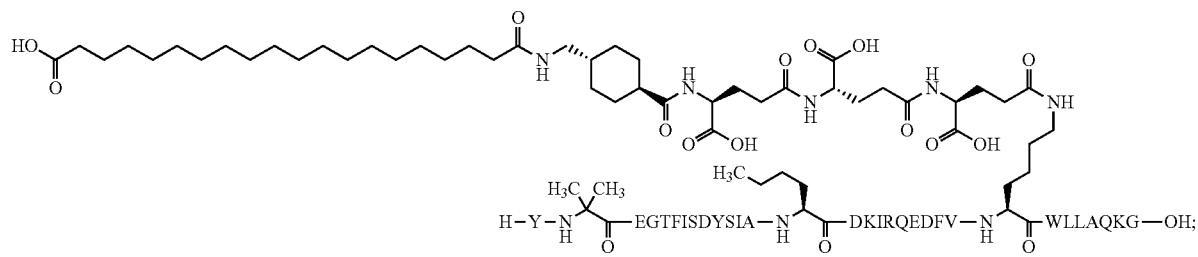

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Aib20,Lys24]-hGIP(1-31) (Compound 11; SEQ ID NO: 16)

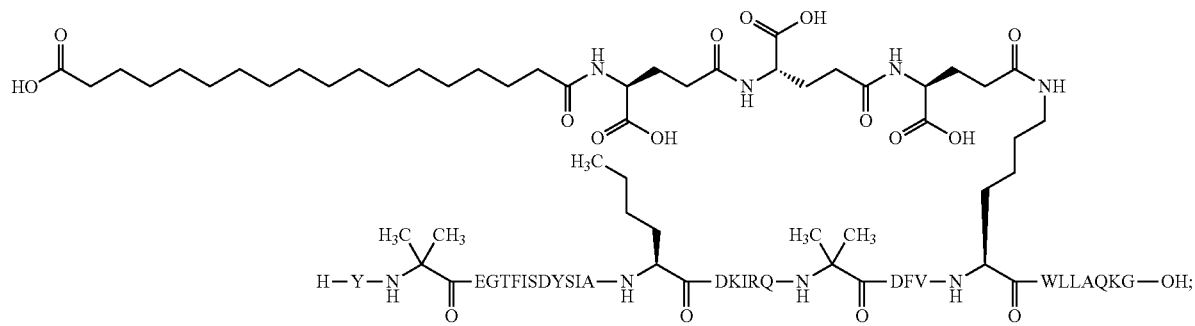

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]-[Aib2,Nle14,Arg18,Aib20,Lys24]-hGIP(1-31) (Compound 12; SEQ ID NO: 17)

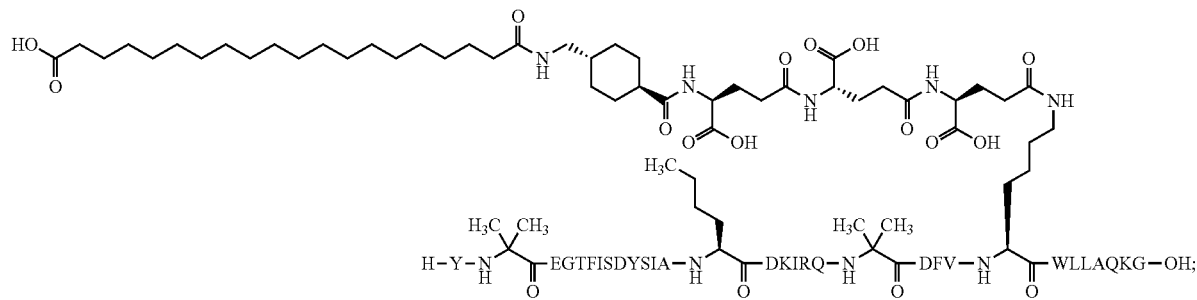

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Ala16,Arg18,Lys24]-hGIP(1-31) (Compound 13; SEQ ID NO: 18)

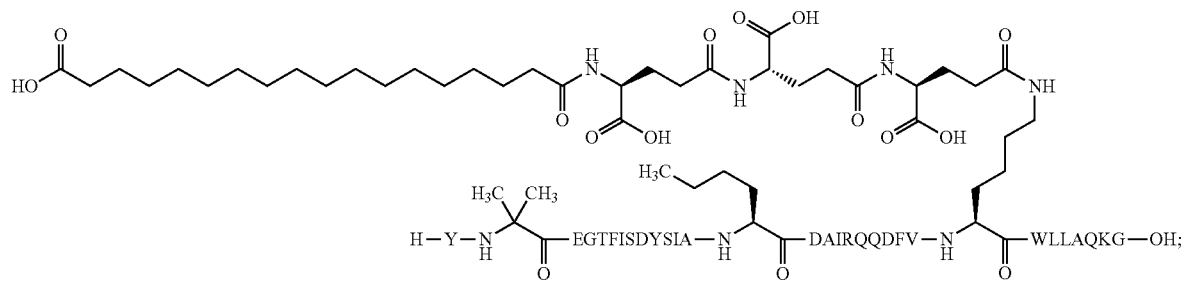

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[Aib2,Nle14,Ala16,Arg18,Lys24]-hGIP(1-31) (Compound 14; SEQ ID NO: 19)

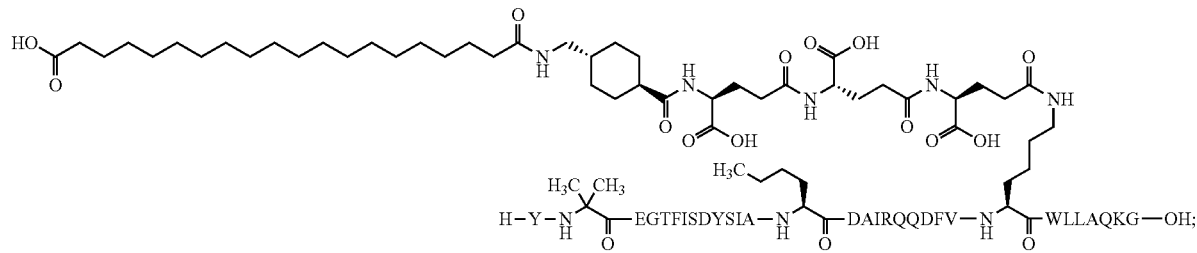

N{1}-acetyl,N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[D-Tyr1,Nle14,Arg18,Lys24]-hGIP(1-31) (Compound 15; SEQ ID NO: 20)

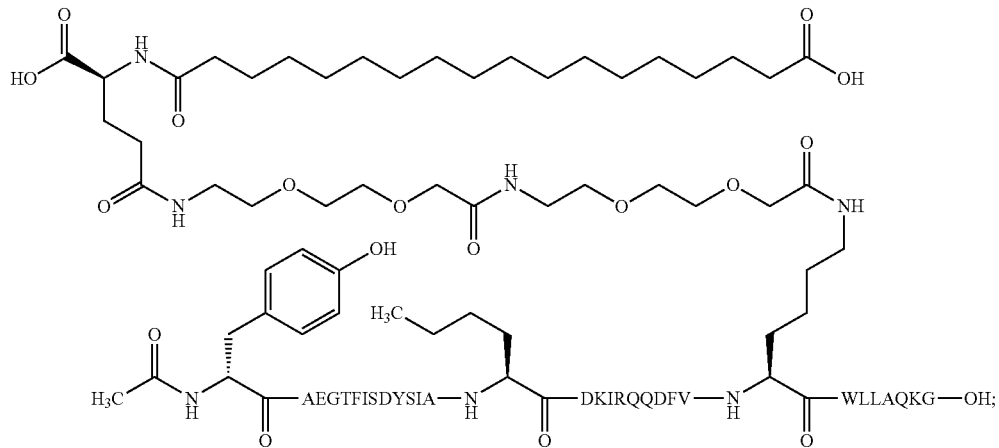

N{1}-acetyl,N{Epsilon-24}-[2-[2-[2-[[2-[2-[2-[[(4S)-4-carboxy-4-(17-carboxy- heptadecanoylamino)butanoyl]amino]ethoxy]ethoxy]acetyl]amino]ethoxy]ethoxy]acetyl]-[D-Tyr1,Nle14,Arg18,Glu20,Lys24]-hGIP(1-31) (Compound 16; SEQ ID NO: 21)

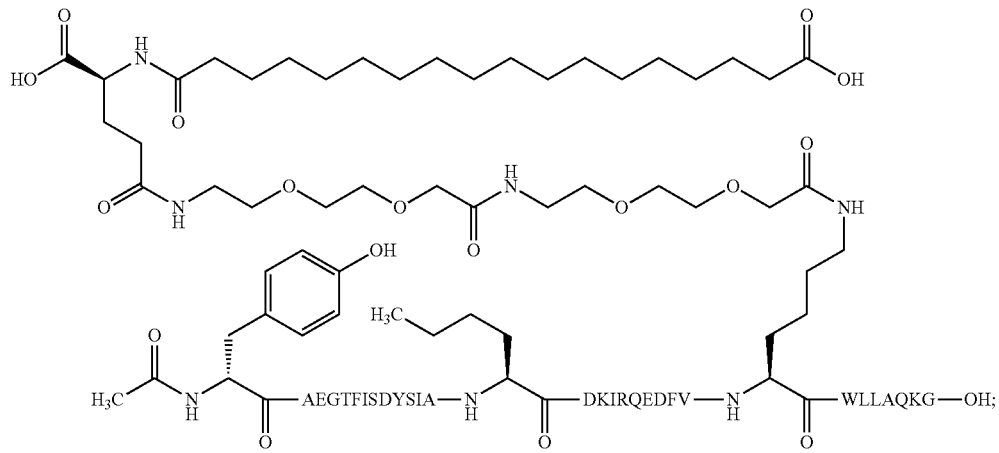

N{1}-acetyl,N{Epsilon-24}-[2-[2-[2-[[2-[2-[2-[[(4S)-4-carboxy-4-[[(4S)-4- carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[D-Tyr1,Nle14,Arg18,Lys24]-hGIP(1-31) (Compound 17; SEQ ID NO: 22)

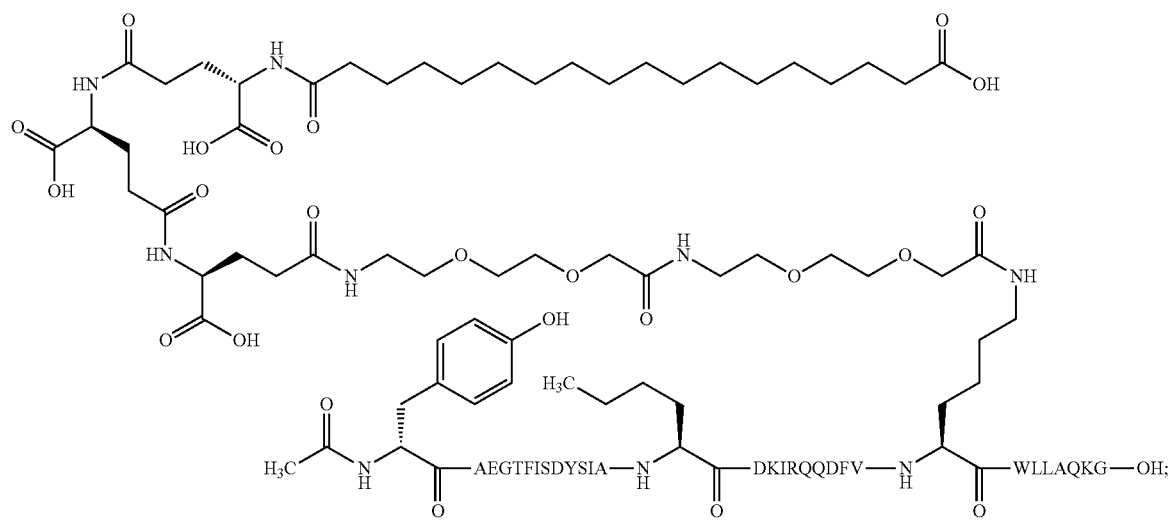
N{1}-acetyl,N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Nle14,Arg18, Lys24]-hGIP(1-31) (Compound 18; SEQ ID NO: 23)
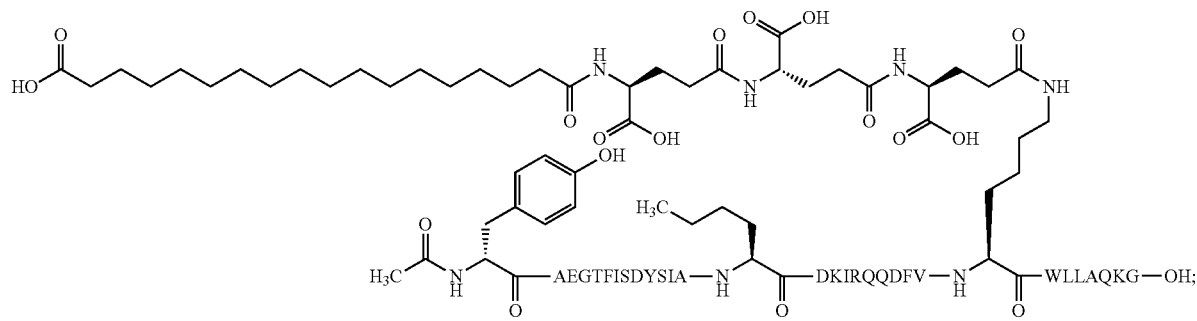
N{1}-acetyl,N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[D-Tyr1,Asp14,Arg18,Glu20,Lys24]-hGIP(1-31) (Compound 19; SEQ ID NO: 24)
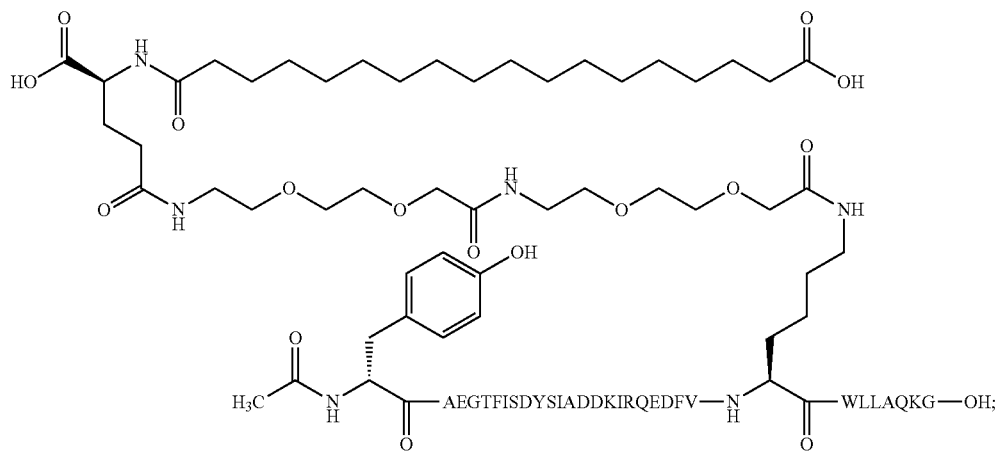

N{Epsilon-24}-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Aib2,Nle14,Glu20,Lys24]-hGIP(1-31) (Compound 20; SEQ ID NO: 25)

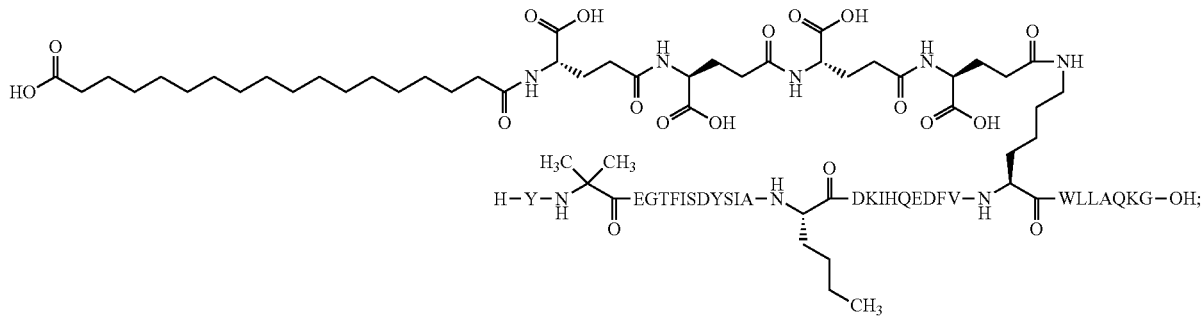

25

N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]amino]butanoyl]-[Aib2,Nle14,Glu20,Lys24]-haP(1-31) (Compound 21; SEQ ID NO: 26)

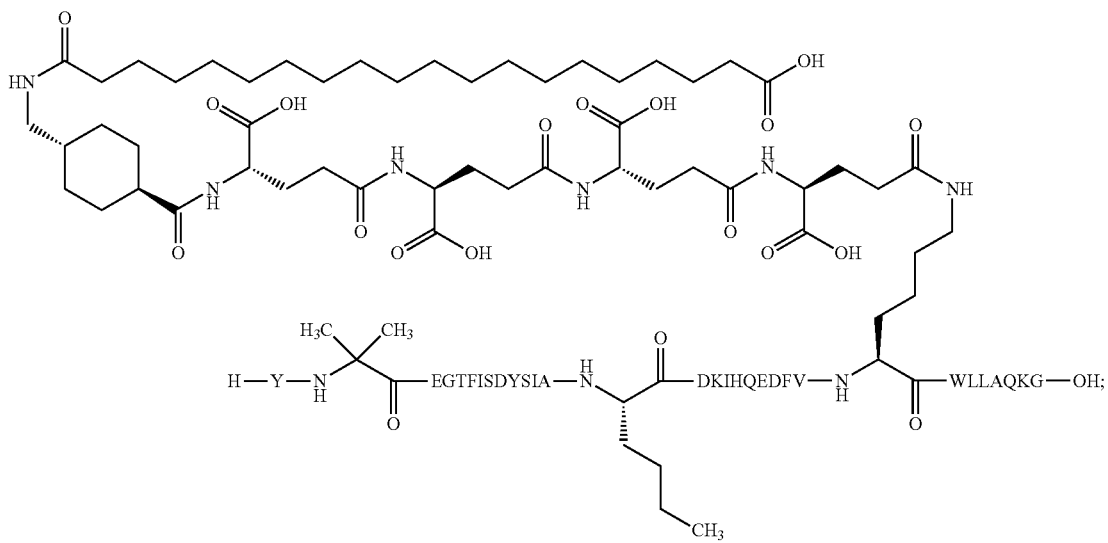

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Glu20,Lys24]-hGIP(1-31) (Compound 22; SEQ ID NO: 27)

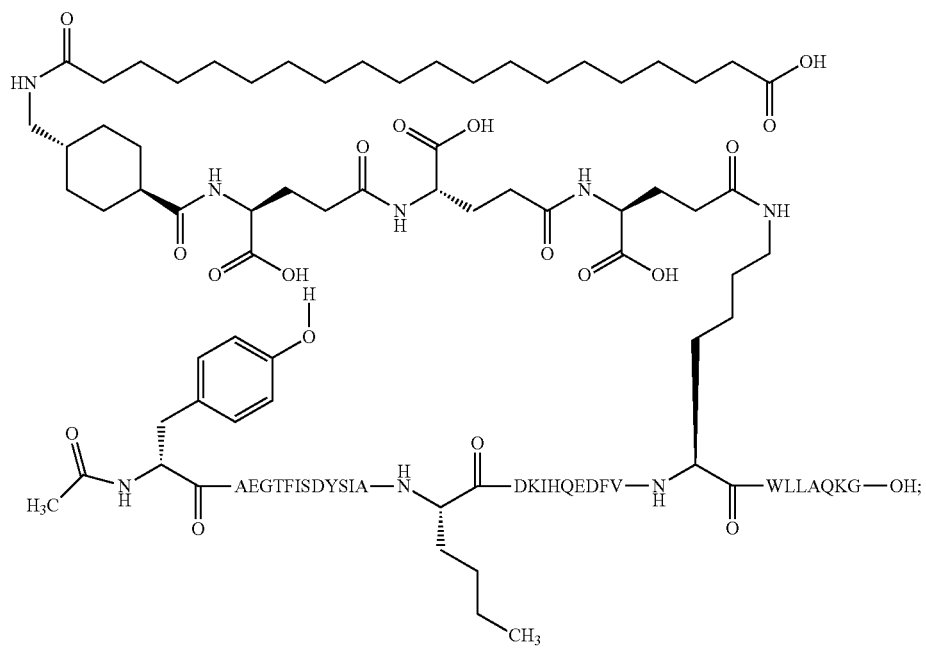

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1, Nle14,Arg18,Glu20,Lys24]-hGIP(1-31) (Compound 23; SEQ ID NO: 28)

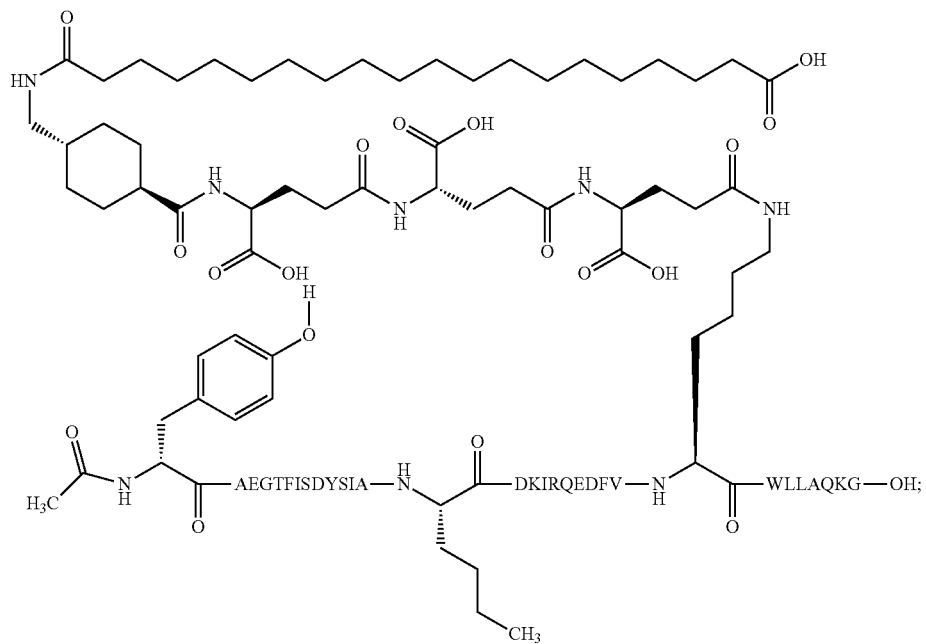

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1, Nle14,Aib20,Lys24]-hGIP(1-31) (Compound 24; SEQ ID NO: 29)

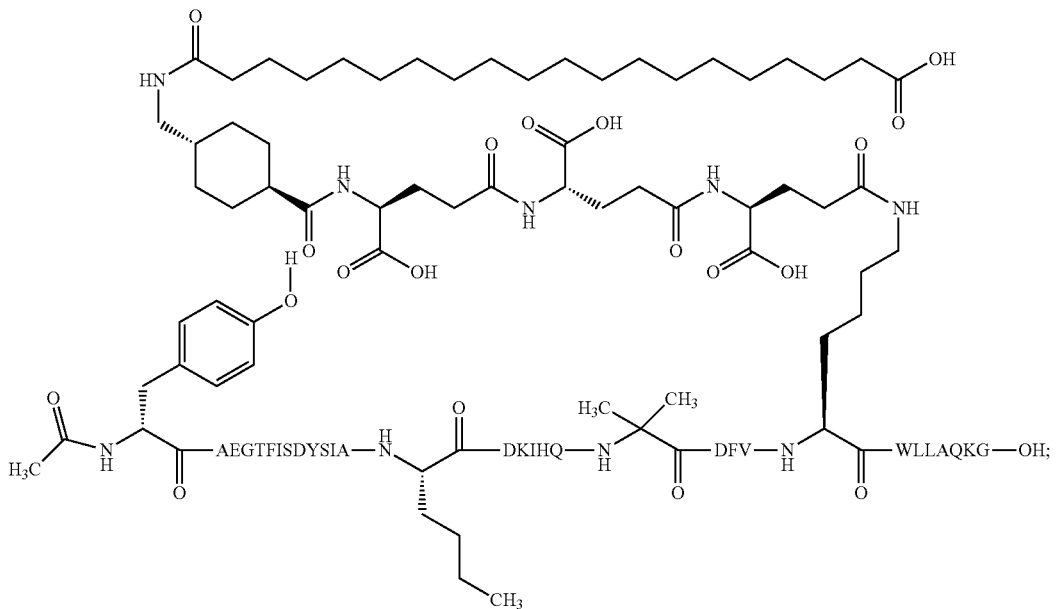

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1, Nle14,Arg18,Aib20,Lys24]-hGIP(1-31) (Compound 25; SEQ ID NO: 30)

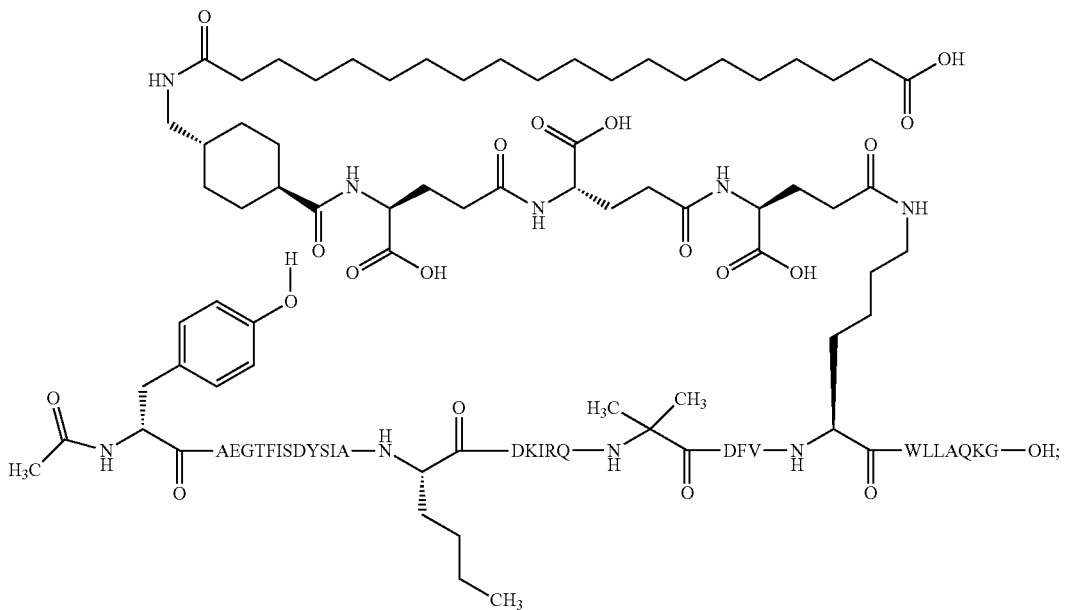

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Arg18,Lys24,Pro31]-hGIP(1-31) amide (Compound 26; SEQ ID NO: 31)

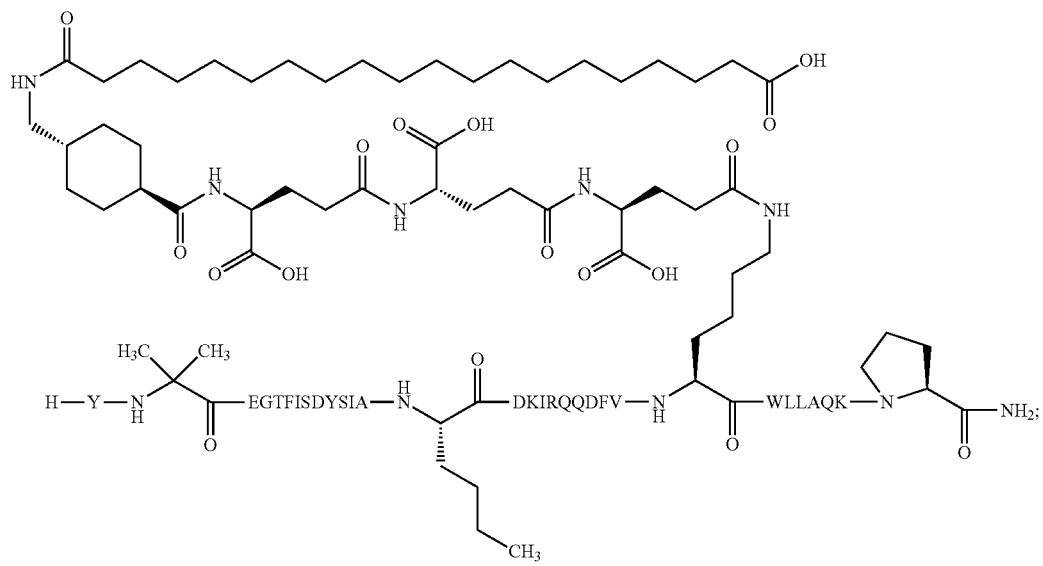

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Lys24,Pro31]-hGIP(1-31) amide (Compound 27; SEQ ID NO: 32)

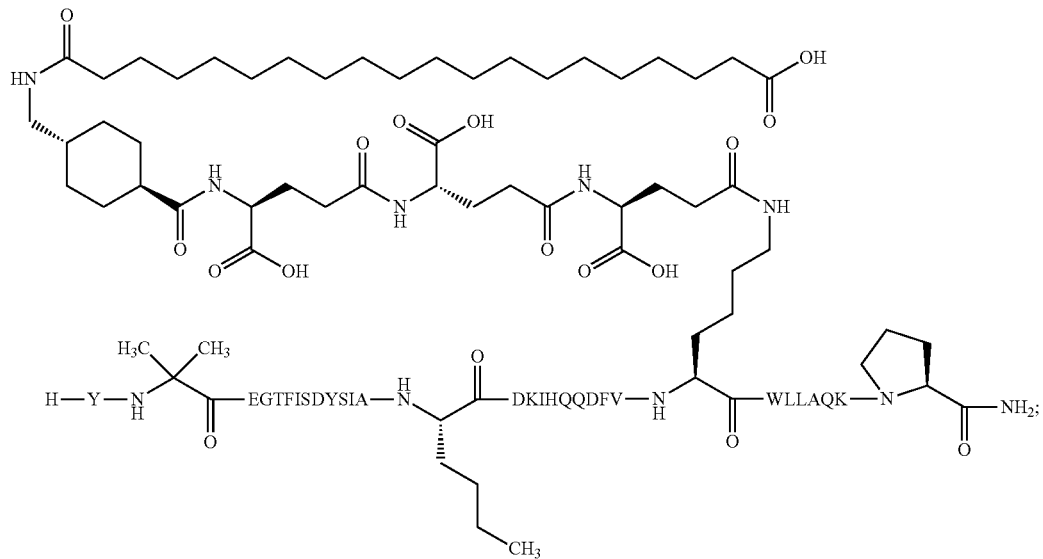

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Arg18,Lys24,Pro31]-hGIP(1-31) amide (Compound 28; SEQ ID NO: 33)

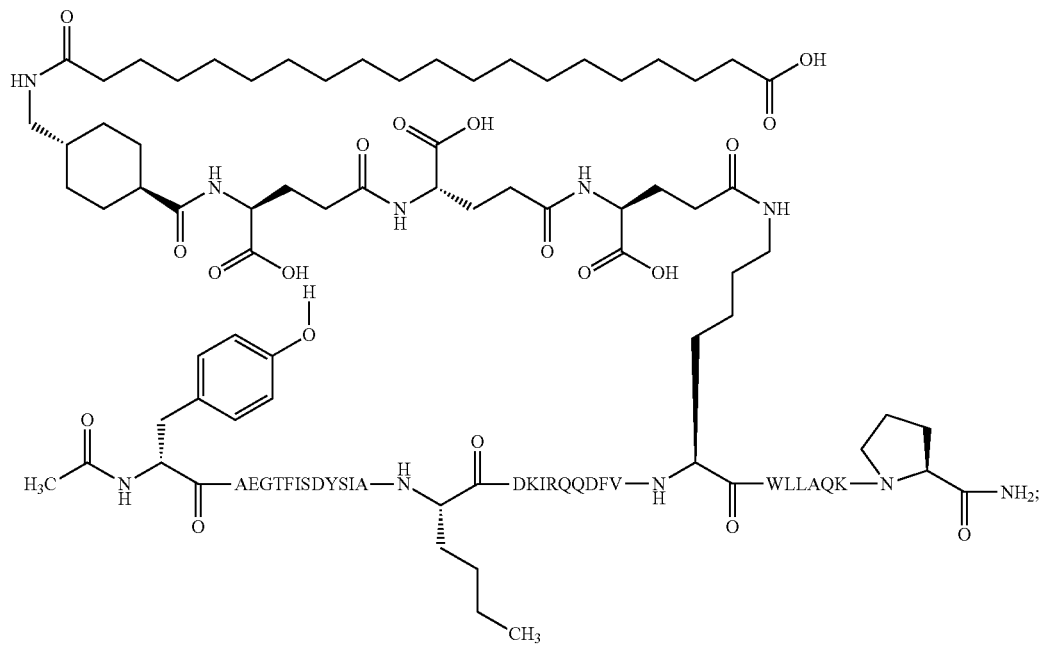

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Lys24,Pro31]-hGIP(1-31) amide (Compound 29; SEQ ID NO: 34)

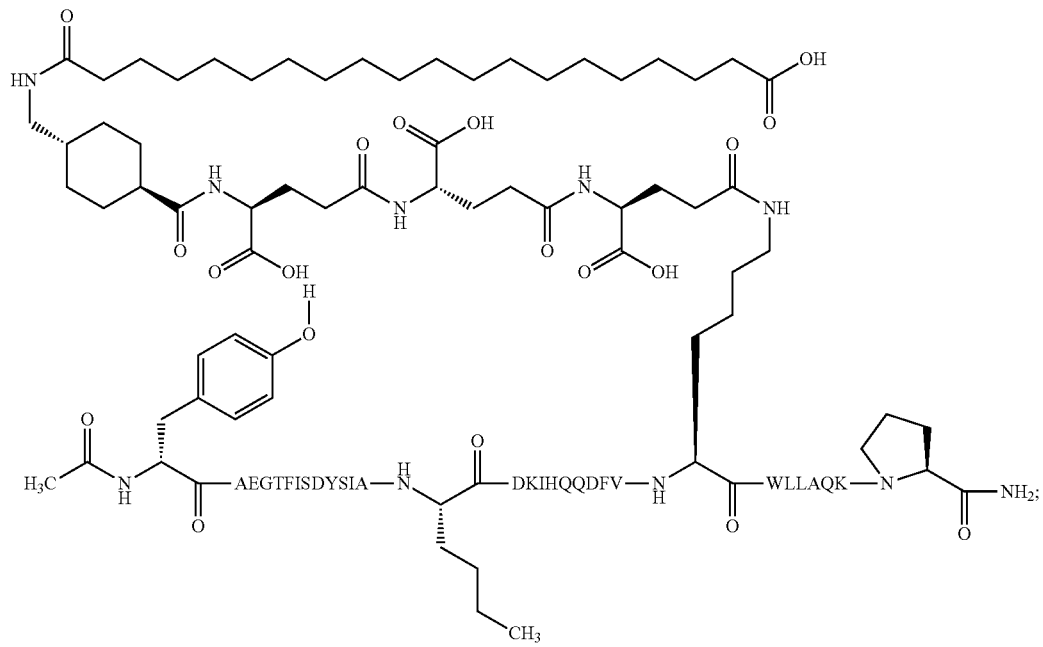

N{1}-acetyl,N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]-amino]butanoyl]amino]butanoyl]amino]butanoyl]amino]butanoyl]-[D-Tyr1,Nle14,Arg18,Lys24]-hGIP(1-31) (Compound 30; SEQ ID NO: 35)

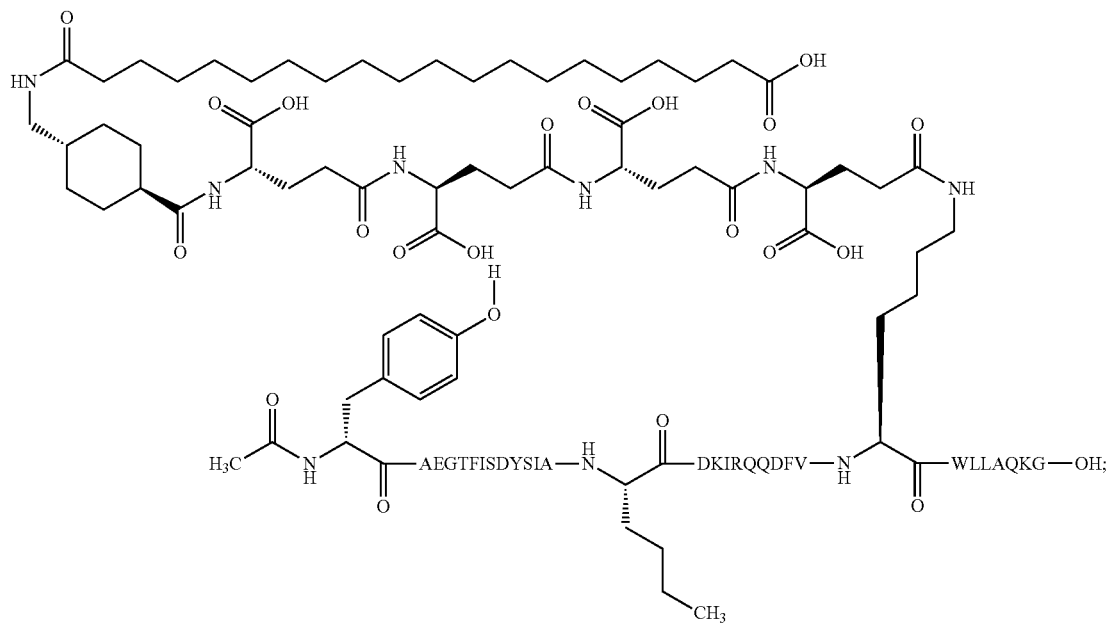

N{1}-acetyl,N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]amino]butanoyl]-[D-Tyr1,Aib2,Nle14,Arg18,Lys24,Pro31]-hGIP(1-31) amide (Compound 31; SEQ ID NO: 36)

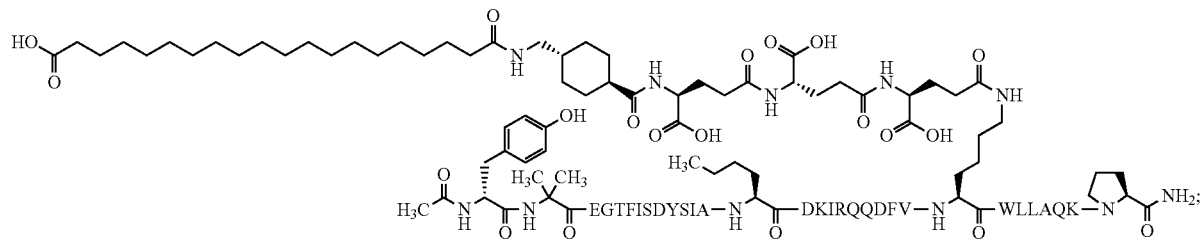

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Aib2,Nle14,Lys24,Pro31]-hGIP(1-31) amide (Compound 32; SEQ ID NO: 37)

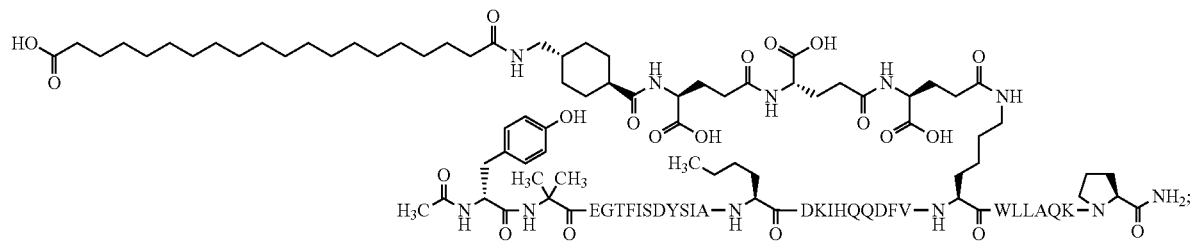

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33]-hGIP (Compound 33; SEQ ID NO: 38)

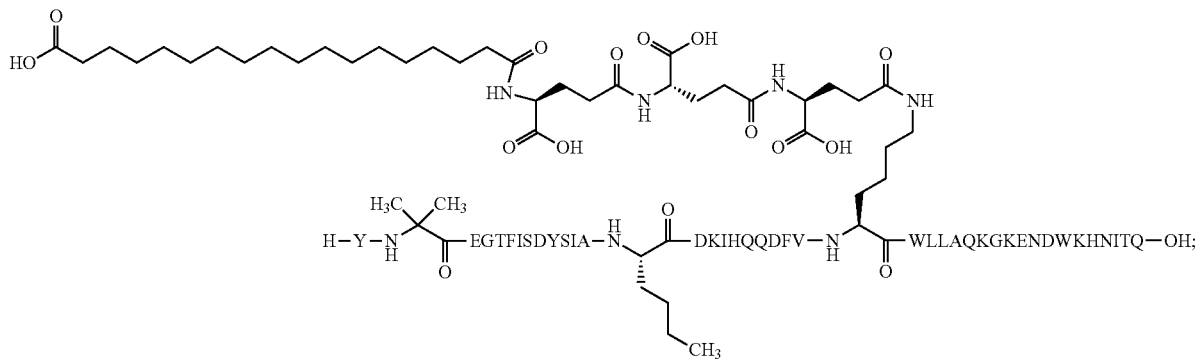

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Lys24,Glu33]-hGIP (Compound 34; SEQ ID NO: 39)

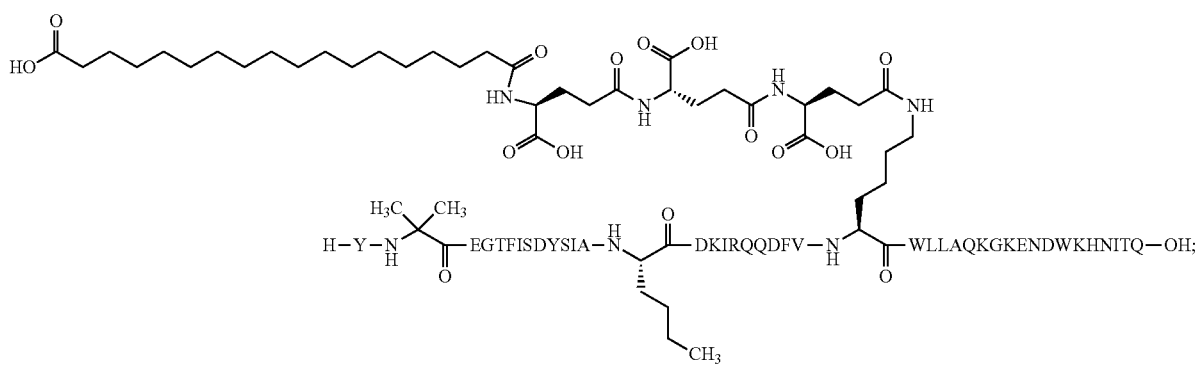

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Glu34]-hGIP (Compound 35; SEQ ID NO: 40)

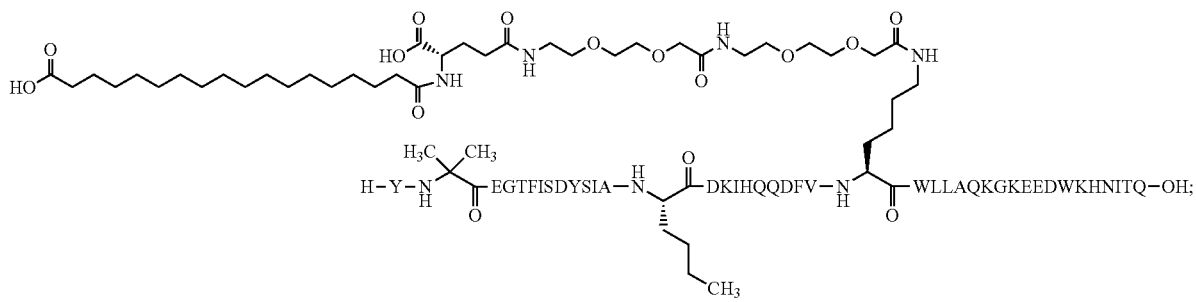

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Asp34]-hGIP (Compound 36, SEQ ID NO: 41)

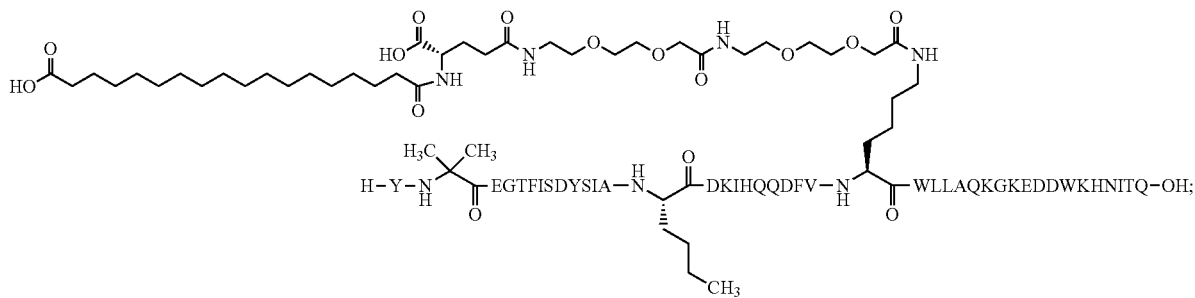

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2, Nle14,Arg18,Lys24,Glu33,Glu34]-hGIP (Compound 37; SEQ ID NO: 42)

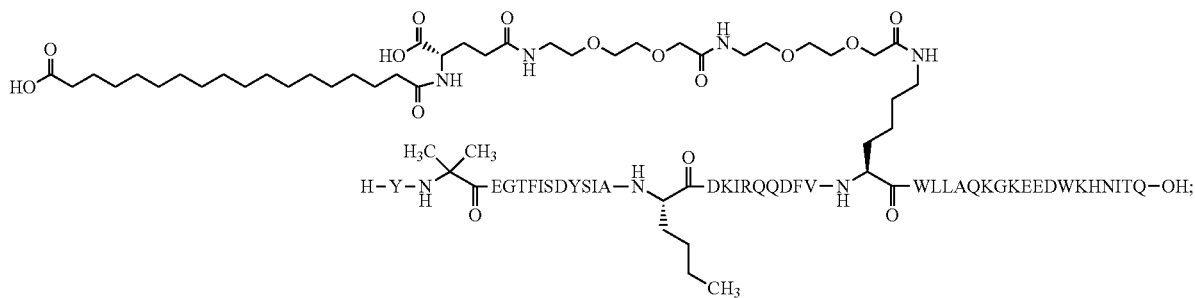

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14, Lys24,Glu33,Glu34]-hGIP (Compound 38; SEQ ID NO: 43)

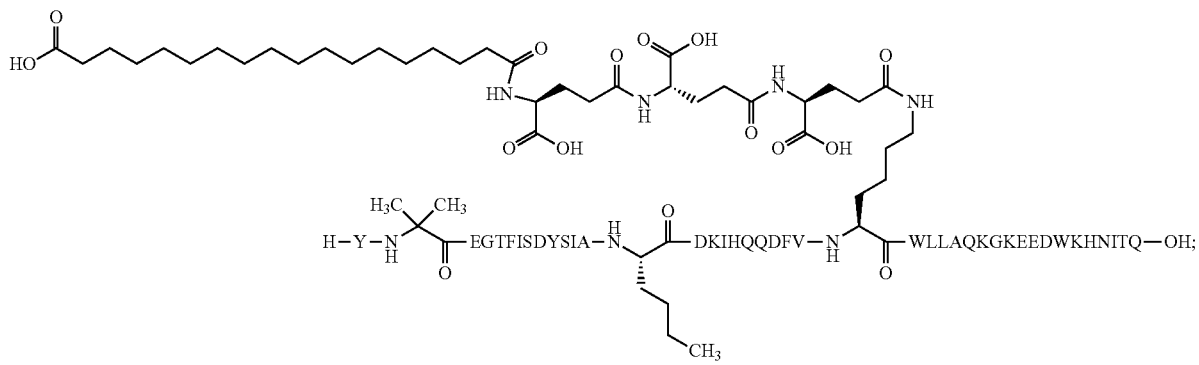

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14, Lys24,Glu33,Asp34]-hGIP (Compound 39; SEQ ID NO: 44)

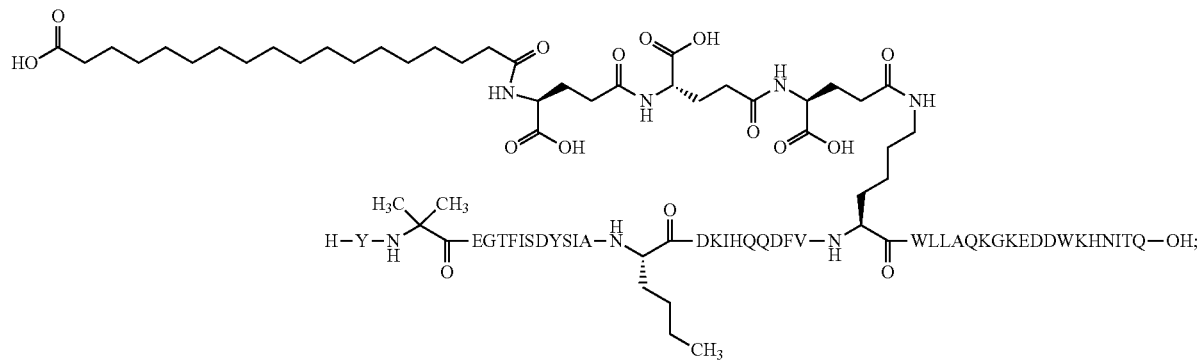
N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Lys24,Glu33,Glu34]-hGIP (Compound 40; SEQ ID NO: 45)
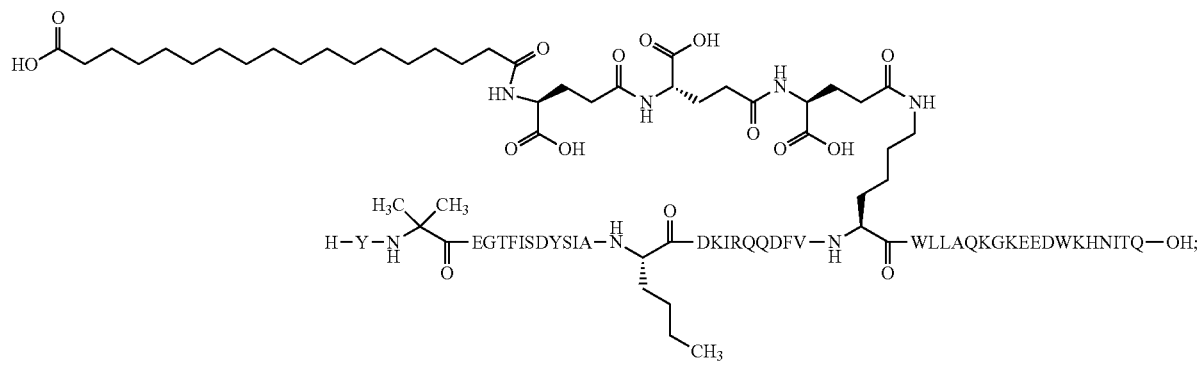
N{Epsilon-24}-[2-[2-[2-[[2-[2-[2-[[(4S)-4-carboxy-4-[[4-[(19-carboxynonadecanoyl- amino)methyl]cyclohexanecarbonyl]amino]butanoyl]amino]ethoxy]ethoxy]acetyl]amino]ethoxy]ethoxy]acetyl]-[Aib2,Nle14,Arg18,Lys24,Glu33,Glu34]-hGIP (Compound 41; SEQ ID NO: 46)
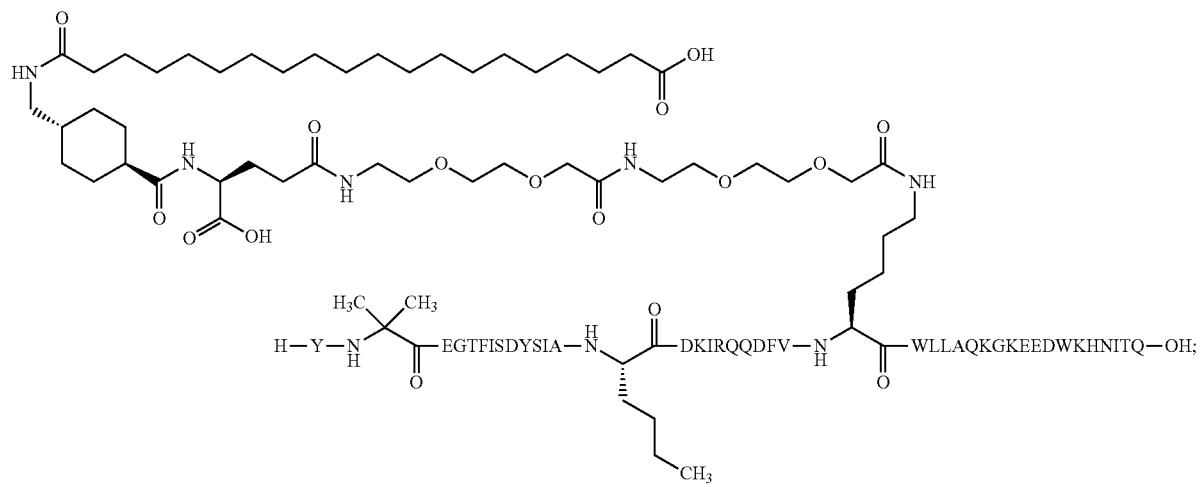

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]-[Aib2,Nle14,Arg18,Lys24,Glu33,Glu34]-hGIP (Compound 42; SEQ ID NO: 47)

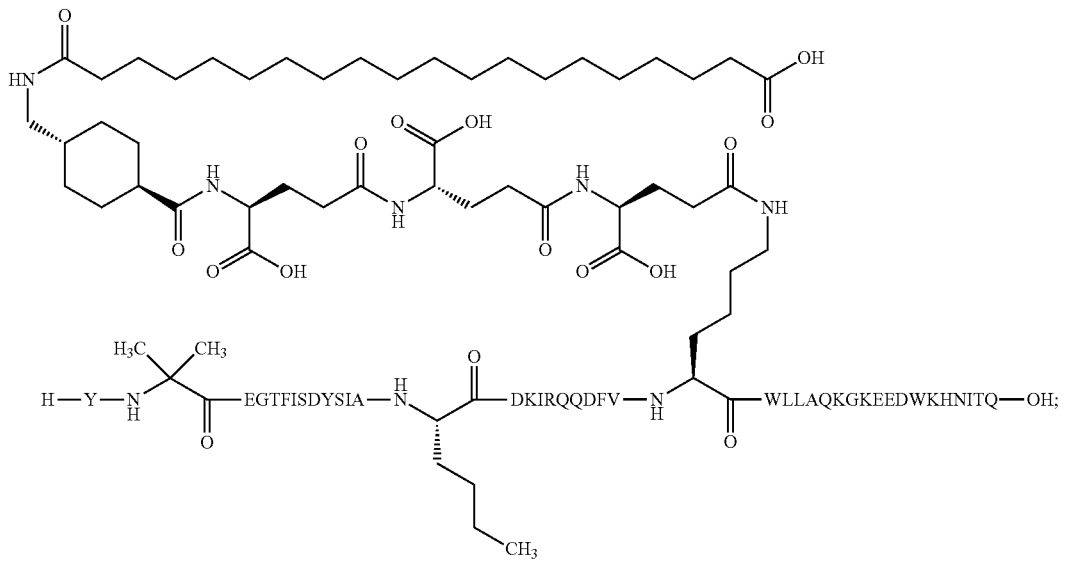

N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Nle14,Arg18,Aib20,Lys24]-hGIP(1-31) (Compound 43; SEQ ID NO: 59)

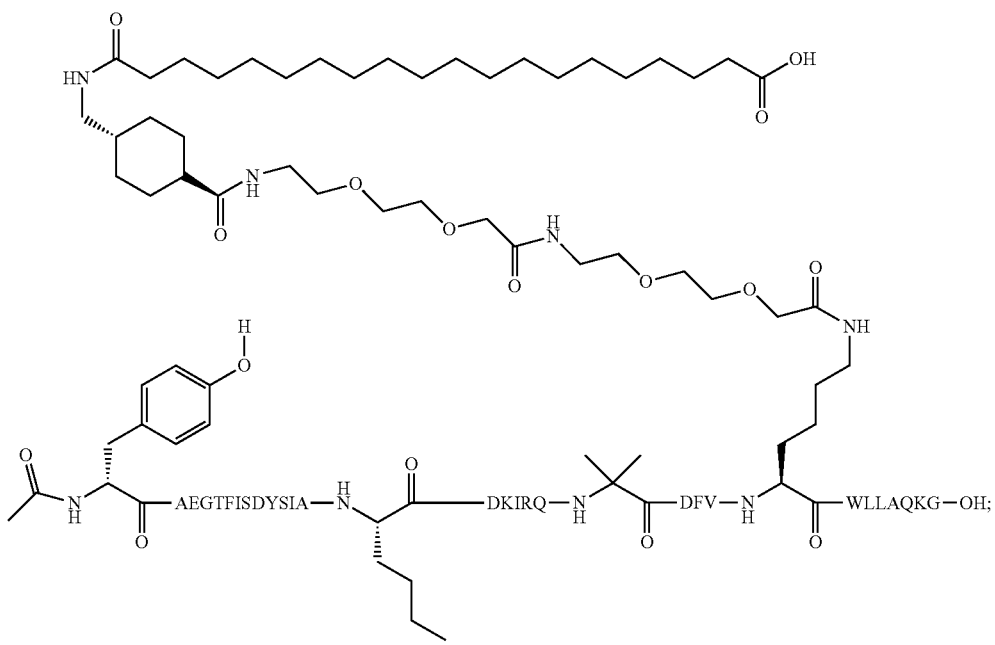

N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Aib2,Nle14,Arg18,Lys24,Pro31]-hGIP(1-31) amide (Compound 44; SEQ ID NO: 60)

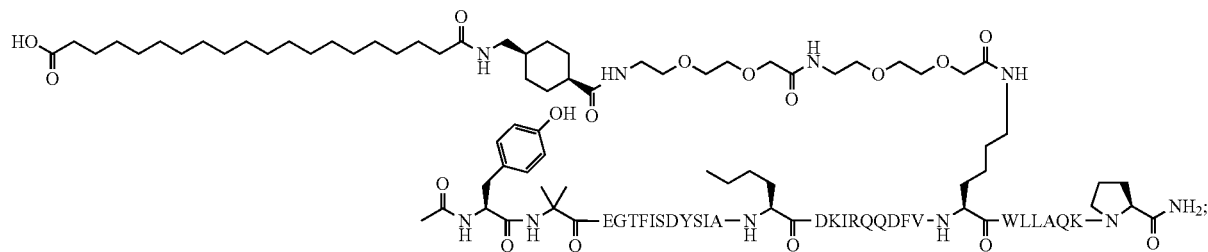

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Leu14,Lys24]-hGIP (Compound 45; SEQ ID NO: 61)

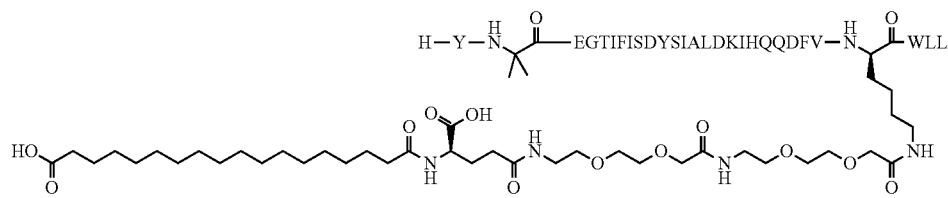

N{1}-acetyl,N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[D-Tyr1,Aib2,Nle14,Arg18,Lys24,Pro31]-hGIP(1-31) amide (Compound 46; SEQ ID NO: 62)

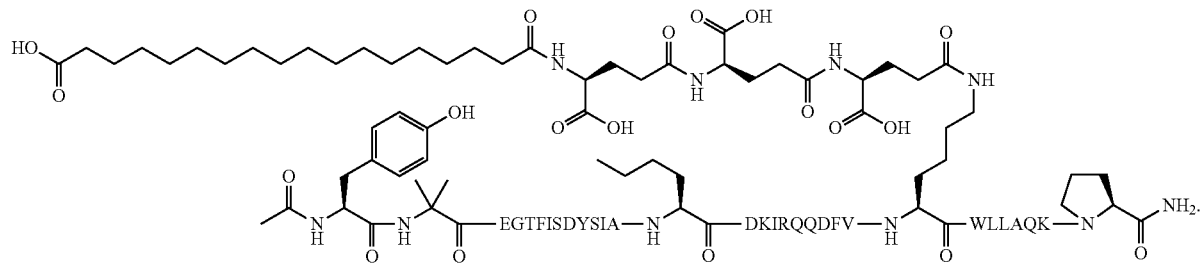

69. The derivative according to embodiment 68 selected from compound no. 1-32, 43-44, 46.
70. The derivative according to any one of embodiments 68-69 selected from compound no. 1-25, 30, 43.
71. The derivative according to any one of embodiments 68-70 which is compound no. 5.
72. The derivative according to any one of embodiments 68-70 which is compound no. 25.
73. The derivative according to any one of embodiments 68-69 selected from compound no. 26-29, 31-32, 44, 46.
74. The derivative according to any one of embodiments 68-69, 73 which is compound no. 31.
75. The derivative according to embodiment 68 selected from compound no. 33-42, 45.
76. The derivative according to any one of the preceding embodiments which is an agonist at the human GIP receptor.
77. The derivative according to any one of the preceding embodiments which is capable of activating the human GIP receptor.
78. The derivative according to any one of the preceding embodiments which is capable of activating the human GIP receptor in an assay with whole cells expressing the human GIP receptor
79. The derivative according to any one of the preceding embodiments which is capable of activating the human GIP receptor in a CRE luciferase assay, such as Example 2 described herein.
80. The derivative according to any one of the preceding embodiments which is an agonist at the human GIP receptor, with an $EC_{50}$ of no more than 900 pM, such as determined in Example 2 described herein.
81. The derivative according to any one of the preceding embodiments which is an agonist at the human GIP receptor, with an $EC_{50}$ of no more than 500 pM, such as determined in Example 2 described herein.
82. The derivative according to any one of the preceding embodiments which is an agonist at the human GIP receptor, with an $EC_{50}$ of no more than 200 pM, such as determined in Example 2 described herein.
83. The derivative according to any one of the preceding embodiments which is selective for the human GIP receptor over the human GLP-1 receptor and human glucagon receptor.
84. The derivative according to any one of the preceding embodiments which has a lower $EC_{50}$ at the human GIP receptor than at the human GLP-1 receptor and the human glucagon receptor.

85. The derivative according to any one of the preceding embodiments which has an $EC_{50}$ at the human GLP-1 receptor of more than 100000 pM in a CRE luciferase assay, such as determined in Example 2 described herein.
86. The derivative according to any one of the preceding embodiments which has an $EC_{50}$ at the human GLP-1 receptor of more than 10000 pM in a CRE luciferase assay, such as determined in Example 2 described herein.
87. The derivative according to any one of the preceding embodiments which has an $EC_{50}$ at the human glucagon receptor of more than 100000 pM in a CRE luciferase assay, such as Example 2 described herein.
88. The derivative according to any one of the preceding embodiments which has improved pharmacokinetic properties.
89. The derivative according to any one of the preceding embodiments which has an increased half-life.
90. The derivative according to any one of the preceding embodiments which has an increased half-life when determined in minipigs.
91. The derivative according to any one of the preceding embodiments which has improved physical stability.
92. The derivative according to any one of the preceding embodiments which has more than 95 percent recovery in a ThT fibrillation assay, such as determined in Example 4 described herein.
93. The derivative according to any one of the preceding embodiments which has more than 45 hours lag-time in a ThT fibrillation assay, such as determined in Example 4 described herein.
94. The derivative according to any one of the preceding embodiments which has a low DLS-SI value.
95. The derivative according to any one of the preceding embodiments which has a DLS-SI value of less than 7, preferably less than 2 such as determined in Example 4 described herein.
96. The derivative according to any one of the preceding embodiments which has no precipitates in a DLS-SI assay, such as determined in Example 4 described herein.
97. The derivative according to any one of the preceding embodiments which has improved chemical stability.
98. The derivative according to any one of the preceding embodiments which has a formation of HMWP of no more than 2 percent per month, such as determined in Example 5 described herein.
99. The derivative according to any one of the preceding embodiments which has a purity loss of no more than 35 percent per month, such as determined in Example 5 described herein.
100. The derivative according to any one of the preceding embodiments which has a purity loss of no more than 6 percent per month, such as determined in Example 5 described herein.
101. The derivative according to any one of the preceding embodiments which has the effect in vivo of reducing food intake as determined in a sub-chronic study in DIO mice, such as Example 6 described herein.
102. The derivative according to any one of the preceding embodiments which has the effect in vivo of inducing body weight loss as determined in a sub-chronic study in DIO mice, such as Example 6 described herein.
103. The derivative according to any one of the preceding embodiments which has the effect of improving glucose tolerance in vivo as determined in a sub-chronic study in DIO mice, such as Example 6 described herein.
104. A pharmaceutical composition comprising the derivative according to any one of the preceding embodiments, and at least one pharmaceutically acceptable excipient.
105. A pharmaceutical composition comprising the derivative according to any one of embodiments 1-103, a GLP-1 receptor agonist, and at least one pharmaceutically acceptable excipient.
106. A pharmaceutical composition comprising the derivative according to any one of embodiments 1-103, a GLP-1/glucagon receptor co-agonist, and at least one pharmaceutically acceptable excipient.
107. The pharmaceutical composition according to embodiment 105, wherein the GLP-1 receptor agonist is liraglutide.
108. The pharmaceutical composition according to embodiment 105, wherein the GLP-1 receptor agonist is semaglutide (SEQ ID NO: 57).
109. The pharmaceutical composition according to embodiment 106, wherein the GLP-1/glucagon receptor co-agonist is N{Epsilon-28}-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Leu27,Lys28]-Glucagon amide (SEQ ID NO: 52):

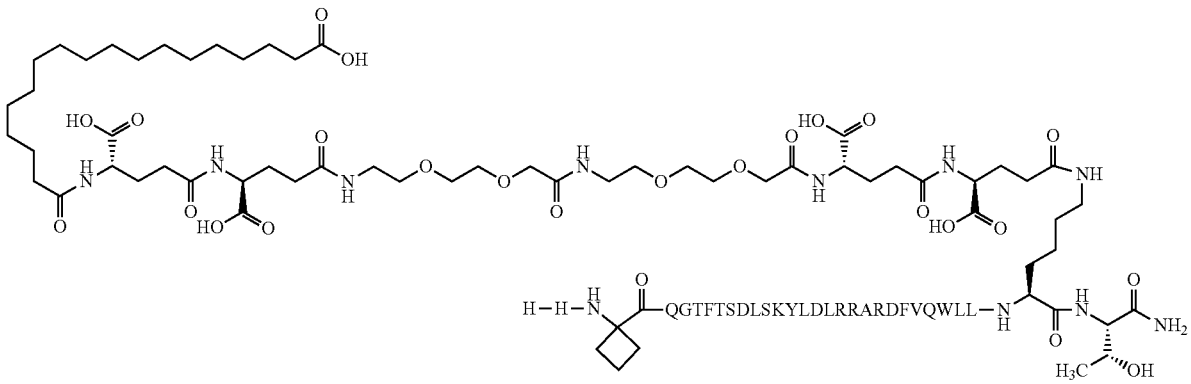

110. The pharmaceutical composition according to embodiment 106, wherein the GLP-1/glucagon receptor co-agonist is N{Epsilon-28}-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Glu21,Leu27,Lys28]-Glucagon amide (SEQ ID NO: 53):

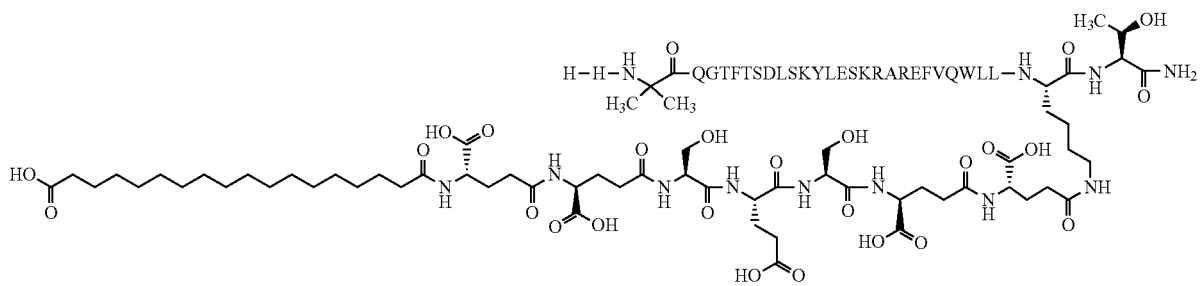

111. The pharmaceutical composition according to embodiment 106, wherein the GLP-1/glucagon receptor co-agonist is N{Epsilon-28}-[(4S)-4-carboxy-4-[[(4S)-4-carboxy-4-[[2-[2-[2-[[2-[2-[2-[[(4S)-4-carboxy-4-(17-carboxyheptadecanoylamino) butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Leu27,Lys28]-Glucagon amide (SEQ ID NO: 54):

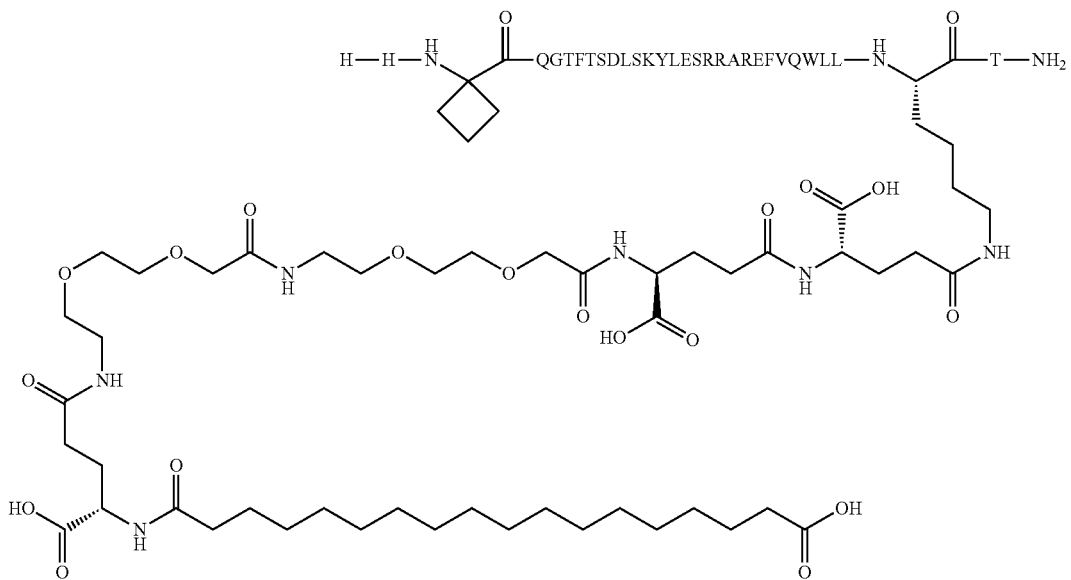

112. The pharmaceutical composition according to embodiment 106, wherein the GLP-1/glucagon receptor co-agonist is N{Epsilon-28}-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Lys17,Arg20,Glu21,Leu27,Lys28]-Glucagon amide (SEQ ID NO: 55):

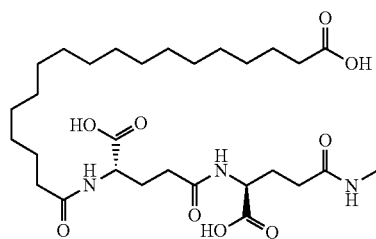
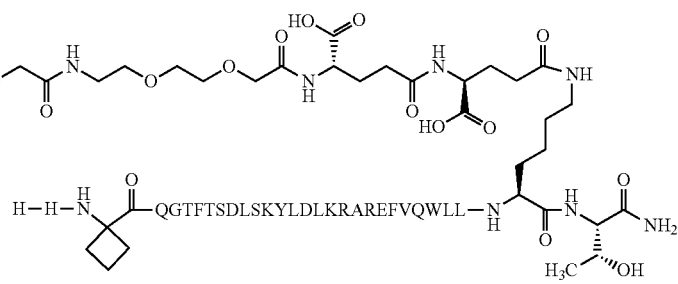

113. The pharmaceutical composition according to embodiment 106, wherein the GLP-1/glucagon receptor co-agonist is N{Epsilon-28}-[2-[2-[2-[[2-[2-[2-[[(4S)-4-carboxy-4-[[(4S)-4-carboxy-4-[[(4S)-4-carboxy-4-(17-carboxyheptadecanoylamino) butanoyl]amino]butanoyl]amino]butanoyl]amino]ethoxy]ethoxy]acetyl]amino]ethoxy]ethoxy]acetyl]-[Aib2,Leu10,Ala16,Arg20,Leu27,Lys28]-Glucagon amide (SEQ ID NO: 56):

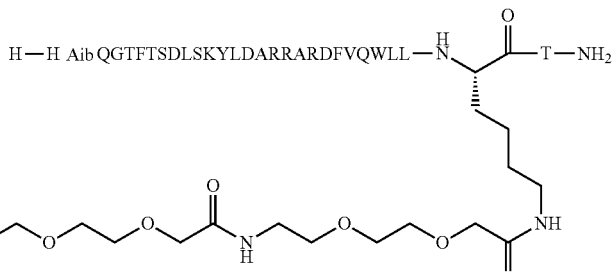
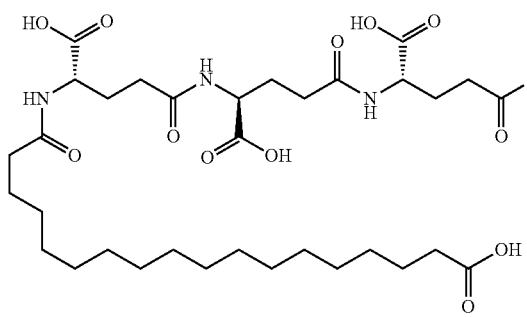

114. The pharmaceutical composition according to any one of embodiments 104-113, wherein the derivative is SEQ ID NO: 10.
115. The pharmaceutical composition according to any one of embodiments 104-113, wherein the derivative is SEQ ID NO: 30.
116. The pharmaceutical composition according to any one of embodiments 104-113, wherein the derivative is SEQ ID NO: 36.
117. The pharmaceutical composition according to any one of embodiments 104-116 for use as a medicament.
118. The derivative according to any one of embodiments 1-103 for use as a medicament.
119. The derivative according to any one of embodiments 1-103 for use in the treatment of:
  (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
  (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
  (iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
  (iv) weight maintenance after successful weight loss (either drug induced or by diet and exercise)—i.e. prevention of weight gain after successful weight loss;
  (v) prevention and/or treatment of liver disorders, such as hepatic steatosis, non-alcoholic fatty liver disease (NAFLD), non-alcoholic steatohepatitis (NASH), liver inflammation or fatty liver.
120. The derivative according to any one of embodiments 1-103 for use in prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C.

121. The derivative according to any one of embodiments 1-103 for use in delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes.

122. The derivative according to any one of embodiments 1-103 for use in prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

123. The derivative according to any one of embodiments 1-103 for use in weight maintenance after successful weight loss (either drug induced or by diet and exercise)—i.e. prevention of weight gain after successful weight loss.

124. The derivative according to any one of embodiments 1-103 for use in prevention and/or treatment of liver disorders, such as hepatic steatosis, non-alcoholic fatty liver disease (NAFLD), non-alcoholic steatohepatitis (NASH), liver inflammation or fatty liver.

125. The derivative according to any one of embodiments 1-103 for use in the treatment and/or prevention of weight management, obesity and obesity related disorders.

126. The derivative according to any one of embodiments 1-103 for use in the treatment and/or prevention of all forms of diabetes, e.g. type 2 diabetes, and diabetes related disorders.

127. Use of the derivative according to any one of embodiments 1-103 for the manufacture of a medicament for
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
(iv) weight maintenance after successful weight loss (either drug induced or by diet and exercise)—i.e. prevention of weight gain after successful weight loss;
(v) prevention and/or treatment of liver disorders, such as hepatic steatosis, non-alcoholic fatty liver disease (NAFLD), non-alcoholic steatohepatitis (NASH), liver inflammation or fatty liver.

128. Use of the derivative according to any one of embodiments 1-103 for the manufacture of a medicament for prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C.

129. Use of the derivative according to any one of embodiments 1-103 for the manufacture of a medicament for delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes.

130. Use of the derivative according to any one of embodiments 1-103 for the manufacture of a medicament for prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

131. Use of the derivative according to any one of embodiments 1-103 for the manufacture of a medicament for weight maintenance after successful weight loss (either drug induced or by diet and exercise)—i.e. prevention of weight gain after successful weight loss.

132. Use of the derivative according to any one of embodiments 1-103 for the manufacture of a medicament for prevention and/or treatment of liver disorders, such as hepatic steatosis, non-alcoholic fatty liver disease (NAFLD), non-alcoholic steatohepatitis (NASH), liver inflammation or fatty liver.

133. Use of the derivative according to any one of embodiments 1-103 for the manufacture of a medicament for the treatment and/or prevention of weight management, obesity and obesity related disorders.

134. Use of the derivative according to any one of embodiments 1-103 for the manufacture of a medicament for treatment and/or prevention of all forms of diabetes, e.g. type 2 diabetes, and diabetes related disorders.

135. A method of prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C comprising administering a pharmaceutically active amount of the derivative according to any one of embodiments 1-103.

136. A method of delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes comprising administering a pharmaceutically active amount of the derivative according to any one of embodiments 1-103.

137. A method of prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence comprising administering a pharmaceutically active amount of the derivative according to any one of embodiments 1-103.

138. A method of weight maintenance after successful weight loss (either drug induced or by diet and exercise)—i.e. prevention of weight gain after successful weight loss comprising administering a pharmaceutically active amount of the derivative according to any one of embodiments 1-103.

139. A method of treatment and/or prevention of liver disorders, such as hepatic steatosis, non-alcoholic fatty liver disease (NAFLD), non-alcoholic steatohepatitis (NASH), liver inflammation or fatty liver comprising administering a pharmaceutically active amount of the derivative according to any one of embodiments 1-103.

140. A method of treatment and/or prevention of weight management, obesity and obesity related disorders comprising administering a pharmaceutically active amount of the derivative according to any one of embodiments 1-103.

141. A method of treatment and/or prevention of all forms of diabetes, e.g. type 2 diabetes, and diabetes related disorders comprising administering a pharmaceutically active amount of the derivative according to any one of embodiments 1-103.

EXAMPLES

This experimental part starts with a list of abbreviations, and is followed by a section including general methods for synthesising and characterising analogues and derivatives of the invention. Then follows a number of examples which relate to the preparation of specific derivatives of the invention, and at the end a number of examples have been included relating to the activity and properties of these analogues and derivatives (section headed pharmacological methods).

Examples serve to illustrate the invention.
Materials and Methods

LIST OF ABBREVIATIONS

The following abbreviations are used in the following, in alphabetical order:
Ac: acetyl
Ado: 8-amino-3,6-dioxaoctanoic acid
Aib: alpha-aminoisobutyric acid
AUC: Area under the curve
BHK: Baby Hamster Kidney
Boc: t-butyloxycarbonyl
BW: body weight
DCC: dicyclohexylcarbodiimide
DCM: dichloromethane
DIC: diisopropylcarbodiimide
DIO: diet-induced obese
DIPEA: N,N-diisopropylethylamine or Hünig's base
DLS-SI: Dynamic Light Scattering Stability Index
DMEM: Dulbecco's Modified Eagle's Medium
DMF: dimethyl formamide
DODT: 3,6-dioxa-1,8-octanedithiol
EDTA: ethylene-diamine-tetraacetic acid
ELISA: Enzyme Linked Immuno Sorbent Assay
FBS: Fetal Bovine Serum
Fmoc: 9-fluorenylmethyloxycarbonyl
GIP: glucose-dependent insulinotropic polypeptide
GLP-1: glucagon-like peptide 1
HFIP: 1,1,1,3,3,3-hexafluoro-2-propanol or hexafluoroisopropanol
HMWP: High Molecular Weight Protein
HOBt: 1-hydroxybenzotriazole
HPLC: High Performance Liquid Chromatography
HSA: Human Serum Albumin
i.p.: intraperitoneal
IPGTT: intraperitoneal glucose tolerance test
i.v.: intravenously
kcal: kilocalorie
kg: kilogram
LCMS: Liquid Chromatography Mass Spectroscopy
MeCN: acetonitrile
mM: millimolar
Mtt: 4-methyltrityl
Nle: norleucine
NMP: N-methyl pyrrolidone
Oxyma Pure®: Cyano-hydroxyimino-acetic acid ethyl ester
PBS: Phosphate Buffered Saline
PK: pharmacokinetic
pM: picomolar
QTof: Quantitative Time of Flight
$R_h$: Stoke radius
s.c.: subcutaneously
SD: Standard deviation
SEC-HPLC: Size Exclusion High Performance Liquid Chromatography
SEC-MS: Size Exclusion Chromatography Mass Spectrometry
SEM: Standard error on the mean
tBu: t-butyl
TFA: trifluoroacetic acid
ThT: Thioflavin T
TIS: triisopropylsilane
Trt: triphenylmethyl (trityl)
Trx: tranexamic acid
UPLC: Ultra Performance Liquid Chromatography
General Methods of Preparation This section relates to methods for solid phase peptide synthesis (SPPS methods, including methods for de-protection of amino acids, methods for cleaving the peptide from the resin, and for its purification), as well as methods for detecting and characterising the resulting peptide (LCMS methods).

Resins employed for the preparation of C-terminal peptide amides were PAL Amide AM resin (loading e.g. 0.6 mmol/g) or H-Rink Amide-ChemMatrix resin (loading e.g. 0.5 mmol/g) or Rink Amide AM polystyrene resin (loading e.g. 0.3-0.7 mmol/g). The resin employed for the preparation of C-terminal peptide glycyl-acids was Fmoc-Gly-Wang polystyrene resin (loading e.g. 0.3-0.7 mmol/g).

The Fmoc-protected amino acid derivatives used, unless specifically stated otherwise, were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp (Boc)-OH (in case of method SPPS_A and SPPS_D) or Fmoc-Trp-OH (in case of methods SPPS_B and SPPS_C), Fmoc-Tyr(tBu)-OH, Fmoc-Val-OH, Fmoc-Lys(Mtt)-OH, Fmoc-Aib-OH, Fmoc-Nle-OH, Fmoc-D-Tyr-(tBu)-OH, etc. supplied from e.g. AAPPTEC, Anaspec, Bachem, Chemlmpex, Iris Biotech, Midwest Biotech, Gyros Protein Technologies or Novabiochem. Where nothing else is specified the natural L-form of the amino acids are used. When the N-terminal amino acid was not acetylated, the N-terminal amino acid was Boc protected at the alpha amino group, either by using a reagent with the Boc group pre-installed (e.g. Boc-Tyr(tBu)-OH for peptides with Tyr at the N-terminus) or by exchanging the N-terminal Fmoc protective group for the Boc protective group after installation of the amino acid at the peptide N-terminus.

In case of modular albumin binding moiety attachment using SPPS, the following suitably protected building blocks such as but not limited to Fmoc-8-amino-3,6-dioxaoctanoic acid (Fmoc-Ado-OH), Fmoc-tranexamic acid (Fmoc-Trx-OH), Fmoc-Glu-OtBu, octadecanedioic acid mono-tert-butyl ester, nonadecanedioic acid mono-tert-butyl ester, eicosanedioic acid mono-tert-butyl ester, tetradecanedioic acid mono-tert-butyl ester, or 4-(9-carboxynonyloxy) benzoic acid tert-butyl ester were used. All operations stated below were performed within a 100-450 µmol synthesis scale range.

Synthesis of Resin-Bound Protected Backbone
Method: SPPS_A

SPPS was performed using Fmoc based chemistry on a SymphonyX Solid Phase Peptide Synthesizer from Protein Technologies (Tucson, Ariz. 85714 U.S.A.). Fmoc-deprotection was achieved with 20% piperidine in DMF, containing 0.1M Oxyma Pure®. Peptide couplings were performed using DIC/Oxyma Pure®. Amino acid/Oxyma Pure® solutions (0.3 M/0.3 M in DMF at a molar excess of 4-8 fold) were added to the resin followed by the same molar equivalent of DIC (1.5M in DMF) and collidine (1.5M in DMF). The step-wise assembly was done using the following steps: 1) pre-swelling of resin with DCM and DMF; 2) Fmoc-deprotection by the use of 20% piperidine in DMF containing 0.1M Oxyma Pure® for two treatments of 10 min each; 3) washes with DMF to remove piperidine; 4) coupling of Fmoc-amino acid with 4-8 eq. of Fmoc-amino acid as a 0.3M solution in 0.3M Oxyma Pure® in DMF mixed with an equimolar volume of DIC and collidine for 1-2 hours; 5) washes with DMF to remove excess reagents; 6) final wash with DCM at the completion of the assembly. For peptides bearing N-terminal acetylation, the Fmoc-deprotected peptidyl resin was treated with 1M acetic anhydride in DMF for 30-60 min, and then washed with DMF and DCM.

Method: SPPS_B

The protected peptidyl resin was synthesized according to the Fmoc strategy on an Applied Biosystems 431A solid-phase peptide synthesizer using the manufacturer supplied general Fmoc protocols. Mixing was accomplished by vortexing and occasional bubbling with nitrogen. The step-wise assembly was done using the following steps: 1) Fmoc-deprotection by the use of 20% piperidine in NMP for one 3 min treatment followed by one 15 min treatment; 2) washes with NMP to remove piperidine; 3) coupling of Fmoc-amino acid with 5-10 eq. of Fmoc-amino acid, DIC, and HOBt in NMP for 45-90 min; 4) washes with NMP to remove excess reagents; 5) final washes with DCM at the completion of the assembly. The standard protected amino acid derivatives listed above were supplied in preweighed cartridges (from e.g. Midwest Biotech), and non-standard derivatives were weighed by hand. Some amino acids such as, but not limited to, those following a sterically hindered amino acid (e.g. Aib) were "double coupled" to ensure reaction completion, meaning that after the first coupling (e.g. 45 min) the resin is drained, more reagents are added (Fmoc-amino acid, DIC, HOBt), and the mixture allowed to react again (e.g. 45 min). For peptides bearing N-terminal acetylation, the Fmoc-deprotected peptidyl resin was removed from the synthesizer and manually treated with 10% (v/v) acetic anhydride/10% (v/v) pyridine in DMF for 30-60 min, then washed with DMF and DCM.

Method: SPPS_C

The protected peptidyl resin was synthesized according to the Fmoc strategy on a Protein Technologies SymphonyX solid-phase peptide synthesizer using the manufacturer supplied protocols with minor modifications. The step-wise assembly was done on a 0.2 mmol basis using the following steps: 1) pre-swelling of resin in DMF (3×8 mL for 15 min each); 2) Fmoc-deprotection by the use of 20% (v/v) piperidine in DMF (2×8 mL for 10 min each); 3) washes with DMF to remove piperidine (5×6 mL); 4) coupling of Fmoc-amino acid by addition of a mixture of Fmoc-amino acid (12 equvi., 2.4 mmol) and Oxyma Pure® (12 equvi., 2.4 mmol) as a 0.6 M solution in DMF (4 mL), followed by addition of DIC (12 equvi., 2.4 mmol) as a 1.2 M solution in DMF (2 mL), and addition of additional DMF (2 mL), then mixing for 0.5-4 h; 4) washes with DMF to remove excess reagents (3×6 mL); 5) final wash with DCM at the completion of the assembly. Some amino acids such as, but not limited to, those following a sterically hindered amino acid (e.g. Aib) were coupled with an extended reaction time (e.g. 4 h) to ensure reaction completion. For peptides bearing N-terminal acetylation, or for peptides which required installation of an N-terminal protecting group prior to side chain assembly (e.g. exchange of Fmoc for Boc protecting group), the N-terminal Fmoc group was removed by treatment with 20% (v/v) piperidine in DMF as described above in step 2. Then the peptidyl resin was removed from the synthesizer and manually treated with 10% (v/v) acetic anhydride/10% (v/v) DIPEA in DMF for 30-60 min, then washed with DMF and DCM.

Method: SPPS_D

The protected peptidyl resin was synthesized according to the Fmoc strategy on a Prelude solid phase peptide synthesiser (Protein Technologies, Tucson, USA) using the manufacturer supplied machine protocols. Coupling was done by the use of DCC and Oxyma Pure® (Merck, Novabiochem, Switzerland) mediated couplings in NMP. The coupling of the Fmoc-amino acid was done as described above using 4-8 time excess of amino acid relative to resin substitution (4-8 equvi.). Coupling time ranged from 1-6 h. The Fmoc-Arg (pbf)-OH was coupled using a double coupling procedure (1 h+1 h). The step-wise solid phase assembly on the Prelude was done using the following steps: 1) deprotection (removal of Fmoc) by the use of 25% piperidine in NMP for 2×4 min., step 2) Wash (removal of piperidine) with NMP and DCM, step 3) Coupling of Fmoc-amino acid (0.3 M Fmoc-amino acid in 0.3 M Oxyma Pure® in NMP) 4-8 equvi. excess for 1-4 h coupling initiated by adding ⅒ volume of 3 M DCC in NMP and ⅒ volume collidine in NMP. Mixing was done by occasional bubbling with nitrogen, step 4) Wash (removal of excess amino acid and reagents by the use of NMP and DCM). The last step included washing with DCM which made the resin ready for attachment of a modifying group on lysine side chain.

Attachment of Side Chains to Resin Bound Protected Peptide Backbone
Method: SC_A The N-epsilon-lysine Mtt protection group was removed by washing the resin with HFIP/TIS/DCM (75:2.5:22.5, v/v/v) (1×5 min and 2×20 min) before washing with piperidine, DMF and DCM.

Acylation was performed on a SymphonyX Solid Phase Peptide Synthesizer from Protein Technologies (Tucson, Ariz. 85714 U.S.A.) as described in method SPPS_A using stepwise addition of building blocks such as, but not limited to, Fmoc-8-amino-3,6-dioxaoctanoic acid (Fmoc-Ado-OH), Fmoc-Glu-OtBu, Fmoc-tranexamic acid (Fmoc-Trx-OH). Introduction of the fatty acid moiety was achieved using method SPPS_A and a suitable building block, such as, but not limited to, octadecanedioic acid mono-tert-butyl-ester or eicosanedioic acid mono-tert-butyl ester.

Method: SC_B

The N-epsilon-lysine protection Mtt protection group was removed by washing the resin with 30% HFIP in DCM for two treatments of 45 min each, following by washing with DCM and DMF.

Acylation was performed on an Applied Biosystems 431A solid-phase peptide synthesizer using the protocols described in method SPPS_B using stepwise addition of building blocks, such as, but not limited to, Fmoc-8-amino-3,6-dioxaoctanoic acid, Fmoc-tranexamic acid, Fmoc-Glu-OtBu, octadecanedioic acid mono-tert-butyl ester, eicosanedioic acid mono-tert-butyl ester.

Method: SC_C

The N-epsilon-lysine Mtt protective group was removed by washing the resin with 30% (v/v) HFIP in DCM for two treatments of 1 h each, followed by washing with DCM and DMF. Acylation was performed on a SymphonyX Solid Phase Peptide Synthesizer from Protein Technologies (Tucson, Ariz. 85714 U.S.A.) as described in method SPPS_C with 4 h coupling times using stepwise addition of building blocks such as, but not limited to, Fmoc-8-amino-3,6-dioxaoctanoic acid (Fmoc-Ado-OH), Fmoc-Glu-OtBu, Fmoc-tranexamic acid (Fmoc-Trx-OH). Introduction of the fatty acid moiety was achieved using method SPPS_C with 4 h coupling times and a suitable building block, such as, but not limited to, octadecanedioic acid mono-tert-butyl-ester or eicosanedioic acid mono-tert-butyl ester. In certain cases where building blocks were not soluble at a stock concentration of 0.6 M in DMF (e.g. Fmoc-Trx-OH and eicosanedioic acid mono-tert-butyl ester), stock concentrations of 0.3 M were prepared and the addition volume was doubled.

Method: SC_D

The N-epsilon-lysine protection Mtt protection group was removed by washing the resin with 70% HFIP+3% TIS in DCM for two treatments of 15 min each, following by washing with DCM and NMP.

Acylation was performed on a Prelude solid-phase synthesizer using the protocols described in method SPPS_D using stepwise addition of building blocks, such as, but not limited to, Fmoc-8-amino-3,6-dioxaoctanoic acid, Fmoc-tranexamic acid, Fmoc-Glu-OtBu, octadecanedioic acid mono-tert-butyl ester, eicosanedioic acid mono-tert-butyl ester.

Method: SC_E

The N-epsilon-lysine Mtt protection group was removed by washing the resin with HFIP/TIS/DCM (75:5:20, v/v/v) (2×5 min and 2×30 min) before washing with DMF and DCM.

Acylation was performed on a SymphonyX Solid Phase Peptide Synthesizer from Protein Technologies (Tucson, Ariz. 85714 U.S.A.) as described in method SPPS_A using stepwise addition of building blocks such as, but not limited to, Fmoc-8-amino-3,6-dioxaoctanoic acid (Fmoc-Ado-OH), Fmoc-Glu-OtBu, Fmoc-tranexamic acid (Fmoc-Trx-OH). Introduction of the fatty acid moiety was achieved using method SPPS_A and a suitable building block, such as, but not limited to, octadecanedioic acid mono-tert-butyl-ester or eicosanedioic acid mono-tert-butyl ester.

Cleavage of Resin Bound Peptide and Purification

Method: CP_A

After synthesis the resin was washed with DCM, and the peptidyl resin subject to a 1.5-3 h treatment with TFA/TIS/water (95:2.5:2.5, v/v/v) followed by precipitation with diethylether. The precipitate was washed with diethylether and dissolved in a suitable mixture of water, acetic acid and/or MeCN. The crude peptide solution was purified by reversed-phase preparative HPLC (Waters Deltaprep 4000) on a column containing C18-silica gel. Elution was performed with an increasing gradient of MeCN in water containing 0.1% TFA. Relevant fractions were checked by analytical UPLC. Fractions containing the pure target peptide were pooled and freeze-dried.

When further purification was necessary, the lyophilized peptide TFA salt isolated above was dissolved in a neutral aqueous buffer based on common salts such as, but not limited to, sodium hydrogen phosphate and purified with reversed-phase preparative HPLC (Waters Deltaprep 4000) on a column containing C18-silica gel. Elution was performed with an increasing gradient of MeCN in aqueous sodium phosphate (90 mM, pH 7.4). Relevant fractions were checked by analytical UPLC. Fractions containing the pure target peptide were pooled and after dilution with water, applied to a second reversed-phase preparative HPLC (Waters Deltaprep 4000) on a column containing C18-silica gel. Elution was performed with an increasing gradient of MeCN in water containing 0.1% TFA. Relevant fractions were pooled and freeze-dried to afford the TFA salt of the target peptide.

Method: CP_B

Following completion of the sidechain synthesis, the peptidyl resin was washed with DCM and dried, then treated with TFA/water/TIS (92.5:5:2.5 v/v/v, 10 mL) for 2 h, followed by precipitation with diethylether. The precipitate was washed with diethylether and dissolved in a suitable solvent (e.g. 2:1 water/MeCN or 4:1 25 mM aqueous $NH_4HCO_3$/MeCN), with modulation of solution pH if necessary for full peptide dissolution. Purification was performed by reversed-phase preparative HPLC (Waters 2545 binary gradient module, Waters 2489 UV/Visible detector, Waters fraction collector III) on a Phenomenex Luna C8(2) column (10 µM particle size, 100 Å pore size, 250×21.2 mm dimensions). Separation of impurities and product elution was accomplished using an increasing gradient MeCN in water containing 0.1% TFA. Relevant fractions were checked by analytical LCMS. Fractions containing the pure target peptide were pooled and freeze dried to afford the TFA salt of the target peptide.

Method: CP_C

After synthesis the resin was washed with DCM, and the peptidyl resin subject to a 1.5-3 h treatment with TFA/TIS/water/anisole/DODT (90:2.5:2.5:2.5:2.5, v/v/v/v/v) followed by precipitation with diethylether. The precipitate was washed with diethylether and dissolved in aqueous ammonium bicarbonate (concentration e.g. 50 mM) and vortexed. To this was added MeCN to afford a clear, yellow solution. This solution was then filtered via 0.22 um Stericup prior to being purified by reversed-phase preparative HPLC (Waters: 2545 pump, 2489 UV-vis, Fr.Collector III) on a column containing C18-silica gel. Elution was performed with an increasing gradient of MeCN in water containing 0.1% TFA. Relevant fractions were checked by analytical UPLC. Fractions containing the pure target peptide were pooled and freeze dried.

Salt Exchange—Formation of Sodium Salts.

Method: SX_A:

The freeze-dried peptide isolated from method CP_A, CP_B, or CP_C was dissolved in neutral to slightly basic (pH 7-8.5) aqueous sodium containing buffers, e.g. 0.1-0.2M sodium acetate or sodium bicarbonate buffers. The buffered solutions containing the peptide were salt exchanged using a Sep-Pak C18 cartridge (1-5 g): The cartridge was first equilibrated with 4 column volumes of isopropanol, then 4 column volumes of MeCN, then 8 column volumes of water. The peptide solution was applied to the cartridge, and the flow through was reapplied to ensure complete retention of peptide. The cartridge was washed with 2-4 column volumes of water, then 4-15 column volumes of buffer solutions (e.g. pH 7.5) containing sodium salts, such as, but not limited to, NaHCO$_3$, NaOAc, Na$_2$HPO$_4$. The peptide was eluted with 5-10 column volumes of between 50-80% MeCN in water and lyophilized to afford the peptide sodium salt as a white solid, which was used as such.

Method: SX_B:

The peptide solution in H$_2$O/MeCN/TFA was adjusted with NaOH to pH 7-8 with a maximum MeCN content of 20%. The mixture was then applied on a reversed-phase preparative HPLC (Waters Deltaprep 4000) on a column containing C18-silica gel. First an equilibration was performed with ~4 column volumes of 0.1M NaOAc followed by flushing with 2 column volumes of water. Elution was performed with an increasing gradient of MeCN in water. Relevant fractions were checked by analytical UPLC. Fractions containing the pure target peptide sodium salt were pooled and freeze dried.

General Methods of Detection and Characterisation
LCMS Methods:
Method: LCMS_34:

LCMS_34 was performed on a set up consisting of Waters Acquity UPLC H Class system and Waters Xevo G2-XS QTof. Eluents: A: 0.1% formic acid in MQ water; B: 0.1% formic acid in MeCN.

The analysis was performed at RT (column temp 40 C) by injecting an appropriate volume of the sample onto the column which was eluted with a gradient of A and B. The UPLC conditions, detector settings, and mass spectrometer settings were: Column: Waters Acquity BEH, C-18, 1.7 µm, 2.1 mm×50 mm. Gradient: Linear 5%-95% B during 4.0 min at 0.4 ml/min. Detection: MS resolution mode, ionisation method: ES. Scan: 50-4000 amu.

Method: LCMS_27:

LCMS_27 was performed on a setup consisting of Agilent 1290 infinity series UPLC system and Agilent Technologies LC/MSD TOF 6230 (G6230A). Eluents: A: 0.02% TFA in water; B: 0.02% TFA in MeCN.

The analysis was performed at RT (column temp 40 C) by injecting an appropriate volume of the sample onto the column which was eluted with a gradient of A and B. Column: Eclipse C18+, 1.8 µm, 2.1 mm×50 mm. Gradient run time: Linear 5-95% B over 4.5 min, then 95% B for 0.5 min, 95-5% B for 0.5 min, 5% B for 0.5 min at a flow rate of 0.40 ml/min. Detection: linear reflector mode (positive); Ionisation method: Agilent Jet Stream source. Scan: 100-3200 (m/z)

Method: LCMS_01

LCMS_01 was performed on a setup consisting of Waters Acquity UPLC system and LCT Premier XE mass spectrometer from Micromass. Eluents: A: 0.1% Formic acid in MQ water; B: 0.1% Formic acid in MeCN. The analysis was performed at RT (column temp 40 C) by injecting an appropriate volume of the sample onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% B during 4.0 min at 0.4 ml/min. Detection: 214 nm (analogue output from TUV (Tunable UV detector)) MS ionisation mode: API-ES. Scan: 500-2000 amu.

Example 1

Synthesis of GIP Derivatives

The derivatives of the invention were synthesised according to the general methods of preparation as described above.

hGIP(1-42); (SEQ ID NO: 1):
H-Y A E G T F I S D Y S I A M D K I H Q Q D F V N
W L L A Q K G K K N D W K H N I T Q-OH

General methods used: SPPS_D, CP_A
Molecular weight (average) calculated: 4983.53 g/mol.
LCMS01: found (M+4H)4+1246.17 hGIP(1-31); (SEQ ID NO: 2):
H-Y A E G T F I S D Y S I A M D K I H Q Q D F V N
W L L A Q K G-OH

General methods used: SPPS_A, CP_A
Molecular weight (average) calculated: 3589.98 g/mol.
LCMS01: found (M+3H)3+1197.61

Compound 1 (SEQ ID NO: 6):

N{Epsilon-24}-[(4S)-4-carboxy-4-[[(4S)-4-carboxy-4-[[(4S)-4-carboxy-4-(17-carboxyheptadecanoy-lamino)butanoyl]amino]butanoyl]amino]butanoyl]-[Aib2,Nle14,Arg18,Lys24]-hGIP(1-31)

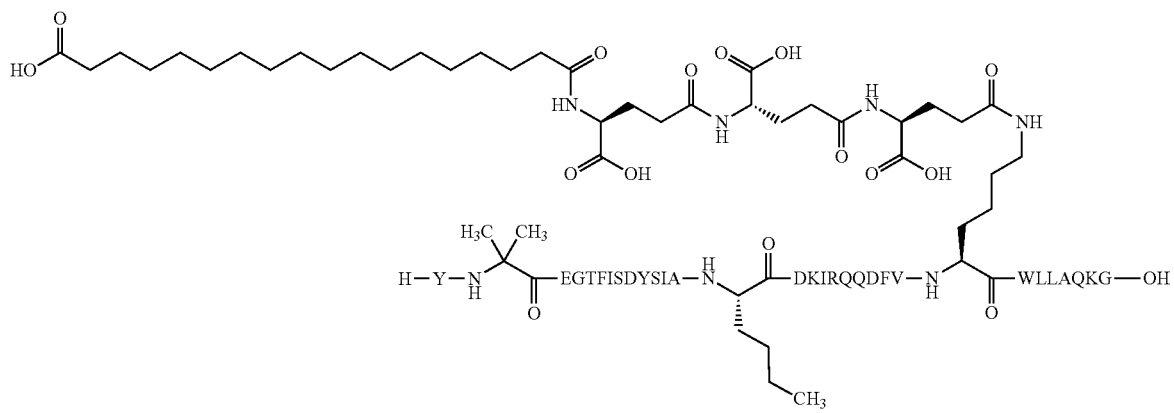

General methods used: SPPS_A, SC_A, CP_A, SX_A
Molecular weight (average) calculated: 4302.87 g/mol
LCMS_34: found (M+4H)4+1076.82

Compound 2 (SEQ ID NO: 7):

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24]-hGIP(1-31)

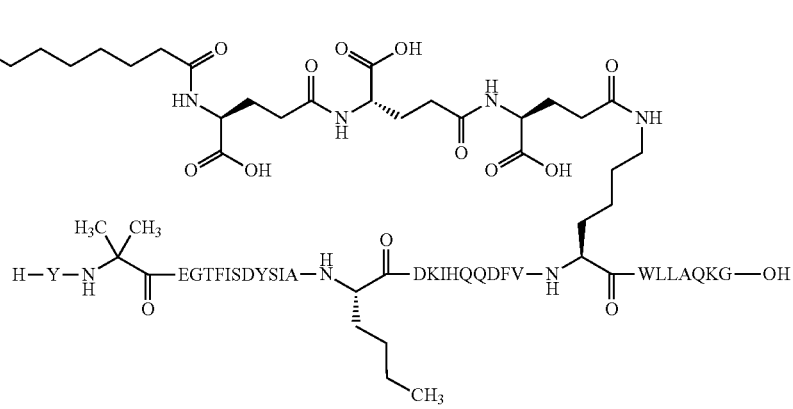

General methods used: SPPS_A, SC_A, CP_A, SX_A
Molecular weight (average) calculated: 4283.82 g/mol
LCMS_34: found (M+4H)4+1071.82

Compound 3 (SEQ ID NO: 8):

N{Epsilon-24}-[2-[2-[2-[[2-[2-[2-[[(4S)-4-carboxy-4-[[4-[(19-carboxynonadecanoylamino) methyl] cyclohexanecarbonyl]amino]butanoyl]amino] ethoxy]ethoxy]acetyl]amino]ethoxy]ethoxy]acetyl]-[Aib2,Nle14,Arg18,Lys24]-hGIP(1-31)

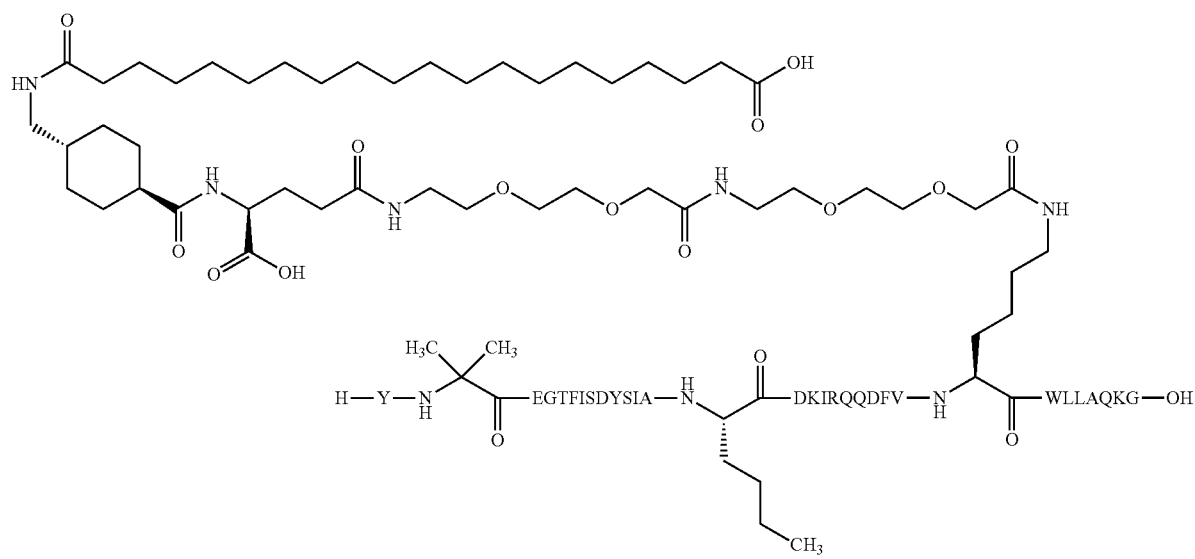

General methods used: SPPS_A, SC_A, CP_A, SX_A
Molecular weight (average) calculated: 4502.20 g/mol
LCMS_27: found (M+3H)3+ 1501.50

Compound 4 (SEQ ID NO: 9):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[Aib2,Nle14,Arg18,Lys24]-hGIP(1-31)

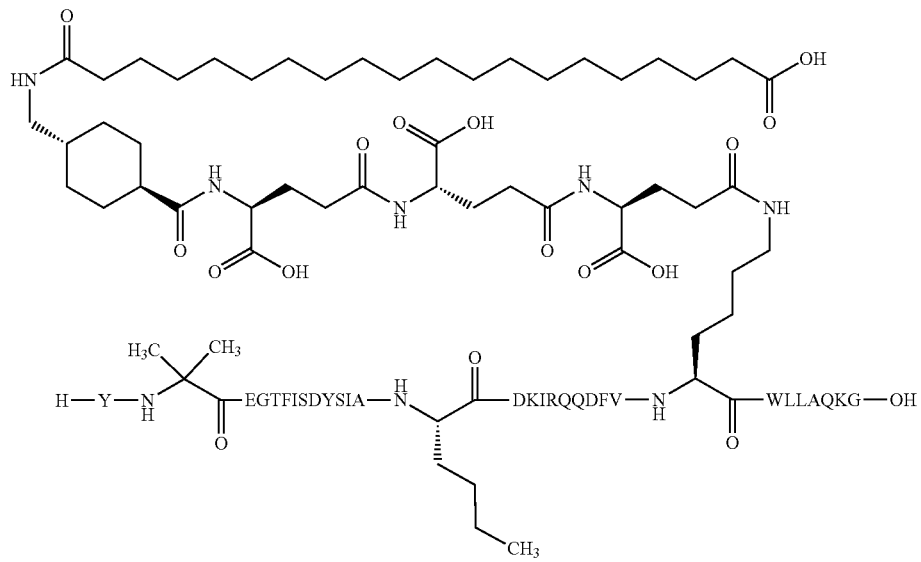

General methods used: SPPS_A, SC_A, CP_A, SX_A
Molecular weight (average) calculated: 4470.12 g/mol
LCMS_27: found (M+4H)4+ 1118.11

Compound 5 (SEQ ID NO: 10):

N{1}-acetyl, N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[D-Tyr1,Aib2,Nle14,Arg18,Lys24]-hGIP(1-31)

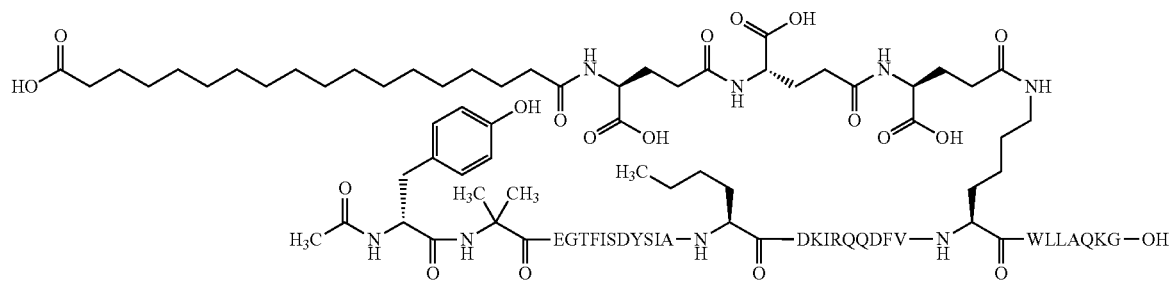

General methods used: SPPS_A, SC_A, CP_A, SX_A
Molecular weight (average) calculated: 4344.91 g/mol
LCMS_27: found (M+3H)3+1449.10

Compound 6 (SEQ ID NO: 11):

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[D-Tyr1,Aib2,Nle14,Arg18,Lys24]-hGIP (1-31)

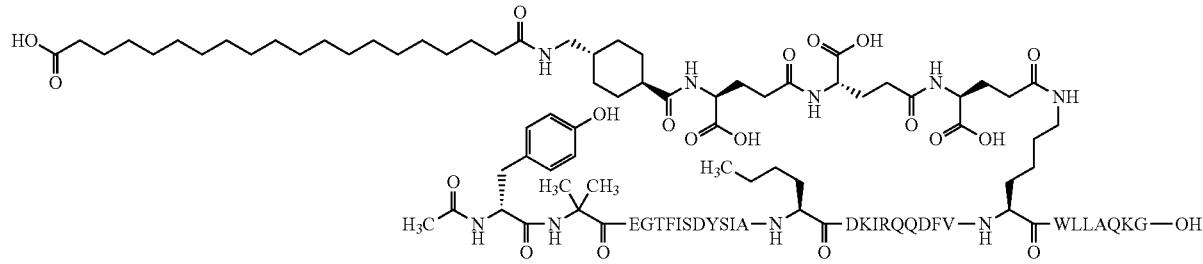

General methods used: SPPS_B, SC_B, CP_B, SX_A
Molecular weight (average) calculated: 4512.16 g/mol
LCMS_27: found (M+3H)3+1504.79

Compound 7 (SEQ ID NO: 12):

N{1}-acetyl,N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[D-Tyr1,Nle14,Arg18,Lys24]-hGIP (1-31)

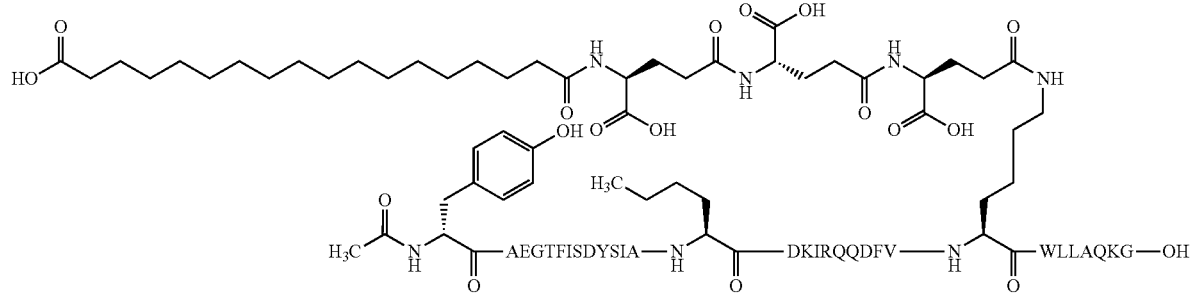

General methods used: SPPS_B, SC_B, CP_B, SX_A
Molecular weight (average) calculated: 4330.88 g/mol
LCMS_27: found (M+3H)3+1444.41

Compound 8 (SEQ ID NO: 13):

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]-butanoyl]amino]butanoyl]amino]butanoyl]-[D-Tyr1,Nle14,Arg18,Lys24]-hGIP(1-31)

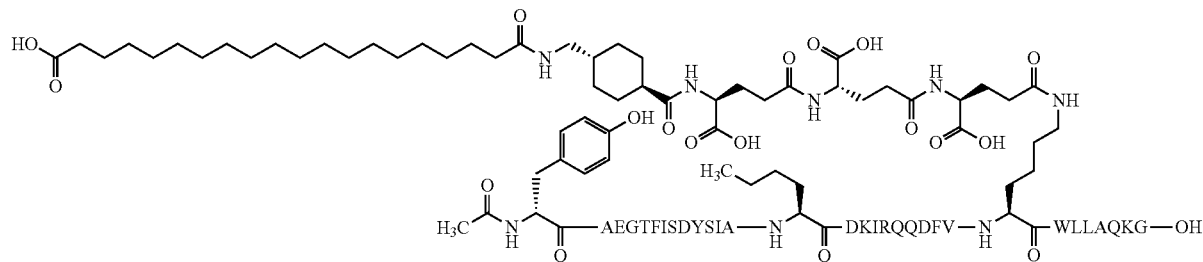

General methods used: SPPS_B, SC_B, CP_B, SX_A
Molecular weight (average) calculated: 4498.13 g/mol
LCMS_27: found (M+3H)3+1500.12
Compound 9 (SEQ ID NO: 14):

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Glu20,Lys24]-hGIP(1-31)

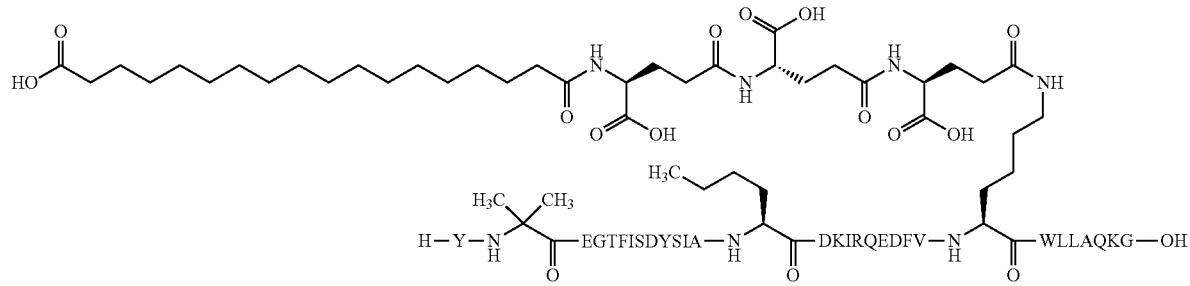

General methods used: SPPS_B, SC_B, CP_B
Molecular weight (average) calculated: 4303.86 g/mol
LCMS_27: found (M+3H)3+1435.08
Compound 10 (SEQ ID NO: 15):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Arg18,Glu20,Lys24]-hGIP(1-31)

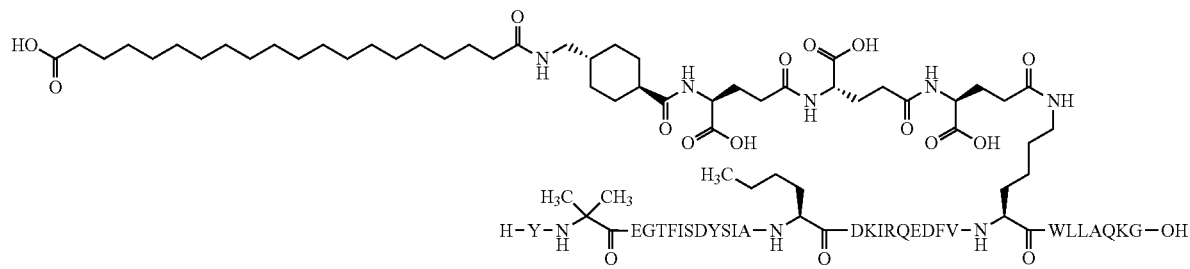

General methods used: SPPS_B, SC_B, CP_B, SX_A
Molecular weight (average) calculated: 4471.10 g/mol
LCMS_27: found (M+3H)3+1490.79
Compound 11 (SEQ ID NO: 16):

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Aib20,Lys24]-hGIP(1-31)

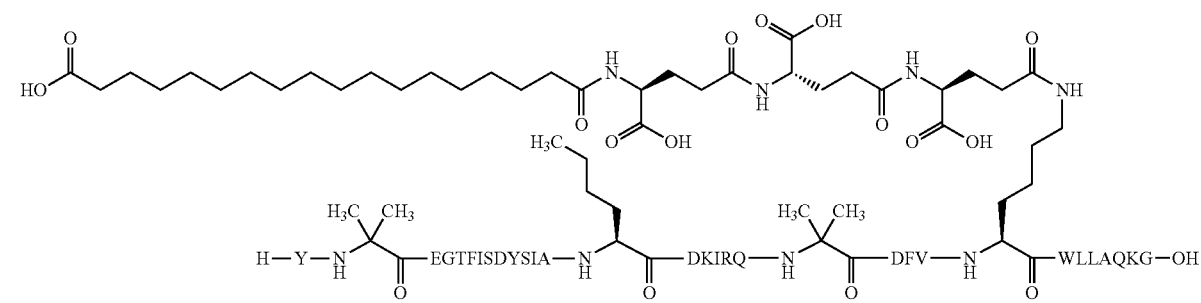

General methods used: SPPS_C, SC_C, CP_C, SX_A
Molecular weight (average) calculated: 4259.85 g/mol
LCMS_27: found (M+3H)3+1420.74

Compound 12 (SEQ ID NO: 17):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Aib20,Lys24]-hGIP(1-31)

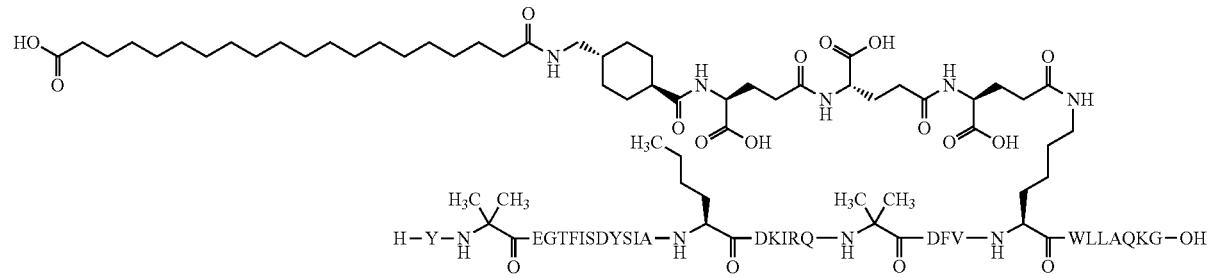

General methods used: SPPS_C, SC_C, CP_C, SX_A
Molecular weight (average) calculated: 4427.09 g/mol
LCMS_27: found (M+3H)3+1476.45

Compound 13 (SEQ ID NO: 18):

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Ala16,Arg18,Lys24]-hGIP(1-31)

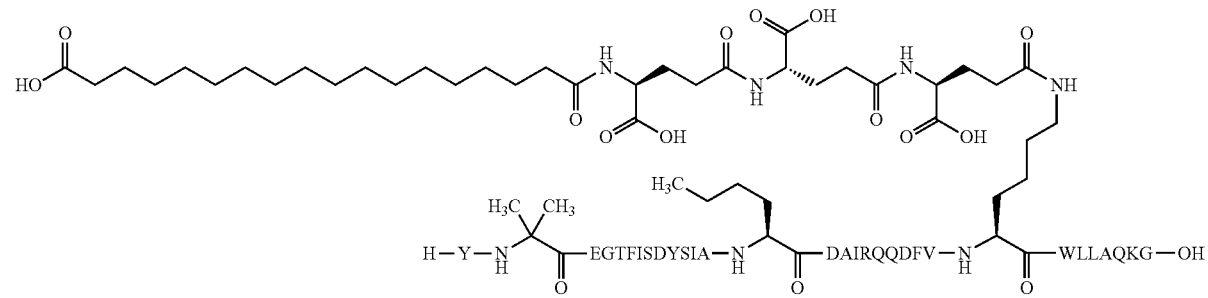

General methods used: SPPS_C, SC_C, CP_C
Molecular weight (average) calculated: 4245.78 g/mol
LCMS_27: found (M+3H)3+1416.06

Compound 14 (SEQ ID NO: 19):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Ala16,Arg18,Lys24]-hGIP(1-31)

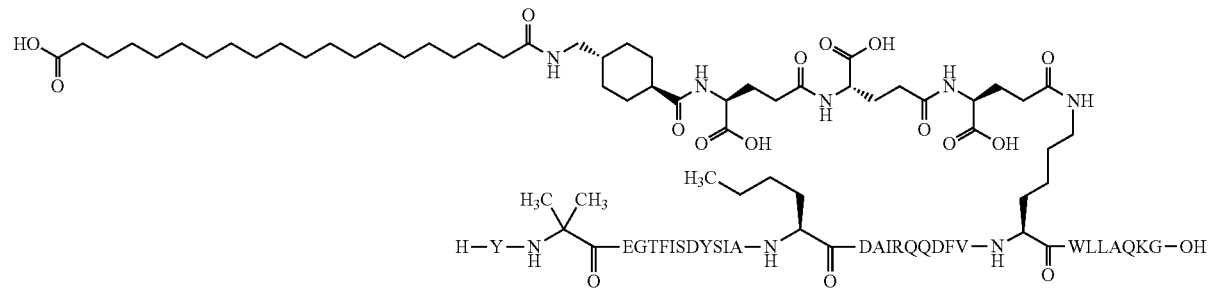

General methods used: SPPS_C, SC_C, CP_C
Molecular weight (average) calculated: 4413.02 g/mol
LCMS_27: found (M+3H)3+1471.77

Compound 15 (SEQ ID NO: 20):

N{1}-acetyl,N{Epsilon-24}-[2-[2-[2-[[2-[2-[2-
[[(4S)-4-carboxy-4-(17-carboxyheptadecanoy-
lamino)butanoyl]amino]ethoxy]ethoxy]acetyl]
amino]ethoxy]ethoxy]acetyl]-[D-Tyr1,Nle14,Arg18,
Lys24]-hGIP(1-31)

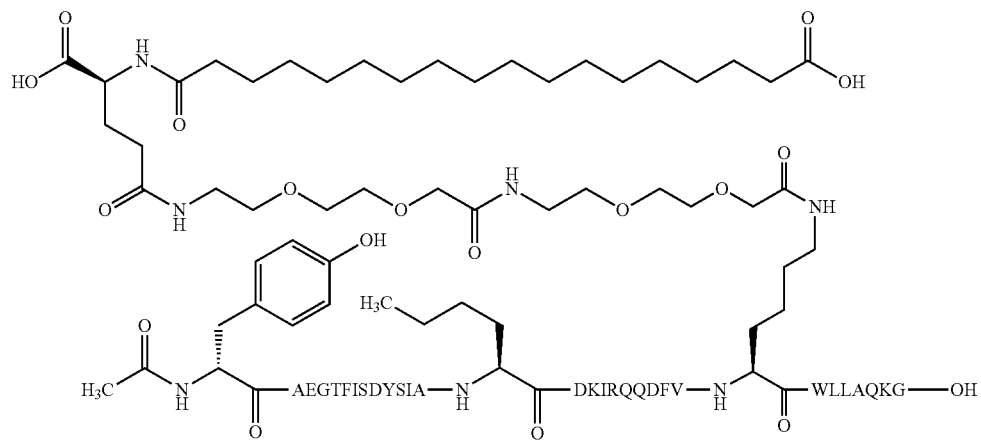

General methods used: SPPS_B, SC_B, CP_B, SX_A
Molecular weight (average) calculated: 4362.97 g/mol
LCMS_27: found (M+3H)3+1455.09

Compound 16 (SEQ ID NO: 21):

N{1}-acetyl,N{Epsilon-24}-[2-[2-[2-[[2-[2-[2-
[[(4S)-4-carboxy-4-(17-carboxy- heptadecanoy-
lamino)butanoyl]amino]ethoxy]ethoxy]acetyl]
amino]ethoxy]ethoxy]acetyl]-[D-Tyr1,Nle14,Arg18,
Glu20,Lys24]-hGIP(1-31)

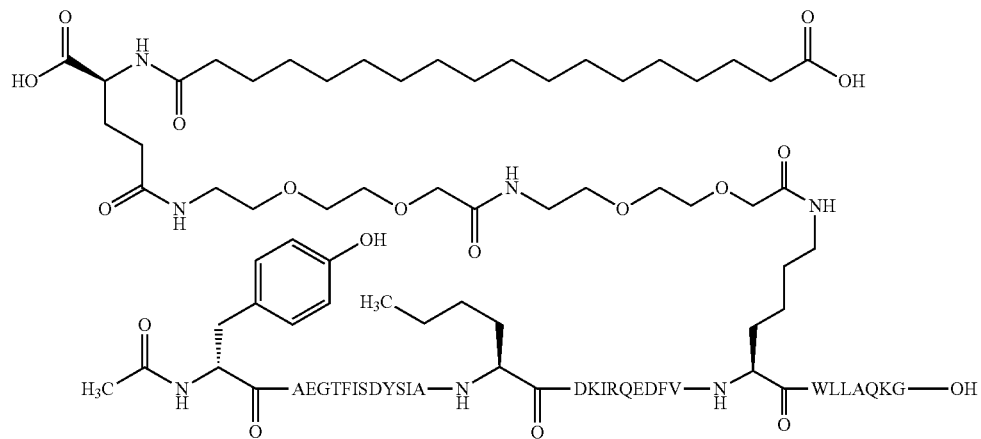

General methods used: SPPS_C, SC_C, CP_C
Molecular weight (average) calculated: 4363.95 g/mol
LCMS_27: found (M+3H)3+1455.42

Compound 17 (SEQ ID NO: 22):

N{1}-acetyl,N{Epsilon-24}-[2-[2-[2-[[2-[2-[2-[[(4S)-4-carboxy-4-[[(4S)-4- carboxy-4-[[(4S)-4-carboxy-4-(17-carboxyheptadecanoylamino)butanoyl]amino]butanoyl]-butanoyl]amino]ethoxy]ethoxy]acetyl]amino]ethoxy]ethoxy]acetyl]-[D-Tyr1,Nle14,Arg18,Lys24]-hGIP(1-31)

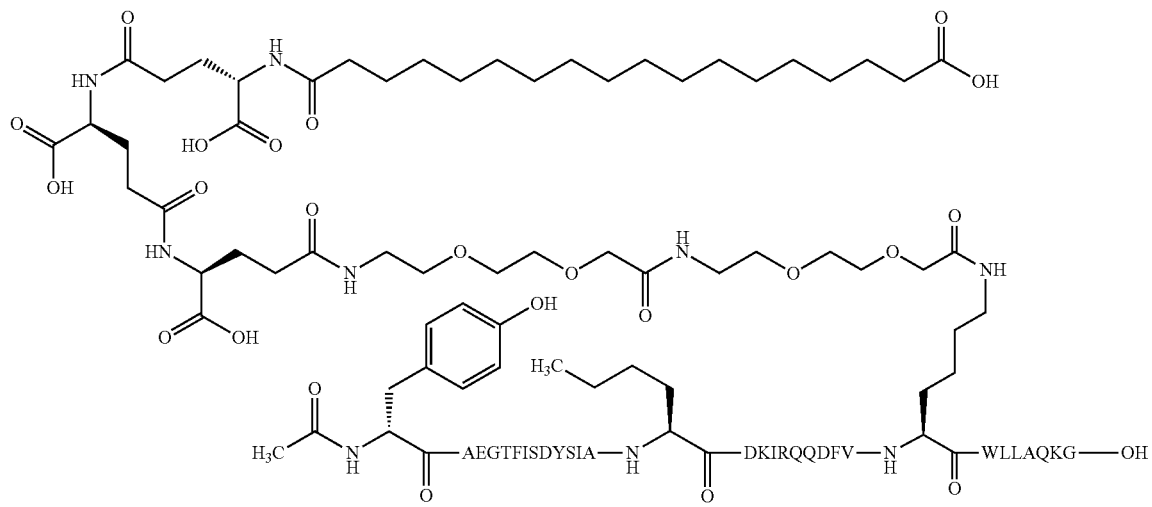

General methods used: SPPS_B, SC_B, CP_B, SX_A
Molecular weight (average) calculated: 4621.19 g/mol
LCMS_27: found (M+3H)3+1541.12

Compound 18 (SEQ ID NO: 23):

N{1}-acetyl,N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Nle14,Arg18,Lys24]-hGIP(1-31)

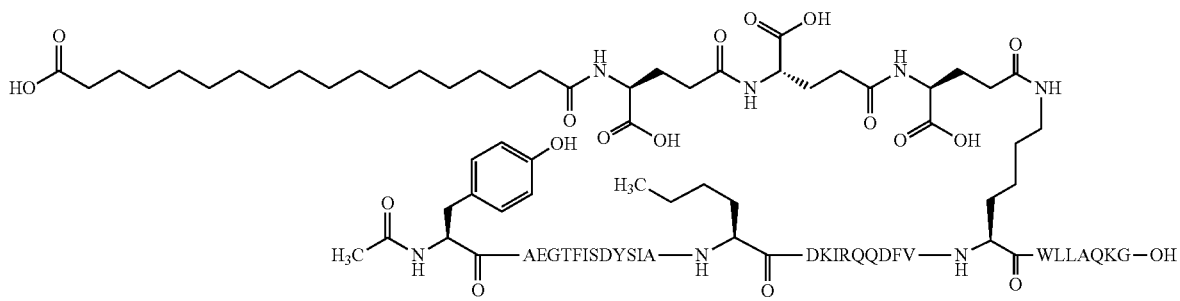

General methods used: SPPS_C, SC_C, CP_C
Molecular weight (average) calculated: 4330.88 g/mol
LCMS_27: found (M+3H)3+1444.40

Compound 19 (SEQ ID NO: 24):

N{1}-acetyl,N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[D-Tyr1,Asp14,Arg18,Glu20, Lys24]-hGIP(1-31)

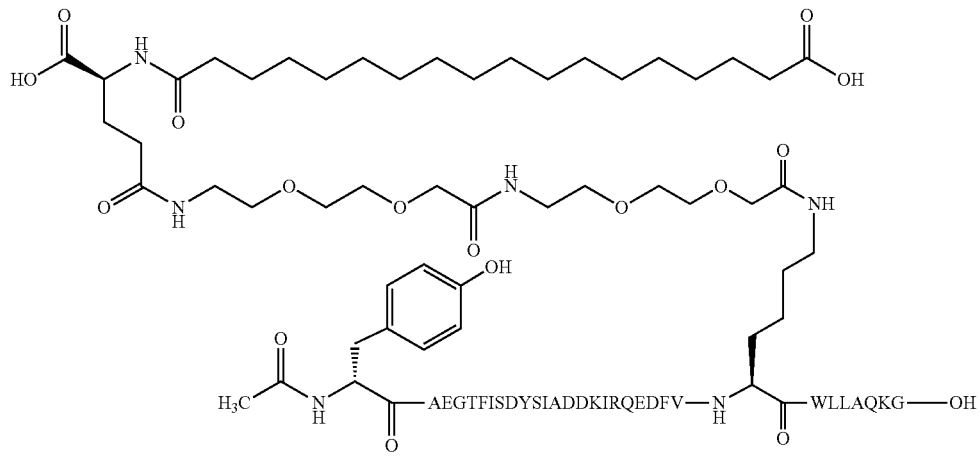

General methods used: SPPS_C, SC_C, CP_C
Molecular weight (average) calculated: 4365.88 g/mol
LCMS_27: found (M+3H)3+1456.07

Compound 20 (SEQ ID NO: 25):

N{Epsilon-24}-[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]-[Aib2,Nle14,Glu20,Lys24]-hGIP(1-31)

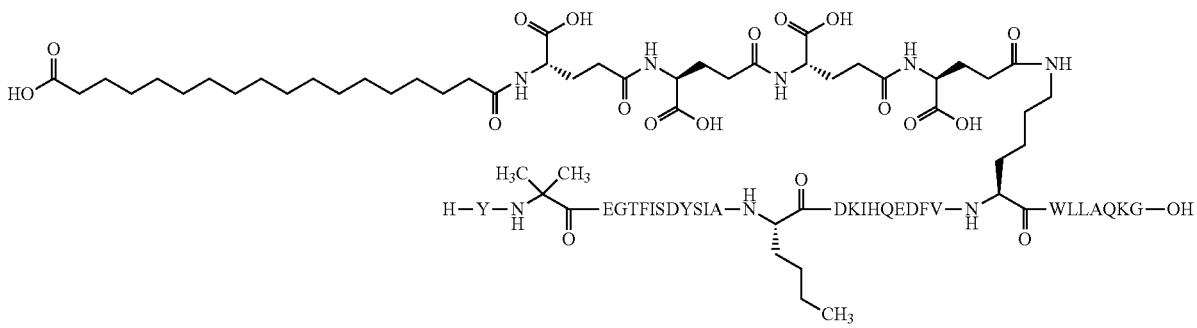

General methods used: SPPS_A, SC_A, CP_A
Molecular weight (average) calculated: 4413.92 g/mol
LCMS_27: found (M+3H)3+1472.07

Compound 21 (SEQ ID NO: 26):
N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]amino]butanoyl]-[Aib2,Nle14,Glu20,Lys24]-hGIP(1-31)
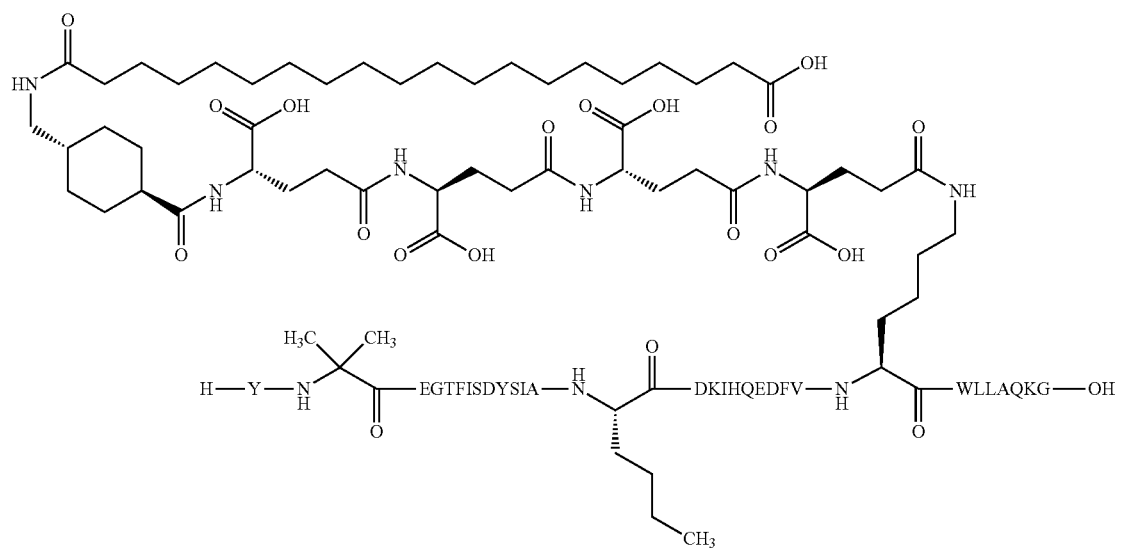
General methods used: SPPS_A, SC_A, CP_A, SX_A
Molecular weight (average) calculated: 4581.17 g/mol
LCMS_27: found (M+3H)3+1527.78

Compound 22 (SEQ ID NO: 27):
N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Glu20,Lys24]-hGIP(1-31)
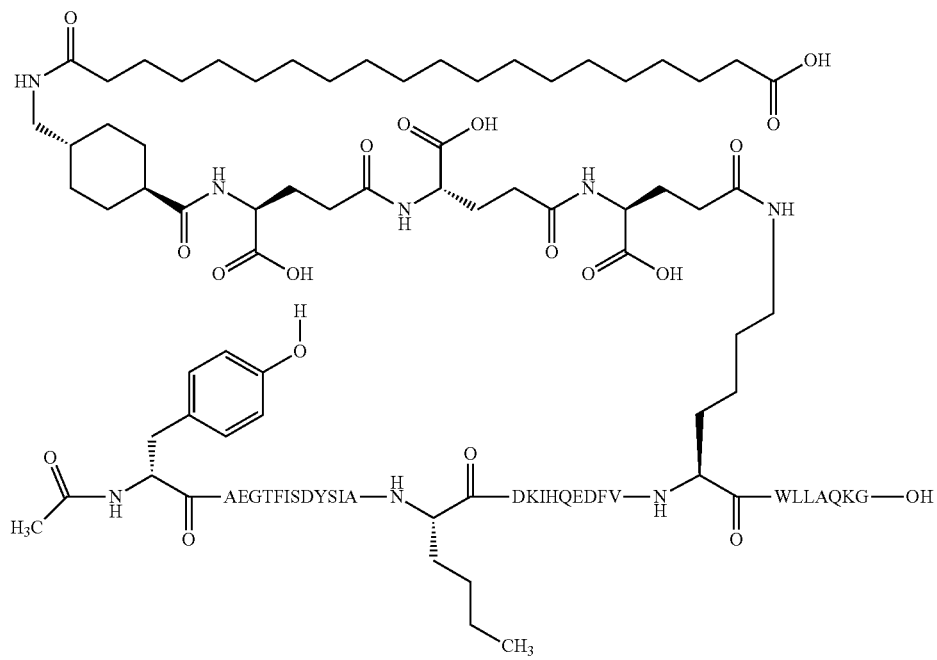
General methods used: SPPS_A, SC_A, CP_A, SX_A
Molecular weight (average) calculated: 4480.07 g/mol
LCMS_27: found (M+3H)3+1494.13

Compound 23 (SEQ ID NO: 28):
N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Arg18,Glu20, Lys24]-hGIP(1-31)
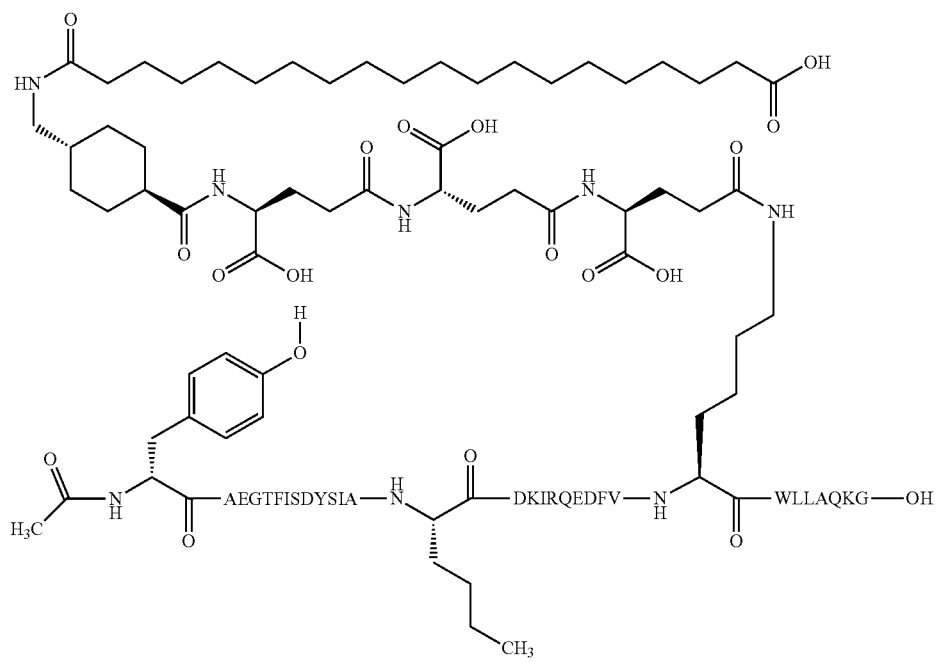
General methods used: SPPS_A, SC_A, CP_A, SX_A
Molecular weight (average) calculated: 4499.11 g/mol
LCMS_27: found (M+3H)3+1500.47

Compound 24 (SEQ ID NO: 29):
N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Aib20,Lys24]-hGIP(1-31)
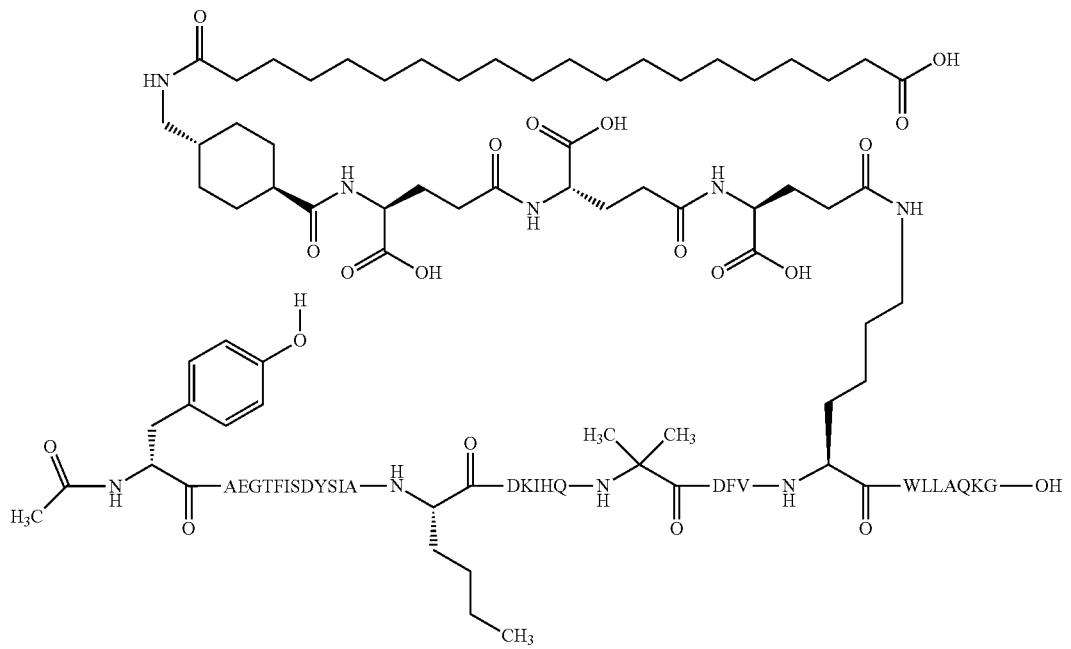
General methods used: SPPS_A, SC_A, CP_A, SX_A
Molecular weight (average) calculated: 4436.06 g/mol
LCMS_27: found (M+3H)3+1479.46

Compound 25 (SEQ ID NO: 30):

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Arg18,Aib20,Lys24]-hGIP(1-31)

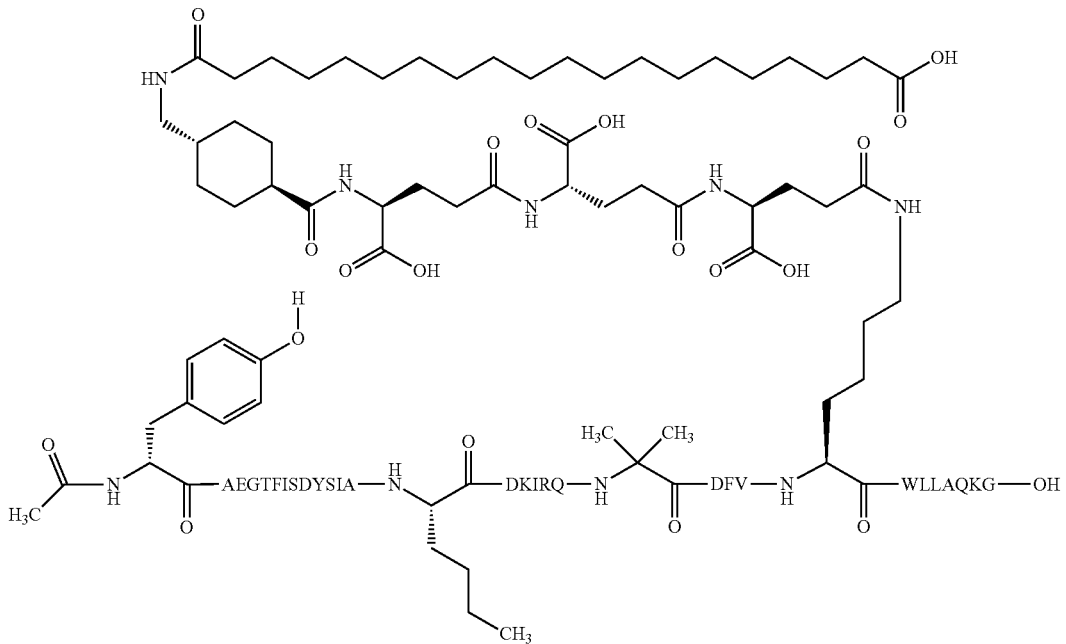

General methods used: SPPS_A, SC_A, CP_A, SX_A
Molecular weight (average) calculated: 4455.10 g/mol
LCMS_27: found (M+3H)3+1485.81

Compound 26 (SEQ ID NO: 31):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Arg18,Lys24,Pro31]-hGIP(1-31) amide

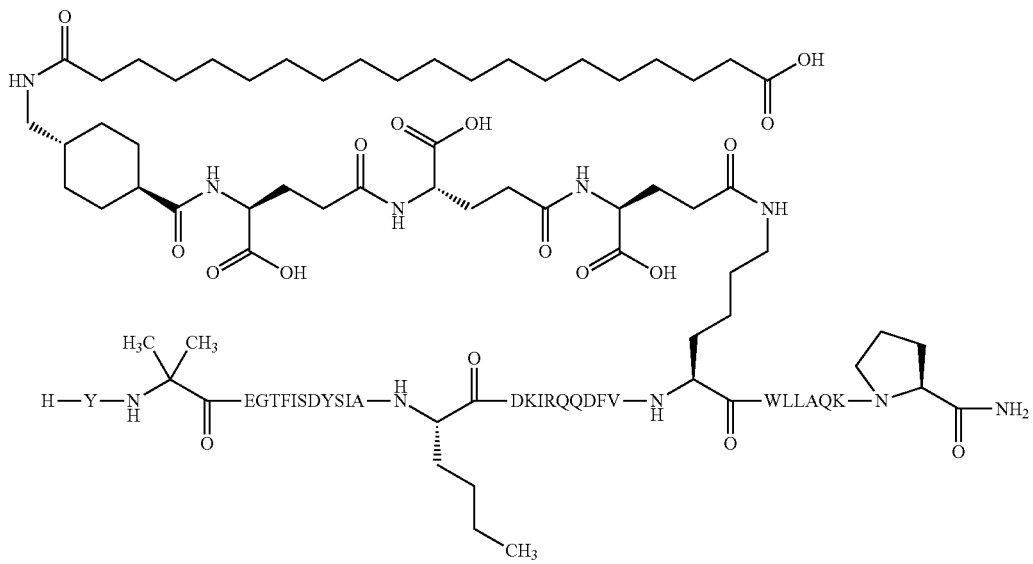

General methods used: SPPS_A, SC_A, CP_A, SX_A
Molecular weight (average) calculated: 4509.20 g/mol
LCMS_27: found (M+3H)3+1503.84

Compound 27 (SEQ ID NO: 32):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Lys24,Pro31]-hGIP(1-31) amide

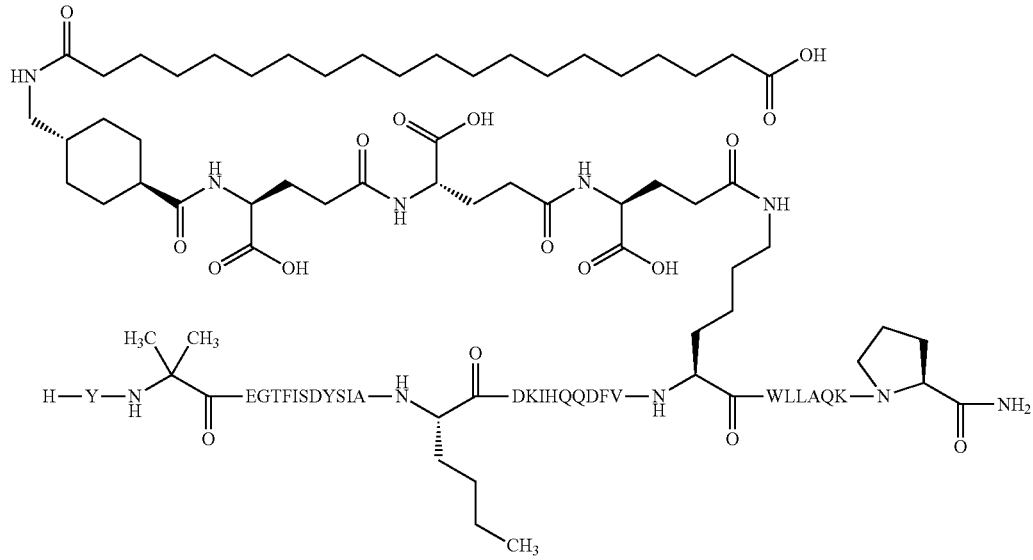

General methods used: SPPS_A, SC_A, CP_A, SX_A
Molecular weight (average) calculated: 4490.15 g/mol
LCMS_27: found (M+3H)3+1497.49

Compound 28 (SEQ ID NO: 33):
N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Arg18,Lys24,Pro31]-hGIP(1-31) amide

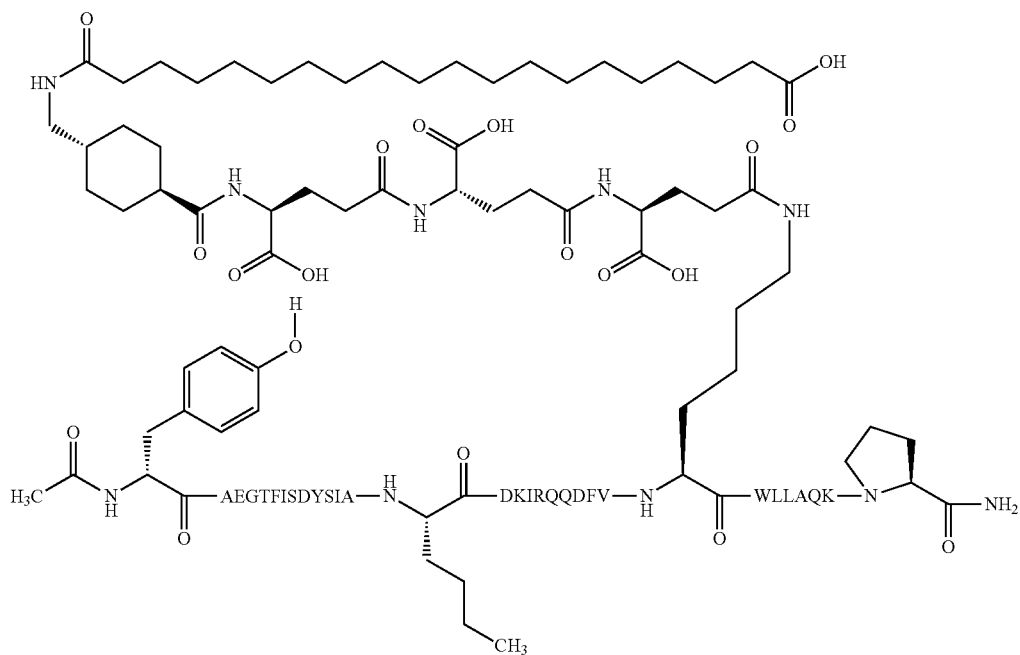

General methods used: SPPS_A, SC_A, CP_A, SX_A
Molecular weight (average) calculated: 4537.21 g/mol
LCMS_34: found (M+4H)4+1135.13

Compound 29 (SEQ ID NO: 34):

N{1}-acetyl,N{Epsilon-24}-[(4S)-4-carboxy-4-
[[(4S)-4-carboxy-4-[[(4S)-4-carboxy-4-[[4-[(19-
carboxynonadecanoylamino)methyl]cyclohexanecar-
bonyl]amino]butanoyl]-amino]butanoyl]amino]
butanoyl]-[D-Tyr1,Nle14,Lys24,Pro31]-hGIP(1-31)
amide

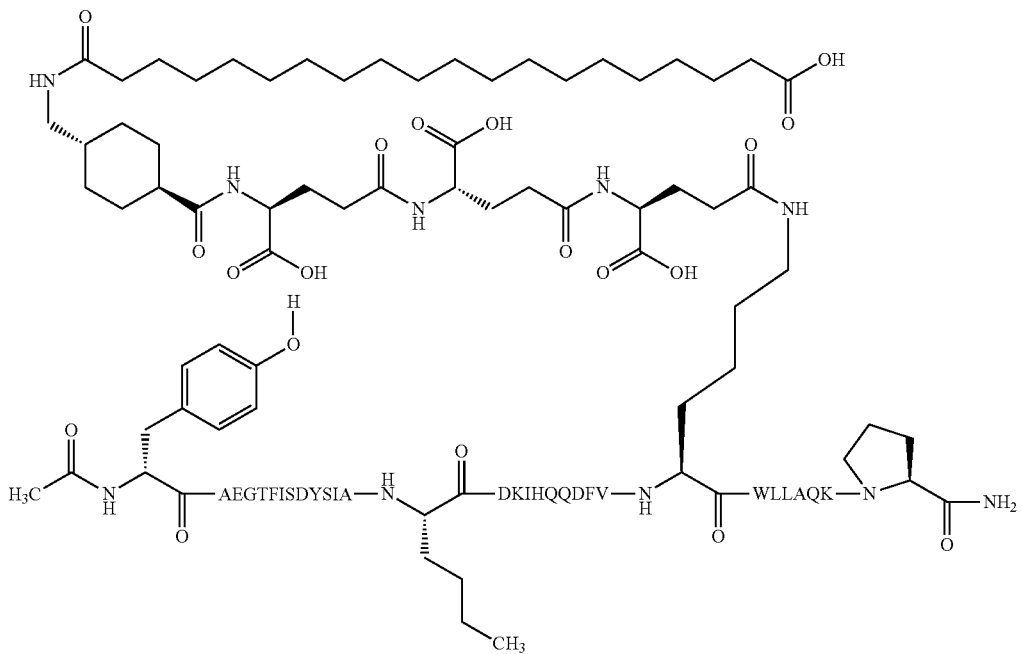

General methods used: SPPS_A, SC_A, CP_A, SX_A
Molecular weight (average) calculated: 4518.16 g/mol
LCMS_34: found (M+4H)4+1130.37

Compound 30 (SEQ ID NO: 35):

N{1}-acetyl,N{Epsilon-24}-[(4S)-4-carboxy-4-
[[(4S)-4-carboxy-4-[[(4S)-4-carboxy-4-[[(4S)-4-
carboxy-4-[[4-[(19-carboxynonadecanoylamino)
methyl]cyclohexanecarbonyl]amino]butanoyl]
amino]butanoyl]amino]butanoyl]amino]butanoyl]-
[D-Tyr1,Nle14,Arg18,Lys24]-hGIP(1-31)

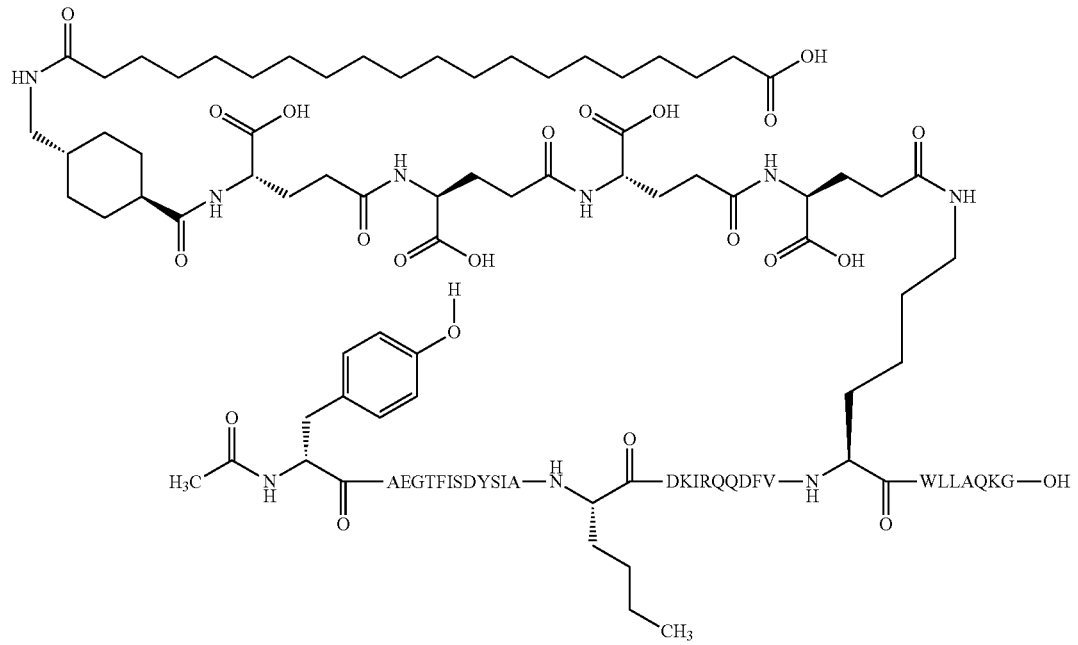

General methods used: SPPS_A, SC_A, CP_A, SX_A
Molecular weight (average) calculated: 4627.24 g/mol
LCMS_34: found (M+4H)4+1130.37

Compound 31 (SEQ ID NO: 36):

N{1}-acetyl,N{Epsilon-24}-[(4S)-4-carboxy-4-
[[(4S)-4-carboxy-4-[[(4S)-4-carboxy-4-[[(4S)-4-
carboxy-4-[[4-[(19-carboxynonadecanoylamino)
methyl]cyclohexanecarbonyl]amino]butanoyl]
amino]butanoyl]amino]butanoyl]amino]butanoyl]-
[D-Tyr1,Aib2,Nle14,Arg18,Lys24,Pro31]-hGIP(1-
31) amide

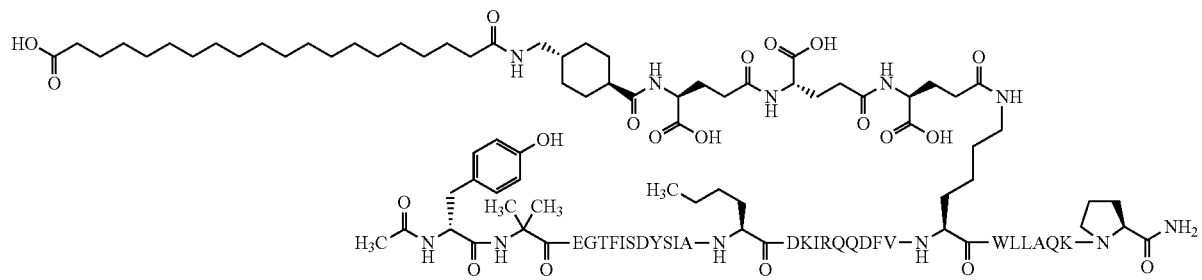

General methods used: SPPS_A, SC_A, CP_A, SX_A
Molecular weight (average) calculated: 4551.23 g/mol
LCMS_27: found (M+3H)3+1517.81

Compound 32 (SEQ ID NO: 37):

N{1}-acetyl,N{Epsilon-24}-[(4S)-4-carboxy-4-
[[(4S)-4-carboxy-4-[[(4S)-4-carboxy-4-[[4-[(19-
carboxynonadecanoylamino)methyl]cyclohexanecar-
bonyl]amino]butanoyl]-amino]butanoyl]amino]
butanoyl]-[D-Tyr1,Aib2, Nle14,Lys24,Pro31]-hGIP
(1-31) amide

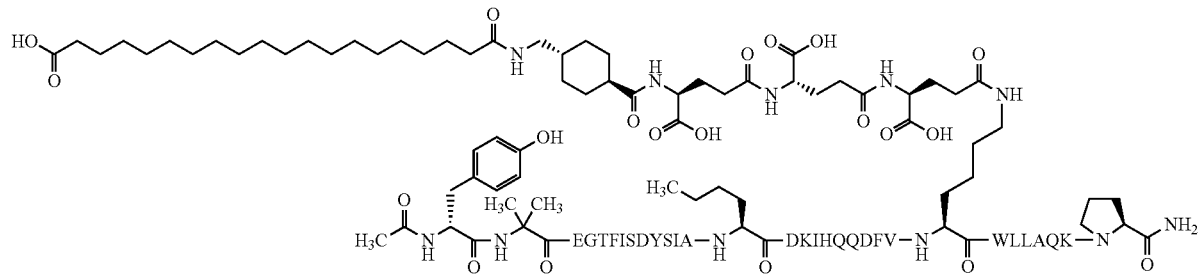

General methods used: SPPS_C, SC_C, CP_C, SX_A
Molecular weight (average) calculated: 4532.19 g/mol
LCMS_27: found (M+3H)3+1511.44

Compound 33 (SEQ ID NO: 38):

N{Epsilon-24}-[(4S)-4-carboxy-4-[[(4S)-4-carboxy-
4-[[(4S)-4-carboxy-4-(17-carboxyheptadecanoy-
lamino)butanoyl]amino]butanoyl]amino]butanoyl]-
[Aib2,Nle14,Lys24,Glu33]-hGIP

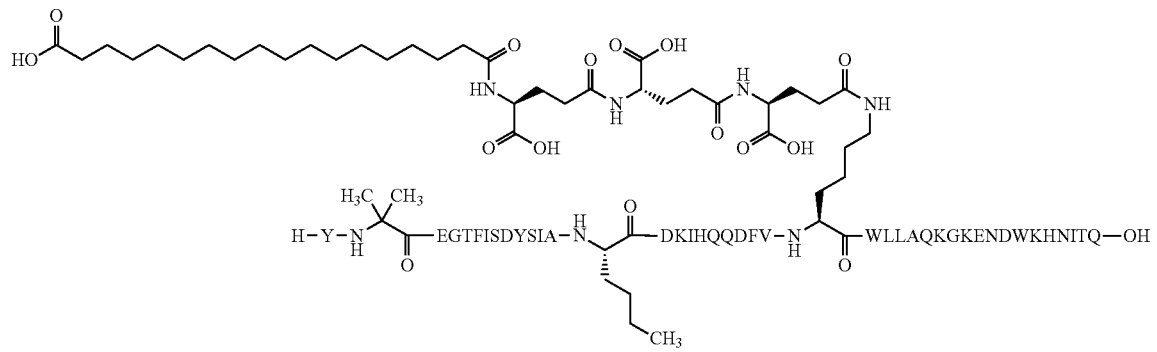

General methods used: SPPS_A, SC_A, CP_A, SX_A
Molecular weight (average) calculated: 5678.32 g/mol
LCMS_27: found (M+4H)4+1420.54

Compound 34 (SEQ ID NO: 39):

N{Epsilon-24}-[(4S)-4-carboxy-4-[[(4S)-4-carboxy-
4-[[(4S)-4-carboxy-4-(17-carboxyheptadecanoy-
lamino)butanoyl]amino]butanoyl]amino]butanoyl]-
[Aib2,Nle14,Arg18,Lys24,Glu33]-hGIP

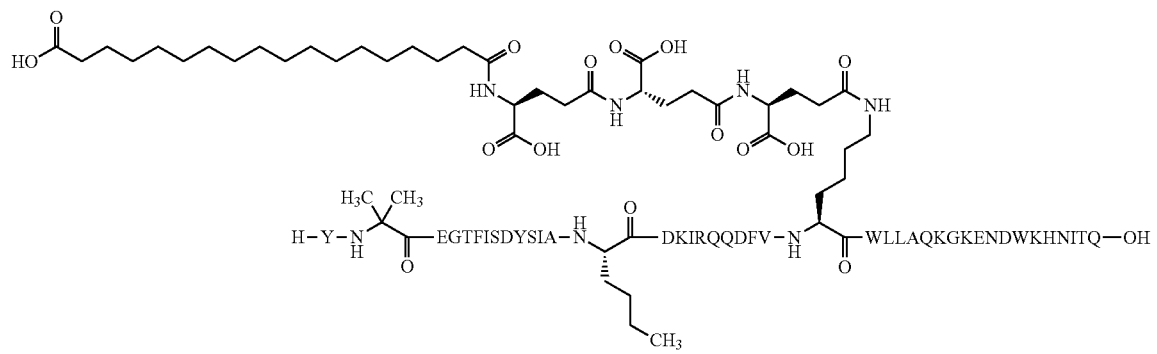

General methods used: SPPS_A, SC_A, CP_A, SX_A
Molecular weight (average) calculated: 5697.36 g/mol
LCMS_27: found (M+4H)4+1425.29

Compound 35 (SEQ ID NO: 40):

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Glu34]-hGIP

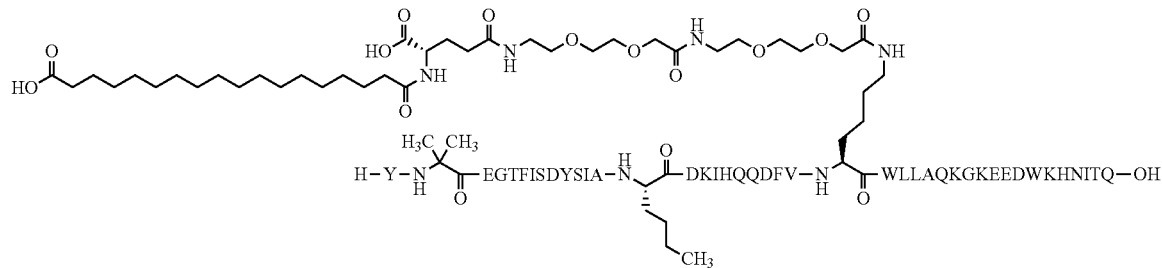

General methods used: SPPS_A, SC_A, CP_A
Molecular weight (average) calculated: 5725.41 g/mol
LCMS_27: found (M+4H)4+1432.25

Compound 36 (SEQ ID NO: 41):

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Asp34]-hGIP

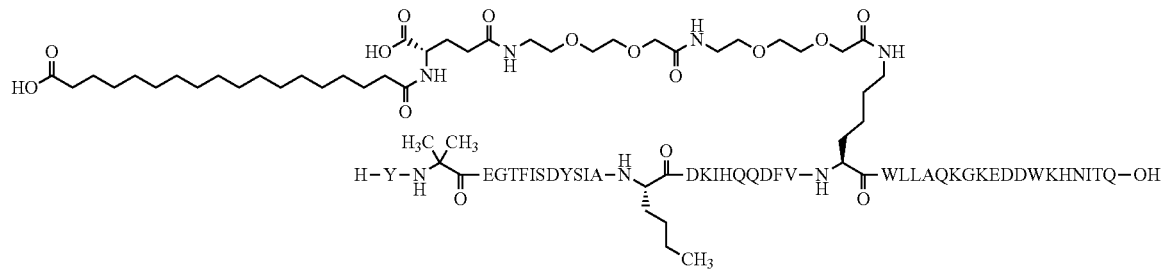

General methods used: SPPS_A, SC_A, CP_A
Molecular weight (average) calculated: 5711.39 g/mol
LCMS_27: found (M+4H)4+1428.75

Compound 37 (SEQ ID NO: 42):

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Arg18,Lys24,Glu33,Glu34]-hGIP

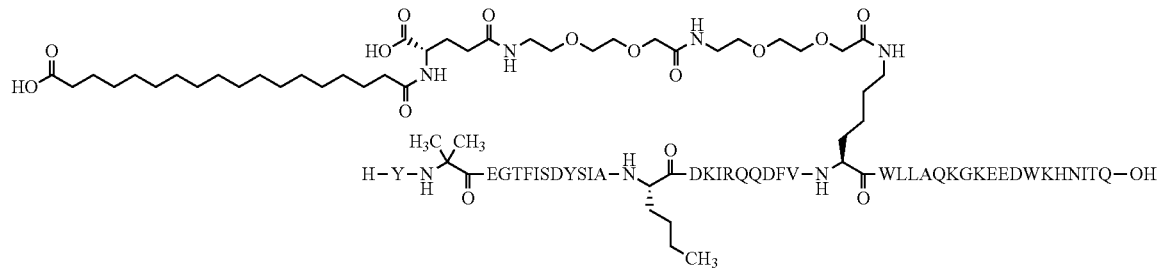

General methods used: SPPS_A, SC_A, CP_A
Molecular weight (average) calculated: 5744.46 g/mol
LCMS_27: found (M+4H)4+1437.03

Compound 38 (SEQ ID NO: 43):

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33,Glu34]-hGIP

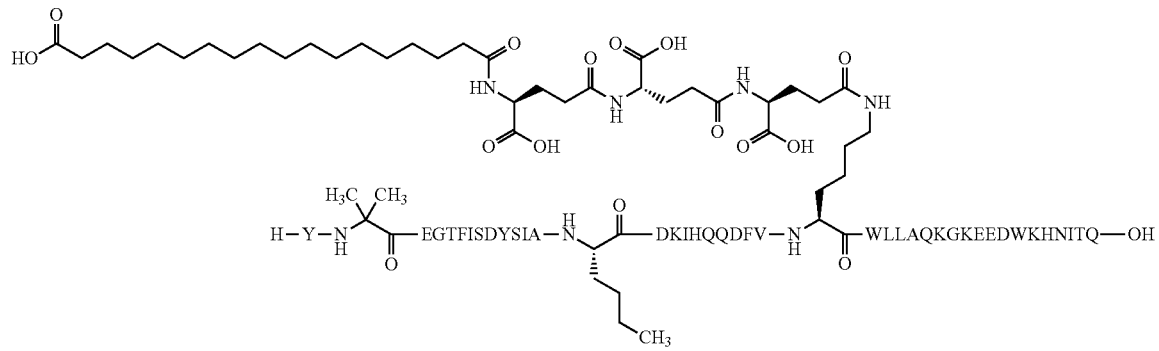

General methods used: SPPS_A, SC_A, CP_A
Molecular weight (average) calculated: 5693.33 g/mol
LCMS_27: found (M+4H)4+1424.24

Compound 39 (SEQ ID NO: 44):

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33,Asp34]-hGIP

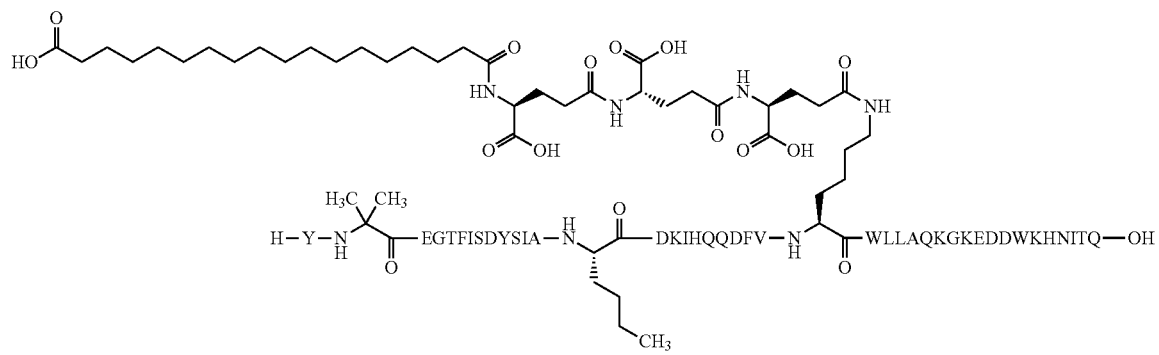

General methods used: SPPS_A, SC_A, CP_A
Molecular weight (average) calculated: 5679.30 g/mol
LCMS_27: found (M+4H)4+1420.79

Compound 40 (SEQ ID NO: 45):

N{Epsilon-24}-[(4S)-4-carboxy-4-[[(4S)-4-carboxy-
4-[[(4S)-4-carboxy-4-(17-carboxyheptadecanoy-
lamino)butanoyl]amino]butanoyl]amino]butanoyl]-
[Aib2,Nle14,Arg18,Lys24,Glu33,Glu34]-hGIP

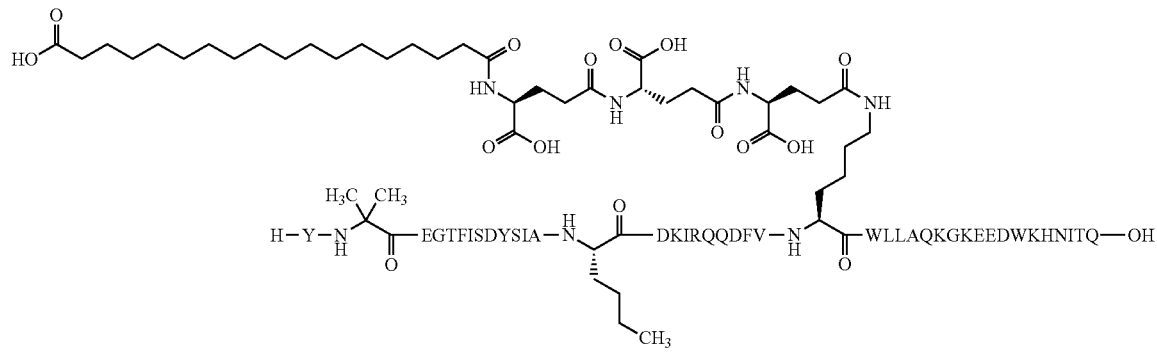

General methods used: SPPS_A, SC_A, CP_A
Molecular weight (average) calculated: 5712.37 g/mol
LCMS_27: found (M+4H)4+1429.00

Compound 41 (SEQ ID NO: 46):

N{Epsilon-24}-[2-[2-[2-[[2-[2-[2-[[(4S)-4-carboxy-
4-[[4-[(19-carboxynonadecanoyl- amino)methyl]
cyclohexanecarbonyl]amino]butanoyl]amino]
ethoxy]ethoxy]acetyl]amino]ethoxy]ethoxy]acetyl]-
[Aib2,Nle14,Arg18,Lys24,Glu33,Glu34]-hGIP

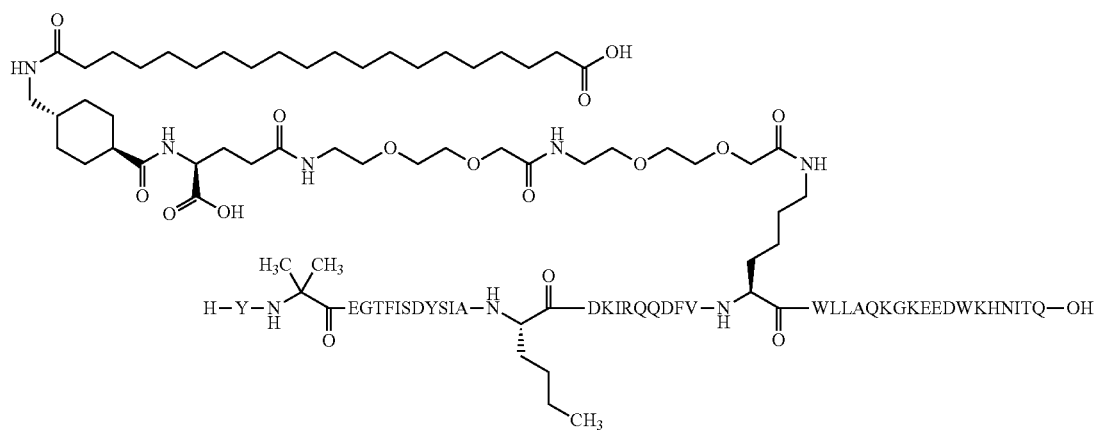

General methods used: SPPS_A, SC_A, CP_A
Molecular weight (average) calculated: 5911.71 g/mol
LCMS_27: found (M+4H)4+1478.81

Compound 42 (SEQ ID NO: 47):

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[Aib2,Nle14,Arg18,Lys24,Glu33,Glu34]-hGIP

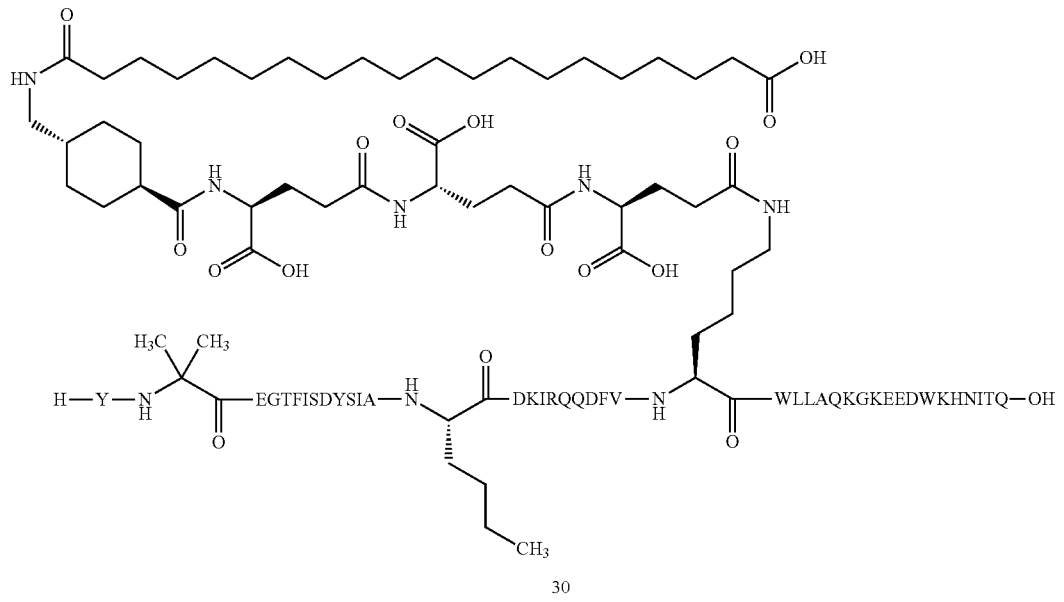

General methods used: SPPS_A, SC_A, CP_A
Molecular weight (average) calculated: 5879.62 g/mol
LCMS_27: found (M+4H)4+1470.81

Compound 43 (SEQ ID NO: 59):

N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Nle14,Arg18,Aib20,Lys24]-hGIP(1-31)

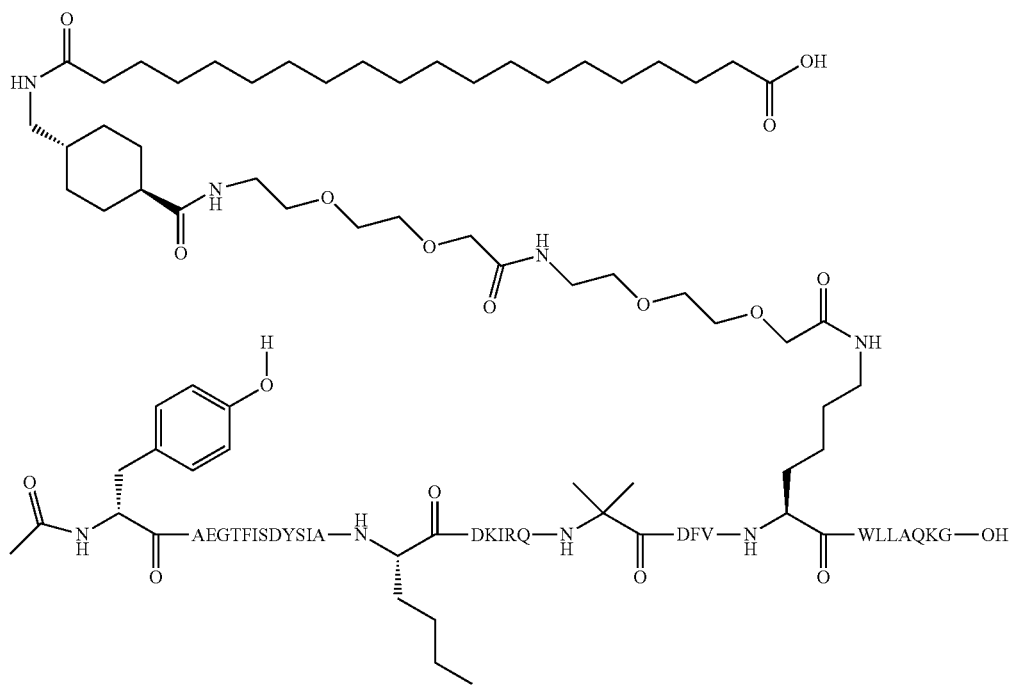

General methods used: SPPS_A, SC_E, CP_A, SX_A
Molecular weight (average) calculated: 4358.08 g/mol
LCMS_34: found (M+3H)3+1452.82
Compound 44 (SEQ ID NO: 60):

N{1}-acetyl,N{Epsilon-24}-[2-[2-[2-[[2-[2-[2-[[4-[[(19-carboxynonadecanoylamino)methyl]cyclohexanecarbonyl]amino]ethoxy]ethoxy]acetyl]amino]ethoxy]ethoxy]acetyl]-[D-Tyr1,Aib2, Nle14,Arg18, Lys24,Pro31]-hGIP(1-31) amide

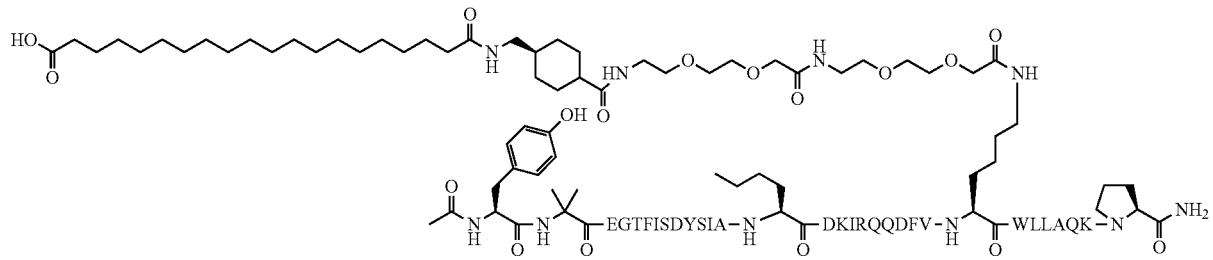

General methods used: SPPS_A, SC_E, CP_A, SX_A
Molecular weight (average) calculated: 4454.21 g/mol
LCMS_34: found (M+3H)3+1484.83
Compound 45 (SEQ ID NO: 61)
N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Leu14,Lys24]-hGIP

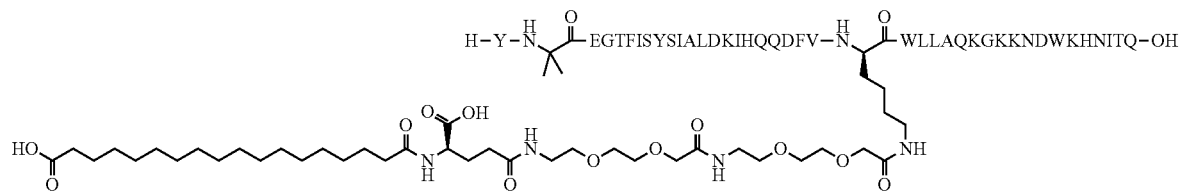

General methods used: SPPS_D, SC_D, CP_A
Molecular weight (average) calculated: 5709.46 g/mol
LCMS_34: found (M+4H)4+1428.36
Compound 46 (SEQ ID NO: 62)

N{1}-acetyl,N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[D-Tyr1,Aib2,Nle14,Arg18,Lys24,Pro31]-hGIP(1-31) amide

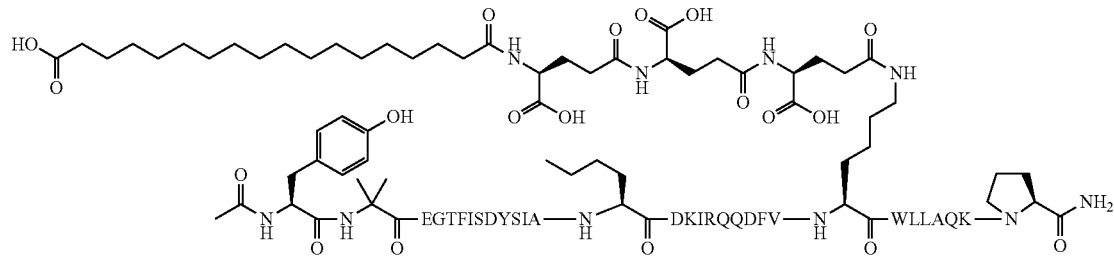

General methods used: SPPS_A, SC_A, CP_A, SX_B
Molecular weight (average) calculated: 4383.99 g/mol
LCMS_34: found (M+3H)3+1461.99

Pharmacological Methods

The utility of the derivatives of the present invention as pharmacologically active agents in the reduction of weight gain and treatment of obesity in mammals, such as humans, and for the treatment of diabetes and NASH may be demonstrated by the activity of the agonists in conventional assays and in the in vitro and in vivo assays described below.

Such assays also provide a means whereby the activities of the derivatives of the invention can be compared with activities of known compounds.

Example 2

In Vitro Potency (CRE Luciferase; Whole Cells)

The purpose of this example is to test the activity, or potency, of the derivatives in vitro at the human GIP receptor as well as at the human GLP-1 receptor and the human glucagon receptor. The in vitro potency is the measure of human GIP, GLP-1 or glucagon receptor activation, respectively, in a whole cell assay.

The potencies of the derivatives of Example 1 were determined as described below. hGIP and C-terminal truncated hGIP(1-31) as well as hGLP-1(7-37) (SEQ ID NO: 4) and human glucagon (hGcg) (SEQ ID NO: 5) were included for comparison.

Principle:

In vitro potency was determined by measuring the response of the human GIP, GLP-1 or glucagon receptor in a reporter gene assay in individual cell lines. The assay was performed in stably transfected BHK cell lines that expresses either the human GIP receptor, the human GLP-1 receptor or the human glucagon receptor and where each contains the DNA for the cAMP response element (CRE) coupled to a promoter and the gene for firefly luciferase (CRE luciferase). When the respective receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (BHK CRE luc2P hGIPR clone #5, BHK CRE luc2P hGLP-1R clone #6, BHK CRE luc2P hGCGR clone #18) were BHK cells with BHKTS13 as a parent cell line. The cells were derived from a clone containing the CRE luciferase element and were established by further transfection with the respective receptor to obtain the current clone.

The cells were cultured at 5% $CO_2$ in Cell Culture Medium. They were aliquoted and stored in liquid nitrogen. The cells were kept in passage and were seeded out the day before each assay.

Materials

The following chemicals were used in the assay: Pluronic F-68 (10%) (Gibco 2404), human serum albumin (HSA) (Sigma A9511), 10% FBS (fetal bovine serum; Invitrogen 16140-071), fetal ovalbumin (Sigma A5503), DMEM w/o phenol red (Gibco 11880-028), 1 M Hepes (Gibco 15630), Glutamax 100× (Gibco 35050), G418 (Invitrogen 10131-027), hygromycin (Invitrogen 10687-010), 1% pen/strep (penicillin/streptomycin; Invitrogen 15140-122) and steadylite plus (PerkinElmer 6016757).

Buffers

Cell Culture Medium consisted of DMEM medium with 10% FBS, 1 mg/ml G418, 1 mg/ml hygromycin and 1% pen/strep (penicillin/streptomycin; Invitrogen 15140-122).

Assay Medium consisted of DMEM w/o phenol red, 10 mM Hepes and 1× Glutamax. The Assay Buffer consisted of 1% ovalbumin and 0.1% Pluronic F-68 in Assay Medium with the addition of human serum albumin at twice the indicated concentrations. The assay Medium was mixed 1:1 with an equal volume of the test compound in Assay Buffer to give the final assay concentration of serum albumin.

Procedure

1) Cells were plated at 5000 cells/well and incubated overnight.
2) Cells were washed three times in PBS.
3) Assay Medium (50 µl aliquot) with or without serum albumin was added to each well in the assay plate.
4) Stocks of the test compounds and reference compounds were diluted to a concentration of 0.2 µM in Assay Buffer. Compounds were diluted 10-fold to give the following concentrations: $2\times10^{-7}$ M, $2\times10^{-8}$ M; $2\times10^{-9}$ M, $2\times10^{-10}$ M, $2\times10^{-11}$ M, $2\times10^{-12}$ M, $2\times10^{-13}$ M, and $2\times10^{-14}$ M.
5) A 50 µl aliquot of compound or blank was transferred from the dilution plate to the assay plate. Compounds were tested at the following final concentrations: $1\times10^{-7}$ M, $1\times10^{-8}$ M; $1\times10^{-9}$ M, $1\times10^{-10}$ M, $1\times10^{-11}$ M, $1\times10^{-12}$ M, $1\times10^{-13}$ M, and $1\times10^{-14}$ M.
6) The assay plate was incubated for 3 h in a 5% $CO_2$ incubator at 37° C.
7) The assay plate was removed from the incubator and allowed to stand at room temperature for 15 min.
8) The cells were washed three times with PBS plus some liquid in each well.
9) A 100 µl aliquot of steadylite plus reagent was added to each well of the assay plate (reagent was light sensitive).
10) Each assay plate was covered with aluminum foil to protect it from light and shaken for 30 min at room temperature.
11) Each assay plate was read in a microtiter plate reader.

Calculations and Results

The data from the microtiter plate reader was transferred to GraphPad Prism software. The software performs a non-linear regression (log(agonist) vs response). $EC_{50}$ values which were calculated by the software and reported in pM are shown in Table 1 below.

A minimum of two replicates was measured for each sample. The reported values are averages of the replicates.

TABLE 1

| | Potencies, $EC_{50}$ | | |
|---|---|---|---|
| Compound No. | hGIP-R, CRE Luc 0.2% HSA $EC_{50}$ (pM) | hGLP-1-R, CRE Luc 0.2% HSA $EC_{50}$ (pM) | hGcg-R CRE Luc 0.2% HSA $EC_{50}$ (pM) |
| hGIP(1-42) | 4.98 | >100000 | >100000 |
| hGIP(1-31) | 2.24 | nd | nd |
| hGLP-1(7-37) | >100000 | 3.9* | >100000* |
| hGcg | >100000 | 1094 | 14.3 |
| 1 | 40.49 | >100000* | >100000* |
| 2 | 49.89 | >100000* | >100000* |
| 3 | 44.74 | nd | nd |
| 4 | 72.12 | nd | nd |
| 5 | 20.90 | >10000* | nd |
| 6 | 134.67 | nd | nd |
| 7 | 48.93 | nd | nd |
| 8 | 179.57 | nd | nd |
| 9 | 62.94 | nd | nd |
| 10 | 252.27 | nd | nd |
| 11 | 9.40 | nd | nd |
| 12 | 71.17 | nd | nd |
| 13 | 72.47 | nd | nd |
| 14 | 265.53 | nd | nd |
| 15 | 30.44 | nd | nd |
| 16 | 25.03 | nd | nd |
| 17 | 43.10 | nd | nd |
| 18 | 545.53 | nd | nd |

TABLE 1-continued

Potencies, EC$_{50}$

| Compound No. | hGIP-R, CRE Luc 0.2% HSA EC$_{50}$ (pM) | hGLP-1-R, CRE Luc 0.2% HSA EC$_{50}$ (pM) | hGcg-R CRE Luc 0.2% HSA EC$_{50}$ (pM) |
|---|---|---|---|
| 19 | 91.53 | nd | nd |
| 20 | 158.46 | nd | nd |
| 21 | 810.27 | nd | nd |
| 22 | 547.20 | nd | nd |
| 23 | 135.62 | nd | nd |
| 24 | 152.88 | nd | nd |
| 25 | 123.86 | >10000* | nd |
| 26 | 61.50 | nd | nd |
| 27 | 67.47 | nd | nd |
| 28 | 76.23 | nd | nd |
| 29 | 71.19 | nd | nd |
| 30 | 84.20 | nd | nd |
| 31 | 26.05 | >10000* | >100000* |
| 32 | 38.35 | nd | nd |
| 33 | 21.29 | >100000* | >100000* |
| 34 | 20.15 | >100000* | >100000* |
| 35 | 5.45 | >100000 | >100000 |
| 36 | 5.97 | >100000 | >100000 |
| 37 | 4.12 | >100000 | >100000 |
| 38 | 9.00 | >100000 | >100000 |
| 39 | 5.90 | >100000 | >100000 |
| 40 | 4.47 | >100000 | >100000 |
| 41 | 14.00 | nd | nd |
| 42 | 22.00 | nd | nd |
| 45 | 56.00 | >100000* | >100000* |
| 46 | 21.2 | >100000 | nd |

*Assay performed in presence of 1% HSA; nd = not determined.

The derivatives of the present invention all display good GIP potency and substantially no activity or no measurable activity at the human GLP-1 receptor and the human glucagon receptor under the given conditions.

Example 3

Pharmacokinetic Study in Minipigs

The purpose of this study is to determine the half-life in vivo of the derivatives of the present invention after i.v. administration to minipigs, i.e. the prolongation of their time in the body and thereby their time of action. This is done in a pharmacokinetic (PK) study, where the terminal half-life of the derivative in question is determined. By terminal half-life is generally meant the period of time it takes to halve a certain plasma concentration, measured after the initial distribution phase.

Study:

Female Göttingen minipigs were obtained from Ellegaard Göttingen Minipigs (Dalmose, Denmark) approximately 7-14 months of age and weighing from approximately 16-35 kg were used in the studies. The minipigs were housed individually and fed restrictedly once daily with SDS minipig diet (Special Diets Services, Essex, UK).

After at 3 weeks of acclimatisation two permanent central venous catheters were implanted in vena cava caudalis in each animal. The animals were allowed 1 week recovery after the surgery, and were then used for repeated pharmacokinetic studies with a suitable wash-out period between successive derivative dosing.

The animals were fasted for approximately 18 hours before dosing and from 0 to 4 hours after dosing, but had ad libitum access to water during the whole period.

The GIP derivatives of Examples 1 were dissolved in an 8 mM sodium phosphate buffer pH 7.8, containing, 236 mM propylene glycol to a concentration of 50 nmol/ml. Intravenous injections (the volume corresponding to usually 5 nmol/kg, for example 0.1 ml/kg) of the compounds were given through one catheter, and blood was sampled at predefined time points for up till 13 days post dosing (preferably through the other catheter). Blood samples (for example 0.8 ml) were collected in EDTA buffer (8 mM) and then centrifuged at 4° C. and 1942G for 10 minutes.

Sampling and Analysis:

Plasma was pipetted into Micronic tubes on dry ice, and kept at −20° C. until analysed for plasma concentration of the respective GIP peptide derivative using ELISA or a similar antibody based assay or LCMS. Individual plasma concentration-time profiles were analysed by a non-compartmental model in Phoenix WinNonLin ver. 6.4. (Pharsight Inc., Mountain View, Calif., USA), and the resulting terminal half-lives (harmonic mean) determined.

Results:

TABLE 2

Half-life ($t_{1/2}$)

| Compounds no. | n | $t_{1/2}$ (hours) harmonic mean (min-max) |
|---|---|---|
| 3 | 3 | 96 (93-98) |
| 4 | 3 | 124 (116-132) |
| 5 | 2 | 79 (73-79) |
| 6 | 3 | 125 (121-130) |
| 7 | 2 | 84 (82-87) |
| 8 | 3 | 106 (92-118) |
| 11 | 2 | 89 (86-91) |
| 12 | 3 | 132 (120-141) |
| 15 | 2 | 81 (80-82) |
| 17 | 3 | 88 (86-91) |
| 23 | 3 | 119 (112-126) |
| 24 | 3 | 125 (122-127) |
| 25 | 2 | 125 (119-134) |
| 26 | 3 | 109 (101-118) |
| 27 | 3 | 147 (145-151) |
| 28 | 3 | 104 (91-116) |
| 29 | 3 | 119 (103-138) |
| 30 | 3 | 99 (88-107) |
| 31 | 2 | 128 (125-130) |
| 32 | 3 | 121 (100-137) |

The tested GIP derivatives have very long half-lives as compared to the half-life of hGIP(1-42) measured in man to be about 5 min [Meier et al., Diabetes, Vol. 59, 2004, 654-662] or 7 min [Deacon et al., J. Clin. Endocrinol. & Metab., Vol. 85, No. 10, 2000, 3575-3581].

Example 4

Physical Stability of Peptide Compositions (ThT Fibrillation Assay and DLS_SI)

The purpose of this study is to assess the physical stability of the derivatives of the invention in aqueous solutions in a ThT assay and DLS-SI assay as explained below.

ThT Assay:

The Thioflavin T assay was performed as outlined in Schlein (2017), AAPS J, 19(2), 397-408.

Low physical stability of a peptide may lead to amyloid fibril formation, which is observed as well-ordered, thread-like macromolecular structures in the sample, which eventually may lead to gel formation. This has traditionally been measured by visual inspection of the sample. However, that kind of measurement is very cumbersome and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq.(1)}$$

Here, F is the ThT fluorescence at the time t. The constant t0 is the time needed to reach 50% of maximum fluorescence. The two important parameters describing fibril formation are the lag-time calculated by $t0-2\tau$ and the apparent rate constant kapp $1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Samples are prepared freshly before each assay. The drug substance was solved with 250 µM of the GIP derivative in 8 mM phosphate, 14 mg/mL propylene glycol, 58 mM phenol, pH 7.4. The pH of the sample was adjusted to the desired value using appropriate amounts of concentrated NaOH and HCl. Thioflavin T was added to the samples from a stock solution in $H_2O$ to a final concentration of 1 µM.

Sample aliquots of 200 µl were placed in each well of a 96 well microtiter plate (Packard OptiPlate™-96, white polystyrene). Four replica of each sample (corresponding to one test condition) was placed in one column of wells. The plate was sealed with Scotch Pad (Qiagen).

Incubation, shaking and measurement of the ThT fluorescence emission were done in a Fluoroskan Ascent FL fluorescence platereader (Thermo Labsystems). The plate was incubated at 37° C. with orbital shaking adjusted to 960 rpm with an amplitude of 1 mm. Fluorescence measurement was done using excitation through a 444 nm filter and measurement of emission through a 485 nm filter. The assay was completed after 45 hours of incubation.

Each run was initiated by incubating the plate at the assay temperature for 10 min. The plate was measured every 20 minutes for a desired period of time. Between each measurement, the plate was shaken and heated as described.

After completion of the ThT assay the replica of each sample was pooled and centrifuged at 20000 rpm for 30 minutes at 18° C. The supernatant was filtered through a 0.22 µm filter and an aliquot was transferred to a HPLC vial. The concentration of the filtered sample relative to the initial sample (in percentage) was reported as the recovery.

The measurement points were saved in Microsoft Excel format for further processing and curve drawing and fitting was performed using GraphPad Prism. The background emission from ThT in the absence of fibrils was negligible. The data points were a mean of the four replica and shown with standard deviation error bars. Only data obtained in the same experiment (i.e. samples on the same plate) were presented in the same graph ensuring a relative measure of fibrillation between experiments.

The data set may be fitted to Eq. (1). However, the lag time before fibrillation reported herein was determined by visual inspection of the curve identifying the time point at which ThT fluorescence increases significantly above the background level. No increase in ThT fluorescence during the duration of the assay was reported as a lag time of 45 hours.

Dynamic Light Scattering Stability Index (DLS-SI) for Evaluation of Physical Stability of Peptides in Solution:

The hydrodynamic radius ($R_h$, synonym: Stokes radius) of a peptide in solution is an indicator for the size and oligomeric state of the biomolecule in solution and can be measured by dynamic light scattering (DLS). Changes in hydrodynamic radius ($R_h$) over time can be an indicator for changes in size and oligomeric state and therefore an indicator for physical instability of the peptide in solution.

Samples were freshly prepared before each assay. The drug substance was solved with 250 µM of the GIP derivative in 8 mM phosphate, 14 mg/mL propylene glycol, 58 mM phenol, pH 7.4. The pH of the sample was adjusted to the desired value using appropriate amounts of concentrated NaOH and HCl.

400 µL of each freshly prepared sample were filtered through non-sterile Whatman® Anotop® 10 syringe filter with 0.02 µm pore size whereby the first two drops were discarded. 25 µL filtered sample was placed per well in a 384 well microtiter plate (Corning® 3540 Polystyrene, black with flat, clear bottom), each sample was analysed as three replicas. Sample in each well was covered with 15 µL Silicone oil (Sigma-Aldrich, viscosity 20 cSt at 25° C.). Plate was centrifuged for 5 min at 1200 rpm (Eppendorf® centrifuge 5430, rotor A 2 MTP) and placed in Wyatt DynaPro Plate Reader II for 30 min before start of measurement for temperature equilibration of sample to 25° C. The Wyatt DynaPro Plate Reader II was equipped with 830 nm laser and the software Dynamics v7.5. Each sample in each well was analysed with a data acquisition interval of 5 sec and 40 acquisitions per sample. After measurement plate was covered with Adhesive Film for Microplates (VWR polypropylene heat resistant film) and incubated for 4 weeks at 25° C. The samples were re-measured by DLS after 1, 2 and 4 weeks with same parameter.

After measurement the data of each sample were first filtered by the Dynamics software v7.5 with Minimum Amplitude: 0.03, Maximum Amplitude: 1, Baseline Limit (1+/−): 0.005 and Maximum SOS: 100. Afterwards the time-autocorrelation function of each measured sample was peer reviewed before calculation of DLS-SI according to Eq. (2).

In the DLS-SI assay changes of cumulant $R_h$ are defined as stability index depending on the time by:

$$DLSSI(t) = \frac{|R_h(t) - R_h(t_0)|}{2\sigma} \qquad \text{Eq. (2)}$$

with DLS-SI as stability index depending on time (t), the difference between the cumulant hydrodynamic radius, $R_h$ at the begin ($t_0$) and end (t) of the stability investigation normalised by the statistical significant variability $2\sigma$. The analytical variability of $R_h$-measurements under such conditions was comprehensive investigated and resulted in $\sigma=0.3$ nm. A DLS-SI value larger than 1 represents a statistical significant change in $R_h$. The larger the DLS-SI value the more changes $R_h$ over time.

Results:

TABLE 3

ThT assay lag time and recovery at pH 7.4, and DLS-SI.

| Compound No. | ThT Assay Lag time (h) | ThT Assay Recovery (%) | DLS-SI Dimensionless | DLS-SI precipitates |
|---|---|---|---|---|
| hGIP(1-42) | 0.33 | 0 | 1[#] | No[#] |
| hGIP(1-31) | 0 | 49 | 1000[##] | Yes[##] |
| 1 | >45 | 104.5 | 1.7 | No |
| 2 | >45 | 111.5 | 0 | No |
| 3 | >45 | 100 | 0 | No |
| 4 | >45 | 100 | 0.6 | No |
| 5 | >45 | 101 | 1.1 | No |
| 6 | >45 | 100 | 1.7 | No |
| 7 | >45 | 100 | 1.7 | No |
| 8 | >45 | 100 | 0.6 | No |
| 10 | >45 | 95 | 1.7 | No |
| 11 | >45 | 100 | 0 | No |
| 12 | >45 | 115 | 0.6 | No |
| 15 | >45 | 101 | 1.7 | No |
| 17 | >45 | 105 | 0.6 | No |
| 21 | >45 | 104 | 0 | No |
| 22 | >45 | 100 | 1.7 | No |
| 23 | >45 | 100 | 1.7 | No |
| 24 | >45 | 100 | 1.7 | No |
| 25 | >45 | 104 | 1.7 | No |
| 26 | >45 | 104 | 0 | No |
| 27 | >45 | 102 | 1.7 | No |
| 28 | >45 | 100 | 0 | No |
| 29 | >45 | 102 | 0 | No |
| 30 | >45 | 100 | 1.1 | No |
| 31 | >45 | 101 | 0.6 | No |
| 32 | >45 | 100 | 1.7 | No |
| 33 | >45 | 88 | nd | nd |
| 34 | >45 | 88 | nd | nd |
| 43* | >45 | 100 | 0 | No |
| 44** | nd | nd | nd | nd |
| 45 | >45 | 93 | 6.7 | No |
| 46 | >45 | 103 | 1.5 | No | nd = not determined;
[#]concentration of hGIP(1-42) in DLS-SI was only 156 μM instead of 250 μM as described under sample preparation.
[##]concentration of hGIP(1-31) in DLS-SI was only 5 μM instead of 250 μM as described under sample preparation.
*concentration was only 162 μM instead of 250 μM as described under sample preparation.
**Compound not soluble at given pH.

The GIP derivatives tested in ThT assay shows no fibril formation after 45 hours (lag time) and very high recovery, i.e. the concentration of GIP derivative recovered after the assay relative to the initial concentration compared to hGIP (1-42) and hGIP(1-31). Further, the tendency of hGIP(1-42) and hGIP(1-31) to form fibrils in solution is shown.

DLS-SI data shows no or only little increase in hydrodynamic radius for the hGIP(1-42) and the GIP derivatives of the invention, precipitation was not visible. The change of $R_h$ over time was significant for hGIP(1-31) and the formation of large aggregates became visible as precipitation in the DLS instrument.

Accordingly, the GIP derivatives of the invention have a high physical stability as compared to hGIP(1-42) and hGIP(1-31).

Example 5

Chemical Stability of GIP Derivative Compositions

The aim of this study is to determine the chemical stability of GIP derivative compositions. As a measure of stability of the GIP derivative composition, the formation of high molecular weight peptide formation (% HMWP) as a function of time was analysed by size-exclusion chromatography (SEC-MS). Further, the purity loss of the GIP derivative compositions was measured by LCMS.

Formulations:

Samples for chemical stability assays were freshly prepared before each assay. The drug substance was solved with 250 μM of the GIP derivative in 8 mM phosphate, 14 mg/mL propylene glycol, 58 mM phenol, pH 7.4. The pH of the sample was adjusted to the desired value using appropriate amounts of concentrated NaOH and HCl.

Incubation:

The formulations of the respective GIP derivatives were stored in an incubator at 37° C. for 4 weeks before being tested on HMWP formation and purity loss, as described below.

HMWP Formation Analysis:

Formation of covalent oligomers (HMWPs) was analysed and identified by a SEC-MS method. A Waters Acquity i-class UPLC equipped with Acquity BEH200 SEC column, 4.6 mm×150 mm, 1.7 μm particle size and pore size of 200 Å. Isocratic elution with 0.05% TFA in 55% MeCN was performed at a column temperature of 45° C. and a flow rate of 0.2 ml/min. The LC system was coupled to both a TUV detector operated at 215 nm, 10 Hz and a high resolution QToF mass spectrometer from Waters (Synapt G2S) operated in positive ion mode and m/z range of 100 to 4000 with normal resolution setting. Lock mass correction against Leu-Enkephalin was done every 31 sec. Spectra were processed in MassLynx version 4.1 and MaxEnt deconvoluted. Results are shown in table 5.

Purity Analysis by LCMS:

For accelerated chemical stability testing relevant samples were analysed on a Waters Acquity I-class UPLC system coupled with a Waters Synapt G2S high resolution QToF mass spectrometry system for purity and impurity identification and characterisation. The UPLC system was fitted with a Waters Acquity CSH C18 column with a particle size of 1.7 μm and internal diameter of 1 mm and length of 150 mm. The column oven was kept at 55° C. The solvent used was 0.1% formic acid in water (Eluent A), premixed from Thermo (Optima LS118-1) and for the B eluent 0.1% formic acid in MeCN also premixed from Thermo (Optima LS120-1). The solvents were pumped from a binary solvent manager system and mixed on the high pressure side in a mixer with a volume of 50 μl. The gradient and flow can be seen in table 4:

TABLE 4

LC Gradient table

| Time (min) | Flow rate (ml/min) | % A | % B | Curve |
|---|---|---|---|---|
| 0 | 0.1 | 70 | 30 | Initial |
| 40 | 0.1 | 46 | 54 | 6 |
| 41 | 0.1 | 5 | 95 | 6 |
| 45 | 0.1 | 5 | 95 | 6 |
| 46 | 0.1 | 70 | 30 | 6 |
| 50 | 0.1 | 70 | 30 | 6 |

A Flow-through-needle auto sampler at 8° C. was used to inject 1 μl of each sample. The effluent passed through a tuneable UV detector (TUV) tuned to 215 nm. The outlet from the UV detector passed to the electrospray source of the mass spectrometer. The capillary was held at 3 kV and dry nitrogen gas was purged at a flow of 750 l/h and a temperature of 250° C. The source block was kept at 120° C. and the large bore cone was flushed with nitrogen at 50 l/h with standard electrode potentials on the rest of the instrument. The MS was operated in high resolution mode with a nominal resolution of 35000. The ToF analyser was operated in ADC mode with an m/z window from 100-2000. A second function with higher collision energy in the trap T-wave region was used for MSE type experiment with the high energy ramp having a voltage between 32 and 52 V.
Results:

TABLE 5

HMWP Formation and purity loss at 37° C.

| Compound No. | HMWP formation (%/month) | Purity loss (%/month) |
|---|---|---|
| hGIP(1-42) | 2.0 | 73.1 |
| hGIP(1-31) | 0.15 | 86.9 |
| 1 | 0.30 | 5.60 |
| 2 | 0.25 | 3.47 |

TABLE 5-continued

HMWP Formation and purity loss at 37° C.

| Compound No. | HMWP formation (%/month) | Purity loss (%/month) |
|---|---|---|
| 3 | 0.90 | 2.80 |
| 4 | 0.50 | 2.00 |
| 5 | 0.15 | 2.89 |
| 6 | 0.50 | 5.20 |
| 7 | 0.00 | 1.70 |
| 8 | 0.80 | 6.00 |
| 10 | 1.50 | 4.80 |
| 11 | −0.44 | 2.64 |
| 12 | 0.70 | 4.40 |
| 15 | 0.24 | 0.74 |
| 17 | −0.30 | 4.00 |
| 21 | 0.40 | 3.20 |
| 22 | 0.10 | 4.80 |
| 23 | 0.40 | 1.60 |
| 24 | 0.70 | 3.60 |
| 25 | 0.40 | 2.00 |
| 26 | 1.30 | 4.40 |
| 27 | 0.85 | 1.09 |
| 28 | 0.08 | 1.49 |
| 29 | 0.31 | 2.10 |
| 30 | 0.10 | 1.14 |
| 31 | −0.24 | 0.49 |
| 32 | 0.66 | 2.80 |
| 33 | 0.32 | 34.50 |
| 45 | 8.17 | 47.22 |
| 46 | −0.09 | 2.96 |

As seen from table 5, the GIP derivatives of the present invention shows low formation of HMWPs and have low purity loss per month. Accordingly, they are considered to be chemically stable in solution.

Example 6

Sub-Chronic In Vivo Studies in Obese Mice

The purpose of this example is to assess the in vivo effect of the GIP derivatives of the present invention alone and in combination with a GLP-1 receptor agonist on food intake, body weight, and glucose tolerance in diet-induced obese (DIO) mice. The GLP-1 receptor agonist used for this example was a semaglutide-like molecule that has the same pharmacological properties as semaglutide, but a slightly different structure. The compound may be synthesised using methods known in the art, e.g. as described by methods of present Example 1 or as described in WO 2006/097537, example 4.

Semaglutide-like molecule (compound no. 47; SEQ ID NO: 58):

$N^{6,26}$-{18-[N-(17-carboxyheptadecanoyl)-D-γ-glutamyl]-10-oxo-3,6,12,15-tetraoxa-9,18-diazaoctadecanoyl}-[8-(2-amino-2-propanoic acid), 34-L-arginine]human glucagon-like peptide 1(7-37)

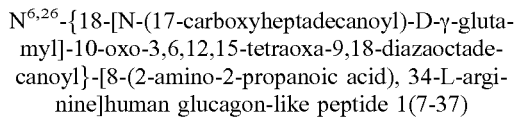

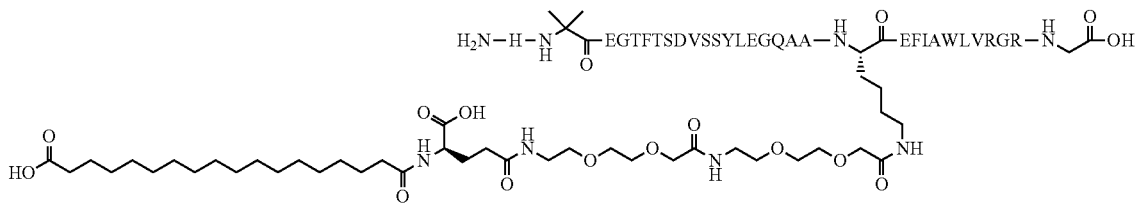

The animals were treated once daily with the GLP-1 receptor agonist (compound no. 47) and/or a GIP derivative of the present invention exemplified by compound no.'s 5, 25 and 31, to assess weight loss, efficacy and glucose tolerance.

Animals and Diet

All animal protocols were approved by an Institutional Animal Care and Use Committee and Ethical Review Committee of Novo Nordisk. Animals were housed according to Novo Nordisk rodent housing standards, and were given ad libitum access to food and water under controlled lighting (12 h:12 h light/dark cycle; lights off 18:00-06:00), temperature (23±2° C.) and relative humidity (50±20%) conditions. DIO male C57BL/6J mice maintained on a high fat diet (45% kcal fat, RD12451, Research Diets, New Brunswick, N.J., USA) for 22 weeks were obtained from Charles River (France). Upon arrival, the mice were single-housed (one mouse per cage) and allowed to acclimate to their new environment for two weeks prior to the start of treatment.

Group Allocation and Dosing

Prior to initiation of the study, animals were single-housed and acclimated to handling for 7 days. The DIO mice were distributed into groups (n=8/group) such that statistical variations in the mean and standard deviations of fat mass and body weight were minimized between groups. Animals were dosed once daily, subcutaneously with either vehicle or test compound.

Formulation Buffers

All compounds in the study were formulated in the following buffer: 50 mM phosphate; 70 mM sodium chloride; 0.05% polysorbate 80, pH 7.4. Dosing solutions were formulated in glass vials and stored at 2-8° C. Dosing solutions were brought to room temperature before dosing and returned to 2-8° C. after dosing.

Body Weight and Food Intake

Body weight (BW) and food intake were measured immediately prior to dosing each day. The average starting body weight of the mice prior to start of treatment was 45.2±0.2 grams. Results are shown in Tables 6-8.

IPGTT (Intraperitoneal Glucose Tolerance Test)

On the day of the glucose tolerance test (day 15), animals were fasted for 4 h. Food was removed and animals were transferred to fresh cages. Animals had access to water but not to food. Tail blood glucose levels were measured and mice were injected (t=0) with an intra-peritoneal (i.p.) glucose load of 2 g/kg (200 mg/ml glucose solution, dose volume 10 ml/kg). Tail blood glucose levels were measured at times 0, 15, 30, 60, 90, 120 minutes following the i.p. glucose load. Stratification of the animals during the IPGTT was such that for example two mice from group 1 are dosed followed by two mice from group 2, 3, 4, before the next two mice from group 1, 2, 3 etc. were handled. This was to allow for equal distribution of "time of day" throughout all groups.

Results:

TABLE 6

Study 1, Effects on food intake, body weight and glucose tolerance in DIO mice treated with the GLP-1 receptor agonist (compound no. 47, 2 nmol/kg) and/or GIP compound no. 5 (30 nmol/kg).

| Compound no. | Cumulative food intake (kcals) Day 14 | Absolute BW (grams) Day 0 | Absolute BW (grams) Day 14 | Change in BW (%) Day 14 | iAUC, IPGTT (mM*min) Day 15 |
|---|---|---|---|---|---|
| Vehicle | 197.0 ± 12.2 $^a$ | 43.8 ± 1.2 $^a$ | 43.6 ± 1.0 $^a$ | −0.6 ± 3.6 $^a$ | 1038 ± 157 $^a$ |
| 5 | 181.6 ± 8.1 $^b$ | 43.9 ± 1.1 $^a$ | 42.2 ± 1.1 $^{ab}$ | −3.8 ± 3.4 $^b$ | 812 ± 141 $^a$ |
| 47 | 146.3 ± 6.8 $^b$ | 44.4 ± 1.0 $^a$ | 38.5 ± 1.2 $^{bc}$ | −13.2 ± 3.3 $^c$ | 543 ± 94 $^a$ |
| 5 + 47 | 117.1 ± 8.2 $^b$ | 44.6 ± 1.2 $^a$ | 35.4 ± 0.7 $^c$ | −20.7 ± 2.7 $^d$ | 482 ± 154 $^b$ |

$^{a\text{-}d}$ p < 0.05, one-way ANOVA and Tukey's multiple comparison test for each day; groups not connected by the same letter (in each column) are significantly different from each other. Results expressed as mean ± SEM, n = 6-8. iAUC = baseline subtracted area under the curve

TABLE 7

Study 2, Effects on food intake, body weight and glucose tolerance in DIO mice treated with the GLP-1 receptor agonist (compound no. 47, 2 nmol/kg) and/or GIP compound no. 25 (30 nmol/kg).

| Compound no. | Cumulative food intake (kcals) Day 14 | Absolute BW (grams) Day 0 | Absolute BW (grams) Day 14 | Change in BW (%) Day 14 | iAUC, IPGTT (mM*min) Day 15 |
|---|---|---|---|---|---|
| Vehicle | 180.7 ± 7.3 $^a$ | 40.8 ± 1.0 $^a$ | 40.1 ± 0.7 $^a$ | −1.6 ± 1.5 $^a$ | 1078 ± 123 $^a$ |
| 25 | 170.2 ± 7.3 $^b$ | 41.1 ± 1.0 $^a$ | 38.8 ± 1.0 $^a$ | −5.6 ± 0.8 $^b$ | 518 ± 36 $^b$ |
| 47 | 134.9 ± 4.3 $^b$ | 40.2 ± 1.2 $^a$ | 34.8 ± 1.2 $^b$ | −13.6 ± 0.7 $^c$ | 503 ± 55 $^b$ |
| 25 + 47 | 111.0 ± 8.6 $^b$ | 40.8 ± 1.2 $^a$ | 31.9 ± 0.9 $^b$ | −21.8 ± 1.0 $^d$ | 375 ± 76 $^b$ |

$^{a\text{-}d}$ p < 0.05, one-way ANOVA and Tukey's multiple comparison test for each day; groups not connected by the same letter (in each column) are significantly different from each other. Results expressed as mean ± SEM, n = 8. iAUC = baseline subtracted area under the curve

TABLE 8

Study 3, Effects on food intake, body weight and glucose tolerance in DIO mice treated with the GLP-1 receptor agonist (compound no. 47, 2 nmol/kg) and GIP compound no. 31 (30 nmol/kg).

| Compound no. | Cumulative food intake (kcals) Day 14 | Absolute BW (grams) Day 0 | Absolute BW (grams) Day 14 | Change in BW (%) Day 14 | iAUC, IPGTT (mM*min) Day 15 |
|---|---|---|---|---|---|
| Vehicle | 178.2 ± 8.9 $^a$ | 44.4 ± 1.2 $^a$ | 44.4 ± 1.4 $^a$ | −0.2 ± 0.8 $^a$ | 1882 ± 119 $^a$ |
| 31 | 161.9 ± 5.7 $^b$ | 43.9 ± 1.2 $^a$ | 41.6 ± 1.0 $^a$ | −5.2 ± 0.9 $^b$ | 727 ± 76 $^b$ |
| 47 | 140.2 ± 6.7 $^b$ | 45.2 ± 1.4 $^a$ | 40.0 ± 1.3 $^a$ | −11.2 ± 1.6 $^c$ | 1441 ± 135 $^c$ |
| 31 + 47 | 110.0 ± 6.0 $^b$ | 44.3 ± 1.5 $^a$ | 36 ± 1.3 $^b$ | −18.7 ± 1.6 $^d$ | 1045 ± 113 $^{bc}$ |

$^{a\text{-}d}$ p < 0.05, one-way ANOVA and Tukey's multiple comparison test for each day; groups not connected by the same letter (in each column) are significantly different from each other. Results expressed as mean ± SEM, n = 8. iAUC = baseline subtracted area under the curve From Tables 6-8, it is seen that monotherapy with the GLP-1 receptor agonist compound no. 47 (2 nmol/kg) induced a reduction in food intake that resulted in body weight loss and improvement in glucose tolerance. Monotherapy with the GIP derivatives of the invention (compounds 5, 25, 31; 30 nmol/kg) had a minor effect on food intake resulting in a minor body weight loss than for compound 47. Monotherapy with GIP derivatives 5, 25, 31 all improved glucose tolerance. Combination therapy of compound 47 (2 nmol/kg) with each of the GIP derivatives 5, 25, 31 (30 nmol/kg) potentiated the reduction in food intake and body weight loss at an effect greater than additive compared with monotherapies. Glucose tolerance of combination therapy was not improved beyond that achieved with GIP derivative monotherapy (Tables 6-8).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A GIP analogue derivative comprising a GIP analogue and a modifying group,
wherein the GIP analogue is (SEQ ID NO: 48):

X$_1$-X$_2$-Glu-Gly-Thr-Phe-Ile-Ser-Asp-Tyr-Ser-Ile-Ala-X$_{14}$-Asp-X$_{16}$-Ile-X$_{18}$-Gln-X$_{20}$-Asp-Phe-Val-Lys-Trp-Leu-Leu-Ala-Gln-Lys-X$_{31}$;

wherein
X$_1$ is Tyr or D-Tyr;
X$_2$ is Aib, Ala, or D-Ala;
X$_{14}$ is Leu, Nle, Asp or Met;
X$_{16}$ is Lys or Ala;
X$_{18}$ is Arg or His;
X$_{20}$ is Gln, Glu or Aib;
X$_{31}$ is Gly or Pro;
wherein the modifying group is A-B-C;
wherein A is

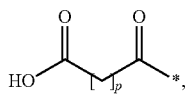  (Chem. 1)

wherein p is an integer in the range of 14-20, and
wherein * denotes the position of an amide bond connecting A- and B-;
wherein B is

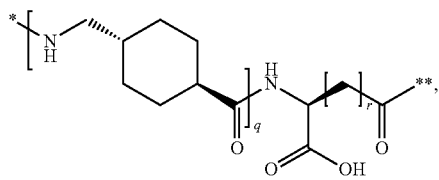  (Chem. 2)

wherein q is an integer in the range of 0-1,
wherein r is an integer in the range of 1-3,
wherein * denotes the position of the amide bond connecting A- and B-,
wherein ** denotes the position of an amide bond connecting B- and C-; and
wherein C is

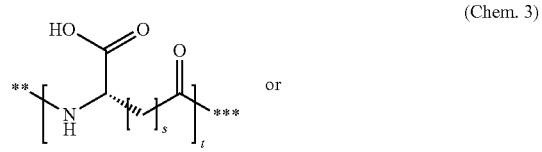  (Chem. 3)

or

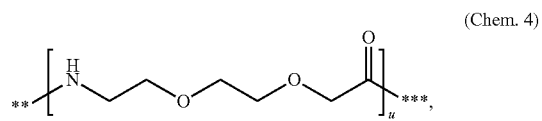  (Chem. 4)

wherein s is an integer in the range of 1-3,
wherein t is an integer in the range of 1-4,
wherein u is an integer in the range of 1-3,
wherein ** denotes the position of the amide bond connecting B- and C-, and
wherein *** denotes the position of an amide bond connecting C- and the epsilon amino group of the lysine at position 24.

2. The derivative according to claim 1, selected from the group consisting of:
N{Epsilon-24}-[2-[2-[2-[[2-[2-[2-[[(4S)-4-carboxy-4-[[4-[(19-carboxynonadecanoylamino) methyl]cyclohexanecarbonyl]amino]butanoyl]amino]ethoxy] ethoxy]acetyl]amino]ethoxy]ethoxy]acetyl]-[Aib2, Nle14,Arg18,Lys24]-hGIP(1-31) (Compound 3; SEQ ID NO: 8)

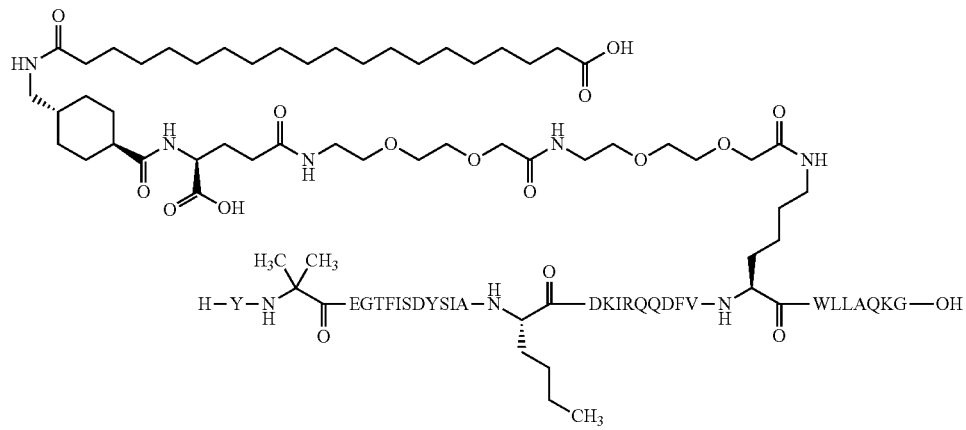

N{Epsilon-24}-[(4S)-4-carboxy-4-[[(4S)-4-carboxy-4-[[(4S)-4-carboxy-4-(17-carboxyheptadecanoylamino) butanoyl]amino]butanoyl]amino]butanoyl]-[Aib2, Nle14,Arg18,Glu20,Lys24]-hGIP(1-31) (Compound 9; SEQ ID NO: 14)

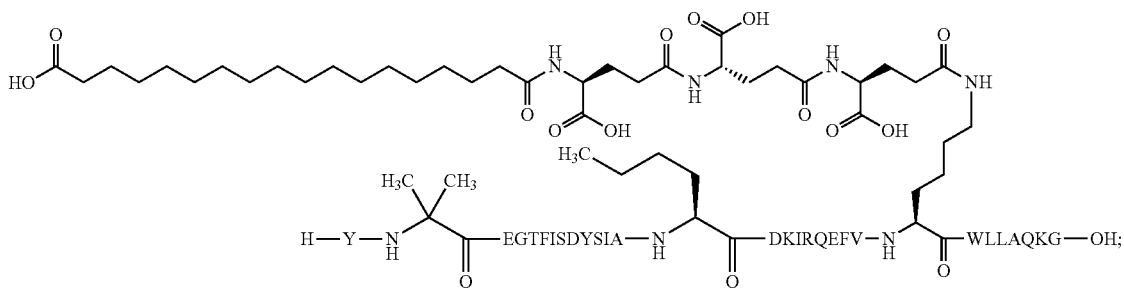

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Arg18,Glu20,Lys24]-hGIP(1-31) (Compound 10; SEQ ID NO: 15)

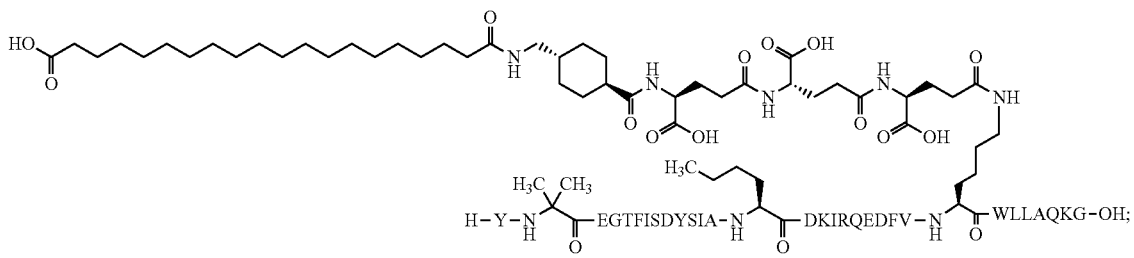

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Ala16,Arg18,Lys24]-hGIP(1-31) (Compound 13; SEQ ID NO: 18)

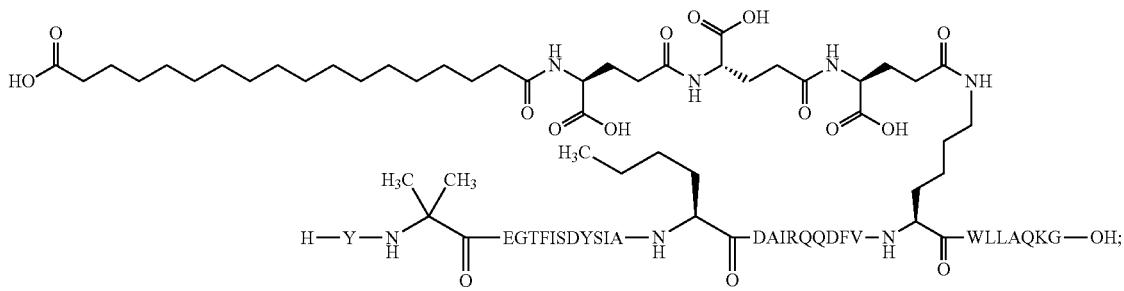

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Ala16,Arg18,Lys24]-hGIP(1-31) (Compound 14; SEQ ID NO: 19)

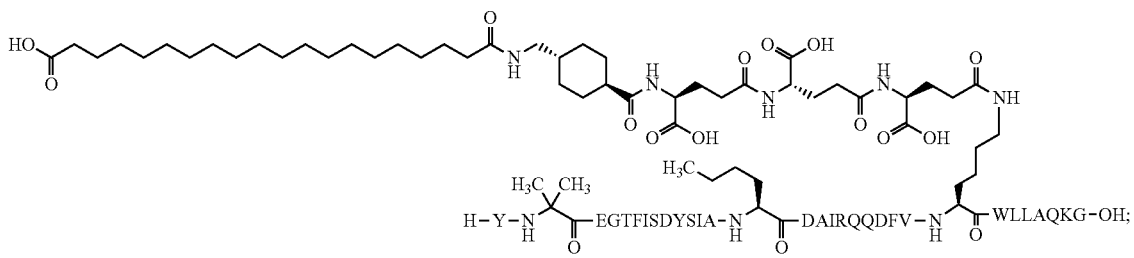

N{1}-acetyl,N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[D-Tyr1,Nle14,Arg18,Lys24]-hGIP(1-31) (Compound 15; SEQ ID NO: 20)

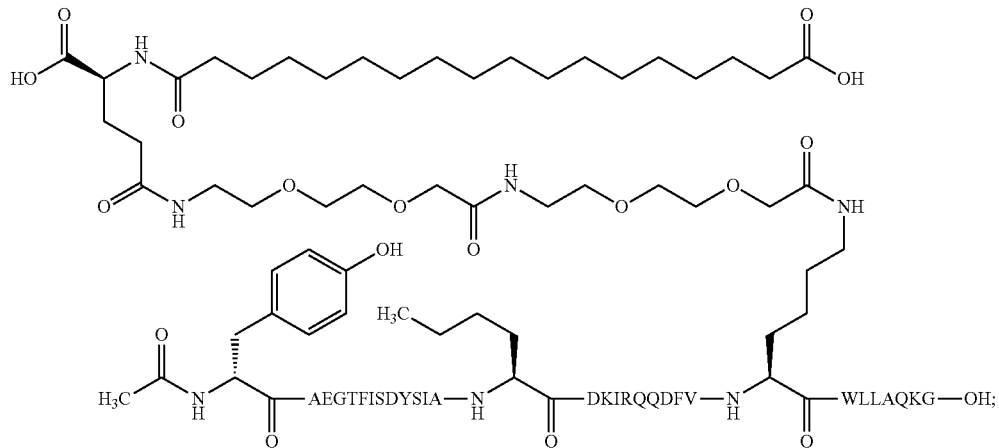

N{1}-acetyl,N{Epsilon-24}-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[D-Tyr1,Nle14,Arg18,Glu20,Lys24]-hGIP(1-31) (Compound 16; SEQ ID NO: 21)

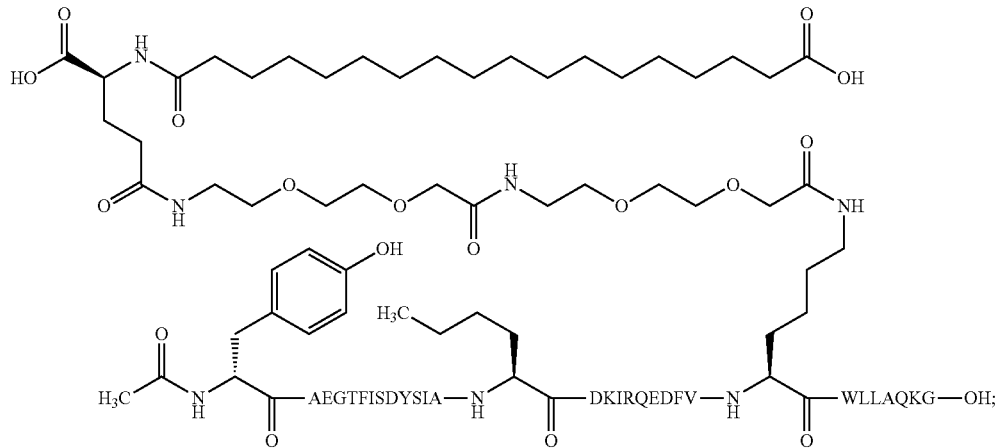

N{1}-acetyl,N{Epsilon-24}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]-butanoyl]amino]ethoxy]ethoxy]acetyl]amino]ethoxy]ethoxy]acetyl]-[D-Tyr1,Nle14,Arg18,Lys24]-hGIP(1-31) (Compound 17; SEQ ID NO: 22)

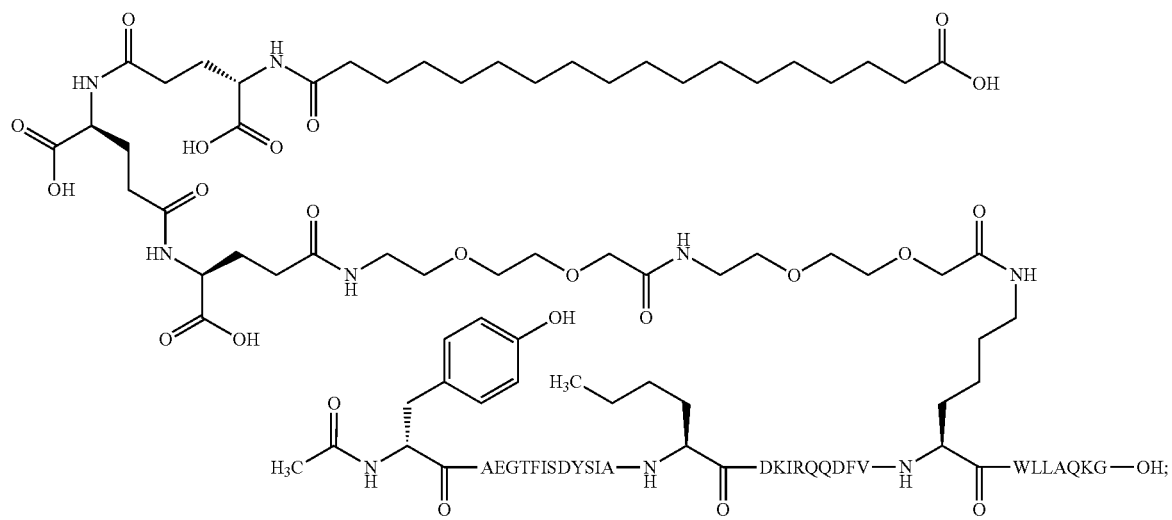
N{1}-acetyl,N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[D-Tyr1,Asp14,Arg18,Glu20,Lys24]-hGIP(1-31) (Compound 19; SEQ ID NO: 24)
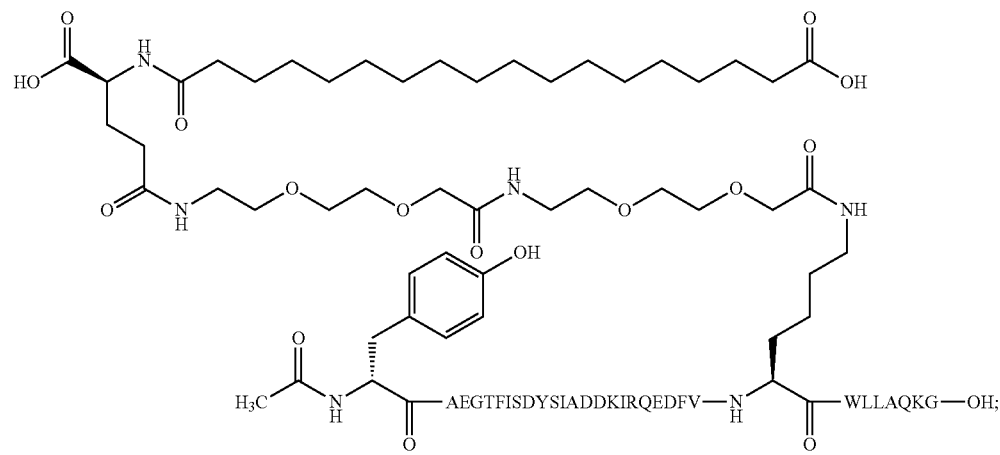
N{Epsilon-24}-[(4S)-4-carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]-amino]butanoyl]-[Aib2,Nle14,Glu20,Lys24]-hGIP(1-31) (Compound 20; SEQ ID NO: 25)
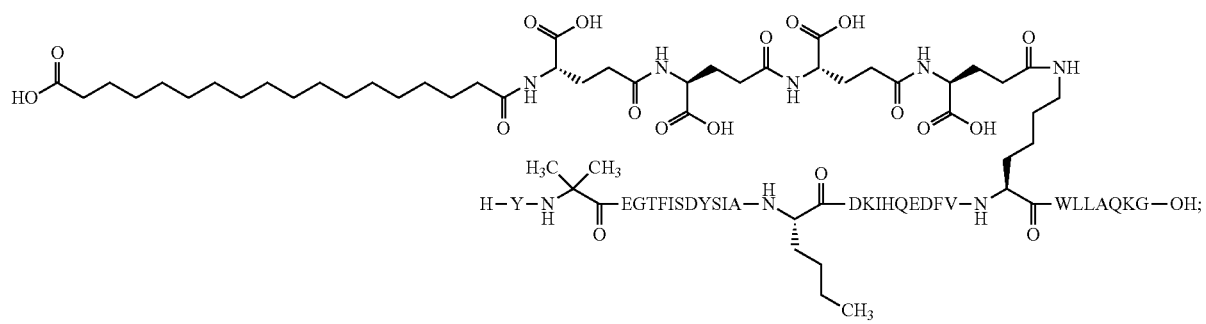

N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]-amino]butanoyl]-amino]butanoyl]amino]butanoyl]amino]butanoyl]-[Aib2,Nle14,Glu20,Lys24]-hGIP(1-31) (Compound 21; SEQ ID NO: 26)

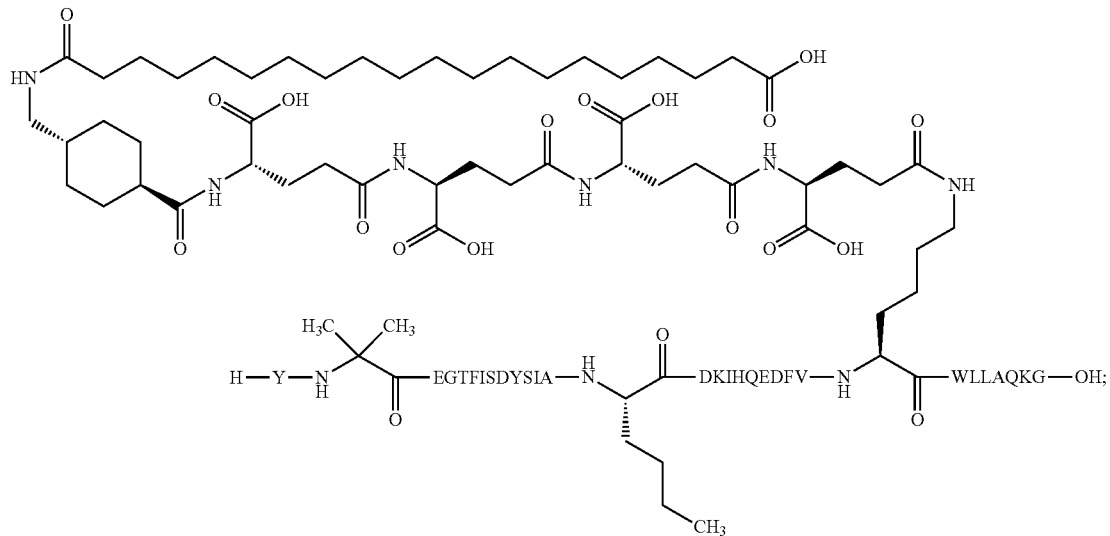

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Glu20,Lys24]-hGIP(1-31) (Compound 22; SEQ ID NO: 27)

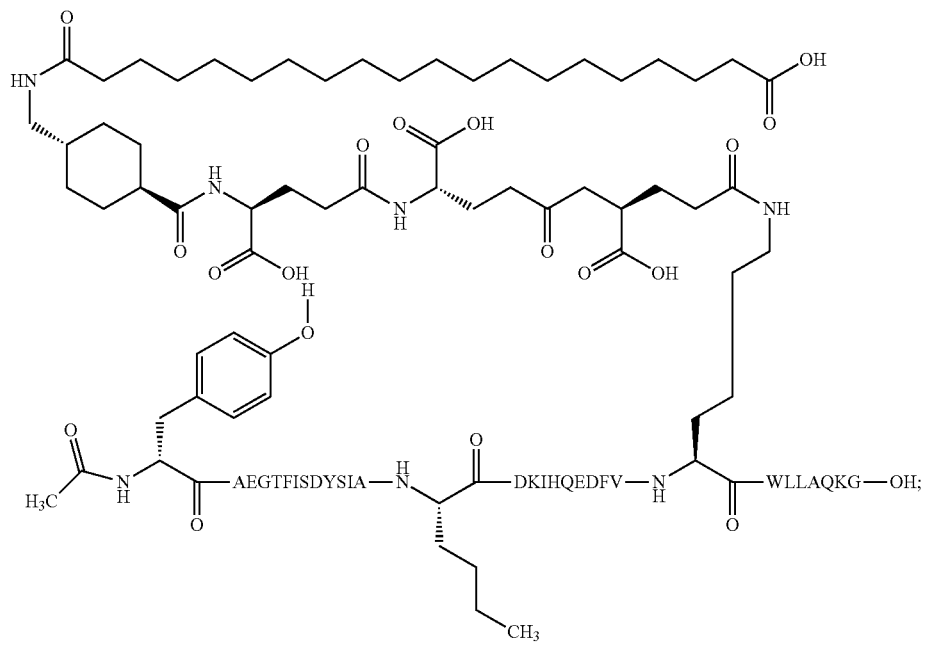

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1,Nle14,Arg18,Glu20,Lys24]-hGIP(1-31) (Compound 23; SEQ ID NO: 28)

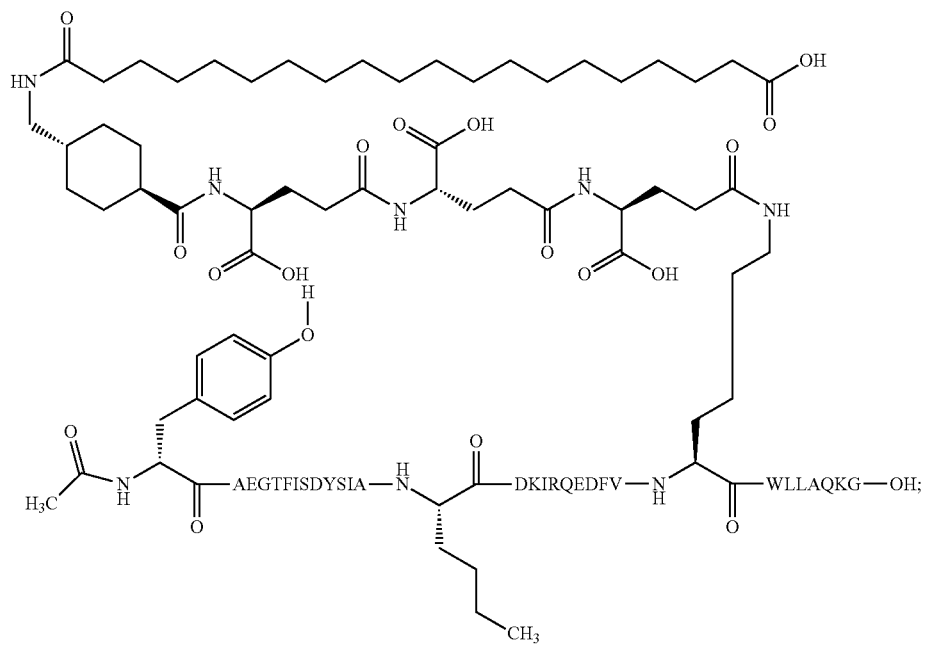

N{1}-acetyl,N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]-amino]butanoyl]amino]butanoyl]amino]butanoyl]amino]butanoyl]-[D-Tyr1,Nle14,Arg18,Lys24]-hGIP(1-31) (Compound 30; SEQ ID NO: 35)

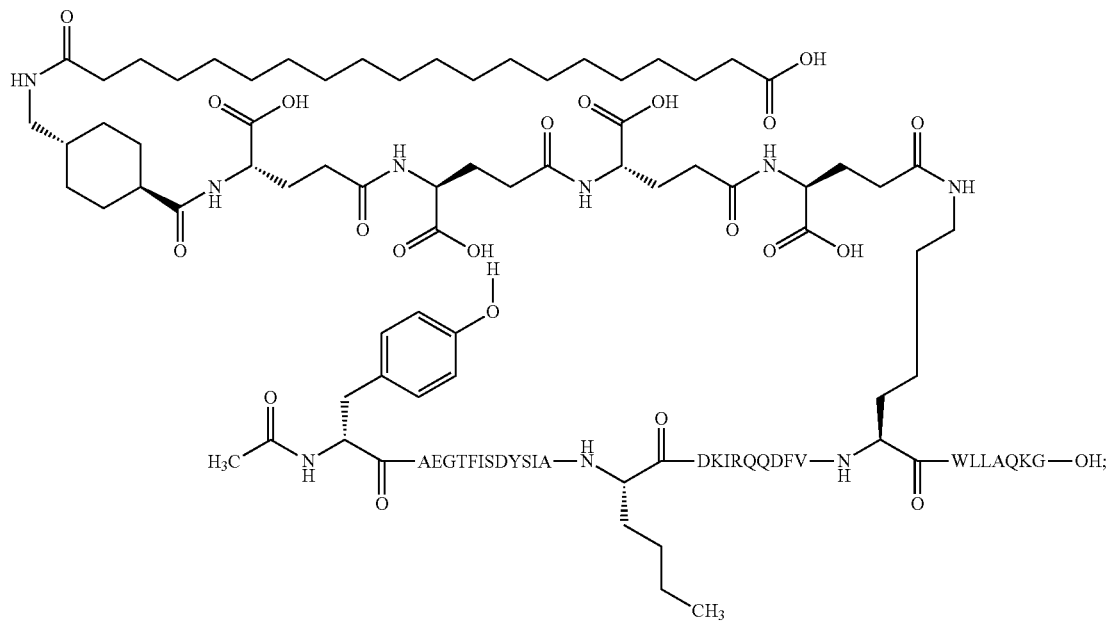

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33]-hGIP (Compound 33; SEQ ID NO: 38)

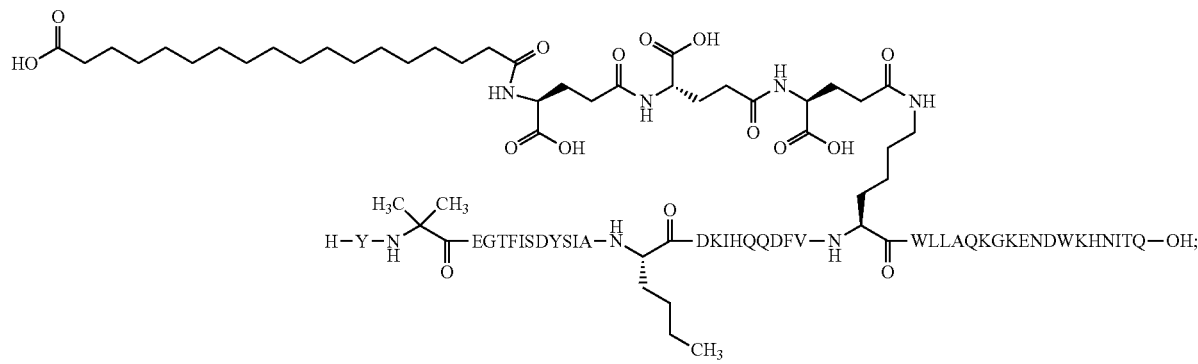

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Lys24,Glu33]-hGIP (Compound 34; SEQ ID NO: 39)

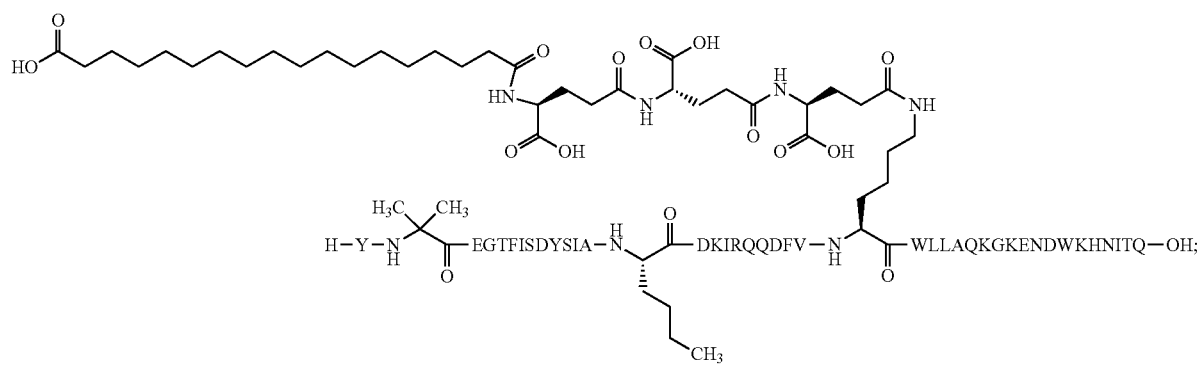

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Glu34]-hGIP (Compound 35; SEQ ID NO: 40)

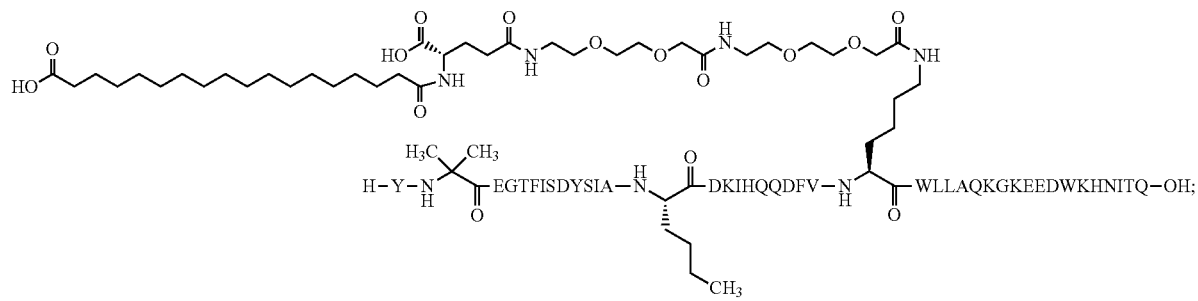

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Asp34]-hGIP (Compound 36, SEQ ID NO: 41)

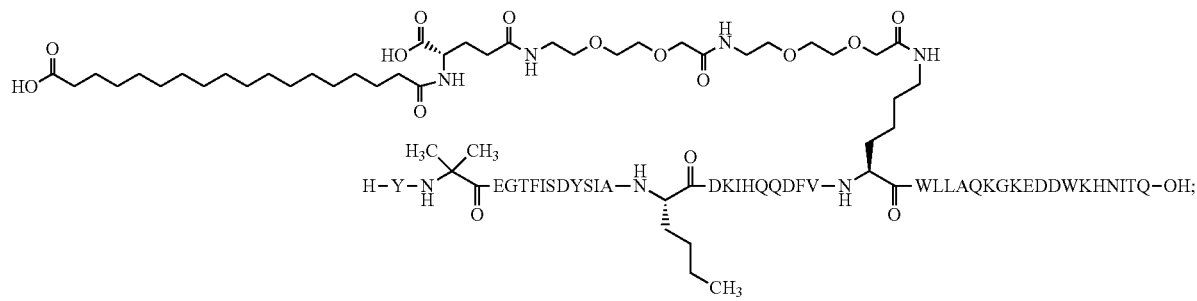

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Arg18,Lys24,Glu33,Glu34]-hGIP (Compound 37; SEQ ID NO: 42)

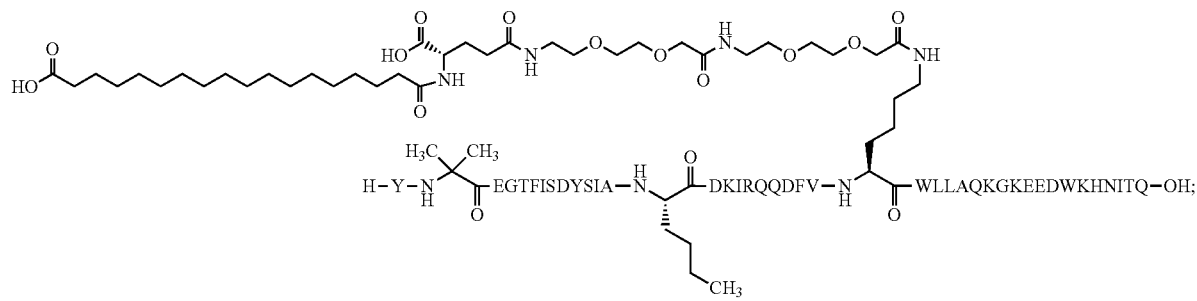

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33,Glu34]-hGIP (Compound 38; SEQ ID NO: 43)

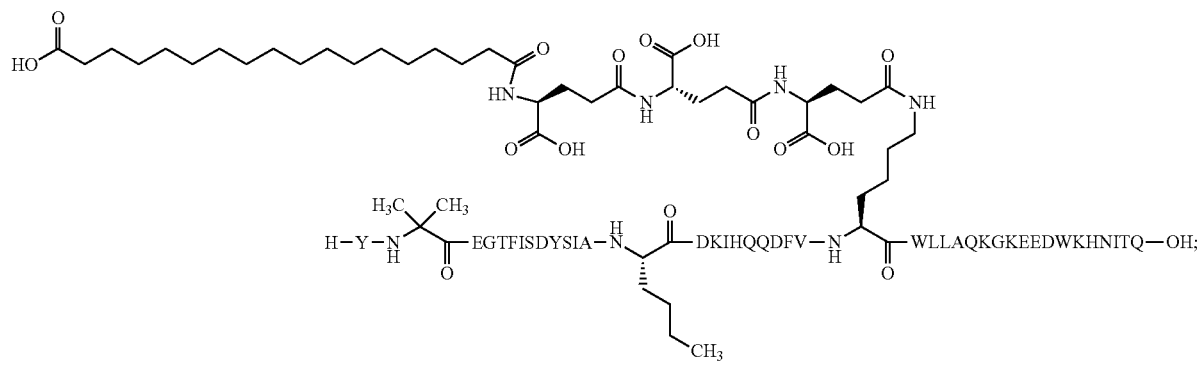

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33,Asp34]-hGIP (Compound 39; SEQ ID NO: 44)

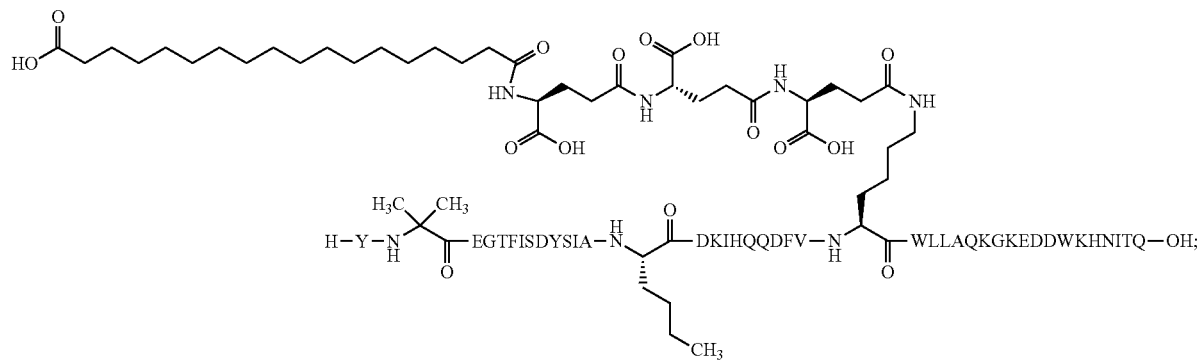
N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2, Nle14,Arg18,Lys24,Glu33,Glu34]-hGIP (Compound 40; SEQ ID NO: 45)
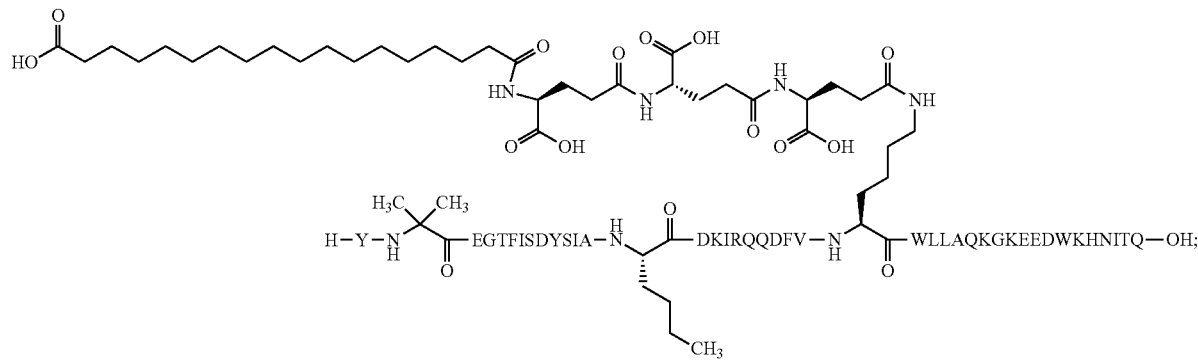
N{Epsilon-24}-[2-[2-[2-[[2-[2-[2-[[(4S)-4-carboxy-4-[[4-[(19-carboxynonadecanoyl-amino)methyl]cyclohexanecarbonyl]amino]butanoyl]amino]ethoxy]ethoxy]acetyl]amino]ethoxy]ethoxy]acetyl]-[Aib2, Nle14,Arg18,Lys24,Glu33,Glu34]-hGIP (Compound 41; SEQ ID NO: 46)
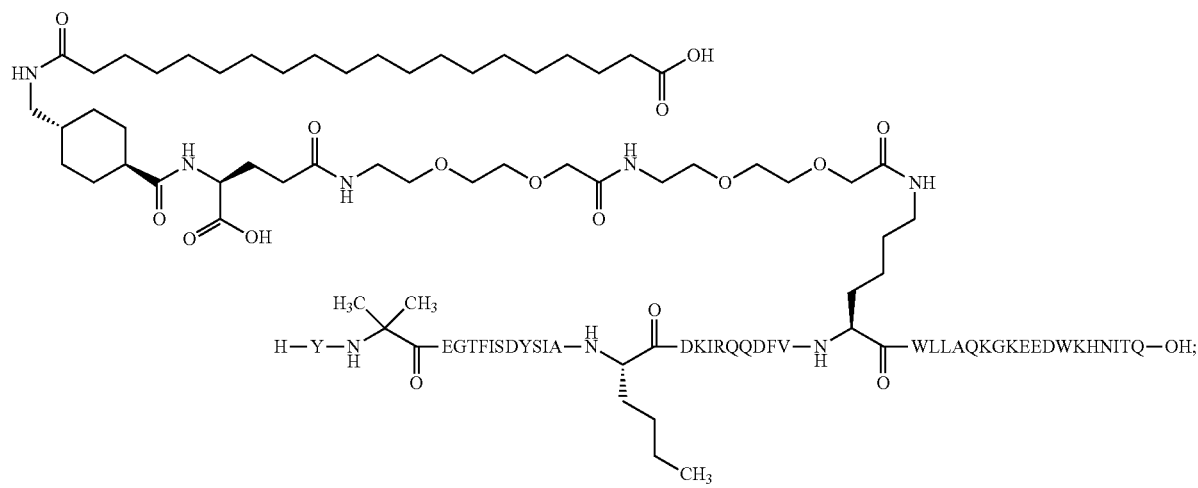

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]-[Aib2,Nle14,Arg18,Lys24,Glu33,Glu34]-hGIP (Compound 42; SEQ ID NO: 47)

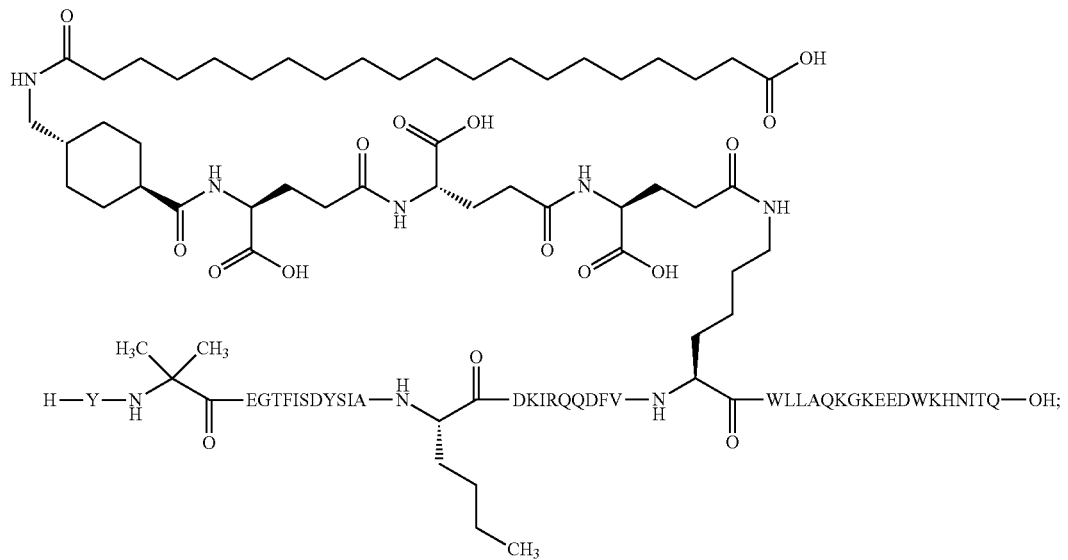

N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Nle14,Arg18,Aib20,Lys24]-hGIP(1-31) (Compound 43; SEQ ID NO: 59)

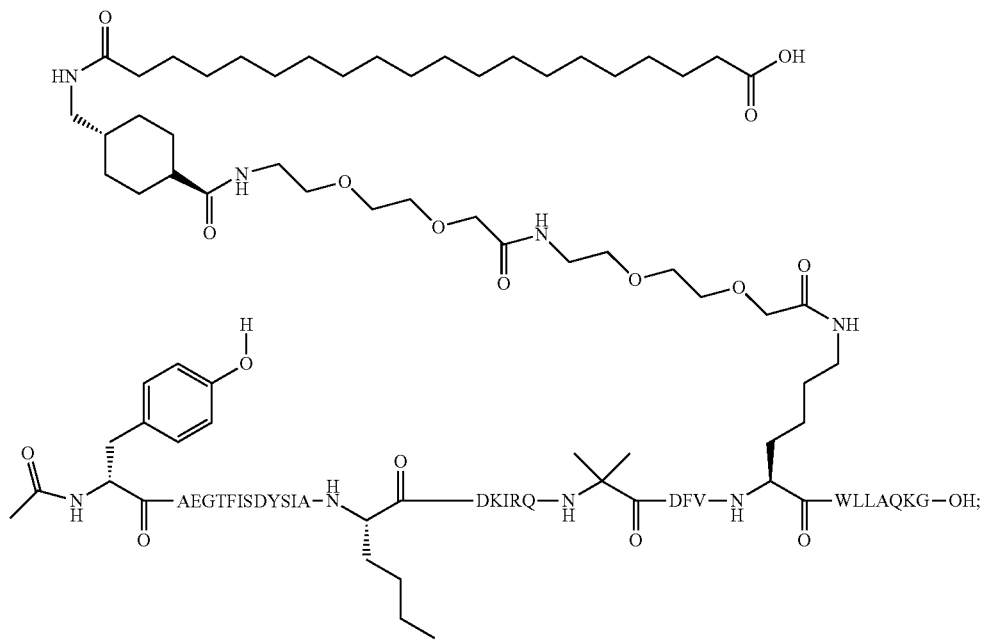

N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Aib2,Nle14,Arg18,Lys24,Pro31]-hGIP(1-31) amide (Compound 44; SEQ ID NO: 60)

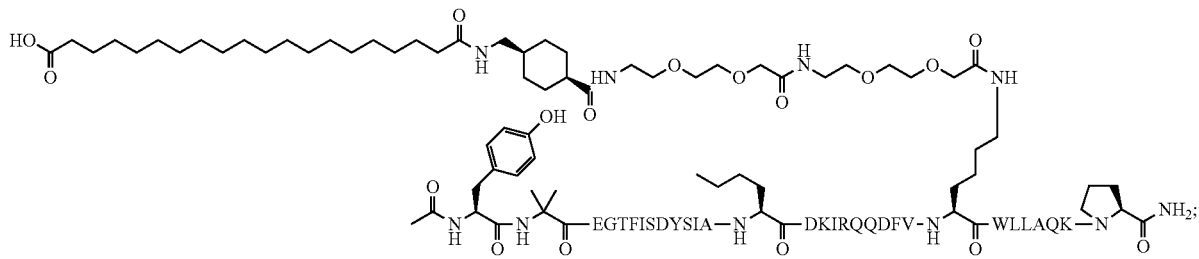

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Leu14,Lys24]-hGIP (Compound 45; SEQ ID NO: 61)

16. The pharmaceutical composition according to claim 15, wherein the GLP-1 receptor agonist is semaglutide.

17. A method of treating type II diabetes by administering an effective amount of a pharmaceutical composition to a subject in need thereof,

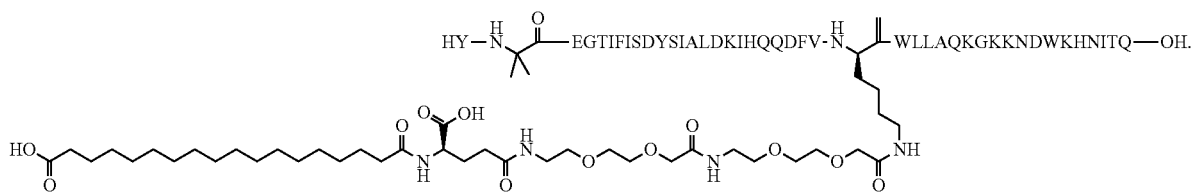

3. A pharmaceutical composition comprising the derivative according to claim 1 and at least one pharmaceutically acceptable excipient.

4. The pharmaceutical composition according to claim 3, further comprising a GLP-1 receptor agonist or a GLP-1/glucagon receptor co-agonist.

5. The pharmaceutical composition according to claim 4, wherein the GLP-1 receptor agonist is semaglutide.

6. The pharmaceutical composition according to claim 4, comprising the GIP analogue derivative as a first unit dosage form and the GLP-1 receptor agonist as a second unit dosage form.

7. The pharmaceutical composition according to claim 6, wherein the GLP-1 receptor agonist is semaglutide.

8. The pharmaceutical composition according to claim 4, wherein the pharmaceutical composition is a single-dosage form comprising both the GIP analogue derivative and the GLP-1 receptor agonist.

9. The pharmaceutical composition according to claim 8, wherein the GLP-1 receptor agonist is semaglutide.

10. A pharmaceutical composition comprising the derivative according to claim 2 and at least one pharmaceutically acceptable excipient.

11. The pharmaceutical composition according to claim 10, further comprising a GLP-1 receptor agonist or a GLP-1/glucagon receptor co-agonist.

12. The pharmaceutical composition according to claim 11, wherein the GLP-1 receptor agonist is semaglutide.

13. The pharmaceutical composition according to claim 11, comprising the GIP analogue derivative as a first unit dosage form and the GLP-1 receptor agonist as a second unit dosage form.

14. The pharmaceutical composition according to claim 13, wherein the GLP-1 receptor agonist is semaglutide.

15. The pharmaceutical composition according to claim 11, wherein the pharmaceutical composition is a single-dosage form comprising both the GIP analogue derivative and the GLP-1 receptor agonist.

wherein the pharmaceutical composition comprises a GIP analogue derivative and a GLP-1 receptor agonist;

wherein the GIP analogue derivative comprises a GIP analogue and a modifying group;

wherein the GIP analogue is (SEQ ID NO: 48):

$X_1$-$X_2$-Glu-Gly-Thr-Phe-Ile-Ser-Asp-Tyr-Ser-Ile-Ala-$X_{14}$-Asp-$X_{16}$-Ile-$X_{18}$-Gln-$X_{20}$-Asp-Phe-Val-Lys-Trp-Leu-Leu-Ala-Gln-Lys-$X_{31}$;

wherein $X_1$ is Tyr or D-Tyr;

$X_2$ is Aib, Ala, or D-Ala;

$X_{14}$ is Leu, Nle, Asp or Met;

$X_{16}$ is Lys or Ala;

$X_{18}$ is Arg or His;

$X_{20}$ is Gln, Glu or Aib;

$X_{31}$ is Gly or Pro;

wherein the modifying group is A-B-C;

wherein A is (Chem. 1)

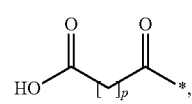

wherein p is an integer in the range of 14-20, and wherein * denotes the position of an amide bond connecting A- and B-;

wherein B is (Chem. 2)

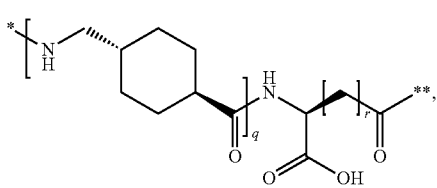

wherein q is an integer in the range of 0-1,
wherein r is an integer in the range of 1-3,
wherein * denotes the position of the amide bond connecting A- and B-,
wherein ** denotes the position of an amide bond connecting B- and C-; and
wherein C is (Chem. 3)

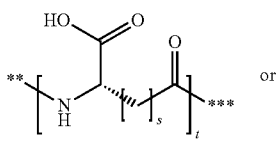 or

-continued (Chem. 4)

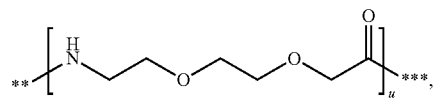

wherein s is an integer in the range of 1-3,
wherein t is an integer in the range of 1-4,
wherein u is an integer in the range of 1-3,
wherein ** denotes the position of the amide bond connecting B- and C-, and
wherein *** denotes the position of an amide bond connecting C- and the epsilon amino group of the lysine at position 24.

18. The method according to claim 17, wherein the GIP analogue derivative is selected from the group consisting of N{Epsilon-24}-[2-[2-[2-[[2-[2-[2-[[(4S)-4-carboxy-4-[[4-[(19-carboxynonadecanoylamino) methyl]cyclohexanecarbonyl]amino]butanoyl]amino]ethoxy]ethoxy]acetyl]amino]ethoxy]ethoxy]acetyl]-[Aib2,Nle14,Arg18,Lys24]-hGIP(1-31) (Compound 3; SEQ ID NO: 8)

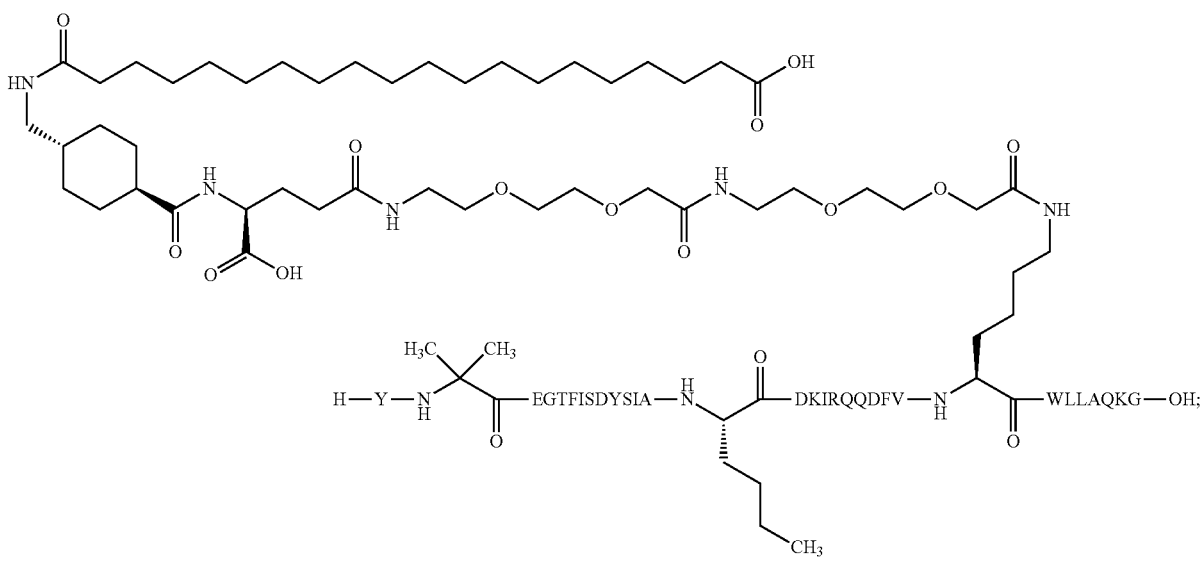

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Glu20,Lys24]-hGIP(1-31) (Compound 9; SEQ ID NO: 14)

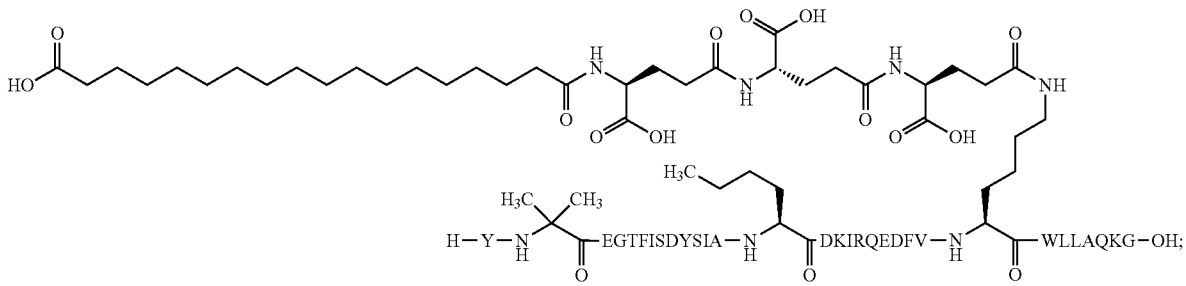

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Arg18,Glu20,Lys24]-hGIP(1-31) (Compound 10; SEQ ID NO: 15)

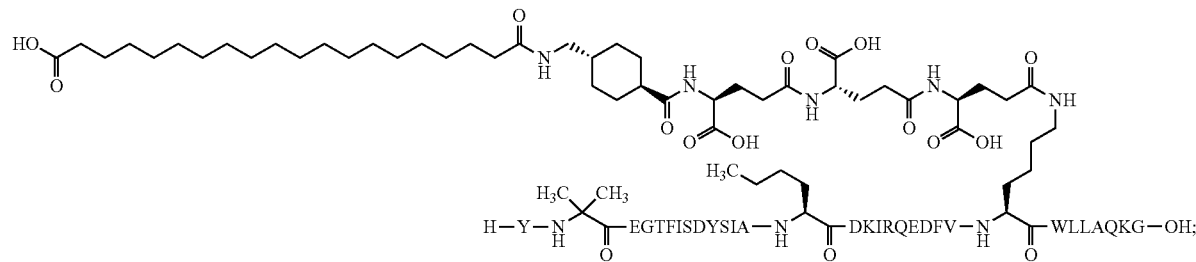

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Ala16,Arg18,Lys24]-hGIP(1-31) (Compound 13; SEQ ID NO: 18)

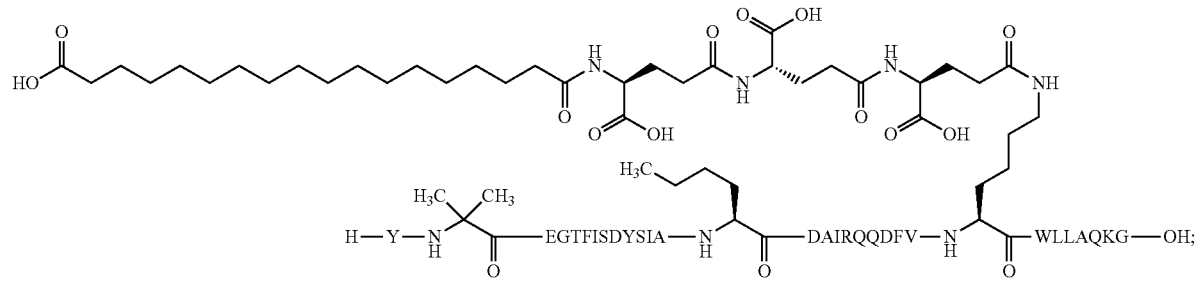

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]-butanoyl]amino]butanoyl]-[Aib2,Nle14,Ala16,Arg18,Lys24]-hGIP(1-31) (Compound 14; SEQ ID NO: 19)

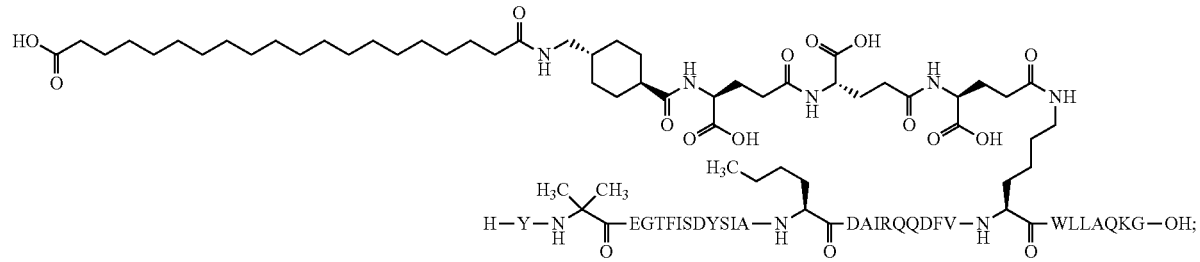

N{1}-acetyl,N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[D-Tyr1,Nle14,Arg18,Lys24]-hGIP(1-31) (Compound 15; SEQ ID NO: 20)

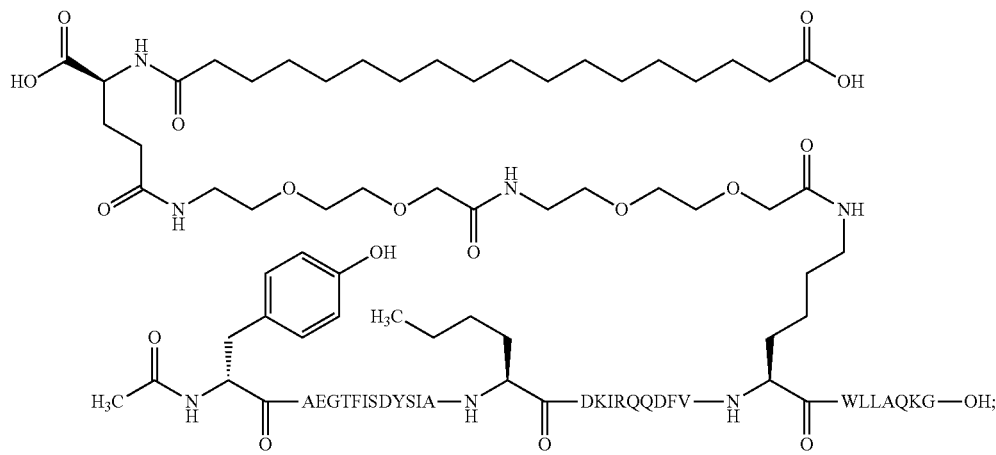

N{1}-acetyl,N{Epsilon-24}-[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]-[D-Tyr1,Nle14,Arg18,Glu20,Lys24]-hGIP(1-31) (Compound 16; SEQ ID NO: 21)

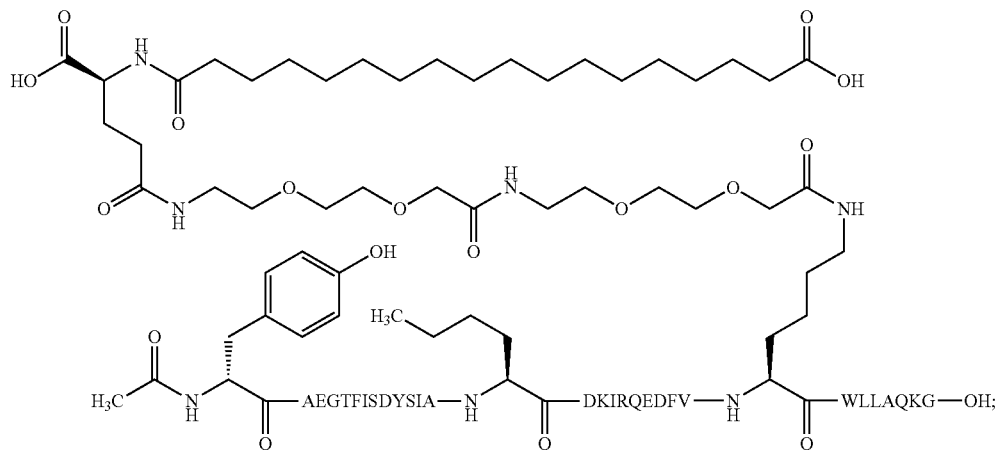

N{1}-acetyl,N{Epsilon-24}-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]-butanoyl]amino]ethoxy]ethoxy]acetyl]amino]ethoxy]ethoxy]acetyl]-[D-Tyr1,Nle14,Arg18,Lys24]-hGIP(1-31) (Compound 17; SEQ ID NO: 22)

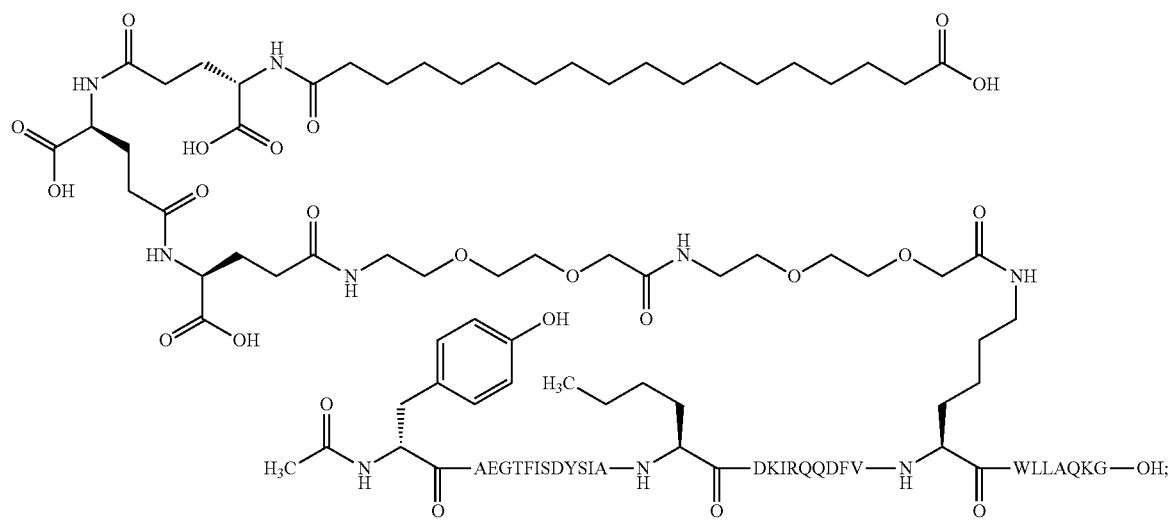
N{1}-acetyl,N{Epsilon-24}-[2-[2-[2-[[2-[2-[2-[[(4S)-4-
carboxy-4-(17-carboxyheptadecanoylamino)butanoyl]
amino]ethoxy]ethoxy]acetyl]amino]ethoxy]ethoxy]
acetyl]-[D-Tyr1,Asp14,Arg18,Glu20,Lys24]-hGIP(1-
31) (Compound 19; SEQ ID NO: 24)
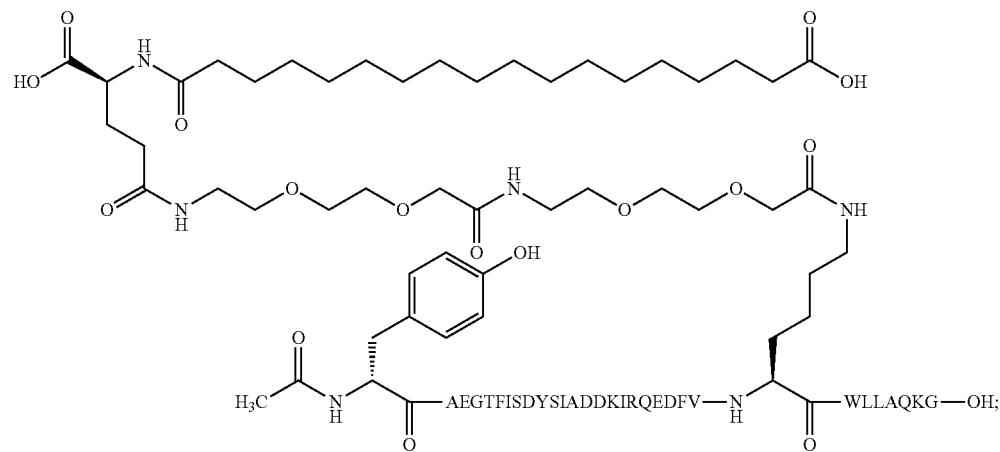
N{Epsilon-24}-[(4S)-4-carboxy-4-[[(4S)-4-carboxy-4-
[[(4S)-4-carboxy-4-[[(4S)-4-carboxy-4-(17-carboxy-
heptadecanoylamino)butanoyl]amino]butanoyl]amino]
butanoyl]-amino]butanoyl]-[Aib2,Nle14,Glu20,
Lys24]-hGIP(1-31) (Compound 20; SEQ ID NO: 25)
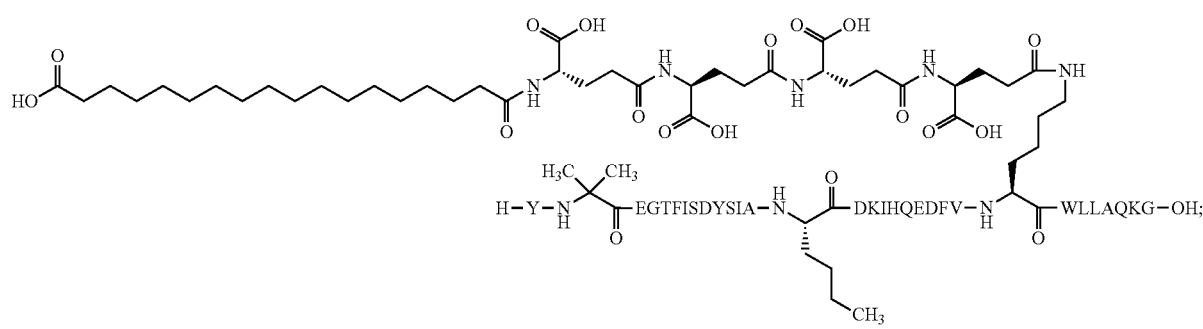

N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]-amino]butanoyl]-amino]butanoyl]amino]butanoyl]amino]butanoyl]-[Aib2,Nle14,Glu20,Lys24]-hGIP(1-31) (Compound 21; SEQ ID NO: 26)

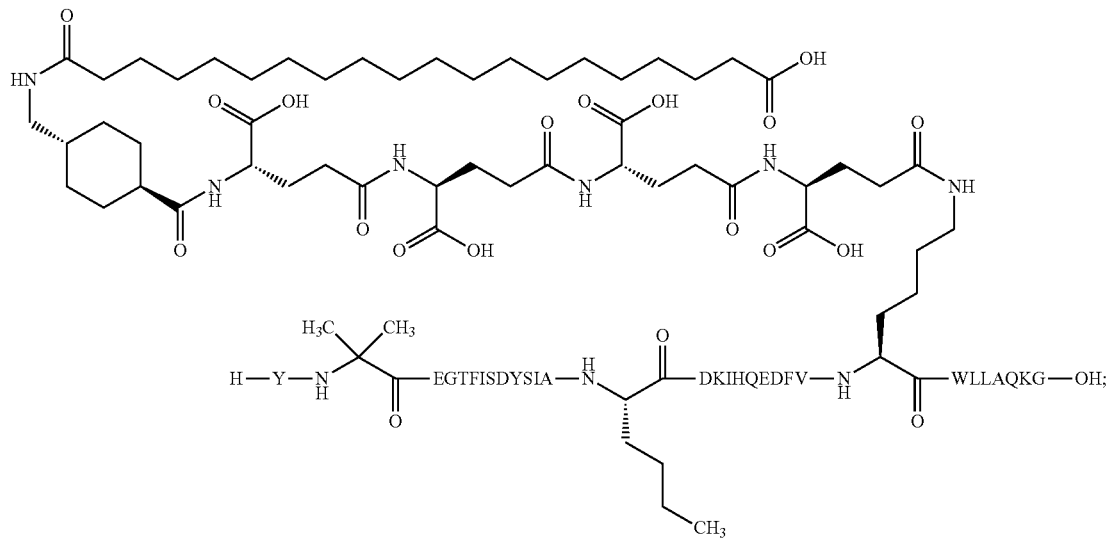

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1, Nle14,Glu20,Lys24]-hGIP(1-31) (Compound 22; SEQ ID NO: 27)

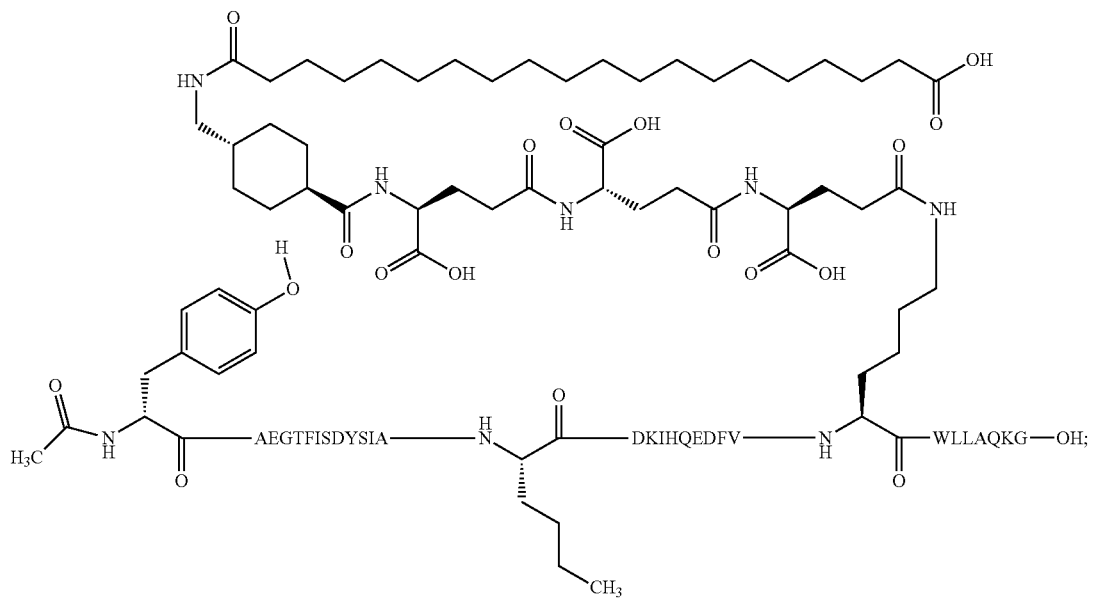

N{1}-acetyl,N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]-amino]butanoyl]amino]butanoyl]-[D-Tyr1, Nle14,Arg18,Glu20,Lys24]-hGIP(1-31) (Compound 23; SEQ ID NO: 28)

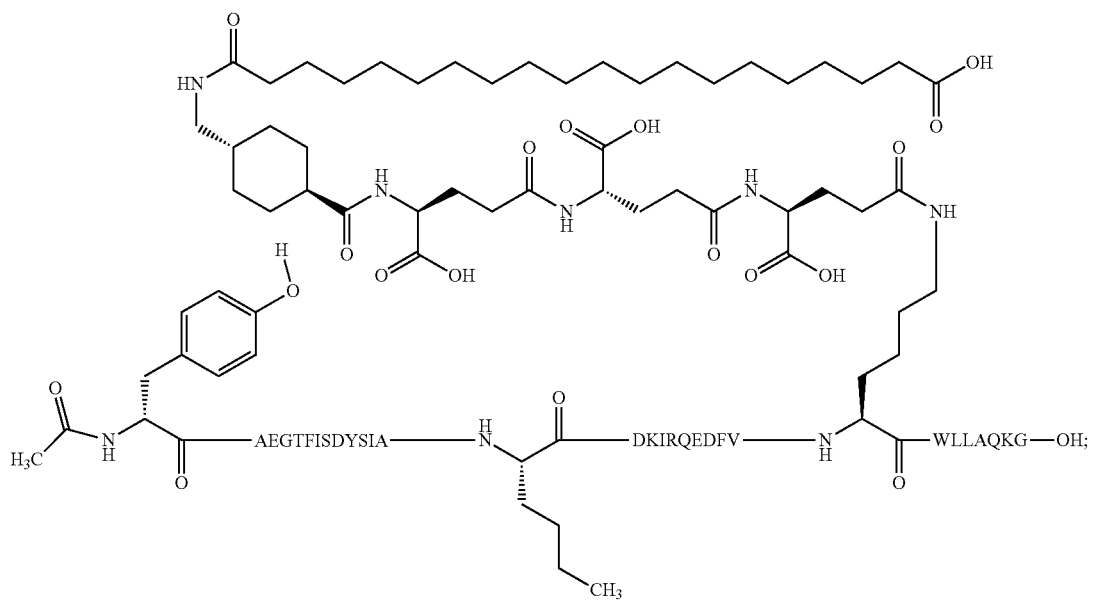

N{1}-acetyl,N{Epsilon-24}-[(4S)-4-carboxy-4-[[(4S)-4-carboxy-4-[[(4S)-4-carboxy-4-[[(4S)-4-carboxy-4-[[4-[(19-carboxynonadecanoylamino)methyl]cyclohexanecarbonyl]-amino]butanoyl]amino]butanoyl]amino]butanoyl]amino]butanoyl]-[D-Tyr1,Nle14,Arg18,Lys24]-hGIP(1-31) (Compound 30; SEQ ID NO: 35)

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33]-hGIP (Compound 33; SEQ ID NO: 38)

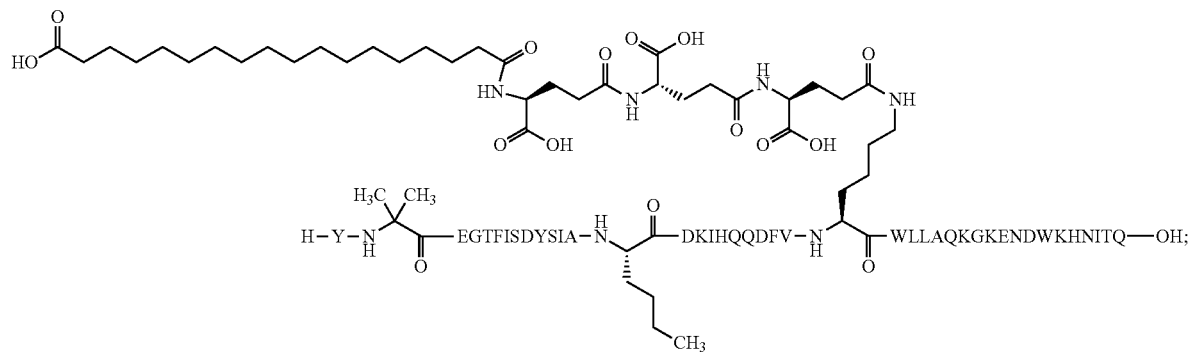

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Lys24,Glu33]-hGIP (Compound 34; SEQ ID NO: 39)

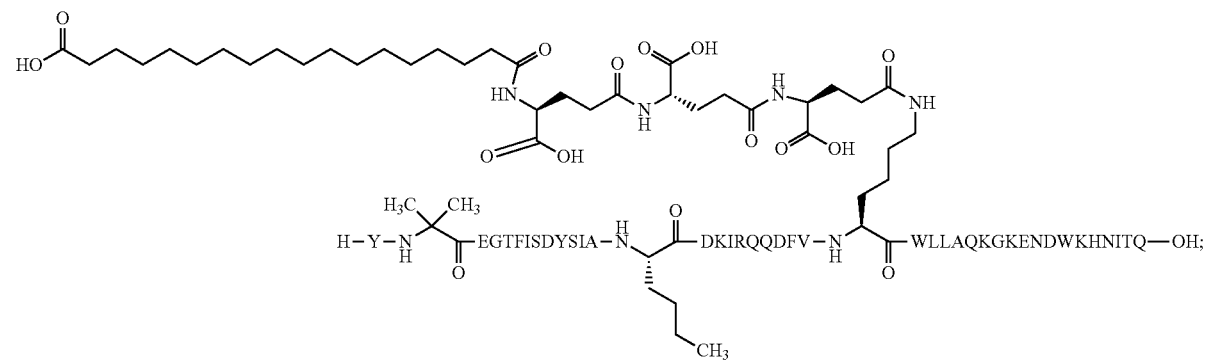

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Glu34]-hGIP (Compound 35; SEQ ID NO: 40)

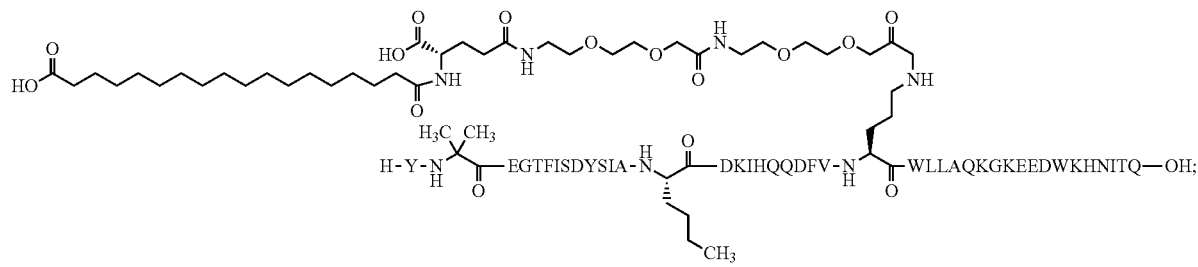

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Lys24,Glu33,Asp34]-hGIP (Compound 36, SEQ ID NO: 41)

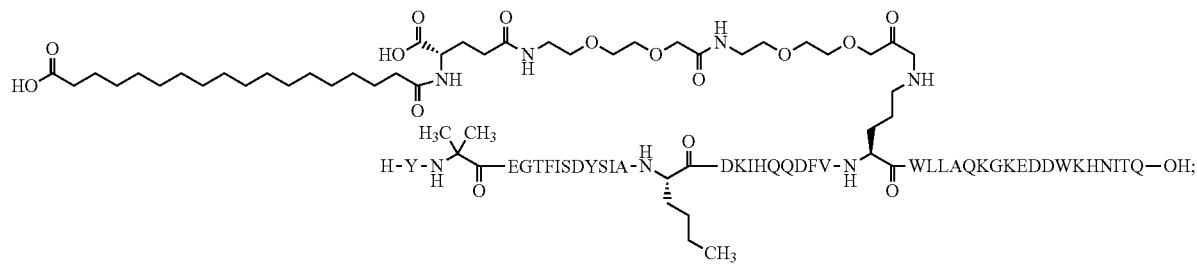

N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Nle14,Arg18,Lys24,Glu33,Glu34]-hGIP (Compound 37; SEQ ID NO: 42)

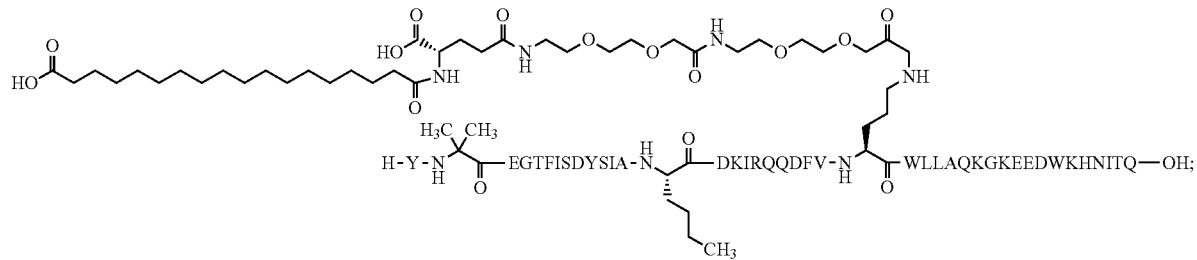

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33,Glu34]-hGIP (Compound 38; SEQ ID NO: 43)

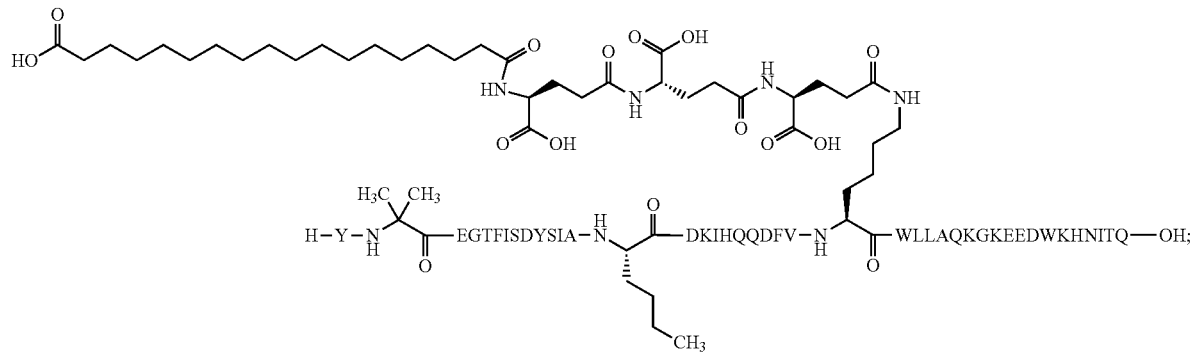

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Lys24,Glu33,Asp34]-hGIP (Compound 39; SEQ ID NO: 44)

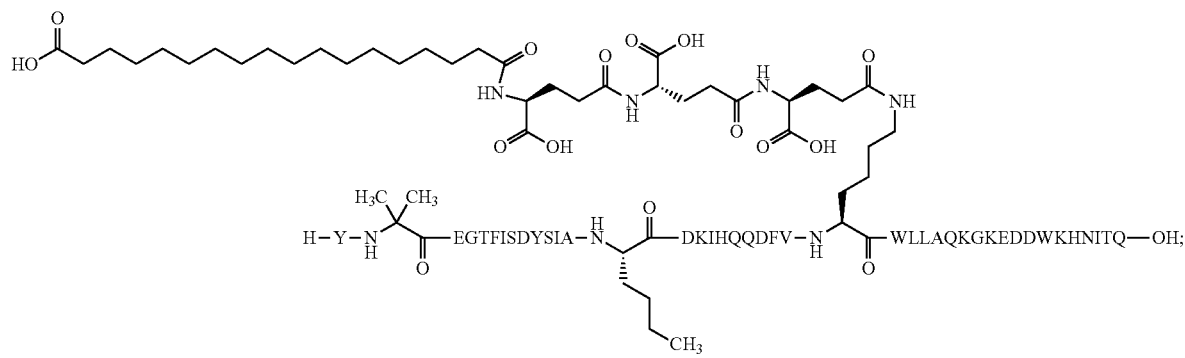

N{Epsilon-24}-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Nle14,Arg18,Lys24,Glu33,Glu34]-hGIP (Compound 40; SEQ ID NO: 45)

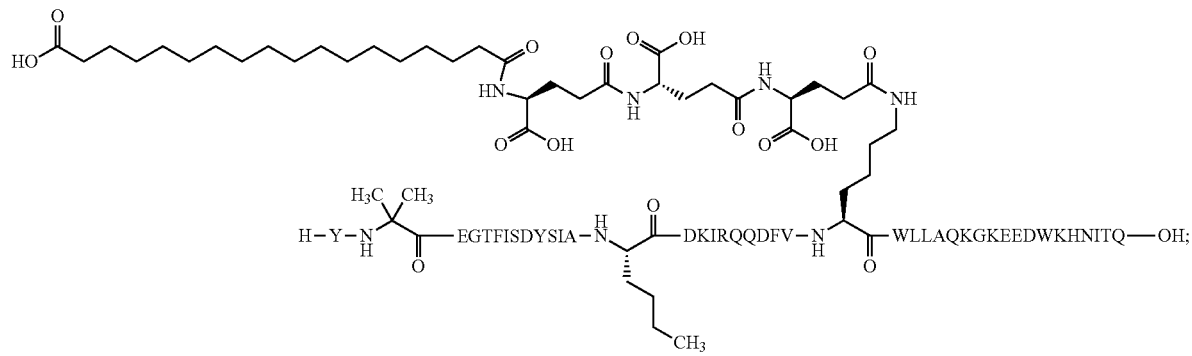

N{Epsilon-24}-[2-[2-[2-[[2-[2-[2-[[(4S)-4-carboxy-4-[[4-[(19-carboxynonadecanoyl- amino)methyl]cyclohexanecarbonyl]amino]butanoyl]amino]ethoxy]ethoxy]acetyl]amino]ethoxy]ethoxy]acetyl]-[Aib2,Nle14,Arg18,Lys24,Glu33,Glu34]-hGIP (Compound 41; SEQ ID NO: 46)

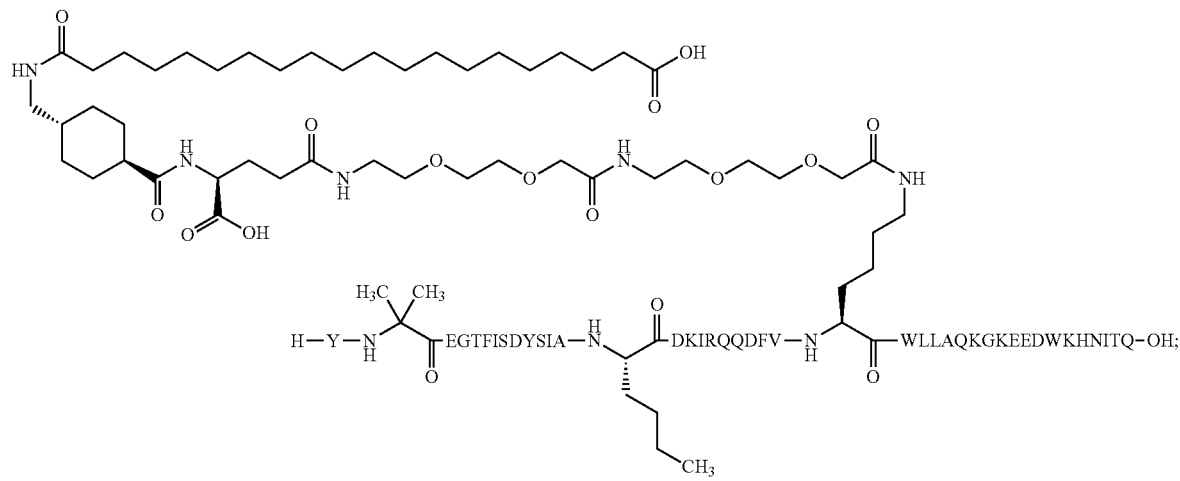

N{Epsilon-24}-[(4S)-4-carboxy-4-[[(4S)-4-carboxy-4-[[(4S)-4-carboxy-4-[[4-[(19-carboxynonadecanoylamino)methyl]cyclohexanecarbonyl]amino]butanoyl]amino]butanoyl]amino]butanoyl]-[Aib2,Nle14,Arg18,Lys24,Glu33,Glu34]-hGIP (Compound 42; SEQ ID NO: 47)

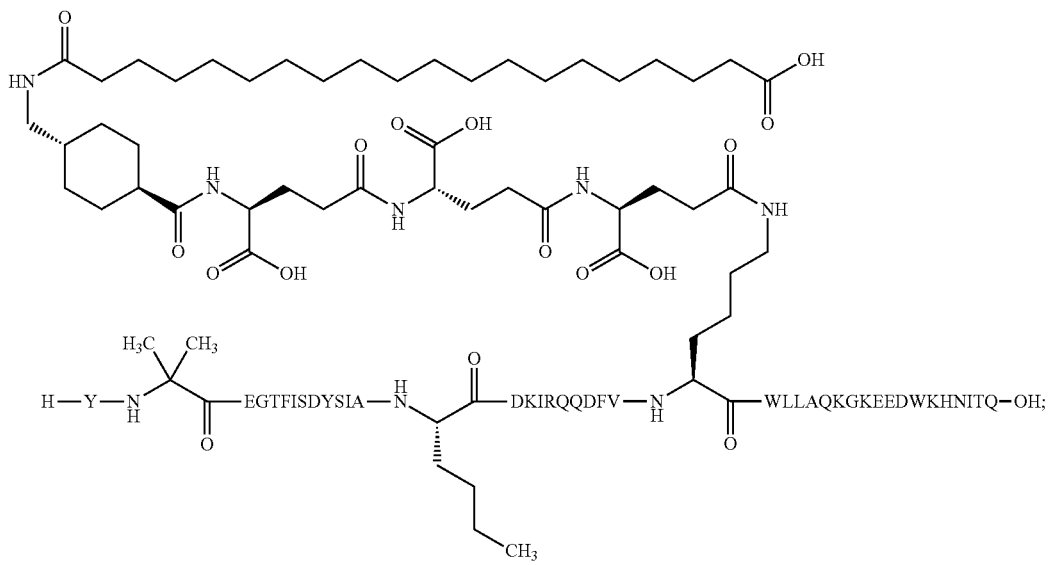
N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Nle14,Arg18,Aib20,Lys24]-hGIP(1-31) (Compound 43; SEQ ID NO: 59)
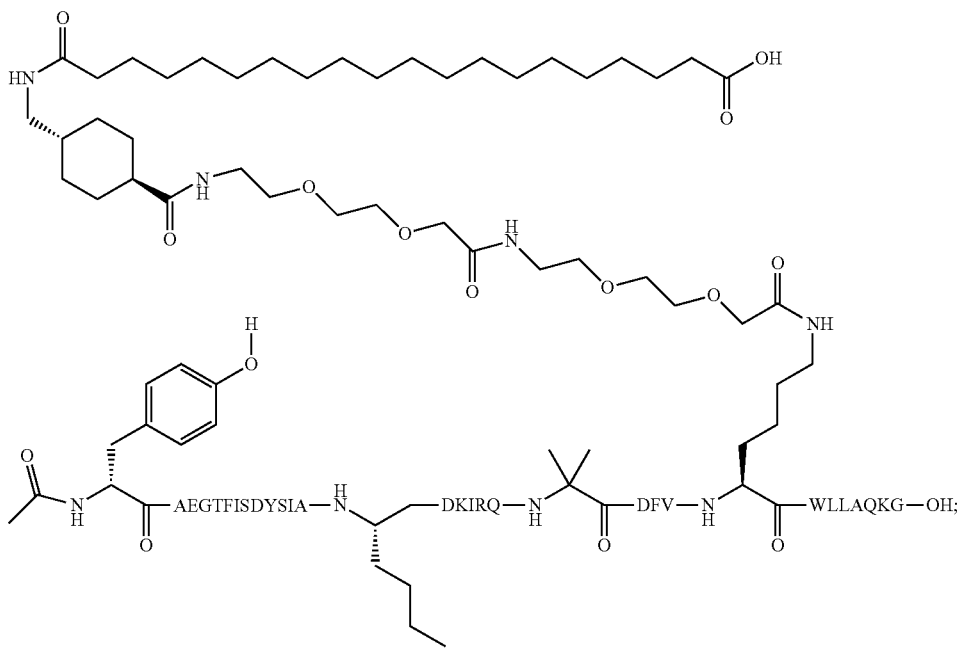
N{1}-acetyl,N{Epsilon-24}-[2-[2-[2-[[2-[2-[2-[[4-[(19-carboxynonadecanoylamino)methyl]cyclohexanecarbonyl]amino]ethoxy]ethoxy]acetyl]amino]ethoxy]ethoxy]acetyl]-[D-Tyr1,Aib2,Nle14,Arg18,Lys24,Pro31]-hGIP(1-31) amide (Compound 44; SEQ ID NO: 60)

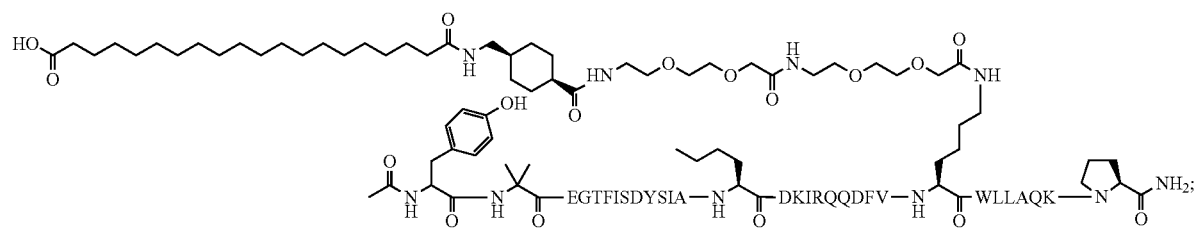
and
N{Epsilon-24}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib2,Leu14,Lys24]-hGIP (Compound 45; SEQ ID NO: 61)
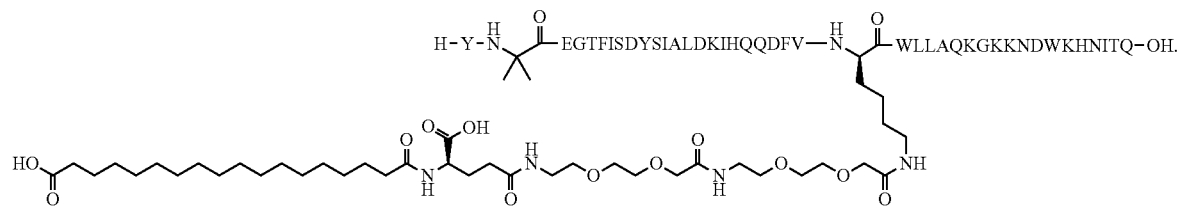
19. The method according to claim 17, wherein the GLP-1 receptor agonist is semaglutide.
* * * * *

UNITED STATES PATENT AND TRADEMARK OFFICE
CERTIFICATE OF CORRECTION

PATENT NO. : 11,633,459 B2  
APPLICATION NO. : 17/052702  
DATED : April 25, 2023  
INVENTOR(S) : Wouter Frederik Johan Hogendorf et al.

Page 1 of 1

It is certified that error appears in the above-identified patent and that said Letters Patent is hereby corrected as shown below:

In the Claims

At Column 194, Claim number 2, Line number 10, please delete:

"
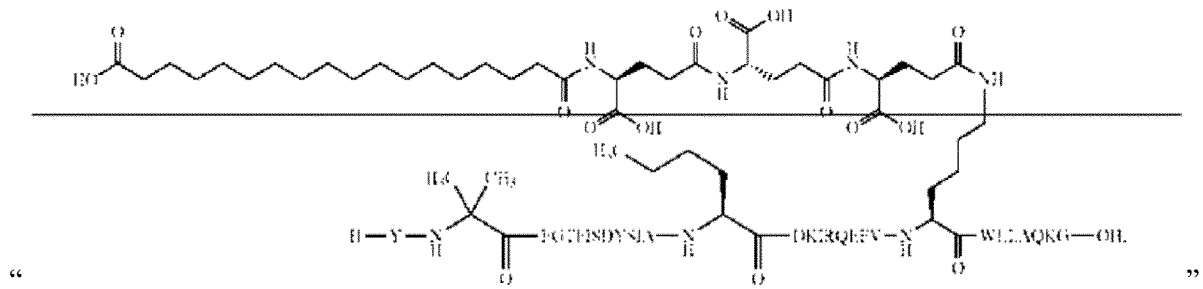
"

And replace with:

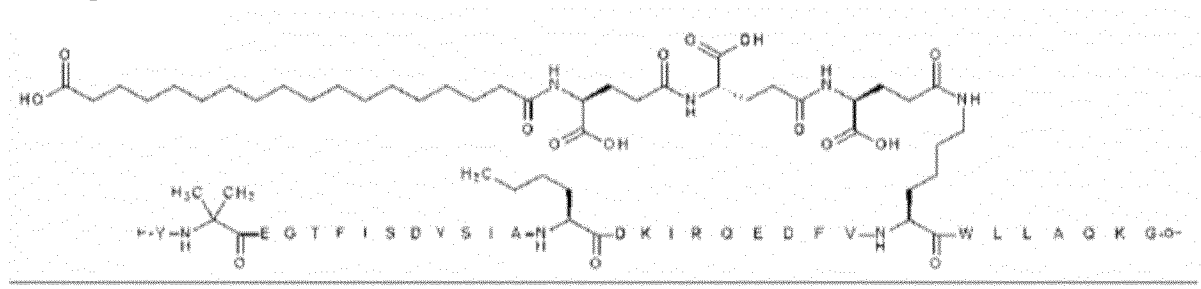

Signed and Sealed this  
Fifteenth Day of April, 2025

Coke Morgan Stewart  
*Acting Director of the United States Patent and Trademark Office*

SEQUENCE LISTING

```
<160> NUMBER OF SEQ ID NOS: 65

<210> SEQ ID NO 1
<211> LENGTH: 42
<212> TYPE: PRT
<213> ORGANISM: HOMO SAPIENS
<220> FEATURE:
<221> NAME/KEY: misc_feature
<223> OTHER INFORMATION: hGIP(1-42)

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Truncated human GIP(1-31)

<400> SEQUENCE: 2

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly
            20                  25                  30

<210> SEQ ID NO 3
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Formula I
<220> FEATURE:
<221> NAME/KEY: misc_feature
<222> LOCATION: (24)..(24)
<223> OTHER INFORMATION: Modifying group attached to epsilon amino group
      of lysine

<400> SEQUENCE: 3

Tyr Ala Glu Gly Thr Phe Ile Ser Asp Tyr Ser Ile Ala Met Asp Lys
1               5                   10                  15

Ile His Gln Gln Asp Phe Val Lys Trp Leu Leu Ala Gln Lys Gly
            20                  25                  30
```

```
<210> SEQ ID NO 4
<211> LENGTH: 31
<212> TYPE: PRT
<213> ORGANISM: HOMO SAPIENS
<220> FEATURE:
<221> NAME/KEY: misc_feature
<223> OTHER INFORMATION: human GLP-1(7-37)

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 29
<212> TYPE: PRT
<213> ORGANISM: HOMO SAPIENS
<220> FEATURE:
<221> NAME/KEY: misc_feature
<223> OTHER INFORMATION: human glucagon

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 6
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 1
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 6

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 7
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 2
```

```
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 7

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Gly
            20                  25                  30

<210> SEQ ID NO 8
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 3
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: Epsilon amino group of Lys:
      [2-[2-[2-[[2-[2-[2-[[(4S)-4-carboxy-4-[[4-[(19-
      carboxynonadecanoylamino)methyl]cyclohexanecarbonyl]amino]
      butanoyl]amino]ethoxy]ethoxy]acetyl]amino]ethoxy] ethoxy]acetyl]-

<400> SEQUENCE: 8

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 9
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 4
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
```

```
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]butanoyl]amino]butanoyl]-

<400> SEQUENCE: 9

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 10
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 5
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 10

Xaa Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 11
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 6
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
``` cyclohexanecarbonyl]amino]butanoyl]amino]butanoyl]amino]butanoyl]-

<400> SEQUENCE: 11

```
Xaa Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30
```

<210> SEQ ID NO 12
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 7
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
    following substituent: [(4S)-4-carboxy-4-[[(4S)-4-carboxy-4-
    [[(4S)-4-carboxy-4-(17-carboxyheptadecanoylamino)butanoyl]amino]
    butanoyl]amino]butanoyl]-

<400> SEQUENCE: 12

```
Xaa Ala Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30
```

<210> SEQ ID NO 13
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 8
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
    following substituent: [(4S)-4-carboxy-4-[[(4S)-4-carboxy-4-
    [[(4S)-4-carboxy-4-[[4-[(19-carboxynonadecanoylamino)methyl]
    cyclohexanecarbonyl]amino]-butanoyl]amino]butanoyl]amino]
    butanoyl]-

<400> SEQUENCE: 13

```
Xaa Ala Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30
```

```
<210> SEQ ID NO 14
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 9
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 14

Tyr Xaa Glu Gly Thr Phe Ile Ser Asp Tyr Ser Ile Ala Xaa Asp Lys
1               5                   10                  15

Ile Arg Gln Glu Asp Phe Val Lys Trp Leu Leu Ala Gln Lys Gly
            20                  25                  30

<210> SEQ ID NO 15
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 10
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]-butanoyl]amino]
      butanoyl]-

<400> SEQUENCE: 15

Tyr Xaa Glu Gly Thr Phe Ile Ser Asp Tyr Ser Ile Ala Xaa Asp Lys
1               5                   10                  15

Ile Arg Gln Glu Asp Phe Val Lys Trp Leu Leu Ala Gln Lys Gly
            20                  25                  30

<210> SEQ ID NO 16
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 11
```

-continued

```
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (20)..(20)
<223> OTHER INFORMATION: Xaa is Aib (alpha-aminoisobutyric acid)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 16

Tyr Xaa Glu Gly Thr Phe Ile Ser Asp Tyr Ser Ile Ala Xaa Asp Lys
1               5                   10                  15

Ile Arg Gln Xaa Asp Phe Val Lys Trp Leu Leu Ala Gln Lys Gly
            20                  25                  30

<210> SEQ ID NO 17
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 12
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (20)..(20)
<223> OTHER INFORMATION: Xaa is Aib (alpha-aminoisobutyric acid)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]-butanoyl]amino]
      butanoyl]-

<400> SEQUENCE: 17

Tyr Xaa Glu Gly Thr Phe Ile Ser Asp Tyr Ser Ile Ala Xaa Asp Lys
1               5                   10                  15

Ile Arg Gln Xaa Asp Phe Val Lys Trp Leu Leu Ala Gln Lys Gly
            20                  25                  30

<210> SEQ ID NO 18
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 13
<220> FEATURE:
<221> NAME/KEY: misc_feature
```

```
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 18

Tyr Xaa Glu Gly Thr Phe Ile Ser Asp Tyr Ser Ile Ala Xaa Asp Ala
1               5                   10                  15

Ile Arg Gln Gln Asp Phe Val Lys Trp Leu Leu Ala Gln Lys Gly
            20                  25                  30

<210> SEQ ID NO 19
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 14
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]-butanoyl]amino]
      butanoyl]-

<400> SEQUENCE: 19

Tyr Xaa Glu Gly Thr Phe Ile Ser Asp Tyr Ser Ile Ala Xaa Asp Ala
1               5                   10                  15

Ile Arg Gln Gln Asp Phe Val Lys Trp Leu Leu Ala Gln Lys Gly
            20                  25                  30

<210> SEQ ID NO 20
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 15
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
```

```
                     following substituent: [2-[2-[2-[[2-[2-[2-[[(4S)-4-carboxy-4-(17-
                     carboxyheptadecanoylamino)butanoyl]amino]ethoxy]ethoxy]acetyl]
                     amino]ethoxy]ethoxy]acetyl]-

<400> SEQUENCE: 20

Xaa Ala Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 21
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 16
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [2-[2-[2-[[2-[2-[2-[[(4S)-4-carboxy-4-(17-
      carboxy-heptadecanoylamino)butanoyl]amino]ethoxy]ethoxy]acetyl]
      amino]ethoxy]ethoxy]acetyl]-

<400> SEQUENCE: 21

Xaa Ala Glu Gly Thr Phe Ile Ser Asp Tyr Ser Ile Ala Xaa Asp Lys
1               5                   10                  15

Ile Arg Gln Glu Asp Phe Val Lys Trp Leu Leu Ala Gln Lys Gly
            20                  25                  30

<210> SEQ ID NO 22
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 17
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: Epsilon NH2 group of Lys has:[2-[2-[2-[[2-[2-
      [2-[[(4S)-4-carboxy-4-[[(4S)-4-carboxy-4-[[(4S)-4-carboxy-4-(17-
      carboxyheptadecanoylamino)butanoyl]amino]butanoyl]amino]-
      butanoyl]amino]ethoxy]ethoxy]acetyl]amino]ethoxy]ethoxy]acetyl]-

<400> SEQUENCE: 22

Xaa Ala Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30
```

```
<210> SEQ ID NO 23
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 18
<220> FEATURE:
<221> NAME/KEY: misc_feature
<222> LOCATION: (1)..(1)
<223> OTHER INFORMATION: N-terminal Acetyl
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 23

Tyr Ala Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 24
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 19
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (24)..(24)
<223> OTHER INFORMATION: The epsilon amino group of Lys has the
      following substituent: [2-[2-[2-[[2-[2-[2-[[(4S)-4-carboxy-4-(17-
      carboxyheptadecanoylamino)butanoyl]amino]ethoxy]ethoxy]acetyl]
      amino]ethoxy]ethoxy]acetyl]-

<400> SEQUENCE: 24

Xaa Ala Glu Gly Thr Phe Ile Ser Asp Tyr Ser Ile Ala Asp Asp Lys
1               5                   10                  15

Ile Arg Gln Glu Asp Phe Val Lys Trp Leu Leu Ala Gln Lys Gly
            20                  25                  30

<210> SEQ ID NO 25
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 20
<220> FEATURE:
<221> NAME/KEY: misc_feature
<222> LOCATION: (2)..(2)
<223> OTHER INFORMATION: Xaa is Aib (alpha-aminoisobutyric acid)
```

```
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[(4S)-4-carboxy-4-(17-
      carboxyheptadecanoylamino)butanoyl]amino]butanoyl]amino]butanoyl]-
      amino]butanoyl]-

<400> SEQUENCE: 25

Tyr Xaa Glu Gly Thr Phe Ile Ser Asp Tyr Ser Ile Ala Xaa Asp Lys
1               5                   10                  15

Ile His Gln Glu Asp Phe Val Lys Trp Leu Leu Ala Gln Lys Gly
            20                  25                  30

<210> SEQ ID NO 26
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 21
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: Epsilon amino group of Lys has:[(4S)-4-carboxy-
      4-[[(4S)-4-carboxy-4-[[(4S)-4-carboxy-4-[[(4S)-4-carboxy-4-[[4-
      [(19-carboxynonadecanoylamino)methyl]cyclohexanecarbonyl]-amino]
      butanoyl]-amino]butanoyl]amino]butanoyl]amino]butanoyl]-

<400> SEQUENCE: 26

Tyr Xaa Glu Gly Thr Phe Ile Ser Asp Tyr Ser Ile Ala Xaa Asp Lys
1               5                   10                  15

Ile His Gln Glu Asp Phe Val Lys Trp Leu Leu Ala Gln Lys Gly
            20                  25                  30

<210> SEQ ID NO 27
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 22
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
``` cyclohexanecarbonyl]amino]butanoyl]-amino]butanoyl]amino]
butanoyl]-

<400> SEQUENCE: 27

Xaa Ala Glu Gly Thr Phe Ile Ser Asp Tyr Ser Ile Ala Xaa Asp Lys
1               5                   10                  15

Ile His Gln Glu Asp Phe Val Lys Trp Leu Leu Ala Gln Lys Gly
            20                  25                  30

<210> SEQ ID NO 28
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 23
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]-amino]butanoyl]amino]
      butanoyl]-

<400> SEQUENCE: 28

Xaa Ala Glu Gly Thr Phe Ile Ser Asp Tyr Ser Ile Ala Xaa Asp Lys
1               5                   10                  15

Ile Arg Gln Glu Asp Phe Val Lys Trp Leu Leu Ala Gln Lys Gly
            20                  25                  30

<210> SEQ ID NO 29
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 24
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (20)..(20)
<223> OTHER INFORMATION: Xaa is Aib (alpha-aminoisobutyric acid)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]-amino]butanoyl]amino]
      butanoyl]-

<400> SEQUENCE: 29

```
Xaa Ala Glu Gly Thr Phe Ile Ser Asp Tyr Ser Ile Ala Xaa Asp Lys
1               5                   10                  15

Ile His Gln Xaa Asp Phe Val Lys Trp Leu Leu Ala Gln Lys Gly
            20                  25                  30
```

<210> SEQ ID NO 30
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 25
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (20)..(20)
<223> OTHER INFORMATION: Xaa is Aib (alpha-aminoisobutyric acid)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]-amino]butanoyl]amino]
      butanoyl]-

<400> SEQUENCE: 30

```
Xaa Ala Glu Gly Thr Phe Ile Ser Asp Tyr Ser Ile Ala Xaa Asp Lys
1               5                   10                  15

Ile Arg Gln Xaa Asp Phe Val Lys Trp Leu Leu Ala Gln Lys Gly
            20                  25                  30
```

<210> SEQ ID NO 31
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 26
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]-butanoyl]amino]
      butanoyl]-
<220> FEATURE:
<221> NAME/KEY: misc_feature
<222> LOCATION: (31)..(31)
<223> OTHER INFORMATION: C-terminal amidation

<400> SEQUENCE: 31

```
Tyr Xaa Glu Gly Thr Phe Ile Ser Asp Tyr Ser Ile Ala Xaa Asp Lys
```

```
                1               5                   10                  15
Ile Arg Gln Gln Asp Phe Val Lys Trp Leu Leu Ala Gln Lys Pro
            20                  25                  30

<210> SEQ ID NO 32
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 27
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]-butanoyl]amino]
      butanoyl]-
<220> FEATURE:
<221> NAME/KEY: misc_feature
<222> LOCATION: (31)..(31)
<223> OTHER INFORMATION: C-terminal amidation

<400> SEQUENCE: 32

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Pro
            20                  25                  30

<210> SEQ ID NO 33
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 28
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]-amino]butanoyl]amino]
      butanoyl]-
<220> FEATURE:
<221> NAME/KEY: misc_feature
<222> LOCATION: (31)..(31)
<223> OTHER INFORMATION: C-terminal amidation

<400> SEQUENCE: 33

Xaa Ala Glu Gly Thr Phe Ile Ser Asp Tyr Ser Ile Ala Xaa Asp Lys
1               5                   10                  15
```

Ile Arg Gln Gln Asp Phe Val Lys Trp Leu Leu Ala Gln Lys Pro
            20                  25                  30

<210> SEQ ID NO 34
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 29
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]-amino]butanoyl]amino]
      butanoyl]-
<220> FEATURE:
<221> NAME/KEY: misc_feature
<222> LOCATION: (31)..(31)
<223> OTHER INFORMATION: C-terminal amidation

<400> SEQUENCE: 34

Xaa Ala Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Pro
            20                  25                  30

<210> SEQ ID NO 35
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 30
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: Epsilon amino group of Lys has:[(4S)-4-carboxy-
      4-[[(4S)-4-carboxy-4-[[(4S)-4-carboxy-4-[[(4S)-4-carboxy-4-[[4-
      [(19-carboxynonadecanoylamino)methyl]cyclohexanecarbonyl]-
      amino]butanoyl]amino]butanoyl]amino]butanoyl]amino]butanoyl]-

<400> SEQUENCE: 35

Xaa Ala Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly
            20                  25                  30

<210> SEQ ID NO 36

```
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 31
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has:[(4S)-4-
      carboxy-4-[[(4S)-4-carboxy-4-[[(4S)-4-carboxy-4-[[(4S)-4-carboxy-
      4-[[4-[(19-carboxynonadecanoylamino)methyl]cyclohexanecarbonyl]-
      amino]butanoyl]amino]butanoyl]amino]butanoyl]amino]butanoyl]-
<220> FEATURE:
<221> NAME/KEY: misc_feature
<222> LOCATION: (31)..(31)
<223> OTHER INFORMATION: C-terminal amidation

<400> SEQUENCE: 36

Xaa Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Pro
            20                  25                  30

<210> SEQ ID NO 37
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 32
<220> FEATURE:
<221> NAME/KEY: misc_feature
<222> LOCATION: (1)..(1)
<223> OTHER INFORMATION: Xaa is N-acetyl D-Tyr
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]-amino]butanoyl]amino]
      butanoyl]-
<220> FEATURE:
<221> NAME/KEY: misc_feature
<222> LOCATION: (31)..(31)
<223> OTHER INFORMATION: C-terminal amidation

<400> SEQUENCE: 37

Xaa Xaa Glu Gly Thr Phe Ile Ser Asp Tyr Ser Ile Ala Xaa Asp Lys
1               5                   10                  15
```

```
Ile His Gln Gln Asp Phe Val Lys Trp Leu Leu Ala Gln Lys Pro
            20                  25                  30

<210> SEQ ID NO 38
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 33
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 38

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Gly Lys
            20                  25                  30

Glu Asn Asp Trp Lys His Asn Ile Thr Gln
        35                  40

<210> SEQ ID NO 39
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 34
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: [(4S)-4-carboxy-4-[[(4S)-4-carboxy-4-[[(4S)-4-
      carboxy-4-(17-carboxyheptadecanoylamino)butanoyl]amino]butanoyl]
      amino]butanoyl]-

<400> SEQUENCE: 39

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly Lys
            20                  25                  30

Glu Asn Asp Trp Lys His Asn Ile Thr Gln
        35                  40

<210> SEQ ID NO 40
```

```
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 35
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [2-[2-[2-[[2-[2-[2-[[(4S)-4-carboxy-4-(17-
      carboxyheptadecanoylamino)butanoyl]amino]ethoxy]ethoxy]acetyl]
      amino]ethoxy]ethoxy]acetyl]-

<400> SEQUENCE: 40

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Gly Lys
            20                  25                  30

Glu Glu Asp Trp Lys His Asn Ile Thr Gln
        35                  40

<210> SEQ ID NO 41
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 36
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [2-[2-[2-[[2-[2-[2-[[(4S)-4-carboxy-4-(17-
      carboxyheptadecanoylamino)butanoyl]amino]ethoxy]ethoxy]acetyl]
      amino]ethoxy]ethoxy]acetyl]-

<400> SEQUENCE: 41

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Gly Lys
            20                  25                  30

Glu Asp Asp Trp Lys His Asn Ile Thr Gln
        35                  40

<210> SEQ ID NO 42
<211> LENGTH: 42
<212> TYPE: PRT
<213> ORGANISM: ARTIFICIAL
<220> FEATURE:
<223> OTHER INFORMATION: Synthetic polypeptide
```

```
<220> FEATURE:
<221> NAME/KEY: misc_feature
<223> OTHER INFORMATION: Compound 37
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [2-[2-[2-[[2-[2-[2-[[(4S)-4-carboxy-4-(17-
      carboxyheptadecanoylamino)butanoyl]amino]ethoxy]ethoxy]acetyl]
      amino]ethoxy]ethoxy]acetyl]-

<400> SEQUENCE: 42

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly Lys
            20                  25                  30

Glu Glu Asp Trp Lys His Asn Ile Thr Gln
        35                  40

<210> SEQ ID NO 43
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 38
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 43

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Gly Lys
            20                  25                  30

Glu Glu Asp Trp Lys His Asn Ile Thr Gln
        35                  40

<210> SEQ ID NO 44
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 39
<220> FEATURE:
<221> NAME/KEY: misc_feature
```

```
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 44

Tyr Xaa Glu Gly Thr Phe Ile Ser Asp Tyr Ser Ile Ala Xaa Asp Lys
1               5                   10                  15

Ile His Gln Gln Asp Phe Val Lys Trp Leu Leu Ala Gln Lys Gly Lys
            20                  25                  30

Glu Asp Asp Trp Lys His Asn Ile Thr Gln
        35                  40

<210> SEQ ID NO 45
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 40
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-(17-carboxyheptadecanoylamino)butanoyl]amino]
      butanoyl]amino]butanoyl]-

<400> SEQUENCE: 45

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly Lys
            20                  25                  30

Glu Glu Asp Trp Lys His Asn Ile Thr Gln
        35                  40

<210> SEQ ID NO 46
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 41
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
```

```
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [2-[2-[2-[[2-[2-[2-[[(4S)-4-carboxy-4-[[4-
      [(19-carboxynonadecanoyl-amino)methyl]cyclohexanecarbonyl]amino]
      butanoyl]amino]ethoxy]ethoxy]acetyl]amino]ethoxy]ethoxy]acetyl]-

<400> SEQUENCE: 46

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly Lys
            20                  25                  30

Glu Glu Asp Trp Lys His Asn Ile Thr Gln
            35                  40

<210> SEQ ID NO 47
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Compound 42
<220> FEATURE:
<221> NAME/KEY: misc_feature
<222> LOCATION: (2)..(2)
<223> OTHER INFORMATION: Xaa is Aib (alpha-aminoisobutyric acid)
<220> FEATURE:
<221> NAME/KEY: misc_feature
<222> LOCATION: (14)..(14)
<223> OTHER INFORMATION: Xaa is Nle (Norleucine)
<220> FEATURE:
<221> NAME/KEY: misc_feature
<222> LOCATION: (24)..(24)
<223> OTHER INFORMATION: The epsilon amino group of Lys has the
      following substituent: [(4S)-4-carboxy-4-[[(4S)-4-carboxy-4-
      [[(4S)-4-carboxy-4-[[4-[(19-carboxynonadecanoylamino)methyl]
      cyclohexanecarbonyl]amino]butanoyl]amino]butanoyl]amino]butanoyl]-

<400> SEQUENCE: 47

Tyr Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Gly Lys
            20                  25                  30

Glu Glu Asp Trp Lys His Asn Ile Thr Gln
            35                  40

<210> SEQ ID NO 48
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Formula II
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is any amino acid
```

```
<220> FEATURE:
<221> NAME/KEY: misc_feature
<222> LOCATION: (16)..(16)
<223> OTHER INFORMATION: Xaa is any amino acid
<220> FEATURE:
<221> NAME/KEY: misc_feature
<222> LOCATION: (18)..(18)
<223> OTHER INFORMATION: Xaa is any amino acid
<220> FEATURE:
<221> NAME/KEY: misc_feature
<222> LOCATION: (20)..(20)
<223> OTHER INFORMATION: Xaa is any amino acid
<220> FEATURE:
<221> NAME/KEY: misc_feature
<222> LOCATION: (24)..(24)
<223> OTHER INFORMATION: Modifying group attached to epsilon amino group
      of lysine
<220> FEATURE:
<221> NAME/KEY: misc_feature
<222> LOCATION: (31)..(31)
<223> OTHER INFORMATION: Xaa is any amino acid

<400> SEQUENCE: 48

Xaa Xaa Glu Gly Thr Phe Ile Ser Asp Tyr Ser Ile Ala Xaa Asp Xaa
1               5                   10                  15

Ile Xaa Gln Xaa Asp Phe Val Lys Trp Leu Leu Ala Gln Lys Xaa
            20                  25                  30

<210> SEQ ID NO 49
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is Tyr or d-Tyr
<220> FEATURE:
<221> NAME/KEY: misc_feature
<222> LOCATION: (2)..(2)
<223> OTHER INFORMATION: Xaa is Ala, d-Ala, or Aib (alpha-
      aminoisobutyric acid)
<220> FEATURE:
<221> NAME/KEY: misc_feature
<222> LOCATION: (14)..(14)
<223> OTHER INFORMATION: Xaa is Leu, Met, Asp or Nle (norleucine)
<220> FEATURE:
<221> NAME/KEY: misc_feature
<222> LOCATION: (16)..(16)
<223> OTHER INFORMATION: Xaa is Lys or Ala
<220> FEATURE:
<221> NAME/KEY: misc_feature
<222> LOCATION: (18)..(18)
<223> OTHER INFORMATION: Xaa is Arg or His
<220> FEATURE:
<221> NAME/KEY: misc_feature
<222> LOCATION: (20)..(20)
<223> OTHER INFORMATION: Xaa is Gln, Glu, or Aib (alpha-aminoisobutyric
      acid)
<220> FEATURE:
<221> NAME/KEY: misc_feature
<222> LOCATION: (24)..(24)
<223> OTHER INFORMATION: Modifying group attached to epsilon amino group
      of lysine
<220> FEATURE:
<221> NAME/KEY: misc_feature
<222> LOCATION: (31)..(31)
<223> OTHER INFORMATION: Xaa is Gly or Pro

<400> SEQUENCE: 49

Xaa Xaa Glu Gly Thr Phe Ile Ser Asp Tyr Ser Ile Ala Xaa Asp Xaa
1               5                   10                  15

Ile Xaa Gln Xaa Asp Phe Val Lys Trp Leu Leu Ala Gln Lys Xaa
```

```
                    20                  25                  30

<210> SEQ ID NO 50
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is Tyr or d-Tyr
<220> FEATURE:
<221> NAME/KEY: misc_feature
<222> LOCATION: (2)..(2)
<223> OTHER INFORMATION: Xaa is Ala or Aib (alpha-aminoisobutyric acid)
<220> FEATURE:
<221> NAME/KEY: misc_feature
<222> LOCATION: (14)..(14)
<223> OTHER INFORMATION: Xaa is Nle (norleucine)
<220> FEATURE:
<221> NAME/KEY: misc_feature
<222> LOCATION: (16)..(16)
<223> OTHER INFORMATION: Xaa is Lys or Ala
<220> FEATURE:
<221> NAME/KEY: misc_feature
<222> LOCATION: (18)..(18)
<223> OTHER INFORMATION: Xaa is His or Arg
<220> FEATURE:
<221> NAME/KEY: misc_feature
<222> LOCATION: (20)..(20)
<223> OTHER INFORMATION: Xaa is Gln, Glu, or Aib (alpha-aminoisobutyric
      acid)
<220> FEATURE:
<221> NAME/KEY: misc_feature
<222> LOCATION: (24)..(24)
<223> OTHER INFORMATION: Modifying group attached to epsilon amino group
      of lysine
<220> FEATURE:
<221> NAME/KEY: misc_feature
<222> LOCATION: (31)..(31)
<223> OTHER INFORMATION: Xaa is Gly or Pro

<400> SEQUENCE: 50

Xaa Xaa Glu Gly Thr Phe Ile Ser Asp Tyr Ser Ile Ala Xaa Asp Xaa
1               5                   10                  15

Ile Xaa Gln Xaa Asp Phe Val Lys Trp Leu Leu Ala Gln Lys Xaa
            20                  25                  30

<210> SEQ ID NO 51
<211> LENGTH: 11
<212> TYPE: PRT
<213> ORGANISM: ARTIFICIAL
<220> FEATURE:
<223> OTHER INFORMATION: Synthetic polypeptide
<220> FEATURE:
<221> NAME/KEY: misc_feature
<223> OTHER INFORMATION: Formula III
<220> FEATURE:
<221> NAME/KEY: misc_feature
<222> LOCATION: (2)..(2)
<223> OTHER INFORMATION: Xaa is Lys or Glu
<220> FEATURE:
<221> NAME/KEY: misc_feature
<222> LOCATION: (3)..(3)
<223> OTHER INFORMATION: Xaa is Asn, Glu, or Asp

<400> SEQUENCE: 51

Lys Xaa Xaa Asp Trp Lys His Asn Ile Thr Gln
1               5                   10

<210> SEQ ID NO 52
<211> LENGTH: 29
```

```
<212> TYPE: PRT
<213> ORGANISM: ARTIFICIAL
<220> FEATURE:
<223> OTHER INFORMATION: Synthetic polypeptide
<220> FEATURE:
<221> NAME/KEY: Misc_feature
<223> OTHER INFORMATION: Embodiment 109
<220> FEATURE:
<221> NAME/KEY: Misc_feature
<222> LOCATION: (2)..(2)
<223> OTHER INFORMATION: Xaa is Acb (1-aminocyclobutanecarboxylic acid)
<220> FEATURE:
<221> NAME/KEY: Misc_feature
<222> LOCATION: (28)..(28)
<223> OTHER INFORMATION: Epsilon Lys:[(4S)-4-carboxy-4-[[(4S)-4-carboxy-
      4-[[2-[2-[2-[[2-[2-[2-[[(4S)-4-carboxy-4-[[(4S)-4-carboxy-4-(17-
      carboxyheptadecanoylamino)butanoyl]amino]butanoyl]amino]ethoxy]
      ethoxy]acetyl]amino]ethoxy]ethoxy]acetyl]amino]butanoyl]amino]
      butanoyl-
<220> FEATURE:
<221> NAME/KEY: Misc_feature
<222> LOCATION: (29)..(29)
<223> OTHER INFORMATION: C-terminal amidation

<400> SEQUENCE: 52

His Xaa Gln Gly Thr Phe Thr Ser Asp Leu Ser Lys Tyr Leu Asp Leu
1               5                   10                  15

Arg Arg Ala Arg Asp Phe Val Gln Trp Leu Leu Lys Thr
            20                  25

<210> SEQ ID NO 53
<211> LENGTH: 29
<212> TYPE: PRT
<213> ORGANISM: ARTIFICIAL
<220> FEATURE:
<223> OTHER INFORMATION: Synthetic polypeptide
<220> FEATURE:
<221> NAME/KEY: Misc_feature
<223> OTHER INFORMATION: Embodiment 110
<220> FEATURE:
<221> NAME/KEY: Misc_feature
<222> LOCATION: (2)..(2)
<223> OTHER INFORMATION: Xaa is Aib (alpha-aminoisobutyric acid)
<220> FEATURE:
<221> NAME/KEY: Misc_feature
<222> LOCATION: (28)..(28)
<223> OTHER INFORMATION: Epsilon amino Lys:
      [(4S)-4-carboxy-4-[[(4S)-4-carboxy-4-[[(2S)-2-[[(2S)-4-carboxy-2-
      [[(2S)-2-[[(4S)-4-carboxy-4-[[(4S)-4-carboxy-4-(17-
      carboxyheptadecanoylamino)butanoyl]amino]butanoyl]amino]
<220> FEATURE:
<221> NAME/KEY: Misc_feature
<222> LOCATION: (28)..(28)
<223> OTHER INFORMATION: -3-hydroxypropanoyl]amino]butanoyl]amino]-3-
      hydroxypropanoyl]amino]butanoyl]amino]butanoyl-
<220> FEATURE:
<221> NAME/KEY: Misc_feature
<222> LOCATION: (29)..(29)
<223> OTHER INFORMATION: C-terminal amidation

<400> SEQUENCE: 53

His Xaa Gln Gly Thr Phe Thr Ser Asp Leu Ser Lys Tyr Leu Glu Ser
1               5                   10                  15

Lys Arg Ala Arg Glu Phe Val Gln Trp Leu Leu Lys Thr
            20                  25

<210> SEQ ID NO 54
<211> LENGTH: 29
<212> TYPE: PRT
<213> ORGANISM: ARTIFICIAL
<220> FEATURE:
<223> OTHER INFORMATION: Synthetic polypeptide
<220> FEATURE:
```

```
<221> NAME/KEY: Misc_feature
<223> OTHER INFORMATION: Embodiment 111
<220> FEATURE:
<221> NAME/KEY: Misc_feature
<222> LOCATION: (2)..(2)
<223> OTHER INFORMATION: Xaa is Acb (1-aminocyclobutanecarboxylic acid)
<220> FEATURE:
<221> NAME/KEY: Misc_feature
<222> LOCATION: (28)..(28)
<223> OTHER INFORMATION: Epsilon amino of Lys: [(4S)-4-carboxy-4-[[(4S)-
      4-carboxy-4-[[2-[2-[2-[[2-[2-[2-[[(4S)-4-carboxy-4-(17-
      carboxyheptadecanoylamino)butanoyl]amino]ethoxy]ethoxy]acetyl]
      amino]ethoxy]ethoxy]acetyl]amino]butanoyl]amino]butanoyl]-
<220> FEATURE:
<221> NAME/KEY: Misc_feature
<222> LOCATION: (29)..(29)
<223> OTHER INFORMATION: C-terminal amidation

<400> SEQUENCE: 54

His Xaa Gln Gly Thr Phe Thr Ser Asp Leu Ser Lys Tyr Leu Glu Ser
1               5                   10                  15

Arg Arg Ala Arg Glu Phe Val Gln Trp Leu Leu Lys Thr
            20                  25

<210> SEQ ID NO 55
<211> LENGTH: 29
<212> TYPE: PRT
<213> ORGANISM: ARTIFICIAL
<220> FEATURE:
<223> OTHER INFORMATION: Synthetic polypeptide
<220> FEATURE:
<221> NAME/KEY: Misc_feature
<223> OTHER INFORMATION: Embodiment 112
<220> FEATURE:
<221> NAME/KEY: Misc_feature
<222> LOCATION: (2)..(2)
<223> OTHER INFORMATION: Xaa is Acb (1-aminocyclobutanecarboxylic acid)
<220> FEATURE:
<221> NAME/KEY: Misc_feature
<222> LOCATION: (28)..(28)
<223> OTHER INFORMATION: [(4S)-4-carboxy-4-[[(4S)-4-carboxy-4-[2-[2-[2-
      [[2-[2-[2-[[(4S)-4-carboxy-4-[[(4S)-4-carboxy-4-(17-
      carboxyheptadecanoylamino)butanoyl]amino]butanoyl]amino]ethoxy]
      ethoxy]acetyl]amino]ethoxy]ethoxy]acetyl]amino]butanoyl]amino]
      butanoyl]-
<220> FEATURE:
<221> NAME/KEY: Misc_feature
<222> LOCATION: (29)..(29)
<223> OTHER INFORMATION: C-terminal amidation

<400> SEQUENCE: 55

His Xaa Gln Gly Thr Phe Thr Ser Asp Leu Ser Lys Tyr Leu Asp Leu
1               5                   10                  15

Lys Arg Ala Arg Glu Phe Val Gln Trp Leu Leu Lys Thr
            20                  25

<210> SEQ ID NO 56
<211> LENGTH: 29
<212> TYPE: PRT
<213> ORGANISM: ARTIFICIAL
<220> FEATURE:
<223> OTHER INFORMATION: Synthetic polypeptide
<220> FEATURE:
<221> NAME/KEY: Misc_feature
<223> OTHER INFORMATION: Embodiment 113
<220> FEATURE:
<221> NAME/KEY: Misc_feature
<222> LOCATION: (2)..(2)
<223> OTHER INFORMATION: Xaa is Aib (alpha-aminoisobutyric acid)
<220> FEATURE:
<221> NAME/KEY: Misc_feature
<222> LOCATION: (28)..(28)
<223> OTHER INFORMATION: [2-[2-[2-[[2-[2-[2-[[(4S)-4-carboxy-4-[[(4S)-4-
```

```
            carboxy-4-[[(4S)-4-carboxy-4-(17-carboxyheptadecanoylamino)
            butanoyl]amino]butanoyl]amino]butanoyl]amino]ethoxy]ethoxy]acetyl]
            amino]ethoxy]ethoxy]acetyl]-
<220> FEATURE:
<221> NAME/KEY: Misc_feature
<222> LOCATION: (29)..(29)
<223> OTHER INFORMATION: C-terminal amidation

<400> SEQUENCE: 56

His Xaa Gln Gly Thr Phe Thr Ser Asp Leu Ser Lys Tyr Leu Asp Ala
1               5                   10                  15

Arg Arg Ala Arg Asp Phe Val Gln Trp Leu Leu Lys Thr
            20                  25

<210> SEQ ID NO 57
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<223> OTHER INFORMATION: Semaglutide
<220> FEATURE:
<221> NAME/KEY: MISC_FEATURE
<222> LOCATION: (2)..(2)
<223> OTHER INFORMATION: Xaa is Aib (alpha-aminoisobutyric acid)
<220> FEATURE:
<221> NAME/KEY: MISC_FEATURE
<222> LOCATION: (20)..(20)
<223> OTHER INFORMATION: The epsilon amino group of Lys has the
            following substituent:[2-(2-[2-(2-[2-(2-[4-(17-
            Carboxyheptadecanoylamino)-4(S)-carboxybutyrylamino]ethoxy)ethoxy]
            acetylamino)ethoxy]ethoxy)acetyl]-

<400> SEQUENCE: 57

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 58
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<223> OTHER INFORMATION: Semaglutide-like molecule
<220> FEATURE:
<221> NAME/KEY: MISC_FEATURE
<222> LOCATION: (2)..(2)
<223> OTHER INFORMATION: Xaa is Aib (alpha-aminoisobutyric acid)
<220> FEATURE:
<221> NAME/KEY: MISC_FEATURE
<222> LOCATION: (20)..(20)
<223> OTHER INFORMATION: The epsilon amino group of Lys has the
            following substituent: [2-(2-[2-(2-[2-(2-[4-(17-
            Carboxyheptadecanoylamino)-4(R)-carboxybutyrylamino]ethoxy)ethoxy]
            acetylamino)ethoxy]ethoxy)acetyl]-

<400> SEQUENCE: 58

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 59
<211> LENGTH: 31
```

```
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<223> OTHER INFORMATION: Compound 43
<220> FEATURE:
<221> NAME/KEY: MISC_FEATURE
<222> LOCATION: (1)..(1)
<223> OTHER INFORMATION: Xaa is N-acetyl D-Tyr
<220> FEATURE:
<221> NAME/KEY: MISC_FEATURE
<222> LOCATION: (14)..(14)
<223> OTHER INFORMATION: Xaa is Nle (Norleucine)
<220> FEATURE:
<221> NAME/KEY: MISC_FEATURE
<222> LOCATION: (20)..(20)
<223> OTHER INFORMATION: Xaa is Aib (alpha-aminoisobutyric acid)
<220> FEATURE:
<221> NAME/KEY: MISC_FEATURE
<222> LOCATION: (24)..(24)
<223> OTHER INFORMATION: The epsilon amino group of Lys has the
      following substituent: [2-[2-[2-[[2-[2-[2-[[4-[(19-
      carboxynonadecanoylamino)methyl]cyclohexanecarbonyl]amino]ethoxy]
      ethoxy]acetyl]amino]ethoxy]ethoxy]acetyl]-

<400> SEQUENCE: 59

Xaa Ala Glu Gly Thr Phe Ile Ser Asp Tyr Ser Ile Ala Xaa Asp Lys
1               5                   10                  15

Ile Arg Gln Xaa Asp Phe Val Lys Trp Leu Leu Ala Gln Lys Gly
            20                  25                  30

<210> SEQ ID NO 60
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<223> OTHER INFORMATION: Compound 44
<220> FEATURE:
<221> NAME/KEY: MISC_FEATURE
<222> LOCATION: (1)..(1)
<223> OTHER INFORMATION: Xaa is N-acetyl D-Tyr
<220> FEATURE:
<221> NAME/KEY: MISC_FEATURE
<222> LOCATION: (2)..(2)
<223> OTHER INFORMATION: Xaa is Aib (alpha-aminoisobutyric acid)
<220> FEATURE:
<221> NAME/KEY: MISC_FEATURE
<222> LOCATION: (14)..(14)
<223> OTHER INFORMATION: Xaa is Nle (Norleucine)
<220> FEATURE:
<221> NAME/KEY: MISC_FEATURE
<222> LOCATION: (24)..(24)
<223> OTHER INFORMATION: The epsilon amino group of Lys has the
      following substituent: [2-[2-[2-[[2-[2-[2-[[4-[(19-
      carboxynonadecanoylamino)methyl]cyclohexanecarbonyl]amino]ethoxy]
      ethoxy]acetyl]amino]ethoxy]ethoxy]acetyl]-
<220> FEATURE:
<221> NAME/KEY: MISC_FEATURE
<222> LOCATION: (31)..(31)
<223> OTHER INFORMATION: C-terminal amidation

<400> SEQUENCE: 60

Xaa Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Pro
            20                  25                  30

<210> SEQ ID NO 61
```

```
<211> LENGTH: 42
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<223> OTHER INFORMATION: Compound 45
<220> FEATURE:
<221> NAME/KEY: MISC_FEATURE
<222> LOCATION: (2)..(2)
<223> OTHER INFORMATION: Xaa is Aib (alpha-aminoisobutyric acid)
<220> FEATURE:
<221> NAME/KEY: MISC_FEATURE
<222> LOCATION: (24)..(24)
<223> OTHER INFORMATION: The epsilon amino group of Lys has the
      following substituent:[2-[2-[2-[[2-[2-[2-[[(4S)-4-carboxy-4-(17-
      carboxyheptadecanoylamino)butanoyl]amino]ethoxy]ethoxy]acetyl]
      amino]ethoxy]ethoxy]acetyl]-

<400> SEQUENCE: 61

Tyr Xaa Glu Gly Thr Phe Ile Ser Asp Tyr Ser Ile Ala Leu Asp Lys
1               5                   10                  15

Ile His Gln Gln Asp Phe Val Lys Trp Leu Leu Ala Gln Lys Gly Lys
            20                  25                  30

Lys Asn Asp Trp Lys His Asn Ile Thr Gln
        35                  40

<210> SEQ ID NO 62
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<223> OTHER INFORMATION: Compound 46
<220> FEATURE:
<221> NAME/KEY: MISC_FEATURE
<222> LOCATION: (1)..(1)
<223> OTHER INFORMATION: Xaa is N-acetyl D-Tyr
<220> FEATURE:
<221> NAME/KEY: MISC_FEATURE
<222> LOCATION: (2)..(2)
<223> OTHER INFORMATION: Xaa is Aib (alpha-aminoisobutyric acid)
<220> FEATURE:
<221> NAME/KEY: MISC_FEATURE
<222> LOCATION: (14)..(14)
<223> OTHER INFORMATION: Xaa is Nle (Norleucine)
<220> FEATURE:
<221> NAME/KEY: MISC_FEATURE
<222> LOCATION: (24)..(24)
<223> OTHER INFORMATION: The epsilon amino group of Lys
      has:[(4S)-4-carboxy-4-[[(4S)-4-carboxy-4-[[(4S)-4-carboxy-4-(17-
      carboxyheptadecanoylamino)butanoyl]amino]butanoyl]amino]butanoyl]-
<220> FEATURE:
<221> NAME/KEY: MISC_FEATURE
<222> LOCATION: (31)..(31)
<223> OTHER INFORMATION: C-terminal amidation

<400> SEQUENCE: 62

Xaa Xaa Glu Gly Thr Phe Ile Ser Asp Tyr Ser Ile Ala Xaa Asp Lys
1               5                   10                  15

Ile Arg Gln Gln Asp Phe Val Lys Trp Leu Leu Ala Gln Lys Pro
            20                  25                  30

<210> SEQ ID NO 63
<211> LENGTH: 31
<212> TYPE: PRT
<213> ORGANISM: ARTIFICIAL
<220> FEATURE:
<223> OTHER INFORMATION: Synthetic polypeptide
```

```
<220> FEATURE:
<221> NAME/KEY: MISC_FEATURE
<222> LOCATION: (1)..(1)
<223> OTHER INFORMATION: Xaa is Tyr or d-Tyr
<220> FEATURE:
<221> NAME/KEY: MISC_FEATURE
<222> LOCATION: (2)..(2)
<223> OTHER INFORMATION: Xaa is Ala or Aib (alpha-aminoisobutyric acid)
<220> FEATURE:
<221> NAME/KEY: MISC_FEATURE
<222> LOCATION: (14)..(14)
<223> OTHER INFORMATION: Xaa is Asp, Leu, or Nle (norleucine)
<220> FEATURE:
<221> NAME/KEY: MISC_FEATURE
<222> LOCATION: (16)..(16)
<223> OTHER INFORMATION: Xaa is Lys or Ala
<220> FEATURE:
<221> NAME/KEY: MISC_FEATURE
<222> LOCATION: (18)..(18)
<223> OTHER INFORMATION: Xaa is His or Arg
<220> FEATURE:
<221> NAME/KEY: MISC_FEATURE
<222> LOCATION: (20)..(20)
<223> OTHER INFORMATION: Xaa is Gln, Glu, or Aib (alpha-aminoisobutyric
      acid)
<220> FEATURE:
<221> NAME/KEY: MISC_FEATURE
<222> LOCATION: (24)..(24)
<223> OTHER INFORMATION: Modifying group attached to epsilon amino group
      of lysine
<220> FEATURE:
<221> NAME/KEY: MISC_FEATURE
<222> LOCATION: (31)..(31)
<223> OTHER INFORMATION: Xaa is Gly or Pro

<400> SEQUENCE: 63

Xaa Xaa Glu Gly Thr Phe Ile Ser Asp Tyr Ser Ile Ala Xaa Asp Xaa
1               5                   10                  15

Ile Xaa Gln Xaa Asp Phe Val Lys Trp Leu Leu Ala Gln Lys Xaa
            20                  25                  30

<210> SEQ ID NO 64
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is Tyr or d-Tyr
<220> FEATURE:
<221> NAME/KEY: MISC_FEATURE
<222> LOCATION: (2)..(2)
<223> OTHER INFORMATION: Xaa is Ala, d-Ala, or Aib (alpha-
      aminoisobutyric acid)
<220> FEATURE:
<221> NAME/KEY: MISC_FEATURE
<222> LOCATION: (14)..(14)
<223> OTHER INFORMATION: Xaa is Leu, Met, or Nle (norleucine)
<220> FEATURE:
<221> NAME/KEY: MISC_FEATURE
<222> LOCATION: (16)..(16)
<223> OTHER INFORMATION: Xaa is Lys or Ala
<220> FEATURE:
<221> NAME/KEY: MISC_FEATURE
<222> LOCATION: (18)..(18)
<223> OTHER INFORMATION: Xaa is Arg or His
<220> FEATURE:
<221> NAME/KEY: MISC_FEATURE
<222> LOCATION: (20)..(20)
<223> OTHER INFORMATION: Xaa is Gln, Glu, or Aib (alpha-aminoisobutyric
      acid)
<220> FEATURE:
<221> NAME/KEY: MISC_FEATURE
<222> LOCATION: (24)..(24)
```

```
<223> OTHER INFORMATION: Modifying group attached to epsilon amino group
      of lysine
<220> FEATURE:
<221> NAME/KEY: MISC_FEATURE
<222> LOCATION: (31)..(31)
<223> OTHER INFORMATION: Xaa is Gly or Pro

<400> SEQUENCE: 64

Xaa Xaa Glu Gly Thr Phe Ile Ser Asp Tyr Ser Ile Ala Xaa Asp Xaa
1               5                   10                  15

Ile Xaa Gln Xaa Asp Phe Val Lys Trp Leu Leu Ala Gln Lys Xaa
            20                  25                  30

<210> SEQ ID NO 65
<211> LENGTH: 31
<212> TYPE: PRT
<213> ORGANISM: ARTIFICIAL
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is Tyr, Ac-Tyr, d-Tyr or Ac-d-Tyr
<220> FEATURE:
<221> NAME/KEY: MISC_FEATURE
<222> LOCATION: (2)..(2)
<223> OTHER INFORMATION: Xaa is Ala, d-Ala, or Aib (alpha-
      aminoisobutyric acid)
<220> FEATURE:
<221> NAME/KEY: MISC_FEATURE
<222> LOCATION: (14)..(14)
<223> OTHER INFORMATION: Xaa is Leu, Met, Asp or Nle (norleucine)
<220> FEATURE:
<221> NAME/KEY: MISC_FEATURE
<222> LOCATION: (16)..(16)
<223> OTHER INFORMATION: Xaa is Lys or Ala
<220> FEATURE:
<221> NAME/KEY: MISC_FEATURE
<222> LOCATION: (18)..(18)
<223> OTHER INFORMATION: Xaa is Arg or His
<220> FEATURE:
<221> NAME/KEY: MISC_FEATURE
<222> LOCATION: (20)..(20)
<223> OTHER INFORMATION: Xaa is Gln, Glu, or Aib (alpha-aminoisobutyric
      acid)
<220> FEATURE:
<221> NAME/KEY: MISC_FEATURE
<222> LOCATION: (24)..(24)
<223> OTHER INFORMATION: Modifying group attached to epsilon amino group
      of lysine
<220> FEATURE:
<221> NAME/KEY: MISC_FEATURE
<222> LOCATION: (31)..(31)
<223> OTHER INFORMATION: Xaa is Gly or Pro

<400> SEQUENCE: 65

Xaa Xaa Glu Gly Thr Phe Ile Ser Asp Tyr Ser Ile Ala Xaa Asp Xaa
1               5                   10                  15

Ile Xaa Gln Xaa Asp Phe Val Lys Trp Leu Leu Ala Gln Lys Xaa
            20                  25                  30
```